US009393256B2

(12) United States Patent
Ray et al.

(10) Patent No.: US 9,393,256 B2
(45) Date of Patent: *Jul. 19, 2016

(54) METHODS FOR TREATING HCV

(71) Applicant: Gilead Pharmasset LLC, Foster City, CA (US)

(72) Inventors: Adrian S. Ray, Burlingame, CA (US); John O. Link, San Francisco, CA (US); David W. Oldach, Chapel Hill, NC (US); William E. Delaney, IV, Foster City, CA (US); Hongmei Mo, Palo Alto, CA (US); Cheng Yong Yang, Foster City, CA (US)

(73) Assignee: Gilead Pharmasset LLC, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/875,252

(22) Filed: May 1, 2013

(65) Prior Publication Data
US 2013/0243726 A1 Sep. 19, 2013

Related U.S. Application Data

(63) Continuation of application No. PCT/US2012/055621, filed on Sep. 14, 2012.

(60) Provisional application No. 61/535,885, filed on Sep. 16, 2011, provisional application No. 61/561,753, filed on Nov. 18, 2011.

(51) Int. Cl.
| | |
|---|---|
| *A61K 31/505* | (2006.01) |
| *A61K 31/415* | (2006.01) |
| *A61K 31/40* | (2006.01) |
| *A61K 31/34* | (2006.01) |
| *A61K 31/7072* | (2006.01) |
| *A61K 31/381* | (2006.01) |
| *A61K 31/4184* | (2006.01) |
| *A61K 31/4196* | (2006.01) |
| *A61K 31/513* | (2006.01) |
| *A61K 45/06* | (2006.01) |
| *A61K 31/7056* | (2006.01) |
| *A61K 38/21* | (2006.01) |

(52) U.S. Cl.
CPC ........... *A61K 31/7072* (2013.01); *A61K 31/381* (2013.01); *A61K 31/4184* (2013.01); *A61K 31/4196* (2013.01); *A61K 31/513* (2013.01); *A61K 31/7056* (2013.01); *A61K 38/212* (2013.01); *A61K 45/06* (2013.01)

(58) Field of Classification Search
None
See application file for complete search history.

(56) References Cited

U.S. PATENT DOCUMENTS

| | | |
|---|---|---|
| 3,798,209 A | 3/1974 | Robins et al. |
| RE29,835 E | 11/1978 | Witkowski et al. |
| 5,026,687 A | 6/1991 | Yarchoan et al. |
| 5,194,654 A | 3/1993 | Hostetler et al. |
| 5,210,015 A | 5/1993 | Gelfand et al. |
| 5,463,092 A | 10/1995 | Hostetler et al. |
| 5,538,848 A | 7/1996 | Livak et al. |
| 5,703,058 A | 12/1997 | Schinazi et al. |
| 5,858,389 A | 1/1999 | Elsherbini |
| 5,905,070 A | 5/1999 | Schinazi et al. |
| 6,232,300 B1 | 5/2001 | Schinazi et al. |
| 6,348,587 B1 | 2/2002 | Schinazi et al. |
| 6,391,859 B1 | 5/2002 | Schinazi et al. |
| 6,475,985 B1 | 11/2002 | Wagner et al. |
| 6,479,463 B1 | 11/2002 | Wang et al. |
| 6,495,677 B1 | 12/2002 | Ramasamy et al. |
| 6,509,320 B1 | 1/2003 | Wang et al. |
| 6,552,183 B1 | 4/2003 | Ramasamy et al. |
| 6,573,248 B2 | 6/2003 | Ramasamy et al. |
| 6,589,941 B1 | 7/2003 | Fahrig et al. |
| 6,642,206 B2 | 11/2003 | Ramasamy et al. |
| 6,660,721 B2 | 12/2003 | Devos et al. |
| 6,677,314 B2 | 1/2004 | Klecker et al. |
| 6,677,315 B2 | 1/2004 | Klecker et al. |
| 6,680,303 B2 | 1/2004 | Schinazi et al. |
| 6,682,715 B2 | 1/2004 | Klecker et al. |
| 6,683,045 B2 | 1/2004 | Klecker et al. |
| 6,703,374 B1 | 3/2004 | Klecker et al. |
| 6,753,309 B2 | 6/2004 | Klecker et al. |
| 6,777,395 B2 | 8/2004 | Bhat et al. |
| 6,784,166 B2 | 8/2004 | Devos et al. |
| 6,787,526 B1 | 9/2004 | Bryant et al. |
| 6,812,219 B2 | 11/2004 | LaColla et al. |
| 6,815,542 B2 | 11/2004 | Hong et al. |

(Continued)

FOREIGN PATENT DOCUMENTS

| | | |
|---|---|---|
| CN | 101108870 | 1/2008 |
| DE | 102008057284 | 5/2010 |

(Continued)

OTHER PUBLICATIONS

Asselah, et al., "New direct-acting antivirals' combination for the treatment of chronic hepatitis C", Liver International, (2011), 31:68-77.

(Continued)

*Primary Examiner* — Jeffrey S Lundgren
*Assistant Examiner* — Michael Schmitt
(74) *Attorney, Agent, or Firm* — Sheppard Mullin Richter & Hampton LLP

(57) ABSTRACT

This invention relates to combinations of therapeutic molecules useful for treating hepatitis C virus infection. The present invention relates to methods, uses, dosing regimens, and compositions.

4 Claims, No Drawings

(56) References Cited

U.S. PATENT DOCUMENTS

| | | |
|---|---|---|
| 6,846,810 B2 | 1/2005 | Martin et al. |
| 6,908,924 B2 | 6/2005 | Watanabe et al. |
| 6,911,424 B2 | 6/2005 | Schinazi et al. |
| 6,914,054 B2 | 7/2005 | Sommadossi et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,148,206 B2 | 12/2006 | Sommadossi et al. |
| 7,163,929 B2 | 1/2007 | Sommadossi et al. |
| 7,202,224 B2 | 4/2007 | Eldrup et al. |
| 7,268,119 B2 | 9/2007 | Cook et al. |
| 7,307,065 B2 | 12/2007 | Schinazi et al. |
| 7,323,453 B2 | 1/2008 | Olsen et al. |
| 7,365,057 B2 | 4/2008 | LaColla et al. |
| 7,390,791 B2 | 6/2008 | Becker et al. |
| 7,429,572 B2 | 9/2008 | Clark |
| 7,601,820 B2 | 10/2009 | Wang et al. |
| 7,608,597 B2 | 10/2009 | Sommadossi et al. |
| 7,608,600 B2 | 10/2009 | Storer et al. |
| 7,635,689 B2 | 12/2009 | LaColla et al. |
| 7,704,992 B2 | 4/2010 | Bachand et al. |
| 7,754,699 B2 | 7/2010 | Chun et al. |
| 7,820,380 B2 | 10/2010 | Huang |
| 7,879,815 B2 | 2/2011 | Maccoss et al. |
| 7,964,580 B2 | 6/2011 | Sofia et al. |
| 8,088,368 B2 | 1/2012 | Guo et al. |
| 8,148,349 B2 | 4/2012 | Meppen et al. |
| 8,173,621 B2 | 5/2012 | Du et al. |
| 8,178,491 B2 | 5/2012 | Cho et al. |
| 8,273,341 B2 | 9/2012 | Guo et al. |
| 8,334,270 B2 | 12/2012 | Sofia et al. |
| 8,362,068 B2 | 1/2013 | Dousson et al. |
| 8,415,322 B2 | 4/2013 | Clark |
| 8,466,159 B2 | 6/2013 | Bernstein et al. |
| 8,481,713 B2 | 7/2013 | Wang et al. |
| 8,492,386 B2 | 7/2013 | Bernstein et al. |
| 8,492,539 B2 | 7/2013 | Chun et al. |
| 8,513,298 B2 | 8/2013 | Canales et al. |
| 8,546,402 B2 | 10/2013 | Sokoloff et al. |
| 8,551,973 B2 | 10/2013 | Bao et al. |
| 8,563,530 B2 | 10/2013 | Chang et al. |
| 8,569,478 B2 | 10/2013 | Du et al. |
| 8,575,118 B2 | 11/2013 | Guo et al. |
| 8,580,765 B2 | 11/2013 | Sofia et al. |
| 8,618,076 B2 | 12/2013 | Ross et al. |
| 8,629,263 B2 | 1/2014 | Ross et al. |
| 8,633,309 B2 | 1/2014 | Ross et al. |
| 8,642,756 B2 | 2/2014 | Ross et al. |
| 8,669,234 B2 | 3/2014 | Guo et al. |
| 8,685,984 B2 | 4/2014 | Bernstein et al. |
| 8,716,262 B2 | 5/2014 | Sofia et al. |
| 8,716,263 B2 | 5/2014 | Chun et al. |
| 8,735,372 B2 | 5/2014 | Du et al. |
| 8,735,569 B2 | 5/2014 | Ross et al. |
| 8,759,510 B2 | 6/2014 | Du et al. |
| 8,809,265 B2 | 8/2014 | Bernstein et al. |
| 8,822,430 B2 | 9/2014 | Bacon et al. |
| 8,841,275 B2 | 9/2014 | Du et al. |
| 8,841,278 B2 | 9/2014 | Bacon et al. |
| 8,859,756 B2 | 10/2014 | Ross et al. |
| 8,889,159 B2 | 11/2014 | Cleary et al. |
| 8,906,880 B2 | 12/2014 | Du et al. |
| 8,957,045 B2 | 2/2015 | Sofia et al. |
| 8,957,046 B2 | 2/2015 | Du et al. |
| 8,969,588 B2 | 3/2015 | Scott et al. |
| 9,045,520 B2 | 6/2015 | Chun et al. |
| 9,056,860 B2 | 6/2015 | Scott et al. |
| 2001/0034440 A1 | 10/2001 | Shepard et al. |
| 2001/0038833 A1 | 11/2001 | Rybak et al. |
| 2002/0008241 A1 | 1/2002 | Edmond et al. |
| 2002/0058635 A1 | 5/2002 | Averett |
| 2002/0147160 A1 | 10/2002 | Bhat et al. |
| 2002/0198173 A1 | 12/2002 | Schinazi et al. |
| 2003/0050229 A1 | 3/2003 | Sommadossi et al. |
| 2003/0060400 A1 | 3/2003 | LaColla et al. |
| 2003/0109697 A1 | 6/2003 | Shepard et al. |
| 2003/0119752 A1 | 6/2003 | Farmer et al. |
| 2003/0144502 A1 | 7/2003 | Pietrzkowski et al. |
| 2003/0153744 A1 | 8/2003 | Mekouar et al. |
| 2003/0176433 A1 | 9/2003 | Beaulieu et al. |
| 2003/0187018 A1 | 10/2003 | Llinas-Brunet et al. |
| 2003/0207922 A1 | 11/2003 | Neuner et al. |
| 2004/0006007 A1 | 1/2004 | Gosselin et al. |
| 2004/0014108 A1 | 1/2004 | Eldrup et al. |
| 2004/0023901 A1 | 2/2004 | Cook et al. |
| 2004/0024190 A1 | 2/2004 | Beaulieu et al. |
| 2004/0059104 A1 | 3/2004 | Cook et al. |
| 2004/0063622 A1 | 4/2004 | Sommadossi et al. |
| 2004/0067901 A1 | 4/2004 | Bhat et al. |
| 2004/0072788 A1 | 4/2004 | Bhat et al. |
| 2004/0087541 A1 | 5/2004 | Jonaitis et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Carroll et al. |
| 2004/0142989 A1 | 7/2004 | Finzel et al. |
| 2004/0142993 A1 | 7/2004 | Battistini et al. |
| 2004/0167140 A1 | 8/2004 | Schinazi et al. |
| 2004/0171570 A1 | 9/2004 | Allerson et al. |
| 2004/0214844 A1 | 10/2004 | Otto et al. |
| 2004/0229839 A1 | 11/2004 | Babu et al. |
| 2004/0229840 A1 | 11/2004 | Bhat et al. |
| 2004/0254141 A1 | 12/2004 | Schinazi et al. |
| 2004/0259934 A1 | 12/2004 | Olsen et al. |
| 2004/0265969 A1 | 12/2004 | Li et al. |
| 2005/0009737 A1 | 1/2005 | Clark |
| 2005/0026160 A1 | 2/2005 | Allerson et al. |
| 2005/0026853 A1 | 2/2005 | Mekouar et al. |
| 2005/0031588 A1 | 2/2005 | Sommadossi et al. |
| 2005/0043390 A1 | 2/2005 | Bravi et al. |
| 2005/0069522 A1 | 3/2005 | Colonno et al. |
| 2005/0075309 A1 | 4/2005 | Storer et al. |
| 2005/0080034 A1 | 4/2005 | Standring et al. |
| 2005/0082144 A1 | 4/2005 | Maupin et al. |
| 2005/0090432 A1 | 4/2005 | McPhee et al. |
| 2005/0096364 A1 | 5/2005 | Romine et al. |
| 2005/0098125 A1 | 5/2005 | Hathaway et al. |
| 2005/0124532 A1 | 6/2005 | Sommadossi et al. |
| 2005/0130923 A1 | 6/2005 | Bhat et al. |
| 2005/0130931 A1 | 6/2005 | Boyer et al. |
| 2005/0137161 A1 | 6/2005 | Sommadossi et al. |
| 2005/0148534 A1 | 7/2005 | Castellino et al. |
| 2005/0154056 A1 | 7/2005 | Yang et al. |
| 2005/0164960 A1 | 7/2005 | Olsen et al. |
| 2005/0215513 A1 | 9/2005 | Boojamra et al. |
| 2005/0215614 A1 | 9/2005 | Singh et al. |
| 2005/0227947 A1 | 10/2005 | Chen et al. |
| 2005/0228013 A1 | 10/2005 | Thurkauf et al. |
| 2005/0261237 A1 | 11/2005 | Boojamra et al. |
| 2006/0003951 A1 | 1/2006 | Mekouar et al. |
| 2006/0004063 A1 | 1/2006 | Finzel et al. |
| 2006/0035866 A1 | 2/2006 | Cannizzaro et al. |
| 2006/0040890 A1 | 2/2006 | Martin et al. |
| 2006/0040927 A1 | 2/2006 | Blake et al. |
| 2006/0040944 A1 | 2/2006 | Gosselin et al. |
| 2006/0046983 A1 | 3/2006 | Hudyma et al. |
| 2006/0079478 A1 | 4/2006 | Boojamra et al. |
| 2006/0094706 A1 | 5/2006 | Paruch et al. |
| 2006/0110724 A1 | 5/2006 | Burkhardt et al. |
| 2006/0122154 A1 | 6/2006 | Olsen et al. |
| 2006/0166964 A1 | 7/2006 | Hudyma |
| 2006/0194749 A1 | 8/2006 | Keicher et al. |
| 2006/0234962 A1 | 10/2006 | Olsen et al. |
| 2006/0241064 A1 | 10/2006 | Roberts et al. |
| 2006/0276405 A1 | 12/2006 | Albrecht |
| 2006/0276511 A1 | 12/2006 | Serrano-Wu et al. |
| 2006/0287300 A1 | 12/2006 | Klein et al. |
| 2006/0293306 A1 | 12/2006 | Beaulieu et al. |
| 2007/0004669 A1 | 1/2007 | Carroll et al. |
| 2007/0015905 A1 | 1/2007 | LaColla et al. |
| 2007/0024277 A1 | 2/2007 | Cech et al. |
| 2007/0037735 A1 | 2/2007 | Gosselin et al. |
| 2007/0037773 A1 | 2/2007 | Sommadossi et al. |

(56) References Cited

U.S. PATENT DOCUMENTS

| | | |
|---|---|---|
| 2007/0042939 A1 | 2/2007 | LaColla et al. |
| 2007/0042988 A1 | 2/2007 | Klumpp et al. |
| 2007/0042990 A1 | 2/2007 | Gosselin et al. |
| 2007/0049754 A1 | 3/2007 | Boojamra et al. |
| 2007/0054842 A1 | 3/2007 | Blatt et al. |
| 2007/0060498 A1 | 3/2007 | Gosselin et al. |
| 2007/0060541 A1 | 3/2007 | Gosselin et al. |
| 2007/0087960 A1 | 4/2007 | Storer et al. |
| 2007/0123484 A1 | 5/2007 | Bhat et al. |
| 2007/0135363 A1 | 6/2007 | Cook et al. |
| 2007/0142380 A1 | 6/2007 | Beaulieu et al. |
| 2007/0155716 A1 | 7/2007 | Simmen et al. |
| 2007/0197463 A1 | 8/2007 | Chun et al. |
| 2007/0197478 A1 | 8/2007 | Jones et al. |
| 2007/0225249 A1 | 9/2007 | Shi |
| 2007/0231318 A1 | 10/2007 | Saha et al. |
| 2007/0232627 A1 | 10/2007 | Betebenner et al. |
| 2007/0232645 A1 | 10/2007 | Rockway et al. |
| 2007/0265222 A1 | 11/2007 | MacCoss et al. |
| 2007/0265262 A1 | 11/2007 | Schmitz et al. |
| 2007/0275912 A1 | 11/2007 | Bhat et al. |
| 2007/0275930 A1 | 11/2007 | Gentles et al. |
| 2007/0275947 A1 | 11/2007 | Bergstrom |
| 2008/0008682 A1 | 1/2008 | Chong et al. |
| 2008/0021047 A1 | 1/2008 | Butora et al. |
| 2008/0050336 A1 | 2/2008 | Bachand et al. |
| 2008/0057031 A1 | 3/2008 | Casarez et al. |
| 2008/0070861 A1 | 3/2008 | Clark et al. |
| 2008/0108617 A1 | 5/2008 | Desai et al. |
| 2008/0146788 A1 | 6/2008 | Bhat et al. |
| 2008/0182863 A1 | 7/2008 | Simmen et al. |
| 2008/0253995 A1 | 10/2008 | Clark et al. |
| 2008/0280842 A1 | 11/2008 | Maccoss et al. |
| 2009/0004135 A1 | 1/2009 | Clark |
| 2009/0036666 A1 | 2/2009 | Clark |
| 2009/0041716 A1 | 2/2009 | Kim et al. |
| 2009/0062311 A1 | 3/2009 | Simmen et al. |
| 2009/0068140 A1 | 3/2009 | Bachand et al. |
| 2009/0105302 A1 | 4/2009 | Simmen et al. |
| 2009/0137521 A1 | 5/2009 | Hamilton et al. |
| 2009/0156595 A1 | 6/2009 | Raboisson et al. |
| 2009/0202478 A1 | 8/2009 | Bachand et al. |
| 2009/0202483 A1 | 8/2009 | Bachand et al. |
| 2009/0233879 A1 | 9/2009 | Reddy et al. |
| 2009/0269305 A1 | 10/2009 | Seiwert et al. |
| 2009/0280084 A1 | 11/2009 | Schinazi et al. |
| 2009/0281140 A1 | 11/2009 | Simmen et al. |
| 2009/0281141 A1 | 11/2009 | Simmen et al. |
| 2009/0291902 A1 | 11/2009 | Cottrell et al. |
| 2010/0015090 A1 | 1/2010 | Tung et al. |
| 2010/0022468 A1 | 1/2010 | Meppen et al. |
| 2010/0035835 A1 | 2/2010 | Narjes et al. |
| 2010/0048917 A1 | 2/2010 | Wang et al. |
| 2010/0080772 A1 | 4/2010 | Belema et al. |
| 2010/0137576 A1 | 6/2010 | Stec et al. |
| 2010/0152128 A1 | 6/2010 | Attenni et al. |
| 2010/0160335 A1 | 6/2010 | Koh No et al. |
| 2010/0173863 A1 | 7/2010 | Schinazi et al. |
| 2010/0226885 A1 | 9/2010 | Albrecht et al. |
| 2010/0227801 A1 | 9/2010 | Hopkins |
| 2010/0234316 A1 | 9/2010 | Maccoss et al. |
| 2010/0249068 A1 | 9/2010 | Beigelman et al. |
| 2010/0249190 A1 | 9/2010 | Lopez et al. |
| 2010/0267785 A1 | 10/2010 | Wu et al. |
| 2010/0298257 A1 | 11/2010 | Ross et al. |
| 2010/0310512 A1 | 12/2010 | Guo et al. |
| 2010/0316594 A1 | 12/2010 | Sommadossi et al. |
| 2010/0316607 A1 | 12/2010 | Or et al. |
| 2011/0020272 A1 | 1/2011 | Schubert et al. |
| 2011/0077280 A1 | 3/2011 | Bender et al. |
| 2011/0092415 A1 | 4/2011 | Degoey et al. |
| 2011/0137633 A1 | 6/2011 | Hutchins et al. |
| 2011/0142798 A1 | 6/2011 | Qiu et al. |
| 2011/0150827 A1 | 6/2011 | Dousson et al. |
| 2011/0178129 A1 | 7/2011 | Canales et al. |
| 2011/0237621 A1 | 9/2011 | Simmen et al. |
| 2011/0306541 A1 | 12/2011 | Delaney, IV et al. |
| 2012/0094284 A1 | 4/2012 | Lopatin et al. |
| 2012/0107278 A1 | 5/2012 | Berrey et al. |
| 2012/0245335 A1 | 9/2012 | Clark |
| 2012/0246335 A1 | 9/2012 | Liu et al. |
| 2012/0251152 A1 | 10/2012 | Brewington et al. |
| 2012/0264711 A1 | 10/2012 | Guo et al. |
| 2013/0102526 A1 | 4/2013 | Bernstein et al. |
| 2013/0102557 A1 | 4/2013 | Bernstein et al. |
| 2013/0102558 A1 | 4/2013 | Bernstein et al. |
| 2013/0109647 A1 | 5/2013 | Berrey et al. |
| 2013/0136776 A1 | 5/2013 | Cleary et al. |
| 2013/0156732 A1 | 6/2013 | Bacon et al. |
| 2013/0164260 A1 | 6/2013 | Bacon et al. |
| 2013/0165401 A1 | 6/2013 | Ross et al. |
| 2013/0172239 A1 | 7/2013 | Gao et al. |
| 2013/0273005 A1 | 10/2013 | Delaney et al. |
| 2013/0288997 A1 | 10/2013 | Ross et al. |
| 2013/0324496 A1 | 12/2013 | Scott et al. |
| 2013/0324740 A1 | 12/2013 | Scott et al. |
| 2013/0338349 A1 | 12/2013 | Chun et al. |
| 2014/0039021 A1 | 2/2014 | Bacon et al. |
| 2014/0045783 A1 | 2/2014 | Du et al. |
| 2014/0051656 A1 | 2/2014 | Guo et al. |
| 2014/0107016 A1 | 4/2014 | Bernstein et al. |
| 2014/0107017 A1 | 4/2014 | Bernstein et al. |
| 2014/0121366 A1 | 5/2014 | Chun et al. |
| 2014/0187511 A1 | 7/2014 | Du et al. |
| 2014/0212487 A1 | 7/2014 | Mogalian et al. |
| 2014/0249074 A1 | 9/2014 | Bacon et al. |
| 2014/0249101 A1 | 9/2014 | Ding et al. |
| 2014/0343008 A1 | 11/2014 | Yang |
| 2015/0018300 A1 | 1/2015 | Du et al. |
| 2015/0087045 A1 | 3/2015 | Edwards et al. |
| 2015/0141353 A1 | 5/2015 | Delaney et al. |
| 2015/0141659 A1 | 5/2015 | Mogalian et al. |
| 2015/0150896 A1 | 6/2015 | Cleary et al. |

FOREIGN PATENT DOCUMENTS

| | | |
|---|---|---|
| EP | 2583677 | 4/2013 |
| EP | 2583680 | 4/2013 |
| EP | 2797586 | 11/2014 |
| JP | 5238939 | 9/1993 |
| WO | WO-90/00555 | 1/1990 |
| WO | WO-93/00910 | 1/1993 |
| WO | WO-96/29336 | 9/1996 |
| WO | WO-96/32403 | 10/1996 |
| WO | WO-98/16184 | 4/1998 |
| WO | WO-99/15194 | 4/1999 |
| WO | WO-99/37753 | 7/1999 |
| WO | WO-99/43691 | 9/1999 |
| WO | WO-99/59621 | 11/1999 |
| WO | WO-99/64016 | 12/1999 |
| WO | WO-00/09531 | 4/2000 |
| WO | WO-00/18775 | 4/2000 |
| WO | WO-00/37110 | 6/2000 |
| WO | WO-01/07454 | 2/2001 |
| WO | WO-01/32153 | 8/2001 |
| WO | WO-01/60315 | 8/2001 |
| WO | WO-01/79246 | 10/2001 |
| WO | WO-01/81359 | 11/2001 |
| WO | WO-01/90121 | 11/2001 |
| WO | WO-01/91737 | 12/2001 |
| WO | WO-01/92282 | 12/2001 |
| WO | WO-01/96353 | 12/2001 |
| WO | WO-02/08241 | 1/2002 |
| WO | WO-02/08256 | 1/2002 |
| WO | WO-02/18404 | 3/2002 |
| WO | WO-02/32414 | 4/2002 |
| WO | WO-02/32920 | 4/2002 |
| WO | WO-02/57425 | 4/2002 |
| WO | WO-02/48165 | 6/2002 |
| WO | WO-02/057287 | 7/2002 |
| WO | WO-02/100415 | 12/2002 |
| WO | WO-03/000713 | 1/2003 |
| WO | WO-03/006490 | 1/2003 |
| WO | WO-03/010141 | 2/2003 |

(56) References Cited

FOREIGN PATENT DOCUMENTS

| | | |
|---|---|---|
| WO | WO-03/024461 | 3/2003 |
| WO | WO-03/026589 | 4/2003 |
| WO | WO-03/051899 | 6/2003 |
| WO | WO-03/061576 | 7/2003 |
| WO | WO-03/062256 | 7/2003 |
| WO | WO-03/068244 | 8/2003 |
| WO | WO-03/105770 | 12/2003 |
| WO | WO-03/106477 | 12/2003 |
| WO | WO-04/000858 | 12/2003 |
| WO | WO-2004/002422 | 1/2004 |
| WO | WO-2004/002999 | 1/2004 |
| WO | WO-2004/003000 | 1/2004 |
| WO | WO-2004/003138 | 1/2004 |
| WO | WO-2004/007512 | 1/2004 |
| WO | WO-2004/009020 | 1/2004 |
| WO | WO-2004/009610 | 1/2004 |
| WO | WO-2004/014313 | 2/2004 |
| WO | WO-2004/046331 | 6/2004 |
| WO | WO-2004/080466 | 9/2004 |
| WO | WO-2004/096235 | 11/2004 |
| WO | WO-2004/096286 | 11/2004 |
| WO | WO-2005/002626 | 1/2005 |
| WO | WO-2005/003147 | 1/2005 |
| WO | WO-2005/009418 | 2/2005 |
| WO | WO-2005/012327 | 2/2005 |
| WO | WO-2005/020884 | 3/2005 |
| WO | WO-2005/021568 | 3/2005 |
| WO | WO-2005/082144 | 9/2005 |
| WO | WO-2005/121634 | 12/2005 |
| WO | WO 2005/123087 | 12/2005 |
| WO | WO-2006/000922 | 1/2006 |
| WO | WO-2006/012078 | 2/2006 |
| WO | WO-2006/012440 | 2/2006 |
| WO | WO-2006/029081 | 3/2006 |
| WO | WO-2006/031725 | 3/2006 |
| WO | WO-2006/037028 | 4/2006 |
| WO | WO-2006/050161 | 5/2006 |
| WO | WO-2006/065335 | 6/2006 |
| WO | WO-2006/067606 | 6/2006 |
| WO | WO-2006/116557 | 11/2006 |
| WO | WO-2006/121820 | 11/2006 |
| WO | WO-2006/133326 | 12/2006 |
| WO | WO-2007/002602 | 1/2007 |
| WO | WO-2007/020193 | 2/2007 |
| WO | WO-2007/065829 | 6/2007 |
| WO | WO-2007/095269 | 8/2007 |
| WO | WO-2008/005519 | 1/2008 |
| WO | WO-2008/005565 | 1/2008 |
| WO | WO-2008/010921 | 1/2008 |
| WO | WO-2008/021927 | 2/2008 |
| WO | WO-2008/021928 | 2/2008 |
| WO | WO-2008/021936 | 2/2008 |
| WO | WO-2008/045419 | 4/2008 |
| WO | WO-2008/079206 | 7/2008 |
| WO | WO-2008/082601 | 7/2008 |
| WO | WO-2008/085508 | 7/2008 |
| WO | WO-2008/121634 | 10/2008 |
| WO | WO-2008/142055 | 11/2008 |
| WO | WO-2008/144380 | 11/2008 |
| WO | WO-2009/005676 | 1/2009 |
| WO | WO-2009/005677 | 1/2009 |
| WO | WO-2009/005687 | 1/2009 |
| WO | WO-2009/009001 | 1/2009 |
| WO | WO-2009/020825 | 2/2009 |
| WO | WO-2009/020828 | 2/2009 |
| WO | WO-2009/038663 | 3/2009 |
| WO | WO-2009/052287 | 4/2009 |
| WO | WO-2009/089523 | 7/2009 |
| WO | WO-2009/102318 | 8/2009 |
| WO | WO-2009/102325 | 8/2009 |
| WO | WO-2009/102568 | 8/2009 |
| WO | WO-2009/102633 | 8/2009 |
| WO | WO-2009/115893 | 9/2009 |
| WO | WO-2009/120878 | 10/2009 |
| WO | WO-2009/129120 | 10/2009 |
| WO | WO-2009/132123 | 10/2009 |
| WO | WO-2009/152095 | 12/2009 |
| WO | WO-2010/004343 | 1/2010 |
| WO | WO-2010/017401 | 2/2010 |
| WO | WO-2010/062821 | 6/2010 |
| WO | WO-2010/065668 | 6/2010 |
| WO | WO-2010/065674 | 6/2010 |
| WO | WO-2010/065681 | 6/2010 |
| WO | WO-2010/075517 | 7/2010 |
| WO | WO-2010/075549 | 7/2010 |
| WO | WO-2010/075554 | 7/2010 |
| WO | WO-2010/077613 | 7/2010 |
| WO | WO-2010/080878 | 7/2010 |
| WO | WO-2010/081082 | 7/2010 |
| WO | WO-2010/091413 | 8/2010 |
| WO | WO-2010/094977 | 8/2010 |
| WO | WO-2010/096302 | 8/2010 |
| WO | WO-2010/096462 | 8/2010 |
| WO | WO-2010/096777 | 8/2010 |
| WO | WO-2010/099527 | 9/2010 |
| WO | WO-2010/111483 | 9/2010 |
| WO | WO-2010/111534 | 9/2010 |
| WO | WO-2010/111673 | 9/2010 |
| WO | WO-2010/112203 | 10/2010 |
| WO | WO-2010/117635 | 10/2010 |
| WO | WO-2010/117977 | 10/2010 |
| WO | WO-2010/120621 | 10/2010 |
| WO | WO-2010/120935 | 10/2010 |
| WO | WO-2010/122162 | 10/2010 |
| WO | WO-2010/132538 | 11/2010 |
| WO | WO-2010/132601 | 11/2010 |
| WO | WO-2010/135569 | 11/2010 |
| WO | WO-2010/138368 | 12/2010 |
| WO | WO-2010/138488 | 12/2010 |
| WO | WO-2010/138790 | 12/2010 |
| WO | WO-2010/138791 | 12/2010 |
| WO | WO-2010/144646 | 12/2010 |
| WO | WO-2010/148006 | 12/2010 |
| WO | WO-2011/004276 | 1/2011 |
| WO | WO-2011/007454 | 1/2011 |
| WO | WO-2011/009084 | 1/2011 |
| WO | WO-2011/015657 | 2/2011 |
| WO | WO-2011/015658 | 2/2011 |
| WO | WO-2011/026920 | 3/2011 |
| WO | WO-2011/028596 | 3/2011 |
| WO | WO-2011/031904 | 3/2011 |
| WO | WO-2011/031934 | 3/2011 |
| WO | WO-2011/035231 | 3/2011 |
| WO | WO-2011/046811 | 4/2011 |
| WO | WO-2011/050146 | 4/2011 |
| WO | WO-2011/054834 | 5/2011 |
| WO | WO-2011/059850 | 5/2011 |
| WO | WO-2011/059887 | 5/2011 |
| WO | WO-2011/060000 | 5/2011 |
| WO | WO-2011/066241 | 6/2011 |
| WO | WO-2011/075439 | 6/2011 |
| WO | WO-2011/075607 | 6/2011 |
| WO | WO-2011/075615 | 6/2011 |
| WO | WO-2011/079327 | 6/2011 |
| WO | WO-2011/082077 | 7/2011 |
| WO | WO-2011/087740 | 7/2011 |
| WO | WO-2011/088345 | 7/2011 |
| WO | WO-2011/091446 | 7/2011 |
| WO | WO-2011/112429 | 9/2011 |
| WO | WO-2011/123645 | 10/2011 |
| WO | WO-2011/123672 | 10/2011 |
| WO | WO-2011/146401 | 11/2011 |
| WO | WO-2011/150288 | 12/2011 |
| WO | WO-2011/156757 | 12/2011 |
| WO | WO-2012/012465 | 1/2012 |
| WO | WO-2012/027712 | 3/2012 |
| WO | WO-2012/039791 | 3/2012 |
| WO | WO-2012/041014 | 4/2012 |
| WO | WO-2012/048421 | 4/2012 |
| WO | WO-2012/068234 | 5/2012 |
| WO | WO 2012/087596 | 6/2012 |
| WO | WO-2012/087596 | 6/2012 |
| WO | WO-2012/087976 | 6/2012 |
| WO | WO-2012/130862 | 10/2012 |

(56) References Cited

FOREIGN PATENT DOCUMENTS

| WO | WO-2013/000855 | 1/2013 |
| WO | WO 2013/040492 | 3/2013 |
| WO | WO-2013/075029 | 3/2013 |
| WO | WO-2013/059630 | 4/2013 |
| WO | WO-2013/059638 | 4/2013 |
| WO | WO-2013/066748 | 5/2013 |
| WO | WO-2013/082003 | 6/2013 |
| WO | WO-2013/101550 | 7/2013 |
| WO | WO-2013/184698 | 12/2013 |
| WO | WO-2014/120981 | 8/2014 |
| WO | WO-2014/120982 | 8/2014 |
| WO | WO-2014/137929 | 9/2014 |
| WO | WO-2014/185995 | 11/2014 |

OTHER PUBLICATIONS

Lawitz, et al., "2008: Dose-Ranging, Three-Day Monotherapy Study of the HCV NS3 Protease Inhibitor GS-9256", Journal of Heptology, (2010), 52:S466-S467.

Wyles, et al., "Synergy of Small Molecular Inhibitors of Hepatitis C Virus Replication Directed at Multiple Viral Targets," J. Virol., (2007), 81(6):3005-3008.

Zennou, et al., "Combination of two complementary nucleotide analogues, PSI-7977 and PSI-938, effectively clears wild type and NS5b: S282T HCV replicons—Comparison with combinations of other antiviral compounds," Conferences Reports for NATAP, EASL 45th Annual Meeting Apr. 14-18, 2010, Vienna Austria, (http://www.natap.org/2010/EASL/EASL__28.htm).

English Translation of Office Action in Colombian Application No. 14-078.217 dated Dec. 15, 2014, (3 pages).

Examination Report from New Zealand Application No. 623396 dated Dec. 10, 2014 (2 pages).

International Search Report for PCT/US2011/064017 dated Jun. 28, 2012 (6 pages).

International Preliminary Report on Patentability and Written Opinion for PCT/US2011/064017 dated Jun. 25, 2013 (8 pages).

Notification for Vietnam Application No. 1-2014-01180 dated Jul. 24, 2014 (3 pages).

Official Notification for Eurasian Application No. 201490588 dated Jul. 2, 2014. (2 pages).

Opposition by ALAFAR in Ecuador Application No. SP-14-13312 dated Apr. 10, 2015, (18 pages).

Opposition by AG Pharmaceutical Labs Industrial Association in Chilean Application No. 630-2014 dated Apr. 24, 2015, (6 pages).

U.S. Appl. No. 14/013,237, filed Aug. 29, 2013, Du.
U.S. Appl. No. 14/168,329, filed Jan. 30, 2014, Mogalian et al.
U.S. Appl. No. 14/169,004, filed Jan. 30, 2014, Yang.
U.S. Appl. No. 14/195,751, filed Mar. 3, 2014, Hyland et al.
U.S. Appl. No. 14/453,489, filed Aug. 6, 2014, Mogalian et al.
U.S. Appl. No. 14/656,546, filed Mar. 12, 2015, Du et al.
U.S. Appl. No. 61/119,723, filed Jun. 10, 2010, Li et al.
U.S. Appl. No. 61/214,884, filed Sep. 30, 2010, Li et al.
U.S. Appl. No. 60/392,350, filed Jun. 28, 2002, Storer.
U.S. Appl. No. 60/392,351, filed Jun. 28, 2002, Gosselin.

Appel, et al., "Mutational Analysis of Hepatitis C Virus Nonstructural Protein 5A Potential Role of Differential Phosphorylation in RNA Replication and Identification of a Genetically Flexible Domain", Journal of Virology, (2005), 79(5):3187-3194.

Abonyi, et al., "Ribavirin in the Treatment of Hepatitis C", Anticancer Res, (2005) 25:1315-1320.

Afdhal, et al., "Hepatitis C pharmacogenetics: State of the art in 2010", Hepatology, (2011) 53(1 ): 336-345.

Anonymous, "View of NCT01726517 on 2012__12__10: A Phase 2, Randomized, Open-Label Study of Sofosbuvir/GS-5885 Fixed Does Combination +/− Ribavirin in Subjects with Chronic Genotype 1 HCV Infection", ClinicalTrials.gov Archive, http://clinicaltrials.gov/archive/NCT01726517/2012__12__10, retrieved on Mar. 14, 2014.

Anonymous, "View of NCT01726517 on 2013__05__13: A Phase 2, Randomized, Open-Label Study of Sofosbuvir/GS-5885 Fixed Dos Combination +/− Ribavirin in Subjects with Chronic Genotype 1 HCV Infection", Clinical Trials.gov Archive, http://clinicaltrials.giv/archive/NCT01726517/2013__05__13, retrieved on Mar. 14, 2014.

Asselah, et al., "IL28B polymorphism is associated with treatment response in patients with genotype 4 chronic hepatitis C", J Hepatology (2012) 56: 527-532.

Asselah, et al., "Gene expression and hepatitis C virus infection", Gut, (2009) 58: 846-858.

Battaglia, et al., "Combination Therapy with Interferon and Ribavirin in the Treatment of Chronic Hepatitis C Infection", The Annals of Pharmacotherapy, (2000), 34(4):487-494.

Belema, et al., "Discovery and Development of Hepatitis C Virus NS5A Replication Complex Inhibitors", Journal of Medicinal Chemistry, ASAP, (2014), pp. 1-30.

Belema, et al., "Preparation of bi-1H-benzimidazoles end-capped with amino acid or peptide derivatives as hepatitis C virus inhibitors", CAPLUS an 2010: 175961, 2 pages.

Bhat, "Synthesis and Pharmacokinetic Properties of Nucleoside Analogues as Possible Inhibitors of HCV RNA Replication", Oral Session V: Hepatitis C Virus, Flaviviruses, 16th International Conference on Antiviral Research, (Apr. 27-May 1, 2003, Savannah, GA) Abstract # 120, p. A75.

Bodenheimer, et al., "Tolerance and Efficacy of Oral Ribavirin Treatment of Chronic Hepatitis C: A Multicenter Trial", Hepatology, (1997), 26(2):473-477.

Bonkovsky, et al., "Comparative Effects of Different Doses of Ribavirin Plus Interferon-alpha2b for Therapy of Chronic Hepatitis C: Results of a Controlled, Randomized Trial", Digestive Dis & Sci, (2001), 46(10):2051-2059.

Borawski, et al., "Class III Phosphatidylinositol 4-Kinase Alpha and Beta Are Novel Host Factor Regulators of Hepatitis C Virus Replication", Journal of Virology, (2009), 83(19):10058-10074.

Bourliere, "Chronic hepatitis C: Treatments of the future", Clin Res Hepatology & Gastroenterology, (2011), 35: S84-S95.

Caira, "Crystalline Polymorphism of Organic Compounds", Topics in Current Chemistry, (1998), 198:163-208.

Chang, et al., "Deoxycytidine-resistant Stereoisomer Is the Active Form of (+)-2',3'-Dideoxy-3'-thiacytidine in the Inhibition of Hepatitis B Virus Replication", J Bio Chem, (1992), 267(20):13938-13942.

Chemello, et al., "The Effect of Interferon Alfa and Ribavirin Combination Therapy in Naive Patients with Chronic Hepatitis C", J Hepatology, (1995), 23(Suppl. 2):8-12.

Chiou, et al., "Crystallization of Amorphous Components in Spray Dried Powders", Drying Technology, Taylor & Francis, Philadelphia, PA, US, (2007), 25:1427-1435.

Cihlar, et al., "Design and Profiling of GS-9148, a Novel Nucleotide Analog Active against Nucleoside-Resistant Variants of Human Immunodeficiency Virus Type 1, and Its Orally Bioavailable Phosphonoamidate Prodrug, GS-9131", Antimicrobial Agents and Chemotherapy, (2008), 52(2):655-665.

Clark, et al., "Synthesis and antiviral activity of 2'-deoxy-2'-fluoro 2'-C methyl purine nucleosides as inhibitors of hepatitis C virus RNA replication", Bioorg Med Chem Lett, (2006) 16: 1712-1715.

Codington, et al., "Nucleosides XVIII Synthesis of 2'-Fiuorothymidine, 2'-Fluorodeoxyuridine, and Other 2'-Halogeno-2'-deoxy Nucleosides-s 1'2", The Division of Nucleoprotein Chemistry, Sloan-Kettering Institute for Cancer Research, Sloan-Kettering Division of Cornell University Medical College, New York 21, New York, (1963), 29:558-564.

Cornpropst, et al., "The Effect of Renal Impairment and End Stage Renal Disease on the Single-Dose Pharmacokinetics of GS-7977", J Hepatology, (2012), 56:S433 (Abstract #1101).

Cotton, et al., "Current methods of mutation detection", Mutal Res, (1993), 285:125-144.

Cotton, et al., "Reactivity of cytosine and thymine in single-base-pair mismatches with hydroxylamine and osmium tetroxide and its application to the study of mutations", Proc Natl Acad Sci USA (1988), 85: 4397-4401.

Das, et al., "Preparation of dialkyl, dialkenyl and dialkynyl arylene, heteroarylene, heterocyclylene and cycloalkylene linked benzimdazole-imidazoles and related compounds end capped with amino acids or peptide derivatives for treating and preventing flavivirus infections", CAPLUS an 2011: 1236910, 2 pages.

(56) References Cited

OTHER PUBLICATIONS

Davis, "Current Therapy for Chronic Hepatitis C", Gastroenterology, (2000), 118: SI04-SI14.
Di Bisceglie, et al., "Ribavirin as Therapy for Chronic Hepatitis C", Annals of Internal Medicine, (1995), 123(12): 897-903.
Dienstag and McHutchison et al., "American Gastroenterological Association technical review on the management of hepatitis C", Gastroenterology, (2006), 130: 231-264.
Dusheiko, et al., "Ribavirin Treatment for Patients with Chronic Hepatitis C: Results of a Placebo-Controlled Study", J Hepatology, (1996), 25:591-598.
Elazar, et al., "Amphipathic Helix-Dependent Localization of NSSA Mediates Hepatitis C Virus RNA Replication", Journal of Virology, (2003), 77(10):6055-6061.
Evans, et al., "Phosphorylation of hepatitis C virus nonstructural protein 5A modulates its protein interactions and viral RNA replication", PNAS, (2004 ),101 (35), 13038-13043.
Flamm, "Chronic Hepatitis C Virus Infection", J Am Med Assoc, (2003), 289(18):2413-17.
Franciscus, "Hepatitis C Treatments in Current Clinical Development", HCV Advocate, (Mar. 2010), pp. 1-26.
Freundt, et al., "Interfering with interferons: Hepatitis C virus counters innate immunity", PNAS, (2005), 102(49):17539-17540.
Fried, et al., "PegyinterferonAlfa-2a Plus Ribavirin for Chronic Hepatitis C Virus Infection", New England Journal of Medicine, (2002), 324(13):975-982.
Furman, et al., "The Anti-Hepatitis B Virus Activities, Cytoxicities, and Anabolic Profiles of the (−) and (+) Enantiomers of cis-5-Fluoro-1-[2-(Hydroxymenthyl)-1,3-Ozathiolan-5-yl]Cytosine", Antimicrobial Agents and Chemotherapy, (1992), 36(2):2686-2692.
Gane, et al., "Once Daily GS-7977 Plus Ribavirin in HGV Genotypes 1-3: The Electron Trial", Presented at the 47th Annual Meeting of the European Association for the Study of the Liver (Apr. 18-22, 2012), Barcelona, Spain (Poster #1113).
Gane, et al., "Once Daily PSI-7977 Plus RBV: Pegylated Interferon-Alfa Not Required for Complete Rapid Viral Response in Treatment-Naive Patients with HGV GT2 or GT3", Hepatology, (2011), 54(4 Suppl): 377 A (Abstract #34 ).
Gane, "Future Hepatitis C Virus Treatment: Interferon-Sparing Combinations", Liver International, (2011), 31(S1 ): 62-67.
Gane, "Future Treatment for Chronic Hepatitis C: IFN or Ribavirin-Free Regimens", Hepatol Int, (2012), 6:16-17 (Abstract #TCS10-03).
Gane, et al., "Electron: Once Daily PSI-7977 Plus RBV in HGV GT1/2/3", J Hepatology, (2012), 56:S438-S439 (Abstract #1113).
Gao, et al., "Chemical genetics strategy identifies an HCV NS5A inhibitor with a potent clinical effect", Nature, (2010), 465(6):96-102.
Gao, et al., "New BMS HCV NS5A Inhibitor: From Screen Hit to Clinic", (2010), pp. 1-9 [http://www.natao.onz/2008/HCV/101408_01.htm].
Gastaminza, et al., "Antiviral Stilbene 1,2 Diamines Prevent Initiation of Hepatitis C Virus RNA Replication at the Outset of Infection", Journal of Virology, (2011 ), 85(11 ):5513-5523.
Ge, et al., "Genetic variation in IL288 predicts hepatitis C treatment-induced viral clearance", Nature (2009) 461 (17): 399-401.
German, et al., "Lack of Clinically Significant Pharmacokinetic Drug-Drug Interactyion Between Sofosbuvir (GS-7977) and GS-5885 or GS-9669 in Health Volunteers", 63rd Annual Meeting of the American Association for the Study of Liver Diseases, (2012),Abstract 1072A, 3 pages.
Griffith, et al., "HCV Anti-viral Agents", Annual Reports in Medicinal Chemistry, (2004), 39:223-237.
GS-7977 Structure provided by Chem best Research Laboratories Ltd., (2013), 2 pages, [http://biochembest.com/product_detail.asp?m=2&id=1178&classid1=65&nclassid=195].
Guillory, "Generation of Polymorphs, Hydrates, Solvates, and Amorphous Solids", Polymorphism in Pharmaceutical Solids, edited by Harry G. Brittain, Marcel Decker, Inc., Milford, New Jersey (1999), pp. 183-226.
Gunic, et al., "Cyclic monophosphate prodrugs of base=modified 2'-C-methyl ribonucleosides as potent inhibitors of hepatitis C virus RNA replication", Bioorg Med Chem Lett, (2007), 17(9):2456-2458.
Hayashi et al., "PCT-SSCP: a method for detection of mutations", Genet Anal Techn,(1992), 9: 73-79.
Understanding Hepatitis C—Prevention, (2014), 3 pages, [http://www.webmd.com/hepatitis/understanding-hepatitis-c-prevention].
Hepatitis C, (2012), 1 pages, [http://en.wikipedia.org/wiki/Hepatitis C].
Hijikata, et al., "Two Distinct Proteinase Activities Required for the Processing of a Putative Nonstructural Precursor Protein of Hepatitis C Virus", J Viral, (1993), 67(8):4665-4675.
Hilfiker,et al., "Relevance of Solid-state Properties for Pharmaceutical Products", Polymorphism in the Pharmaceutical Industry, edited by Rolf Hilfiker, (2006), pp. 1-19.
Hrebabecky, et al., "Synthesis of 1-(3 azido-2,3-dide-oxy-4-C-hydroxymethyl-alpha-L-threopentofuranosyl) thymine, 1-(2,3-dideoxy-4-C-hydroxy-methyl-alpha-L-glycero-pentofuranosyl)thymine and 1-(2,3-dideoxy-4-C-hydroxymethyl-alpha-L-glycero-pent-2-enofuranosyl)thymine", Collect Czech Chem Commun, (1992), 58: 409-420.
Hrebabecky, et al., "Synthesis of 1-(3-azido-2,3-dideoxy-β-D-allofuranosyl)thymine, 1-(2,3-dideoxy-β-Dallofuranosyl) thymine, and 1-(2,3-dideoxy-—-D-erythro-hex-2-enofuranosyl)thymine", Carbohydrate Research, (1991), 216:179-186.
Huang, et al., "Phosphorylation of hepatitis C virus NS5A nonstructural protein: A new paradigm for phosphorylation-dependent viral RNA replication?", Virology, (2007), 364:1-9.
Hughes, et al., "Domain III of NS5A contributes to both RNA replication and assembly of hepatitis C virus particles", Journal of General Virology, (2009), 90:1329-1334.
Jacobson, et al., "PSI-7977 400 mg OD Safety and Tolerability in the First 450 Patients Treated for 12 Weeks", J Hepatology,(2012), 56:S441 (Abstract #1120).
Jacobson, "GS-7977 400 mg OD Safety and Tolerability in the Over 500 Patients Treated for at Least 12 Weeks", Presented at the 47th Annual Meeting of the European Association for the Study of the Liver, (Apr. 18-22, 2012), Barcelona, Spain (Poster #1120).
Jones, et al., "In-cell click labeling of small molecules to determine subcellular localisation", J Chem Biol, (2011), 4:49-53.
Ishi, et al., "Expression of Hepatitis C Virus NS5B Protein: Characterization of Its RNA Polymerase Activity and RNA Binding", Heptology, (1999), 29: 1227-1235.
Kanda, et al., "Inhibition of Intrahepatic Gamma Interferon Production by Hepatitis C Virus Nonstructural Protein 5A in Transgenic Mice", Journal of Virology, (2009), 83(17):8463-8469.
Katze, et al., "Ser2194 Is a Highly Conserved Major Phosphorylation Site of the Hepatitis C Virus Nonstructural Protein NS5A", Virology, (2000), 278:501-513.
Kaul, et al., "Essential Role of Cyclophilin A for Hepatitis C Virus Replication and Virus Production and Possible Link to Polyprotein Cleavage Kinetics", PLoSPathogens, (2009), 5(8):1-18.
Klumpp, et al., "The Novel Nucleoside Analog R1479(4'-Azidocytidine) Is a Potent Inhibitor of NS5B-dependent RCA Synthesis and Hepatitis C Virus Replication in Cell Culture", J Bio Chem, (2006), 281:3793-3799.
Kowdley, et al., "Atomic: 97% RVR for PSI-7977+PEG/RBV×12 Week Regimen in HGV GT1: An End to Response-Guided Therapy?", J Hepatology (2012) 56:S1 (Abstract #1).
Krieger, et al., "Enhancement of Hepatitis C Virus RNA Replication by Cell Culture-Adaptive Mutations", Journal of Virology, (2001), 75(10):4614-4624.
Kriegs, et al., "The Hepatitis C Virus Non-Structural NS5A Protein Impairs Both the Innate and Adaptive Hepatic Immune Response In Vivo", The Journal of Biological Chemistry, (2009), 284:28343-28351.
Kwo, et al., "Efficacy of boceprevir, an NS3 protease inhibitor, in combination with peginterferon alfa-2b and ribavirin in treatment-naive patients with genotype 1 hepatitis C infection (SPRINT-1): an open-label, randomised, multicentre phase 2 trial", Lancet, (2010), 376(9742):705-16.

(56) References Cited

OTHER PUBLICATIONS

Lalezari, et al., "Once Daily PSI-7977 Plus PegIFN/RBV in a Phase 2B Trial: Rapid Virologic Suppression in Treatment-Naive Patients with HGV GT2/GT3", J Hepatology, (2011), 54:S28 (Abstract #61 ).
Landowski, et al, "Targeted delivery to PEPT1-overexpressing cells: Acidic, basic, and secondary floxurdine amino acid ester prodrugs", MCT, (2005), 4(4):659-667.
Lawitz, et al, "The Effect of Hepatic Impairment on the Safety, Pharmacokinetics, and Antiviral Activity of GS-7977 in Hepatitis C Infected Subjects Treated for Seven Days", Presented at the 47th Annual Meeting of the European Association for the Study of the Liver, (Apr. 18-22, 2012), Barcelona, Spain (Poster #1130).
Lawitz, et al., "A phase 1, randomized, placebo-controlled, 3-day, dose-ranging study of GS-5885, an NS5A inhibitor, in patients with genotype 1 hepatitis C", Journal of Hepatology, (2012, )57(1):24-31.
Lawitz, et al., "Once Daily Dual-Nucleotide Combination of PSI-938 and PSI-7977 Provides 94% HGV RNA <LOD at Day 14: First Purine/Pyrimidine Clinical Combination Data (The Nuclear Study)", J Hepatology, (2011), 54:S543 (Abstract #1370).
Lawitz, et al., "Once-Daily PSI-7977 Plus PEG/RBV in Treatment-Naive Patients with HGV GT1: Robust End of Treatment Response Rates Are Sustained Post-Treatment", J Hepatology, (2011), 54(4 Suppl):472A-473A (Abstract #225).
Lawitz, et al., "PSI-7977 Proton and Electron: 100% Concordance of SVR4 with SVR24 in HGV GT1, GT2 & GT3", J Hepatology, (2012), 56:S4 (Abstract #7).
Lawitz, et al., "The Effect of Hepatic Impairment on the Pharmacokinetics and Antiviral Activity of PSI-7977 in Hepatitis C Infected Subjects Treated for Seven Days", J Hepatology, (2012), 56:S445-S446 (Abstract #1130).
Lee, et al., "The hepatitis C virus NS5A inhibitor (BMS-790052) alters the subcellular localization of the non-structural viral protein", Virology, (2011), 414:10-18.
Lemm, et al., "Discovery of Potent Hepatitis C Virus NS5A Inhibitors with Dimeric Structures", AAC Accepts, (2011) pp. 1-30.
Lemm, et al., "Identification of Hepatitis C Virus NS5A Inhibitors", Journal of Virology, (2010), 84(1):482-491.
Levin, "High Rate of Sustained Virologic Reponses with Response with All Oral Combination Daclatasvir (NS5A Inhibitor) Plus Sofosbuvir (Nucleotide NS5B Inhibitor), With or Without Ribavirin, in Treatment-Naïve Patients Chronically Infected with HCV GT 1, 2, or 3", Nov. 1, 2012, Retrieved from the Internet: http://www.natap.org/2012/AASLC/AASLD_06.htm [retrieved on Apr. 24, 2014].
Lewis, et al., "Second Generation Direct Antiviral and the Way to Interferon-Free Regimens in Chronic HGV", Best Practices & Research: Clinical Gastroenterology, (2012), 26:471-485.
Lin, et al., "A stereospecific synthesis of 2',3'-dideoxy-β-L-cytidine (β-L-ddC), a potent inhibitor against human hepatitis B virus (HBV) and human immunodeficiency virus (HIV)", Tetrahedron Letters, (1994), 35(21):3477-3480.
Lindh, et al., "Interleukin 28B Gene Variation at rs12979860 Determines Early Viral Kinetics During Treatment in Patients Carrying Genotypes 2 or 3 of Hepatitis C Virus", J Infect Dis, (2011) 203: 1748-1752.
Liver Cancer, (2011), 20 pages, [http://www.biomedcentral.com/1471-2458/9/34].
Livercancer2, (2011), 2 pages, [http://www.mayoclinic.com/health/liver-cancer/DS00399/DSECTION=causes].
Lohmann, et al., "Mutations in Hepatitis C Virus RNAs Conferring Cell Culture Adaptation", Journal of Virology, (2001), 75(3):1437-1449.
MacDonald, et al., "Hepatitis C virus NS5A: tales of a promiscuous protein", Journal of General Virology, (2004), 85:2485-2502.
Mangia, et al., "An *IL28B* Polymorphism Determines Treatment Response of Hepatitis C Virus Genotype 2 or 3 Patients Who Do Not Achieve a Rapid Virologic Response", Gastroenterology, (2010), 139: 821-827.
Martel-Laferriere, et al., "GS-7977: a promising nucleotide analog NS5B polymerase inhibitor of HCV", Future Virol, (2012) 7(6):537-546.
McCarthy, et al., "Replicated Association Between an IL28B Gene Variant and a Sustained Response to Pegylated Interferon and Ribavirin", Gastroenterology, (2010) 138: 2307-2314.
McCormick, et al., "Tagging of NS5A expressed from a functional hepatitis C virus replicon", Journal of General Virology, (2006), 87:635-640.
McGuigan, "Phosphoramidate derivatives of stavudine as inhibitors of HIV: unnatural amino acids may substitute for alanine", Antiviral Chemistry & Chemotherapy, (2000), 11:111-116.
McHutchison, et al., "Telaprevir with Peginterferon and Ribavirin for Chronic HGV Genotype 1 Infection", N Engl J Med, (2009), 360(18):1827-1838.
Mills, World Health Organization "Pharmaceutical excipients—an overview including consideration for paefiatric dosing", Federation Internataional Pharm, (Jun. 2010), 44 pages.
Missiha, et al., "Disease Progression in Chronic Hepatitis C: Modifiable and Nonmodifiable Factors", Gastroenterology (2008), 134:1699-1714.
Miyanari, et al., "Hepatitis C Virus Non-structural Proteins in the Probable Membranous Compartment Function in Viral Genome Replication", The Journal of Biological Chemistry, (2003), 278(50):50301-50308.
Moghaddam, et al., "*IL28B* genetic variation and treatment response in patients with hepatitis C virus genotype 3 infection", Hepatology, (2011), 53(3): 746-754.
Moradpour, et al., "Replication of hepatitis C virus", Nature Reviews Microbiology, (2007),5:453-463.
Mourier, et al., "Enantioselective synthesis and biological evaluation of 5-o-carboranyl-pyrimidinenucleosides", Bioorganic & Medicinal Chemistry, (1999), 7:2759-2766.
Myers, et al., "Detection of Single Base Substitutions by Ribonuclease Cleavage at Mismatches in RNA:DNA Duplexes", Science, (1985), 230:1242-1246.
Myers, et al., "Detection of single base substitutions in total genomic DNA", Nature, (1985) 313: 495-498.
Nelson, et al., "Once Daily PSI-7977 Plus PEF-IFN/RBV in HCV GT1: 98% Rapid Virologic Response, Complete Early Virologic Response: The Proton Study", J Hepatology, (2011 ), 54:S544 (Abstract #1372).
Orita, et al., "Detection of polymorphisms of DNA by gel electrophoresis as single-strand conformation polymorphisms", Proc. Natl Acad Sci, USA, (1989), 86:2766-2770.
Pawlotsky, et al., "Antiviral Action of Ribavirin in Chronic Hepatitis C", Gastroenterology, (2004) 126:703-714.
Perrone, Thesis entitled "Design Synthesis and Biological Evaluation of Novel Nucleotide Prodrugs as Potential Anti-Hepatitis C Virus Agents", Welsh School of Pharmacy, Cardiff University, (Feb. 2007), 292 pages.
Perrone, et al., "Design Synthesis and Biological Evalyation of Novel Nucleoside Phorphoramidates as Potential Anti-HCV Agents", Antiviral Research, (2006), 70:Abstract 100, 6 pages.
Pietschmann, et al., "Characterization of Cell Lines Carrying Self-Replicating Hepatitis C Virus RNAs", Journal of Virology, (2001), 75(3):1252-1264.
Pockros, et al., "R1626 Plus Peginterferon Alfa-2a Provides Potent Suppression of Hepatitis C Virus RNA and Significant Antiviral Synergy in Combination with Ribavirin", Hepatology, (2008), 48(2):385-397.
Pockros, et al., "High relapse rate seen at week 72 for patients treated with R1626 combination therapy", Hepatology, (2008) 48(2): 385-397.
Poordad, et al., "A 12-Week Interferon-Free Regimen of ABT-450/r+ABT-333+Ribavirin Achieved SVR12 in More Than 90% of Treatment-naïve HGV Genotype-1-Infected Subjects and 47% of Previous Non-Respoders", EASL 47th Annual Meeting, Barcelona, Spain (Apr. 18-22, 2012), 9 pages, Mar. 23, 2016.
Poordad, et al., "Rapid Virologic Response: A New Milestone in the Management of Chronic Hepatitis C", Clin Infectious Diseases (2008), 46:78-84.
Press Release, Gilead Sciences, Inc., "Gilead Announces Early Sustained Virologic Response Rates for GS-7977 Plus Ribavin in Genotype 1 Hepatitis C Patients", (Apr. 19, 2012), 2 pages.

(56) References Cited

OTHER PUBLICATIONS

Press Release, Gilead Sciences, Inc., "Gilead Announces Sustained Virologic Response Data for 12-Week Regimen of GS-7977 Plus Pegylated Interferon and Ribavin in Genotype 1 Hepatitis C Patients", (Apr. 19, 2012), 2 pages.
Rauch, et al., "Genetic variation in IL28B is associated with chronic hepatitis C and treatment failure: a genome-wide association study", Gastroenterology, (2010,) 138: 1338-1345.
Reed, et al., "The NS5A Proteins of Viruses from Three Genera of the Family Flaviviridae Are Phosphorylated by Associated Serine/Threonine Kinases", Journal of Virology, (2001), 75(3), 1252-1264.
Reichard, et al., "Therapy of Hepatitis C: Alpha Interferon and Ribavirin", Hepatology, (1997) 26(3, Suppl. 1):108S-111S.
Reynolds, et al., "Thermodynamics of Ligand Binding and Efficiency", ACS Medicinal Chemistry Letters, (2011) pp. A-E.
Robins, et al., "Nucleic acid related compounds, 91, Biomimetic reactions are in harmony with loss of 2'-substituents as free radicals (not anions) during mechanism-based inactivation of ribonucleotide reductases, differential interactions of azide, halogen, and alkylthio groups with tributylstannane and triphenylsilane", Journal of the American Chemical Society, (1996), 118(46):11341-11348.
Rodriguez-Torres, et al., "Antiviral activity, pharmacokinetics, safety, and tolerability of PSI-7851, a novel nucleotide polymerase inhibitor for HCV, following single and 3 day multiple ascending oral doses in healthy volunteers and patients with chronic HCV infection", Hepatology, (2009), 50(6):11A (Abstract LB17).
Romine, et al., "Inhibitors of HCV NS5A: From Iminothiazolidinones to Symmetrical Stilbenes", ACS Med Chem Lett, (2010), pp. A-F.
Ruebsam, et al., "Pyrrol[1,2-b]pyridazin-2-ones as potent inhibitors of HCV NS5B polymerase", Bio Org Med Chem Lett, (2008), 18:3616-3621.
Saleeba, et al., "Chemical Cleavage of Mismatch to Detect Mutations", Methods of Enzymology, (1993), 217;286-295.
Sarrazin, et al., "Importance of IL28B gene polymorphisms in hepatitis C virus genotype 2 and 3 infected patients", J Hepatology, (2011), 54: 415-421.
Scheel, et al., "Recombinant HCV Variants with NS5A from Genotypes 1-7 Have Different Sensitivities to an NS5A Inhibitor but Not interferon-a", Gastroenterology, (2011 ), 140(3), 1032-1042.
Schmitz, et al., "NS5A—From Obscurity to New Target for HCV Therapy", Recent Patents on Anti-Infective Drug Discovery, (2008), 3:77-92.
Shimakami, et al., "Hepatitis C: Recent Successes and Continuing Challenges in the Development of Improved Treatment Modalities", Curr Opin Pharmacol, (2009), 9(5):537-544.
Sofia, "Nucleotide prodrugs for HCV therapy", Antivir Chem.& Chemother, (2011), 22:23-49.
Sofia, et al., "Nucleoside, Nucleotide, and Non-Nucleoside Inhibitors of Hepatitis C Virus NS5B RNA-Dependent RNA-Polymerase", J Med Chem, (2012), 55:2481-2531.
Sofia, et al., "Discovery of a β-D-2'-Deoxy-α-fluoro-2'-β-C-methyluridine Nucleotide Prodrug (PSI-7977) for the Treatment of Hepatitis C Virus", Journal of Medicinal Chemistry, (2010), 53(19):7202-7218.
Stephens, et al., "Haplotype Variation and Linkage Disequilibrium in 313 Human Genes", Science ,(2001), 293:489-493.
Sulkowski, M., et al., "Potent Viral Suppression with All-Oral Combination of Daclatasvir (NS5A Inhibitor) and GS-7977 (NS5B Inhibitor),+/− Ribavirin, in Treatment-Naive Patients with Chronic HGV GT1, 2, or 3", J Hepatology, (2012) 56:S560 (Abstract #1422).
Suppiah, et al., "IL28B is associated with response to chronic hepatitis C interferon-αand ribavirin therapy", Nature Genetics, (2009), 41 (10): 1100-1104.
Tan, "Hepatits C Therapeutics: Current Status and Emerging Strategies", Nature Rev Drug Discov, (2002), 1:867-881.
Tanabe, et al., "Synergistic Inhibition of Intracellular Hepatitis C Virus Replication by Combination of Ribavirin and Interferon-alpha", J Infect Dis, (2004), 189(7):1129-1139.

Tanaka, et al., "Genome-wide association of IL28B with response to pegylated interferon-alpha and ribavirin therapy for chronic hepatitis C", Nature Genetics, (2009,) 41 (10): 1105-1109.
Tellinghuisen, et al., "Regulation of Hepatitis C Virion Production via Phosphorylation of the NS5A Protein", PLoS Pathogens, (2008), 4(3):1-17.
Tellinghuisen, et al., "Structure of the Zinc-Binding Domain of an Essential Replicase Component of Hepatitis C Virus Reveals a Novel Fold", Nature, (2005), 435(19):374-379.
Tellinghuisen, et al., "The NS5A Protein of Hepatitis C Virus Is a Zinc Metalloprotein", Journal of Biological Chemistry, (2004), 279(47):48576-48587.
Trousdale, et al., "Activity of 1-(2'-Fluoro-2'-Deoxy-β-D-Arabinofuranosyl)Thymine Against Herpes Simplex Virus in Cell Cultures and Rabbit Eyes", Antimicrobial Agents and Chemotherapy, (1983), 23(6):808-813.
Van Rompaey, et al., "Mycobacterium tuberculosis thymidine monophosphate kinase inhibitors; biological evaluation and conformational analysis of 2'-and 3'-modified thymidine analogues", Eur J Org Chem, (2003) pp. 2911-2918.
Vanheusden, et al., "Discovery of bicyclic thymidine analogues as selective and high-affinity inhibitors of mycobacterium tuberculosis thymidine monophosphate kinase", J Med Chem, (2004), 47:6187-6194.
Vitale, "2-Arylbenzimidazoles as Antiviral and Anti proliferative Agents—Part 1", Medicinal Chemistry, (2008), 4:605-615.
Von Wagner, et al., "Peginteriferon-alpha-2a (40KD) and ribavirin for 16 or 24 weeks in patients with genotype 2 or 3 chronic hepatitis C", Gastroenterology, (2005), 129:522-527.
Yu, et al., "In vitro efficacy of approved and experimental antivirals against novel genotypes 3 hepatitis C virus subgenomic replicons", Antiviral Research, (2013), 100(2):439-445.
Zemlicka, "Lipophilic phosporamidates as antiviral pornucleotides", Biochem Biophys Acta, (2002), pp. 276-286.
Zeuzem, et al., "Review article: management of patients with chronic hepatitis C virus infection and 'normal' alanine aminotransferase activity", Aliment Pharmacol & Ther, (2006), 24:1133-1149.
Zhu, et al, "Virologic Analysis of HGV Genotype 1 Patient Samples from the PROTON Study", Presented at the 47th Annual Meeting of the European Association for the Study of the Liver (Apr. 18-22, 2012), Barcelona, Spain (Poster #1217).
Zhu, et al., "Design and synthesis of HCV agents with sequential triple inhibitory potentials", Bioorg & Med Chem Lett., (2010), 20(17):5212-5213.
Balzarini, et al., "Mechanism of anti-HIV action of masked alaninyl d4t-MP derivatives" PNAS, (1996), 93:7295-7299.
Cahard, et al., "Aryloxy Phosphoramidate Triesters as Pro-Tides," Mini-Reviews in Medicinal Chemisty, (2004), 4:371-381.
Clark, "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, (2005), 48(17):5504-5508.
Defrancesco, et al., "New therapies on the horizon for hepatitis C: are we close?", Clin Liver Dis, (2003), 7:211-242.
Gunic, "6-Hydrazinopurine 2'-methyl ribonucleosides and their 5'-monophosphate prodrugs as potent hepatitis C virus inhibitors," Bioorg & Med Chem Letters, (2007), 17(9): 2456-2458.
Iyer, et al. "Synthesis, in Vitro Anti-Breast Cancer Activity, and Intracellular Decomposition of Amino Acid Methyl Ester and Alkyl Amide Phosphoramidate Monoesters of 3'-Azido-3'-deoxythymidine (AZT)," Journal of Medicinal Chemistry, (2000), 43:2266-2274.
Jones, "Minireview: Nucleotide Prodrugs," Antiviral Research, (1995), 27:1-17.
Kim, et al., "Direct Measurement of Nucleoside Monophosphate Delivery from a Phosphoramidate Pronucleotide by Stable Isotope Labeling and LC-ESI—MS/MS," Molecular Pharmaceutics, (2004), 1 (2):102-111.
Lee, et al., "Selective Intracellular Activation of a Novel Prodrug of the Human Immunodeficiency Virus reverse Transcriptase Inhibitor Tenofovir Leads to Preferential Distribution and Accumulation in Lymphatic Tissue," Antimicrobial Agents and Chemotherapy, (2005), 49(5):1898-1906.

(56) References Cited

OTHER PUBLICATIONS

Ma, "Characterization of the Metabolic Activation of Hepatitis C Virus Nucleoside Inhibitor B-D-2'-Deoxy-2-Fluro-2'-C-Methylcytidine (PSI-6130) and Identification of a Novel Active 5'-Triphosphate Species," The Journal of Biological Chemistry, (2007), 282(41): 29812-29820.

Ma, et al., "Characterization of the Intracellular Metabolism of β-d-2'-Deoxy-2'-Fluoro-2'-C-Methyl-Cytidine and the Inhibition of HCV Polymerase NS5B by its 5'-Triphosphate Species," Antiviral Research, (2007), 74(3): A36; Abstract 23.

McGuigan, et al., "Sub Micromolar Inhibitors of HCV Generated from Inactive Nucleosides by Application of ProTide Technology," Antiviral Research, (2007), 74(3): A36; Abstract 24.

McGuigan, "Phosphoramidate derivatives of d4T as inhibitors of HIV: The effect of amino acid variation," Antiviral Research, (1997), 35(3):95-204.

McGuigan, et al. "Aryl Phosphoramidate Derivatives of d4T Have Improved Anti-HIV Efficacy in Tissue Culture and May Act by the Generation of a Novel Intracellular Metabolite," Journal of Medicinal Chemistry, (1996), 39:1748-1753.

McGuigan, et al. "Application of Phosphoramidate Pro Tide Technology Significantly Improves Antiviral Potency of Carbocyclic Adenosine Derivatives" Journal of Medicinal Chemistry, (2006), 49:7215-7726.

McGuigan, et al., "Certain Phosphoramidate Derivatives of Dideoxy Uridine (ddU) Are Active Against HIV and Successfully By-pass Thymidine Kinase," FEBS Letters, (1994), 351:11-14.

Murakami, et al., "The Mechanism of Action of beta-D-2'-Deoxy-2'-Fluoro-2'-C-Methylcytidine Involves a Second Metabolic Pathway Leading to beta-D-2'-Deoxy-2'-Fluoro-2'-C-Methyluridine 5'-Triphosphate, a Potent Inhibitor of the Hepatitis C Virus RNA-Dependent RNA Polymerase," Antimicrobial Agents and Chemotherapy, (2008), 52(2):458-464.

Murakami, et al., "The Mechanism of Action of β-D-2'-Deoxy-2'-Fluoro-2'-C-Methylcytidine Inhibition of Hepatitis C Virus NS5B RNA Polymerase," Antimicrobial Agents and Chemotherapy, (2007), 52(2):458 -464.

Perrone, et al. "First Example of Phosphoramidate Approach Applied to a 4' Substituted Purine Nucleoside (4'-Azidoadenosine): Conversion of an Inactive Nucleoside to a Submicromolar Compound versus Hepatitis C Virus" Journal of Medicinal Chemistry, (2007), 50:5463-5470.

Saboulard, et al. "Characterization of the Activation Pathway of Phosphoramidate Triester Prodrugs of Stavudine and Zidovudine" American Society for Pharmacology and Experimental Therapeutics, (1999), 56, 693-704.

Sofia, et al., "β-D-2'-Deoxy-2;fluro-2'-C-methyluridine Phosphoramidates: Potent and Selective Inhibitors of HCV RNA Replication," (Sep. 2007), Poster p. 259, 1 page.

Lok, et al., "Combination Therapy with BMS-790052 and BMS-650032 Alone or with Pegylated Interferon and Ribavirin (pegIFN/RBV) Results in Undetectable HCV RNA Through 12 Weeks of Therapy in HCV Genotype 1 Null Responders", AASLD, The Liver Meeting in Boston, MA, Oct. 29-Nov. 2, 2010, poster.

Office Action issued in Eurasian Application No. 201490588 dated Aug. 3, 2015 (with English translation), 4 pages.

Office Action issued in Mexican Application No. MX/a/2014/003145 dated Jul. 23, 2015 (with English translation), 14 pages.

Sharp, "BMS-790052/BMS-650032 Combo Cures Hepatitis C without Interferon", HIV and Hepatitis.com Coverage of the 46th Annual Meeting of the European Association for the Study of the Liver, Mar. 30-Apr. 3, 2011, Berlin, Germany, 3 pages.

Suzuki, et al., Sustained virological response in a patient with chronic hepatitis C treated by monotherapy with the NS3-4A protease inhibitor telaprevir, Journal of Clinical Virology, 2010, vol. 47, pp. 76-78.

Office Action for Chinese Application No. 201280053492.X dated Oct. 9, 2015, with English translation, 7 pages.

Office Action for Thailand patent application No. 1401001362 dated Dec. 29, 2015, with English translation, 2 pages.

Murakami et al., "Mechanism of Activation of PSI-7851 and Its Diastereoisomer PSI-7977," 285(45), 34337-34347 (2010).

International Preliminary Report on Patentability for PCT/US2012/055621 dated Mar. 27, 2014.

International Search Report for PCT/US2012/055621 dated Apr. 26, 2013.

Examination Report issued in Egyptian Application No. PCT 392/2014 dated Jul. 1, 2015 (with English translation), 7 pages.

METHODS FOR TREATING HCV

PRIORITY OF INVENTION

This application claims priority to U.S. Provisional Application No. 61/535,885, filed 16 Sep. 2011; and to U.S. Provisional Application No. 61/561,753, filed 18 Nov. 2011. The entire content of each of these provisional applications is hereby incorporated herein by reference.

FIELD OF THE INVENTION

This invention relates to combinations of therapeutic molecules useful for treating hepatitis C virus infection. The present invention relates to methods, uses, dosing regimens, and compositions.

BACKGROUND OF THE INVENTION

Hepatitis is a disease occurring throughout the world. Hepatitis is generally of viral nature, although, if considered a state of chronic inflammation of the liver, there are other known, non-infectious causes. Viral hepatitis is by far the most common form of hepatitis. The U.S. Centers for Disease Control has estimated that at least 1.8% of the U.S. population has serologic evidence of HCV infection, in the majority of cases associated with chronic active infection. HCV is a positive-stranded RNA virus belonging to the Flaviviridae family and has closest relationship to the pestiviruses that include hog cholera virus and bovine viral diarrhea virus.

The HCV genome is a single-stranded, positive-sense RNA of about 9,600 bp coding for a polyprotein of 3009-3030 amino acids, which is cleaved co- and post-translationally by cellular and two viral proteinases into mature viral proteins (core, E1, E2, p7, NS2, NS3, NS4A, NS4B, NS5A, NS5B). The structural proteins, E1 and E2, are believed to be embedded into a viral lipid envelope and form stable heterodimers. The structural core protein is believed to interact with the viral RNA genome to form the nucleocapsid. The nonstructural proteins designated NS2 to NS5 include proteins with enzymatic functions involved in virus replication and protein processing including a polymerase, protease, and helicase. HCV replicates through the production of a complementary negative-strand RNA template.

HCV is a genetically diverse virus. Within a single infected patient, many variant viruses can be identified, leading to the description 'viral swarm', or viral quasispecies. Within the global human population, HCV is also genetically diverse, with at least 6 major 'genotypes' identified (Genotypes 1-6), and numerous subtypes (i.e., HCV Genotype 1a and 1b). HCV genotypes are defined by genomic phylogenetic analysis, and diagnosed (in a given patient) by HCV RNA sequence-based diagnostic assays.

The main route of infection with HCV is blood exposure. The magnitude of the HCV infection as a health problem is illustrated by the prevalence among high-risk groups. For example, in some surveys, 60% to 90% of hemophiliacs and more than 80% of intravenous drug abusers in western countries had chronic HCV infection. For intravenous drug abusers, the prevalence varies from about 28% to 80% depending on the population studied. The proportion of new HCV infections associated with blood or blood product transfusion has been markedly reduced due to pharmaceutical advances and widespread use of sensitive serologic and RNA detection assays used to screen blood donors, however, a large cohort of aging, chronically infected persons is already established.

One available treatment for HCV infection is pegylated interferon-α (PEG-IFN ala or PEG-IFN α1b), which is, under current treatment guidelines, administered weekly by subcutaneous injection for 24 to 48 weeks, dependent upon the HCV viral genotype being treated. Although greater than 50% of patients with Genotype 1 HCV infection may be expected to have suppression of HCV viremia at the completion of 48 weeks therapy, a significant proportion of these patients will have viral relapse. Accordingly, a Sustained Virologic Response (SVR, defined as HCV RNA negativity 24 weeks post treatment cessation, and considered tantamount to 'cure') is only achieved in 30-40% of Genotype 1 HCV infections treated with PEG-IFN alone. In addition, treatment with PEG-IFN+RBV is not well tolerated, with an adverse event profile that includes flu-like symptoms, thrombocytopenia, anemia, and serious psychiatric side effects. While treatment with the current standard of care is suboptimal, many patients are precluded from ever starting therapy due to comorbidities common in HCV-infected populations, including psychiatric disorders, advanced liver disease, and substance abuse.

Ribavirin is a nucleoside analog antiviral drug. Ribavirin is typically taken orally (by mouth) twice a day. The exact mechanism for ribavirin is unknown. However, it is believed that when ribavirin enters a cell it is phosphorylated; it then acts as an inhibitor of inosine 5'-monophosphate dehydrogenase (IMPDH). IMPDH inhibitors such as ribavirin reduce the intracellular synthesis and storage of guanine, a nucleotide "building block" necessary for DNA and RNA production, thus inhibiting viral replication. IMPDH inhibitors also interfere with the reproduction of rapidly proliferating cells and cells with a high rate of protein turnover. Treatment with ribavirin monotherapy has little effect on HCV RNA levels, but is associated with a decline in serum alanine transferase (ALT). This observation suggests that ribavirin may not be acting as an antiviral agent, but rather as a modulator of immune system function. Ribavirin is only approved for use, for HCV infection, in combination with IFN.

Treatment with the combination of PEG-IFN plus ribavirin improves SVR rates over those observed with PEG-IFN alone, in large part due to reduction in the frequency of viral relapse at the cessation of therapy. Large clinical trial SVR rates for PEG-IFN/ribavirin treated patients with HCV Genotype 1 infection have ranged from 40-55%. At the present time, PEG-IFN/ribavirin therapy is considered the 'standard-of-care' treatment for chronic HCV infection. The standard of care is, however, expected to change rapidly in the near future with approval of direct acting antiviral agents which will, initially, be used in combination with PEG-IFN/ribavirin.

Unfortunately, different genotypes of HCV respond differently to PEG-IFN/ribavirin therapy; for example, HCV genotype 1 is more resistant to therapy than types 2 and 3. Additionally, many current treatments for HCV produce unwanted side effects. Thus, there is currently a need for new anti-viral therapies. In particular there is a need for new antiviral therapies that produce fewer unwanted side-effects, that are more effective against a range of HCV genotypes, or that have less complicated dosing schedules, i.e. that require administration of agents fewer times during a day.

SUMMARY OF THE INVENTION

The present invention provides compositions and therapeutic methods that are useful for treating viral infections (e.g. HCV). Certain compositions and methods of the invention produce fewer unwanted side-effects, are more effective against a range of HCV genotypes, reduce the potential for viral rebound due to resistance selection and have shortened less complicated dosing schedules than currently available therapies.

Accordingly, in one embodiment the invention provides a composition comprising two or more compounds selected from Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16 and pharmaceutically acceptable salts thereof.

In another embodiment the invention provides a method of treating an HCV infection in a human, comprising administering two or more compounds selected from Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16 and pharmaceutically acceptable salts thereof to the human.

In another embodiment the invention provides a method for ameliorating one or more symptoms of an HCV infection in a human, comprising administering two or more compounds selected from Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16 and pharmaceutically acceptable salts thereof to the human.

In another embodiment the invention provides a method for reducing viral load in a human with HCV, comprising administering two or more compounds selected from Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16 and pharmaceutically acceptable salts thereof to the human.

In another embodiment the invention provides a method for reducing emergence of HCV quasispecies with resistance to coadministered oral antiviral agents in a human, comprising administering two or more compounds selected from Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16 and pharmaceutically acceptable salts thereof to the human.

In another embodiment the invention provides the use of two or more compounds selected from Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16 and pharmaceutically acceptable salts thereof in medical therapy.

In another embodiment the invention provides the use of two or more compounds selected from Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16 and pharmaceutically acceptable salts thereof for the prophylactic or therapeutic treatment of a viral (e.g. HCV) infection.

In another embodiment the invention provides the use of a composition of the invention for the prophylactic or therapeutic treatment of a viral (e.g. HCV) infection.

In another embodiment the invention provides the use of two or more compounds selected from Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16 and pharmaceutically acceptable salts thereof to prepare a medicament for treating a viral (e.g. HCV) infection in a human.

In another embodiment the invention provides the use of a composition of the invention to prepare a medicament for treating a viral (e.g. HCV) infection in a human.

In another embodiment the invention provides the use of two or more compounds selected from Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16 and pharmaceutically acceptable salts thereof to prepare a medicament for ameliorating one or more symptoms of a viral (e.g. HCV) infection in a human.

In another embodiment the invention provides the use of a composition of the invention to prepare a medicament for ameliorating one or more symptoms of a viral (HCV) infection in a human.

In another embodiment the invention provides the use of two or more compounds selected from Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16 and pharmaceutically acceptable salts thereof to prepare a medicament for reducing viral load in a human.

In another embodiment the invention provides the use of a composition of the invention to prepare a medicament for reducing viral load in a human.

In another embodiment the invention provides the use of two or more compounds selected from Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16 and pharmaceutically acceptable salts thereof to prepare a medicament for reducing emergence of HCV quasispecies with resistance to coadministered oral antiviral agents in a human.

In another embodiment the invention provides the use of a composition of the invention to prepare a medicament for reducing emergence of HCV quasispecies with resistance to coadministered oral antiviral agents in a human.

The compositions and methods of the invention may provide "synergy" and "synergistic effects", i.e. the effect achieved when the active ingredients (including two or more Combination Compounds) are used together is greater than the sum of the effects that results from using the compounds separately.

The compositions and methods of the invention are beneficial because they provide treatments for a wide range of HCV genotypes and because they cause fewer or less serious side effects than current HCV therapies (e.g. treatments that include the administration of interferon). Additionally, certain combinations of compounds (e.g. Compounds 10 and 5, Compounds 10 and 6, and Compounds 10, 5, and 6) may provide a Sustained Virological Response (SVR) that is a significantly higher than that achieved by current therapies (e.g. HCV therapies). For example, some combinations of compounds may provide an SVR that is at least about 70% or at least about 80%.

DETAILED DESCRIPTION OF THE INVENTION

Definitions

Unless stated otherwise, the following terms and phrases as used herein are intended to have the following meanings. The fact that a particular term or phrase is not specifically defined should not be correlated to indefiniteness or lacking clarity, but rather terms herein are used within their ordinary meaning. When trade names are used herein, applicants intend to independently include the trade name product and the active pharmaceutical ingredient(s) of the trade name product.

As used herein the term "Combination Compounds" refers to Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16.

As used herein, Compound 1 is:

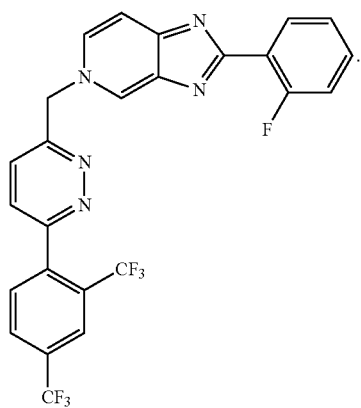 [SMILES: Fc1ccccc1-c1nc2ccn(Cc3ccc(-c4ccc(C(F)(F)F)cc4C(F)(F)F)nn3)cc-2n1]

Compound 1 may also be referred to as 5-((6-(2,4-bis(trifluoromethyl)phenyl)pyridazin-3-yl)methyl)-2-(2-fluorophenyl)-5H-imidazo[4,5-c]pyridine or 5H-imidazo[4,5-c]pyridine, 5-[[6-[2,4-bis(trifluoromethyl)phenyl]pyridazin-3-yl]methyl]-2-(2-fluorophenyl).

As used herein, Compound 2 is:

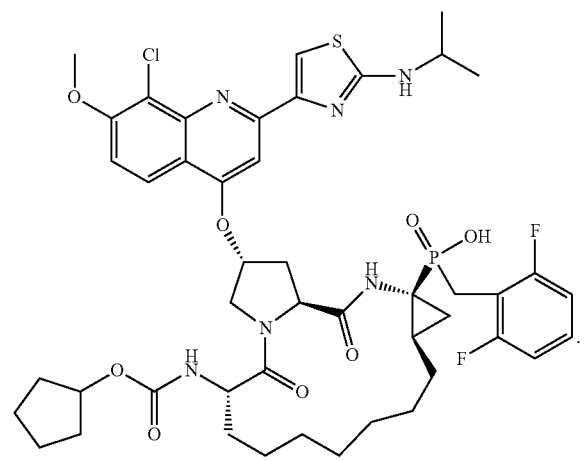 [SMILES: COc1ccc2c(O[C@@H]3C[C@H]4C(=O)N[C@]5(P(=O)(O)Cc6c(F)cccc6F)C[C@H]5CCCCCCC[C@H](NC(=O)OC5CCCC5)C(=O)N4C3)cc(-c3csc(NC(C)C)n3)nc2c1Cl]

Compound 2 may also be referred to as (2R,6S,13aR,14aS,16aS)-2-(8-chloro-2-(2-(isopropylamino)thiazol-4-yl)-7-methoxyquinolin-4-yloxy)-6-(cyclopentyloxycarbonylamino)-5,16-dioxooctadecahydrocyclopropa[e]pyrrolo[1,2-a][1,4]diazacyclopentadecin-14a-yl(2,6-diflurobenzyl) phosphinic acid.

As used herein, Compound 3 is:

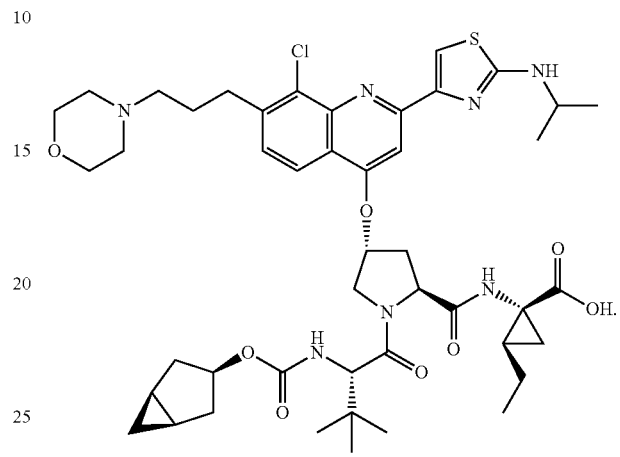

As used herein, Compound 4 is:

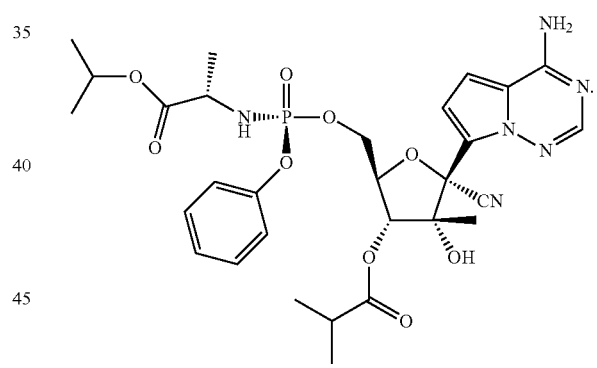

As used herein, Compound 5 is:

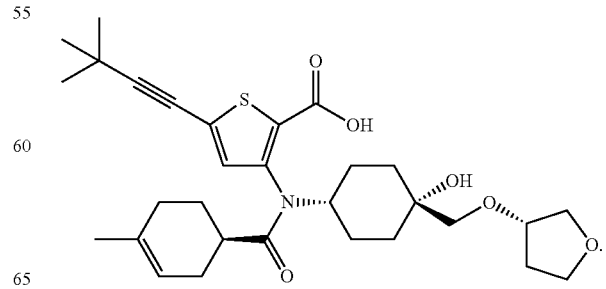

As used herein, Compound 6 is:

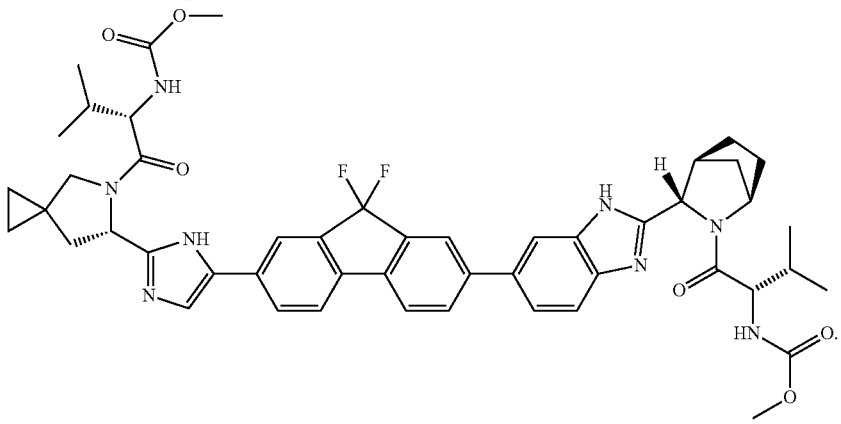 [SMILES: COC(=O)N[C@H](C(=O)N1CC2(CC2)C[C@H]1c1ncc(-c2ccc3c(c2)C(F)(F)c2cc(-c4ccc5nc([C@@H]6[C@H]7CC[C@H](C7)N6C(=O)[C@@H](NC(=O)OC)C(C)C)[nH]c5c4)ccc2-3)[nH]1)C(C)C]

As used herein, Compound 7 is:

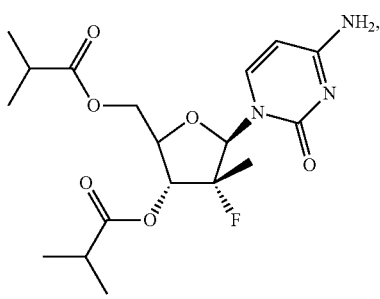 [SMILES: CC(C)C(=O)OCC1O[C@@H](n2ccc(N)nc2=O)[C@](C)(F)[C@@H]1OC(=O)C(C)C]

As used herein, Compound 8 is:

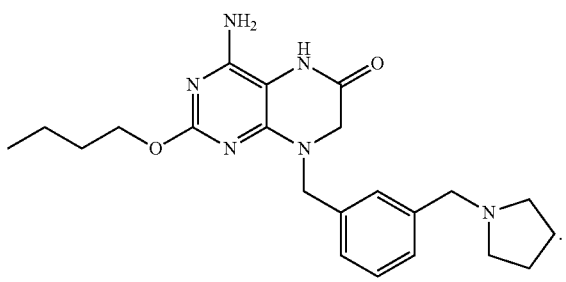

As used herein Compound 9 (diastereomer at P) is:

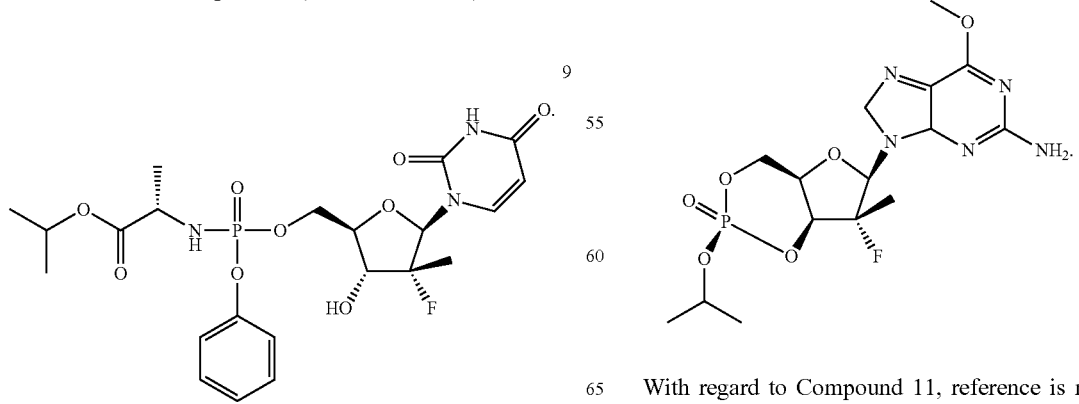

With regard to Compound 9, reference is made to U.S. Pat. No. 7,964,580 and US 2010/0298257, (both of which are incorporated by reference) with regard to manufacture and purification of Compound 9.

As used herein, Compound 10 (S-isomer of Compound 9) is:

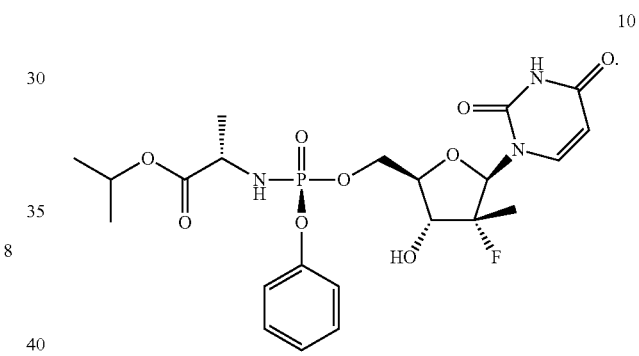

With regard to Compound 10, reference is made to U.S. Pat. No. 7,964,580 and US 2010/0298257, (both of which are incorporated by reference) with regard to manufacture and purification of Compound 10.

As used herein, Compound 11 is:

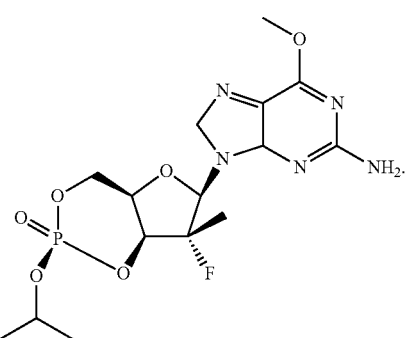

With regard to Compound 11, reference is made to US 2010/0081628 (which is hereby incorporated by reference) with regard to manufacture and purification of Compound 11.

As used herein, Compound 12 (diastereomer at P) is:

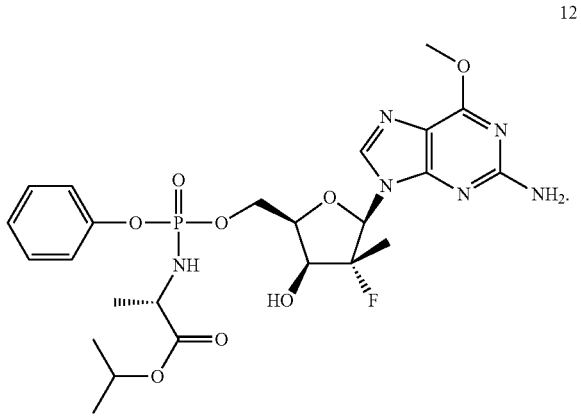 [SMILES: COc1nc(N)nc2c1ncn2[C@@H]1O[C@H](COP(=O)(N[C@@H](C)C(=O)OC(C)C)Oc2ccccc2)[C@H](O)[C@@]1(C)F]

12

With regard to Compound 12, reference is made to US 20110015146 (which is hereby incorporated by reference) with regard to manufacture and purification of Compound 12.

As used herein, Compound 13 (S-diastereomer of Compound 12 at P) is:

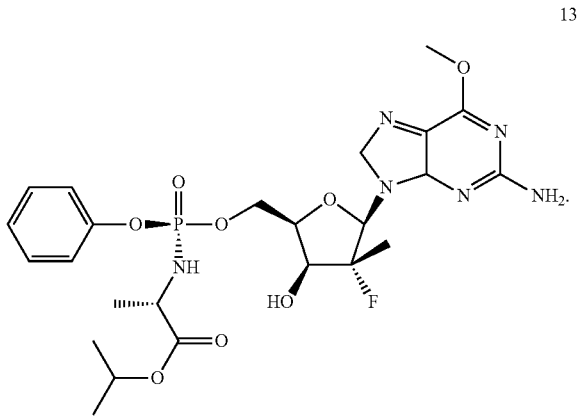 [SMILES: COC1=NC(N)=NC2C1=NCN2[C@@H]1O[C@H](CO[P@@](=O)(N[C@@H](C)C(=O)OC(C)C)Oc2ccccc2)[C@H](O)[C@@]1(C)F]

13

With regard to Compound 13, reference is made to US 20110015146 (which is hereby incorporated by reference) with regard to manufacture and purification of Compound 13.

As used herein, Compound 14 is:

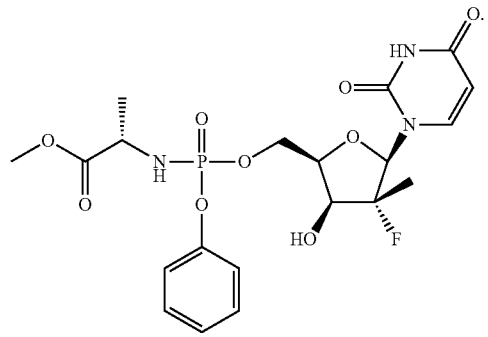

14

With regard to Compound 14, reference is made to U.S. Pat. No. 7,964,580 (which is hereby incorporated by reference) with regard to manufacture and purification of Compound 14.

As used herein, Compound 15 is:

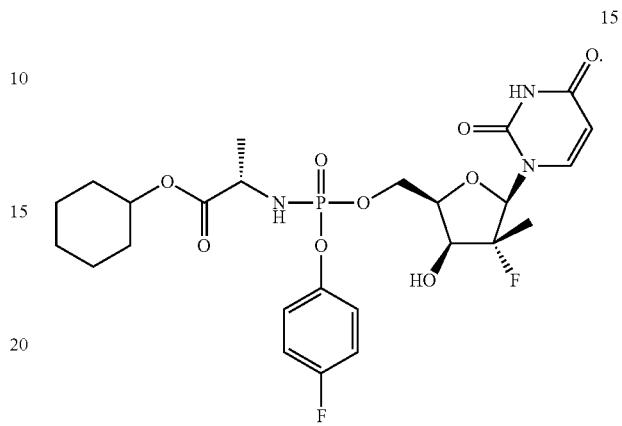

15

With regard to Compound 15, reference is made to U.S. Pat. No. 7,964,580 (which is hereby incorporated by reference) with regard to manufacture and purification of Compound 15.

As used herein, Compound 16 is:

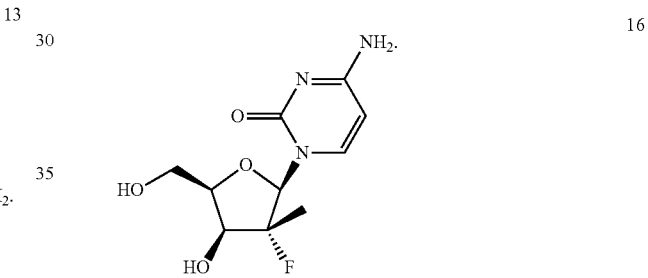

16

With regard to Compound 16, reference is made to U.S. Pat. No. 7,429,572 (which is hereby incorporated by reference) with regard to manufacture and purification of Compound 16.

With regard to ribavirin, reference is made to EP 0 093 401 B1, herein incorporated by reference with regard to a process for manufacture as well as to nomenclature concerning ribavirin. As used herein, ribavirin refers to:

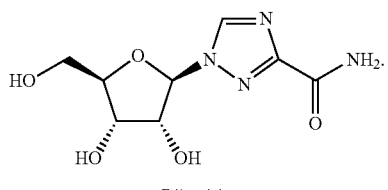

Ribavirin

Ribavirin is also referred to as 1-β-D-ribofuranosyl-1H-1,2,4-Triazole-3-carboxamide; 1-β-D-ribofuranosyl-1,2,4-triazol-3-carboxyamide; 1-β-D-Ribofuranosyl-1,2,4-triazole-3-carboxamide; COPEGUS (Roche); DRG-0028; HSDB 6513; ICN 1229; MegaRibavirin (e.g. in formulations of 100 mg of ribavirin/mL); NSC 163039; RAVANEX (BioPartners); REBETOL (Schering-Plough; Aesca; Bayer Schering Pharma; Essex; Pfizer; Trading Pharma; Zuellig Pharma); Ribamide; RIBAMIDIL (Biopharma, Russia); RIBASPHERE (Three Rivers Pharmaceuticals); Ribavarin; Ribavirina; Tribavirin; VILONA (Valeant Pharmaceuticals; ICN Pharmaceuticals); VIRAMID (ICN Pharmaceuticals; Alfa Wassermann); VIRAZOLE (Valeant Pharmaceuticals); and VIRIZADOLE (Uci-farma, Sao Bernardo do Campo, Sao Paulo, Brazil). In addition, as used herein ribavirin includes analogs of ribavirin, including taribavirin (VIRAMIDINE, ICN 3142).

The term "interferon" includes 1) interferons, e.g., pegylated rIFN-alpha 2b (PEG-Intron, Merck & Co., Inc.), pegylated rIFN-alpha 2a (PEGASYS, Hoffmann-La Roche Inc.), rIFN-alpha 2b (INTRON® A, Merck & Co., Inc.), rIFN-alpha 2a (Roferon®-A, Hoffmann-La Roche Inc.), interferon alpha (MULTIFERON® Viranative AB Corporation, OPC-18, Alfaferone, Alfanative, subalin), interferon alfacon-1 (Valeant), interferon alpha-n1 (Wellferon™, Glaxo Wellcome), interferon alpha-n3 (ALFERON®-Hemispherx Biopharma, Inc.), interferon-beta-1a (AVONEX® Biogen Idec, DL-8234 Daiichi Pharmaceutical Co. Ltd), interferon-omega (omega DUROS®, Alza Corporation, Intarcia Therapeutics, Inc.; Biomed 510, Intarcia Therapeutics, Inc.), albinterferon alpha-2b (ALBUFERON®, Human Genome Sciences, INC.), IFN alpha-2b XL, BLX-883 (LOCTERON®, Biolex Therapeutics, INC.), DA-3021, glycosylated interferon alpha-2b (AVI-005), PEG-INFERGEN®, Amgen, Inc., Pegylated interferon lambda-1(type III) (PEGylated IL-29), and BELEROFON®, Nautilus Biotech.

The term "combination therapy" means compositions or methods or uses or the like that incorporate two or more of the Combination Compounds. Combination therapy may also incorporate other active ingredients in addition to the two or more of the Combination Compounds including, but not limited to: ribavirin, an interferon, an alpha-glucosidase 1 inhibitor, a hepatoprotectant, a Toll-like receptor (TLR)-7 agonist, a cyclophilin inhibitor, an HCV viral entry inhibitor, an HCV maturation inhibitor, and an HCV IRES inhibitor.

The term "active ingredient" means a component of a combination therapy that a exerts or is capable of exerting a pharmaceutical effect including any of the Combination Compounds, ribavirin, an interferon, an alpha-glucosidase 1 inhibitor, a hepatoprotectant, a TLR-7 agonist, a cyclophilin inhibitor, an HCV viral entry inhibitor, an HCV maturation inhibitor, and an HCV IRES inhibitor.

The term "treating" and grammatical equivalents thereof, when used in the context of treating a disease, means slowing or stopping the progression of a disease, or ameliorating at least one symptom of a disease, more preferably ameliorating more than one symptom of a disease. For example, an HCV patient may experience an improvement in one or all of the following symptoms that can be associated with HCV infection: increase in alanine aminotransferase (ALT) levels, fever, headache, muscle aches, jaundice, fatigue, loss of appetite, nausea, vomiting and diarrhea. Treatment of a hepatitis C virus infection can include reducing the HCV viral load in an HCV infected human being.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by the formulae shown herein, as well as any wholly or partially equilibrated mixtures thereof. The present invention also includes the individual isomers of the compounds represented by the formula shown herein as mixtures with isomers thereof in which one or more chiral centers are inverted.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York, herein incorporated by reference in its entirety.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Combinations

The present invention encompasses combinations of two or more of the Combination Compounds. Table I showing possible two-way (Combinations 1-21), three-way (Combinations 22-56), four-way (Combinations 57-92) and five-way (Combinations 93-113) combinations of Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16 of the invention is provided below. Compound 4, Compound 9, Compound 10, Compound 11, Compound 12, Compound 13, Compound 14, Compound 15 and Compound 16 are nucleoside inhibitors of HCV NS5b polymerase and combinations of Combination Compounds will most often include only one of Compound 4, Compound 9, Compound 10, Compound 11, Compound 12, Compound 13, Compound 14, Compound 15 and Compound 16 (See Column 6 of Table I).

TABLE 1

|  | Compound 1 | Compound 2 | Compound 3 | Compound 4<br>Or<br>Compound 9<br>Or<br>Compound 10<br>Or<br>Compound 11<br>Or Compound 12<br>Or<br>Compound 13<br>Or Compound 14<br>Or Compound 15<br>Or<br>Compound 16 | Compound 5 | Compound 6 | Compound 7 |
|---|---|---|---|---|---|---|---|
| Combination 1 | X | X |  |  |  |  |  |
| Combination 2 | X |  | X |  |  |  |  |
| Combination 3 | X |  |  | X |  |  |  |

TABLE 1-continued

|  | Compound 1 | Compound 2 | Compound 3 | Compound 4 Or Compound 9 Or Compound 10 Or Compound 11 Or Compound 12 Or Compound 13 Or Compound 14 Or Compound 15 Or Compound 16 | Compound 5 | Compound 6 | Compound 7 |
|---|---|---|---|---|---|---|---|
| Combination 4 | X |  |  |  | X |  |  |
| Combination 5 | X |  |  |  |  | X |  |
| Combination 6 | X |  |  |  |  |  | X |
| Combination 7 |  | X | X |  |  |  |  |
| Combination 8 |  | X |  | X |  |  |  |
| Combination 9 |  | X |  |  | X |  |  |
| Combination 10 |  | X |  |  |  | X |  |
| Combination 11 |  | X |  |  |  |  | X |
| Combination 12 |  |  | X | X |  |  |  |
| Combination 13 |  |  | X |  | X |  |  |
| Combination 14 |  |  | X |  |  | X |  |
| Combination 15 |  |  | X |  |  |  | X |
| Combination 16 |  |  |  | X | X |  |  |
| Combination 17 |  |  |  | X |  | X |  |
| Combination 18 |  |  |  | X |  |  | X |
| Combination 19 |  |  |  |  | X | X |  |
| Combination 20 |  |  |  |  | X |  | X |
| Combination 21 |  |  |  |  |  | X | X |
| Combination 22 | X | X | X |  |  |  |  |
| Combination 23 | X | X |  | X |  |  |  |
| Combination 24 | X | X |  |  | X |  |  |
| Combination 25 | X | X |  |  |  | X |  |
| Combination 26 | X | X |  |  |  |  | X |
| Combination 27 | X |  | X | X |  |  |  |
| Combination 28 | X |  | X |  | X |  |  |
| Combination 29 | X |  | X |  |  | X |  |
| Combination 30 | X |  | X |  |  |  | X |
| Combination 31 | X |  |  | X | X |  |  |
| Combination 32 | X |  |  | X |  | X |  |
| Combination 33 | X |  |  | X |  |  | X |
| Combination 34 | X |  |  |  | X | X |  |
| Combination 35 | X |  |  |  | X |  | X |
| Combination 36 | X |  |  |  |  | X | X |
| Combination 37 |  | X | X | X |  |  |  |
| Combination 38 |  | X | X |  | X |  |  |
| Combination 39 |  | X | X |  |  | X |  |
| Combination 40 |  | X | X |  |  |  | X |
| Combination 41 |  | X |  | X | X |  |  |
| Combination 42 |  | X |  | X |  | X |  |
| Combination 43 |  | X |  | X |  |  | X |
| Combination 44 |  | X |  |  | X | X |  |
| Combination 45 |  | X |  |  | X |  | X |
| Combination 46 |  | X |  |  |  | X | X |
| Combination 47 |  |  | X | X | X |  |  |
| Combination 48 |  |  | X | X |  | X |  |
| Combination 49 |  |  | X | X |  |  | X |
| Combination 50 |  |  | X |  | X | X |  |
| Combination 51 |  |  | X |  | X |  | X |
| Combination 52 |  |  | X |  |  | X | X |
| Combination 53 |  |  |  | X | X | X |  |
| Combination 54 |  |  |  | X | X |  | X |
| Combination 55 |  |  |  | X |  | X | X |
| Combination 56 |  |  |  |  | X | X | X |
| Combination 57 | X | X | X | X |  |  |  |
| Combination 58 | X | X | X |  | X |  |  |
| Combination 59 | X | X | X |  |  | X |  |
| Combination 60 | X | X | X |  |  |  | X |
| Combination 61 | X | X |  | X | X |  |  |
| Combination 62 | X | X |  | X |  | X |  |
| Combination 63 | X | X |  | X |  |  | X |
| Combination 64 | X | X |  |  | X | X |  |
| Combination 65 | X | X |  |  | X |  | X |
| Combination 66 | X | X |  |  |  | X | X |
| Combination 67 | X |  | X | X | X |  |  |
| Combination 68 | X |  | X | X |  | X |  |

TABLE 1-continued

| | | Compound 1 | Compound 2 | Compound 3 | Compound 4 Or Compound 9 Or Compound 10 Or Compound 11 Or Compound 12 Or Compound 13 Or Compound 14 Or Compound 15 Or Compound 16 | Compound 5 | Compound 6 | Compound 7 |
|---|---|---|---|---|---|---|---|---|
| Combination | 69 | X | | X | X | | | X |
| Combination | 70 | X | | X | | X | X | |
| Combination | 71 | X | | X | | X | | X |
| Combination | 72 | X | | X | | | X | X |
| Combination | 73 | X | | | X | X | X | |
| Combination | 74 | X | | | X | X | | X |
| Combination | 75 | X | | | X | | X | X |
| Combination | 76 | X | | | | X | X | X |
| Combination | 77 | | X | X | X | X | | |
| Combination | 78 | | X | X | X | | X | |
| Combination | 79 | | X | X | X | | | X |
| Combination | 80 | | X | X | | X | X | |
| Combination | 81 | | X | X | | X | | X |
| Combination | 82 | | X | X | | | X | X |
| Combination | 83 | | X | | X | X | X | |
| Combination | 84 | | X | | X | X | | X |
| Combination | 85 | | X | | X | | X | X |
| Combination | 86 | | X | | | X | X | X |
| Combination | 87 | | | X | X | X | X | |
| Combination | 88 | | | X | X | X | | X |
| Combination | 89 | | | X | X | | X | X |
| Combination | 90 | | | X | | X | X | X |
| Combination | 91 | | | | X | X | X | X |
| Combination | 92 | | | | | | | |
| Combination | 93 | X | X | X | X | X | | |
| Combination | 94 | X | X | X | X | | X | |
| Combination | 95 | X | X | X | X | | | X |
| Combination | 96 | X | X | X | | X | X | |
| Combination | 97 | X | X | X | | X | | X |
| Combination | 98 | X | X | X | | | X | X |
| Combination | 99 | X | X | | X | X | X | |
| Combination | 100 | X | X | | X | X | | X |
| Combination | 101 | X | X | | X | | X | X |
| Combination | 102 | X | X | | | X | X | X |
| Combination | 103 | X | | X | X | X | X | |
| Combination | 104 | X | | X | X | X | | X |
| Combination | 105 | X | | X | X | | X | X |
| Combination | 106 | X | | X | | X | X | X |
| Combination | 107 | X | | | X | X | X | X |
| Combination | 108 | | X | X | X | X | X | |
| Combination | 109 | | X | X | X | X | | X |
| Combination | 110 | | X | X | X | | X | X |
| Combination | 111 | | X | X | | X | X | X |
| Combination | 112 | | X | | X | X | X | X |
| Combination | 113 | | | X | X | X | X | X |

Compositions

One aspect of the present invention includes a composition, e.g. a pharmaceutical composition, the composition comprising Compound 1 and further comprising a second compound selected from the group consisting of Compound 2, Compound 3, Compound 4, Compound 5, Compound 6, Compound 7, Compound 9, Compound 10, Compound 11, Compound 12, Compound 13, Compound 14, Compound 15 and Compound 16. In one specific embodiment of the invention, the second compound may be Compound 2, Compound 3, Compound 4, Compound 5 or Compound 6.

Another aspect of the present invention includes a composition, e.g. a pharmaceutical composition, the composition comprising Compound 2 and further comprising a second compound selected from the group consisting of Compound 1, Compound 3, Compound 4, Compound 5, Compound 6, Compound 7, Compound 9, Compound 10, Compound 11, Compound 12, Compound 13, Compound 14, Compound 15 and Compound 16. In one specific embodiment of the invention, the second compound may be Compound 4. In one specific embodiment of the invention, the second compound may be Compound 3. In one specific embodiment of the invention, the second compound may be Compound 5.

Another aspect of the present invention includes a composition, e.g. a pharmaceutical composition, the composition comprising Compound 3 and further comprising a second compound selected from the group consisting of Compound 1, Compound 2, Compound 4, Compound 5, Compound 6, Compound 7, Compound 9, Compound 10, Compound 11, Compound 12, Compound 13, Compound 14, Compound 15 and Compound 16. In one specific embodiment of the invention, the second compound may be Compound 1. In one specific embodiment of the invention, the second compound may be Compound 4. In one specific embodiment of the invention, the second compound may be Compound 5. In one specific embodiment of the invention, the second compound may be Compound 6.

Another aspect of the present invention includes a composition, e.g. a pharmaceutical composition, the composition comprising a first compound selected from the group consisting of Compound 4 and further comprising a second compound selected from the group consisting of Compound 1, Compound 2, Compound 3, Compound 5, Compound 6 and Compound 7. In one specific embodiment of the invention, the second compound may be Compound 1 or Compound 2 or Compound 3 or Compound 6. In one specific embodiment of the invention, the second compound may be Compound 1. In one specific embodiment of the invention, the second compound may be Compound 2. In one specific embodiment of the invention, the second compound may be Compound 3. In one specific embodiment of the invention, the second compound may be Compound 5. In one specific embodiment of the invention, the second compound may be Compound 6.

Another aspect of the present invention includes a composition, e.g. a pharmaceutical composition, the composition comprising Compound 5 and further comprising a second compound selected from the group consisting of Compound 1, Compound 2, Compound 3, Compound 4, Compound 6, Compound 7, Compound 9, Compound 10, Compound 11, Compound 12, Compound 13, Compound 14, Compound 15 and Compound 16. In one specific embodiment of the invention, the second compound may be Compound 1. In one specific embodiment of the invention, the second compound may be Compound 6.

Another aspect of the present invention includes a composition, e.g. a pharmaceutical composition, the composition comprising Compound 6 and further comprising a second compound selected from the group consisting of Compound 1, Compound 2, Compound 3, Compound 4, Compound 5, Compound 7, Compound 9, Compound 10, Compound 11, Compound 12, Compound 13, Compound 14, Compound 15 and Compound 16. In one specific embodiment of the invention, the second compound may be Compound 1. In one specific embodiment of the invention, the second compound may be Compound 2. In one specific embodiment of the invention, the second compound may be Compound 3. In one specific embodiment of the invention, the second compound may be Compound 4.

Another aspect of the present invention includes a composition, e.g. a pharmaceutical composition, the composition comprising Compound 7 and further comprising a second compound selected from the group consisting of Compound 1, Compound 2, Compound 3, Compound 4, Compound 5, Compound 6, Compound 9, Compound 10, Compound 11, Compound 12, Compound 13, Compound 14, Compound 15 and Compound 16.

Another aspect of the present invention includes a composition, e.g. a pharmaceutical composition, the composition comprising a first compound selected from the group consisting of Compound 9, Compound 10, Compound 11, Compound 12, Compound 13, Compound 14, Compound 15 and Compound 16 and further comprising a second compound selected from the group consisting of Compound 1, Compound 2, Compound 3, Compound 5, Compound 6 and Compound 7.

Another aspect of the present invention includes a composition, e.g. a pharmaceutical composition, the composition comprising Compound 1 and further comprising a second compound and a third compound each selected from the group consisting of Compound 2, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 3, or Compound 4, or Compound 5 or Compound 6. The second compound may be Compound 2 and the third compound may be Compound 4. The second compound may be Compound 3 and the third compound may be Compound 4. The second compound may be Compound 2 and the third compound may be Compound 6. The second compound may be Compound 3 and the third compound may be Compound 6. The second compound may be Compound 4 and the third compound may be Compound 6. The second compound may be Compound 2 and the third compound may be Compound 3. The second compound may be Compound 2 and the third compound may be Compound 5. The second compound may be Compound 3 and the third compound may be Compound 5.

Another aspect of the present invention includes a composition, e.g. a pharmaceutical composition, the composition comprising Compound 2 and further comprising a second compound and a third compound each selected from the group consisting of Compound 1, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 4. The second compound may be Compound 1 and the third compound may be Compound 4. The second compound may be Compound 1 and the third compound may be Compound 6. The second compound may be Compound 4 and the third compound may be Compound 6. The second compound may be Compound 3 and the third compound may be Compound 4. The second compound may be Compound 3 and the third compound may be Compound 5. The second compound may be Compound 3 and the third compound may be Compound 6.

Another aspect of the present invention includes a composition, e.g. a pharmaceutical composition, the composition comprising Compound 3 and further comprising a second compound and a third compound each selected from the group consisting of Compound 1, Compound 2, Compound 4, Compound 5, Compound 6, Compound 7, Compound 9, Compound 10, Compound 11, Compound 12, Compound 13, Compound 14, Compound 15 and Compound 16. The second compound may be Compound 1 or Compound 6. The second compound may be Compound 1 and the third compound may be Compound 4. The second compound may be Compound 1 and the third compound may be Compound 6. The second compound may be Compound 4 and the third compound may be Compound 6. The second compound may be Compound 4 and the third compound may be Compound 5.

Another aspect of the present invention includes a composition, e.g. a pharmaceutical composition, the composition comprising a first compound selected from the group consisting of Compound 4 and further comprising a second compound and a third compound each selected from the group consisting of Compound 1, Compound 2, Compound 3, Compound 5, Compound 6 and Compound 7. The second compound may be Compound 1, Compound 2, Compound 3 or Compound 6. The second compound may be Compound 1 and the third compound may be Compound 2. The second compound may be Compound 1 and the third compound may be Compound 3. The second compound may be Compound 1 and the third compound may be Compound 6. The second compound may be Compound 2 and the third compound may be Compound 6. The second compound may be Compound 3 and the third compound may be Compound 6. The second compound may be Compound 1 and the third compound may be Compound 5. The second compound may be Compound 2 and the third compound may be Compound 5.

Another aspect of the present invention includes a composition, e.g. a pharmaceutical composition, the composition comprising Compound 5 and further comprising a second compound and a third compound each selected from the group consisting of Compound 1, Compound 2, Compound 3, Compound 4, Compound 6, Compound 7, Compound 9, Compound 10, Compound 11, Compound 12, Compound 13, Compound 14, Compound 15 and Compound 16. The second compound may be Compound 1.

Another aspect of the present invention includes a composition, e.g. a pharmaceutical composition, the composition comprising Compound 6 and further comprising a second compound and a third compound each selected from the group consisting of Compound 1, Compound 2, Compound 3, Compound 4, Compound 5, Compound 7, Compound 9, Compound 10, Compound 11, Compound 12, Compound 13, Compound 14, Compound 15 and Compound 16. The second compound may be Compound 1, Compound 2, Compound 3 or Compound 4. The second compound may be Compound 1 and the third compound may be Compound 2. The second compound may be Compound 1 and the third compound may be Compound 3. The second compound may be Compound 4 and the third compound may be Compound 6. The second compound may be Compound 2 and the third compound may be Compound 4. The second compound may be Compound 3 and the third compound may be Compound 4. The second compound may be Compound 1 and the third compound may be Compound 5. The second compound may be Compound 2 and the third compound may be Compound 5. The second compound may be Compound 3 and the third compound may be Compound 5.

Another aspect of the present invention includes a composition, e.g. a pharmaceutical composition, the composition comprising Compound 7 and further comprising a second compound and a third compound each selected from the group consisting of Compound 1, Compound 2, Compound 3, Compound 4, Compound 5, Compound 6, Compound 9, Compound 10, Compound 11, Compound 12, Compound 13, Compound 14, Compound 15 and Compound 16.

Another aspect of the present invention includes a composition, e.g. a pharmaceutical composition, the composition comprising a first compound selected from the group consisting of Compound 9, Compound 10, Compound 11, Compound 12, Compound 13, Compound 14, Compound 15 and Compound 16 and further comprising a second compound and a third compound each selected from the group consisting of Compound 1, Compound 2, Compound 3, Compound 5, Compound 6 and Compound 7.

Another aspect of the present invention includes a composition, e.g. a pharmaceutical composition, the composition comprising Compound 1 and further comprising a second compound, a third compound and a fourth compound each selected from the group consisting of Compound 2, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 3, Compound 4, Compound 5, or Compound 6. The second compound may be Compound 2 and the third compound may be Compound 4. The second compound may be Compound 3 and the third compound may be Compound 4. The second compound may be Compound 2 and the third compound may be Compound 6. The second compound may be Compound 3 and the third compound may be Compound 6. The second compound may be Compound 4 and the third compound may be Compound 6. The second compound may be Compound 6. The second compound may be Compound 2, the third compound may be Compound 4, and the fourth compound may be Compound 6. The second compound may be Compound 3, the third compound may be Compound 4, and the fourth compound may be Compound 6.

Another aspect of the present invention includes a composition, e.g. a pharmaceutical composition, the composition comprising Compound 2 and further comprising a second compound, a third compound and a fourth compound each selected from the group consisting of Compound 1, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 4. The second compound may be Compound 1 and the third compound may be Compound 4. The second compound may be Compound 1 and the third compound may be Compound 6. The second compound may be Compound 4 and the third compound may be Compound 6.

Another aspect of the present invention includes a composition, e.g. a pharmaceutical composition, the composition comprising Compound 3 and further comprising a second compound, a third compound and a fourth compound each selected from the group consisting of Compound 1, Compound 2, Compound 4, Compound 5, Compound 6, Compound 7, Compound 9, Compound 10, Compound 11, Compound 12, Compound 13, Compound 14, Compound 15 and Compound 16. The second compound may be Compound 1 or Compound 6. The second compound may be Compound 1 and the third compound may be Compound 4. The second compound may be Compound 1 and the third compound may be Compound 6. The second compound may be Compound 4 and the third compound may be Compound 6. The second compound may be Compound 4, the third compound may be Compound 5, and the fourth compound may be Compound 6.

Another aspect of the present invention includes a composition, e.g. a pharmaceutical composition, the composition comprising a first compound selected from the group consisting of Compound 4 and further comprising a second compound, a third compound and a fourth compound each selected from the group consisting of Compound 1, Compound 2, Compound 3, Compound 5, Compound 6 and Compound 7. The second compound may be Compound 1, Compound 2, Compound 3, or Compound 6. The second compound may be Compound 1 and the third compound may be Compound 2. The second compound may be Compound 1 and the third compound may be Compound 3. The second compound may be Compound 1 and the third compound may be Compound 6. The second compound may be Compound 2 and the third compound may be Compound 6. The second compound may be Compound 3 and the third compound may be Compound 6.

Another aspect of the present invention includes a composition, e.g. a pharmaceutical composition, the composition comprising Compound 5 and further comprising a second compound, a third compound and a fourth compound each selected from the group consisting of Compound 1, Compound 2, Compound 3, Compound 4, Compound 6, Compound 7, Compound 9, Compound 10, Compound 11, Compound 12, Compound 13, Compound 14, Compound 15 and Compound 16. The second compound may be Compound 1.

Another aspect of the present invention includes a composition, e.g. a pharmaceutical composition, the composition comprising Compound 6 and further comprising a second compound, a third compound and a fourth compound each selected from the group consisting of Compound 1, Compound 2, Compound 3, Compound 4, Compound 5, Compound 7, Compound 9, Compound 10, Compound 11, Compound 12, Compound 13, Compound 14, Compound 15 and Compound 16. The second compound may be Compound 1, Compound 2, Compound 3, or Compound 4. The second compound may be Compound 1 and the third compound may be Compound 2. The second compound may be Compound 1 and the third compound may be Compound 3. The second compound may be Compound 4 and the third compound may be Compound 6. The second compound may be Compound 2 and the third compound may be Compound 4. The second compound may be Compound 3 and the third compound may be Compound 4.

Another aspect of the present invention includes a composition, e.g. a pharmaceutical composition, the composition comprising Compound 7 and further comprising a second compound, a third compound and a fourth compound each selected from the group consisting of Compound 1, Compound 2, Compound 3, Compound 4, Compound 5, Compound 6, Compound 9, Compound 10, Compound 11, Compound 12, Compound 13, Compound 14, Compound 15 and Compound 16.

Another aspect of the present invention includes a composition, e.g. a pharmaceutical composition, the composition comprising a first compound selected from the group consisting of Compound 9, Compound 10, Compound 11, Compound 12, Compound 13, Compound 14, Compound 15 and Compound 16 and further comprising a second compound, a third compound and a fourth compound each selected from the group consisting of Compound 1, Compound 2, Compound 3, Compound 5, Compound 6 and Compound 7.

Another aspect of the present invention includes a composition, e.g. a pharmaceutical composition, the composition comprising Compound 1 and further comprising a second compound, a third compound, a fourth compound and a fifth compound each selected from the group consisting of Compound 2, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 3, Compound 4, Compound 5 or Compound 6. The second compound may be Compound 2 and the third compound may be Compound 4. The second compound may be Compound 3 and the third compound may be Compound 4. The second compound may be Compound 2 and the third compound may be Compound 6. The second compound may be Compound 3 and the third compound may be Compound 6. The second compound may be Compound 4 and the third compound may be Compound 6.

Another aspect of the present invention includes a composition, e.g. a pharmaceutical composition, the composition comprising Compound 2 and further comprising a second compound, a third compound, a fourth compound and a fifth compound each selected from the group consisting of Compound 1, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 4. The second compound may be Compound 1 and the third compound may be Compound 4. The second compound may be Compound 1 and the third compound may be Compound 6. The second compound may be Compound 4 and the third compound may be Compound 6.

Another aspect of the present invention includes a composition, e.g. a pharmaceutical composition, the composition comprising Compound 3 and further comprising a second compound, a third compound, a fourth compound and a fifth compound each selected from the group consisting of Compound 1, Compound 2, Compound 4, Compound 5, Compound 6, Compound 7, Compound 9, Compound 10, Compound 11, Compound 12, Compound 13, Compound 14, Compound 15 and Compound 16. The second compound may be Compound 1 or Compound 6. The second compound may be Compound 1 and the third compound may be Compound 4. The second compound may be Compound 1 and the third compound may be Compound 6. The second compound may be Compound 4 and the third compound may be Compound 6.

Another aspect of the present invention includes a composition, e.g. a pharmaceutical composition, the composition comprising a first compound selected from the group consisting of Compound 4 and further comprising a second compound, a third compound, a fourth compound and a fifth compound each selected from the group consisting of Compound 1, Compound 2, Compound 3, Compound 5, Compound 6 and Compound 7. The second compound may be Compound 1, Compound 2, Compound 3 or Compound 6. The second compound may be Compound 1 and the third compound may be Compound 2. The second compound may be Compound 1 and the third compound may be Compound 3. The second compound may be Compound 1 and the third compound may be Compound 6. The second compound may be Compound 2 and the third compound may be Compound 6. The second compound may be Compound 3 and the third compound may be Compound 6.

Another aspect of the present invention includes a composition, e.g. a pharmaceutical composition, the composition comprising Compound 5 and further comprising a second compound, a third compound, a fourth compound and a fifth compound each selected from the group consisting of Compound 1, Compound 2, Compound 3, Compound 4, Compound 6, Compound 7, Compound 9, Compound 10, Compound 11, Compound 12, Compound 13, Compound 14, Compound 15 and Compound 16.
The second compound may be Compound 1.

Another aspect of the present invention includes a composition, e.g. a pharmaceutical composition, the composition comprising Compound 6 and further comprising a second compound, a third compound, a fourth compound and a fifth compound each selected from the group consisting of Compound 1, Compound 2, Compound 3, Compound 4, Compound 5, Compound 7, Compound 9, Compound 10, Compound 11, Compound 12, Compound 13, Compound 14, Compound 15 and Compound 16. The second compound may be Compound 1, Compound 2, Compound 3, and Compound 4. The second compound may be Compound 1 and the third compound may be Compound 2. The second compound may be Compound 1 and the third compound may be Compound 3. The second compound may be Compound 4 and the third compound may be Compound 6. The second compound may be Compound 2 and the third compound may be Compound 4. The second compound may be Compound 3 and the third compound may be Compound 4.

Another aspect of the present invention includes a composition, e.g. a pharmaceutical composition, the composition comprising Compound 7 and further comprising a second compound, a third compound, a fourth compound and a fifth compound each selected from the group consisting of Compound 1, Compound 2, Compound 3, Compound 4, Compound 5, Compound 6, Compound 9, Compound 10, Compound 11, Compound 12, Compound 13, Compound 14, Compound 15 and Compound 16.

Another aspect of the present invention includes a composition, e.g. a pharmaceutical composition, the composition comprising a first compound selected from the group consisting of Compound 9, Compound 10, Compound 11, Compound 12, Compound 13, Compound 14, Compound 15 and Compound 16 and further comprising a second compound, a third compound, a fourth compound and a fifth compound each selected from the group consisting of Compound 1, Compound 2, Compound 3, Compound 5, Compound 6 and Compound 7.

Salts

The Combination Compounds and other active ingredients can be in the form of a salt. Typically, but not absolutely, the salts of the Combination Compounds and other active ingredients are pharmaceutically acceptable salts. Salts encompassed within the term "pharmaceutically acceptable salts" refer to non-toxic salts of the Combination Compounds and/or other active ingredients. Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

Pharmaceutical Formulations

The Combination Compounds and/or other active ingredients can be formulated with conventional carriers or excipients, which can be selected in accord with ordinary practice. Tablets typically contain excipients, glidants, fillers, binders and the like. Aqueous formulations can be prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like.

The pH of the formulations ranges from about 3 to about 11, but is ordinarily about 7 to 10.

While it is possible for an active ingredient to be administered alone it may be preferable to present one or more active ingredients as pharmaceutical formulations. The formulations of the invention, both for veterinary and for human use, comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the administration routes set forth below. The formulations may conveniently be presented in unit dosage form and may be prepared by any of the methods well known in the art of pharmacy. Techniques and formulations generally can be found in Remington's Pharmaceutical Sciences (Mack Publishing Co., Easton, Pa.), herein incorporated by reference in its entirety. Such methods include the step of bringing into association an active ingredient with the carrier which constitutes one or more accessory ingredients. In general the formulations can be prepared by uniformly and intimately bringing into association one or more active ingredients with liquid carriers or finely divided solid carriers or both, and then, if necessary, shaping the product.

Formulations of the present invention suitable for oral administration may be presented as discrete units such as capsules, cachets or tablets each containing a predetermined amount of an active ingredient; as a powder or granules; as a solution or a suspension in an aqueous or non-aqueous liquid; or as an oil-in-water liquid emulsion or a water-in-oil liquid emulsion. An active ingredient may also be administered as a bolus, electuary or paste.

A tablet can made by compression or molding, optionally with one or more accessory ingredients. Compressed tablets may be prepared by compressing in a suitable machine an active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally can be formulated so as to provide slow or controlled release of an active ingredient.

For administration to the eye or other external tissues e.g., mouth and skin, the formulations can be preferably applied as a topical ointment or cream containing an active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, an active ingredient may be employed with either a paraffinic or a water-miscible ointment base. Alternatively, an active ingredient may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of an active ingredient through the skin or other affected areas. Examples of such dermal penetration enhancers include dimethyl sulphoxide and related analogs.

The oily phase of the emulsions of Combination Compounds and/or other active ingredients may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60 (ICI Americas Inc.), Span 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Pharmaceutical formulations according to the present invention comprise one or more active together with one or more pharmaceutically acceptable carriers or excipients and optionally other therapeutic agents. Pharmaceutical formulations containing active ingredients may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing an active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where an active ingredient(s) is mixed with an inert solid diluent, for example calcium phosphate or kaolin, or as soft gelatin capsules wherein an active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending an active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide an active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of an active ingredient per milliliter of solution in order that infusion of a suitable volume at a rate of about 30 mL/hr can occur.

Formulations suitable for administration to the eye include eye drops wherein an active ingredient is dissolved or suspended in a suitable carrier, especially an aqueous solvent for an active ingredient. An active ingredient is preferably present in such formulations in a concentration of 0.5 to 20%, advantageously 0.5 to 10% particularly about 1.5% w/w.

Formulations suitable for topical administration in the mouth include lozenges comprising an active ingredient in a flavored basis, usually sucrose and acacia or tragacanth; pastilles comprising an active ingredient in an inert basis such as gelatin and glycerin, or sucrose and acacia; and mouthwashes comprising an active ingredient in a suitable liquid carrier. Formulations for rectal administration may be presented as a suppository with a suitable base comprising for example cocoa butter or a salicylate.

Formulations suitable for intrapulmonary or nasal administration have a particle size for example in the range of 0.1 to 500 μm (including particle sizes in a range between 0.1 and 500 μm in increments such as 0.5 μm, 1 μm, 30 μm, 35 μm, etc.), which is administered by rapid inhalation through the nasal passage or by inhalation through the mouth so as to reach the alveolar sacs. Suitable formulations include aqueous or oily solutions of an active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to an active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations can be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions can be prepared from sterile powders, granules and tablets of the kind previously described. Preferred unit dosage formulations can be those containing a daily dose or unit daily sub-dose, as herein above recited, or an appropriate fraction thereof, of an active ingredient.

It should be understood that in addition to the ingredients particularly mentioned above the formulations of Combination Compounds and/or other active ingredients may include other agents conventional in the art having regard to the type of formulation in question, for example those suitable for oral administration may include flavoring agents.

Combination Compounds and other active ingredients can also be formulated to provide controlled release of an active ingredient to allow less frequent dosing or to improve the pharmacokinetic or toxicity profile of an active ingredient. Accordingly, the invention also provides compositions comprising two or more of the Combination Compounds formulated for sustained or controlled release.

Dosages

The effective dose of an active ingredient depends at least on the nature of the condition being treated, toxicity, whether the compound is being used prophylactically (lower doses) or against an active disease or condition, the method of delivery, and the pharmaceutical formulation, and can be determined by the clinician using conventional dose escalation studies.

By way of example, compositions of the invention (e.g. tablets) can be formulated to provide effective doses. For example, with respect to Compound 1, or a pharmaceutically acceptable salt thereof, the composition may comprise from 1.0 mg to 100 mg, from 5 mg to 40 mg, from 30 mg to 50 mg, or 20 mg or 40 mg and can be adapted to be administered one or more times daily to a human being in need thereof in combination with any one or more of Compound 2, Compound 3, Compound 6, Compound 4, Compound 5, Compound 7, Compound 9, Compound 10, Compound 11, Compound 12, Compound 13, Compound 14, Compound 15 and Compound 16. With respect to Compound 2 or a pharmaceutically acceptable salt thereof, the composition may comprise from 25 mg to 800 mg, from 50 mg to 400 mg, or from 60 mg to 300 mg or from 70 mg to 200 mg or may be 150 mg and can be adapted to be administered one or more times daily to a human being in need thereof in combination with any one or more of Compound 1, Compound 3, Compound 6, Compound 4, Compound 5, Compound 7, Compound 9, Compound 10, Compound 11, Compound 12, Compound 13, Compound 14, Compound 15 and Compound 16. With respect to Compound 3, or a pharmaceutically acceptable salt thereof, the composition may comprise from 10 mg to 1000 mg, or 50 to 400 mg, or 100 mg to 400 mg or 200 mg to 400 mg and can be adapted to be administered one or more times daily to a human being in need thereof in combination with any one or more of Compound 1, Compound 2, Compound 6, Compound 4, Compound 5, Compound 7, Compound 9, Compound 10, Compound 11, Compound 12, Compound 13, Compound 14, Compound 15 and Compound 16. With respect to Compound 4, or a pharmaceutically acceptable salt thereof, the composition may comprise from 25 mg to 400 mg or from 25 mg to 200 mg can be adapted to be administered one or more times daily to a human being in need thereof in combination with any one or more of Compound 1, Compound 2, Compound 3, Compound 6, Compound 5 and Compound 7. With respect to Compound 5, or a pharmaceutically acceptable salt thereof, the composition may comprise from 50 mg to 1000 mg or 100 mg to 750 mg can be adapted to be administered one or more times daily to a human being in need thereof in combination with any one or more of Compound 1, Compound 2, Compound 3, Compound 6, Compound 4, Compound 7, Compound 9, Compound 10, Compound 11, Compound 12, Compound 13, Compound 14, Compound 15 and Compound 16. With respect to Compound 6, or a pharmaceutically acceptable salt thereof, the composition may comprise from 1 mg to 500 mg or from 3 mg to 300 mg or from 3 mg to 200 mg or from 3 mg to 100 mg or from 10 mg to 90 mg or from 30 mg to 90 mg can be adapted to be administered one or more times daily to a human being in need thereof in combination with any one or more of Compound 1, Compound 2, Compound 3, Compound 4, Compound 5, Compound 7, Compound 9, Compound 10, Compound 11, Compound 12, Compound 13, Compound 14, Compound 15 and Compound 16. With respect to Compound 7, or a pharmaceutically acceptable salt thereof, the composition may comprise from 100 micrograms up to 3000 mg, from 25 mg up to 2000 mg, or from 50 mg up to 1000 mg and can be adapted to be administered one or more times daily (e.g. four times daily) to a human being in need thereof in combination with any one or more of Compound 1, Compound 2, Compound 3, Compound 4, Compound 5, Compound 6, Compound 9, Compound 10, Compound 11, Compound 12, Compound 13, Compound 14, Compound 15 and Compound 16. With respect to Compounds 9 and 10, or pharmaceutically acceptable salts thereof, the composition may comprise 10 mg to 1000 mg per day (according to US 2010/0298257). With respect to Compound 11, or pharmaceutically acceptable salts thereof, the composition may comprise 1 mg to 1000 mg per day (according to US 2010/

0081628). Dosages for Compounds 1-7 that are co-administered may need to be adjusted to account for potential drug-drug interactions. For example, although it does not appear that Compound 1 affects drug metabolizing systems, Compound 2 appears to have the effect of increasing the exposure of Compound 1 approximately 2-3×. Therefore, a dose reduction (e.g. 2×-3×) of Compound 1 would be anticipated when Compound 1 is combined with Compound 2. In combination with Compound 16, Compound 2 appears to have the effect of increasing the exposure of Compound 6 approximately 5×, so dose reduction (e.g. 3×-5×) of Compound 16 would be anticipated when Compound 16 is dosed with Compound 2. Therefore, a 10 mg dose of Compound 6 when coadministered with Compound 2 approximate to a 30 mg dose.

The two or more Combination Compounds may be administered in conjunction with Ribavirin in amounts of about 800 mg, 1000 mg or 1200 mg per day in single or multiple dosages (e.g. about 400 mg, 500 mg or 600 mg twice daily).

Use of Combinations of the Invention

In practice of this aspect of the invention, Combination Compounds may be used in the dosages set forth above.

One aspect of the present invention includes Compound 1 for use in a method of treating HCV infections, wherein compound 1 is used in combination with a second compound selected from the group consisting of Compound 2, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 3, Compound 4, Compound 5 or Compound 6.

Another aspect of the present invention includes Compound 2 for use in a method of treating HCV infections, wherein compound 2 is used in combination with a second compound selected from the group consisting of Compound 1, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 4.

Another aspect of the present invention includes Compound 3 for use in a method of treating HCV infections, wherein compound 3 is used in combination with a second compound selected from the group consisting of Compound 1, Compound 2, Compound 4, Compound 5, Compound 6, Compound 7, Compound 9, Compound 10, Compound 11, Compound 12, Compound 13, Compound 14, Compound 15 and Compound 16. The second compound may be Compound 1 or Compound 6.

Another aspect of the present invention includes Compound 4 for use in a method of treating HCV infections, wherein Compound 4 is used in combination with a second compound selected from the group consisting of Compound 1, Compound 2, Compound 3, Compound 5, Compound 6 and Compound 7. The second compound may be Compound 1 or Compound 2 or Compound 3 or Compound 6.

Another aspect of the present invention includes Compound 5 for use in a method of treating HCV infections, wherein Compound 5 is used in combination with a second compound selected from the group consisting of Compound 1, Compound 2, Compound 3, Compound 4, Compound 6, Compound 7, Compound 9, Compound 10, Compound 11, Compound 12, Compound 13, Compound 14, Compound 15 and Compound 16. The second compound may be Compound 1.

Another aspect of the present invention includes Compound 6 for use in a method of treating HCV infections, wherein Compound 6 is used in combination with a second compound selected from the group consisting of Compound 1, Compound 2, Compound 3, Compound 4, Compound 5, Compound 7, Compound 9, Compound 10, Compound 11, Compound 12, Compound 13, Compound 14, Compound 15 and Compound 16. The second compound may be Compound 1, Compound 2, Compound 3 or Compound 4.

Another aspect of the present invention includes Compound 7 for use in a method of treating HCV infections, wherein Compound 7 is used in combination with a second compound selected from the group consisting of Compound 1, Compound 2, Compound 3, Compound 4, Compound 5, Compound 6, Compound 9, Compound 10, Compound 11, Compound 12, Compound 13, Compound 14, Compound 15 and Compound 16.

Another aspect of the present invention includes Compound 9 for use in a method of treating HCV infections, wherein Compound 9 is used in combination with a second compound selected from the group consisting of Compound 1, Compound 2, Compound 3, Compound 5, Compound 6, and Compound 7.

Another aspect of the present invention includes Compound 10 for use in a method of treating HCV infections, wherein Compound 10 is used in combination with a second compound selected from the group consisting of Compound 1, Compound 2, Compound 3, Compound 5, Compound 6, and Compound 7.

Another aspect of the present invention includes Compound 11 for use in a method of treating HCV infections, wherein Compound 11 is used in combination with a second compound selected from the group consisting of Compound 1, Compound 2, Compound 3, Compound 5, Compound 6, and Compound 7.

Another aspect of the present invention includes Compound 12 for use in a method of treating HCV infections, wherein Compound 12 is used in combination with a second compound selected from the group consisting of Compound 1, Compound 2, Compound 3, Compound 5, Compound 6, and Compound 7.

Another aspect of the present invention includes Compound 13 for use in a method of treating HCV infections, wherein Compound 13 is used in combination with a second compound selected from the group consisting of Compound 1, Compound 2, Compound 3, Compound 5, Compound 6, and Compound 7.

Another aspect of the present invention includes Compound 14 for use in a method of treating HCV infections, wherein Compound 14 is used in combination with a second compound selected from the group consisting of Compound 1, Compound 2, Compound 3, Compound 5, Compound 6, and Compound 7.

Another aspect of the present invention includes Compound 15 for use in a method of treating HCV infections, wherein Compound 15 is used in combination with a second compound selected from the group consisting of Compound 1, Compound 2, Compound 3, Compound 5, Compound 6, and Compound 7.

Another aspect of the present invention includes Compound 16 for use in a method of treating HCV infections, wherein Compound 16 is used in combination with a second compound selected from the group consisting of Compound 1, Compound 2, Compound 3, Compound 5, Compound 6, and Compound 7.

Another aspect of the present invention includes Compound 1 for use in a method of treating HCV infections, wherein compound 1 is used in combination with a second compound and a third compound each selected from the group consisting of Compound 2, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 3, or Compound 4, or Compound 5 or Compound 6. The second compound may be Compound 2 and the third compound may be Compound 4. The second compound may be Compound 3 and the third compound may be Compound 4. The second compound may be Compound 2 and the third compound may be Compound 6. The second compound may be Compound 3 and the third compound may be Compound 6. The second compound may be Compound 4 and the third compound may be Compound 6.

Another aspect of the present invention includes Compound 2 for use in a method of treating HCV infections, wherein compound 2 is used in combination with a second compound and a third compound each selected from the group consisting of Compound 1, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 4. The second compound may be Compound 1 and the third compound may be Compound 4. The second compound may be Compound 1 and the third compound may be Compound 6. The second compound may be Compound 4 and the third compound may be Compound 6.

Another aspect of the present invention includes Compound 3 for use in a method of treating HCV infections, wherein compound 3 is used in combination with a second compound and a third compound each selected from the group consisting of Compound 1, Compound 2, Compound 4, Compound 5, Compound 6, Compound 7, Compound 9, Compound 10, Compound 11, Compound 12, Compound 13, Compound 14, Compound 15 and Compound 16. The second compound may be Compound 1 or Compound 6. The second compound may be Compound 1 and the third compound may be Compound 4. The second compound may be Compound 1 and the third compound may be Compound 6. The second compound may be Compound 4 and the third compound may be Compound 6.

Another aspect of the present invention includes Compound 4 for use in a method of treating HCV infections, wherein Compound 4 is used in combination with a second compound and a third compound each selected from the group consisting of Compound 1, Compound 2, Compound 3, Compound 5, Compound 6 and Compound 7. The second compound may be Compound 1, Compound 2, Compound 3 or Compound 6. The second compound may be Compound 1 and the third compound may be Compound 2. The second compound may be Compound 1 and the third compound may be Compound 3. The second compound may be Compound 1 and the third compound may be Compound 6. The second compound may be Compound 2 and the third compound may be Compound 6. The second compound may be Compound 3 and the third compound may be Compound 6.

Another aspect of the present invention includes Compound 5 for use in a method of treating HCV infections, wherein Compound 5 is used in combination with a second compound and a third compound each selected from the group consisting of Compound 1, Compound 2, Compound 3, Compound 4, Compound 6, Compound 7, Compound 9, Compound 10, Compound 11, Compound 12, Compound 13, Compound 14, Compound 15 and Compound 16. The second compound may be Compound 1.

Another aspect of the present invention includes Compound 6 for use in a method of treating HCV infections, wherein Compound 6 is used in combination with a second compound and a third compound each selected from the group consisting of Compound 1, Compound 2, Compound 3, Compound 4, Compound 5, Compound 7, Compound 9, Compound 10, Compound 11, Compound 12, Compound 13, Compound 14, Compound 15 and Compound 16. The second compound may be Compound 1, Compound 2, Compound 3 or Compound 4. The second compound may be Compound 1 and the third compound may be Compound 2. The second compound may be Compound 1 and the third compound may be Compound 3. The second compound may be Compound 4 and the third compound may be Compound 6. The second compound may be Compound 2 and the third compound may be Compound 4. The second compound may be Compound 3 and the third compound may be Compound 4.

Another aspect of the present invention includes Compound 7 for use in a method of treating HCV infections, wherein Compound 7 is used in combination with a second compound and a third compound each selected from the group consisting of Compound 1, Compound 2, Compound 3, Compound 4, Compound 5, Compound 6, Compound 9, Compound 10, Compound 11, Compound 12, Compound 13, Compound 14, Compound 15 and Compound 16.

Another aspect of the present invention includes Compound 9 for use in a method of treating HCV infections, wherein Compound 9 is used in combination with a second compound and a third compound each selected from the group consisting of Compound 1, Compound 2, Compound 3, Compound 5, Compound 6 and Compound 7.

Another aspect of the present invention includes Compound 10 for use in a method of treating HCV infections, wherein Compound 10 is used in combination with a second compound and a third compound each selected from the group consisting of Compound 1, Compound 2, Compound 3, Compound 5, Compound 6 and Compound 7.

Another aspect of the present invention includes Compound 11 for use in a method of treating HCV infections, wherein Compound 11 is used in combination with a second compound and a third compound each selected from the group consisting of Compound 1, Compound 2, Compound 3, Compound 5, Compound 6 and Compound 7.

Another aspect of the present invention includes Compound 1 for use in a method of treating HCV infections, wherein compound 1 is used in combination with a second compound, a third compound and a fourth compound each selected from the group consisting of Compound 2, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 3, Compound 4, Compound 5, or Compound 6. The second compound may be Compound 2 and the third compound may be Compound 4. The second compound may be Compound 3 and the third compound may be Compound 4. The second compound may be Compound 2 and the third compound may be Compound 6. The second compound may be Compound 3 and the third compound may be Compound 6. The second compound may be Compound 4 and the third compound may be Compound 6.

Another aspect of the present invention includes Compound 2 for use in a method of treating HCV infections, wherein compound 2 is used in combination with a second compound, a third compound and a fourth compound each selected from the group consisting of Compound 1, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 4. The second compound may be Compound 1 and the third compound may be Compound 4. The second compound may be Compound 1 and the third compound may be Compound 6. The second compound may be Compound 4 and the third compound may be Compound 6.

Another aspect of the present invention includes Compound 3 for use in a method of treating HCV infections, wherein compound 3 is used in combination with a second compound, a third compound and a fourth compound each selected from the group consisting of Compound 1, Compound 2, Compound 4, Compound 5, Compound 6, Compound 7, Compound 9, Compound 10, Compound 11, Compound 12, Compound 13, Compound 14, Compound 15 and Compound 16. The second compound may be Compound 1 or Compound 6. The second compound may be Compound 1 and the third compound may be Compound 4. The second compound may be Compound 1 and the third compound may be Compound 6. The second compound may be Compound 4 and the third compound may be Compound 6.

Another aspect of the present invention includes Compound 4 for use in a method of treating HCV infections, wherein Compound 4 is used in combination with a second compound, a third compound and a fourth compound each selected from the group consisting of Compound 1, Compound 2, Compound 3, Compound 5, Compound 6 and Compound 7. The second compound may be Compound 1, Compound 2, Compound 3, or Compound 6. The second compound may be Compound 1 and the third compound may be Compound 2. The second compound may be Compound 1 and the third compound may be Compound 3. The second compound may be Compound 1 and the third compound may be Compound 6. The second compound may be Compound 2 and the third compound may be Compound 6. The second compound may be Compound 3 and the third compound may be Compound 6.

Another aspect of the present invention includes Compound 5 for use in a method of treating HCV infections, wherein Compound 5 is used in combination with a second compound, a third compound and a fourth compound each selected from the group consisting of Compound 1, Compound 2, Compound 3, Compound 4, Compound 6, Compound 7, Compound 9, Compound 10, Compound 11, Compound 12, Compound 13, Compound 14, Compound 15 and Compound 16. The second compound may be Compound 1.

Another aspect of the present invention includes Compound 6 for use in a method of treating HCV infections, wherein Compound 6 is used in combination with a second compound, a third compound and a fourth compound each selected from the group consisting of Compound 1, Compound 2, Compound 3, Compound 4, Compound 5, Compound 7, Compound 9, Compound 10, Compound 11, Compound 12, Compound 13, Compound 14, Compound 15 and Compound 16. The second compound may be Compound 1, Compound 2, Compound 3, or Compound 4. The second compound may be Compound 1 and the third compound may be Compound 2. The second compound may be Compound 1 and the third compound may be Compound 3. The second compound may be Compound 4 and the third compound may be Compound 6. The second compound may be Compound 2 and the third compound may be Compound 4. The second compound may be Compound 3 and the third compound may be Compound 4.

Another aspect of the present invention includes Compound 7 for use in a method of treating HCV infections, wherein Compound 7 is used in combination with a second compound, a third compound and a fourth compound each selected from the group consisting of Compound 1, Compound 2, Compound 3, Compound 4, Compound 5, Compound 6, Compound 9, Compound 10, Compound 11, Compound 12, Compound 13, Compound 14, Compound 15 and Compound 16.

Another aspect of the present invention includes Compound 9 for use in a method of treating HCV infections, wherein Compound 9 is used in combination with a second compound, a third compound and a fourth compound each selected from the group consisting of Compound 1, Compound 2, Compound 3, Compound 5, Compound 6 and Compound 7.

Another aspect of the present invention includes Compound 10 for use in a method of treating HCV infections, wherein Compound 10 is used in combination with a second compound, a third compound and a fourth compound each selected from the group consisting of Compound 1, Compound 2, Compound 3, Compound 5, Compound 6 and Compound 7.

Another aspect of the present invention includes Compound 11 for use in a method of treating HCV infections, wherein Compound 11 is used in combination with a second compound, a third compound and a fourth compound each selected from the group consisting of Compound 1, Compound 2, Compound 3, Compound 5, Compound 6 and Compound 7.

Another aspect of the present invention includes Compound 1 for use in a method of treating HCV infections, wherein compound 1 is used in combination with a second compound, a third compound, a fourth compound and a fifth compound each selected from the group consisting of Compound 2, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 3, Compound 4, Compound 5 or Compound 6. The second compound may be Compound 2 and the third compound may be Compound 4. The second compound may be Compound 3 and the third compound may be Compound 4. The second compound may be Compound 2 and the third compound may be Compound 6. The second compound may be Compound 3 and the third compound may be Compound 6. The second compound may be Compound 4 and the third compound may be Compound 6.

Another aspect of the present invention includes Compound 2 for use in a method of treating HCV infections, wherein compound 2 is used in combination with a second compound, a third compound, a fourth compound and a fifth compound each selected from the group consisting of Compound 1, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 4. The second compound may be Compound 1 and the third compound may be Compound 4. The second compound may be Compound 1 and the third compound may be Compound 6. The second compound may be Compound 4 and the third compound may be Compound 6.

Another aspect of the present invention includes Compound 3 for use in a method of treating HCV infections, wherein compound 3 is used in combination with a second compound, a third compound, a fourth compound and a fifth compound each selected from the group consisting of Compound 1, Compound 2, Compound 4, Compound 5, Compound 6, Compound 7, Compound 9, Compound 10, Compound 11, Compound 12, Compound 13, Compound 14, Compound 15 and Compound 16. The second compound may be Compound 1 or Compound 6. The second compound may be Compound 1 and the third compound may be Compound 4. The second compound may be Compound 1 and the third compound may be Compound 6. The second compound may be Compound 4 and the third compound may be Compound 6.

Another aspect of the present invention includes Compound 4 for use in a method of treating HCV infections, wherein Compound 4 is used in combination with a second compound, a third compound, a fourth compound and a fifth compound each selected from the group consisting of Compound 1, Compound 2, Compound 3, Compound 5, Compound 6 and Compound 7. The second compound may be Compound 1, Compound 2, Compound 3 or Compound 6. The second compound may be Compound 1 and the third compound may be Compound 2. The second compound may be Compound 1 and the third compound may be Compound 3. The second compound may be Compound 1 and the third compound may be Compound 6. The second compound may be Compound 2 and the third compound may be Compound 6. The second compound may be Compound 3 and the third compound may be Compound 6.

Another aspect of the present invention includes Compound 5 for use in a method of treating HCV infections, wherein Compound 5 is used in combination with a second compound, a third compound, a fourth compound and a fifth compound each selected from the group consisting of Compound 1, Compound 2, Compound 3, Compound 4, Compound 6, Compound 7, Compound 9, Compound 10, Compound 11, Compound 12, Compound 13, Compound 14, Compound 15 and Compound 16. The second compound may be Compound 1.

Another aspect of the present invention includes Compound 6 for use in a method of treating HCV infections, wherein Compound 6 is used in combination with a second compound, a third compound, a fourth compound and a fifth compound each selected from the group consisting of Compound 1, Compound 2, Compound 3, Compound 4, Compound 5, Compound 7, Compound 9, Compound 10, Compound 11, Compound 12, Compound 13, Compound 14, Compound 15 and Compound 16. The second compound may be Compound 1, Compound 2, Compound 3, or Compound 4. The second compound may be Compound 1 and the third compound may be Compound 2. The second compound may be Compound 1 and the third compound may be Compound 3. The second compound may be Compound 4 and the third compound may be Compound 6. The second compound may be Compound 2 and the third compound may be Compound 4. The second compound may be Compound 3 and the third compound may be Compound 4.

Another aspect of the present invention includes Compound 7 for use in a method of treating HCV infections, wherein Compound 7 is used in combination with a second compound, a third compound, a fourth compound and a fifth compound each selected from the group consisting of Compound 1, Compound 2, Compound 3, Compound 4, Compound 5, Compound 6, Compound 9, Compound 10, Compound 11, Compound 12, Compound 13, Compound 14, Compound 15 and Compound 16.

Another aspect of the present invention includes Compound 9 for use in a method of treating HCV infections, wherein Compound 9 is used in combination with a second compound, a third compound, a fourth compound and a fifth compound each selected from the group consisting of Compound 1, Compound 2, Compound 3, Compound 5, Compound 6 and Compound 7.

Another aspect of the present invention includes Compound 10 for use in a method of treating HCV infections, wherein Compound 10 is used in combination with a second compound, a third compound, a fourth compound and a fifth compound each selected from the group consisting of Compound 1, Compound 2, Compound 3, Compound 5, Compound 6 and Compound 7.

Another aspect of the present invention includes Compound 11 for use in a method of treating HCV infections, wherein Compound 11 is used in combination with a second compound, a third compound, a fourth compound and a fifth compound each selected from the group consisting of Compound 1, Compound 2, Compound 3, Compound 5, Compound 6 and Compound 7.

One aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 1 and further comprising administering a second compound selected from the group consisting of comprising Compound 2, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 3, Compound 4, Compound 5 or Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 2 and further comprising administering a second compound selected from the group consisting of Compound 1, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 4.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 3 and further comprising administering a second compound selected from the group consisting of Compound 1, Compound 2, Compound 4, Compound 5, Compound 6, Compound 7, Compound 9, Compound 10, Compound 11, Compound 12, Compound 13, Compound 14, Compound 15 and Compound 16. The second compound may be Compound 1 or Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 4 and further comprising administering a second compound selected from the group consisting of Compound 1, Compound 2, Compound 3, Compound 5, Compound 6 and Compound 7. The second compound may be Compound 1 or Compound 2 or Compound 3 or Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 5 and further comprising administering a second compound selected from the group consisting of Compound 1, Compound 2, Compound 3, Compound 4, Compound 6, Compound 7, Compound 9, Compound 10, Compound 11, Compound 12, Compound 13, Compound 14, Compound 15 and Compound 16. The second compound may be Compound 1.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 6 and further comprising administering a second compound selected from the group consisting of Compound 1, Compound 2, Compound 3, Compound 4, Compound 5, Compound 7, Compound 9, Compound 10, Compound 11, Compound 12, Compound 13, Compound 14, Compound 15 and Compound 16. The second compound may be Compound 1, Compound 2, Compound 3 or Compound 4.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 7 and further comprising administering a second compound selected from the group consisting of Compound 1, Compound 2, Compound 3, Compound 4, Compound 5, Compound 6, Compound 9, Compound 10, Compound 11, Compound 12, Compound 13, Compound 14, Compound 15 and Compound 16.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 9 and further comprising administering a second compound selected from the group consisting of Compound 1, Compound 2, Compound 3, Compound 5, Compound 6 and Compound 7.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 10 and further comprising administering a second compound selected from the group consisting of Compound 1, Compound 2, Compound 3, Compound 5, Compound 6 and Compound 7.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 11 and further comprising administering a second compound selected from the group consisting of Compound 1, Compound 2, Compound 3, Compound 5, Compound 6 and Compound 7.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 1 and further comprising administering a second compound and a third compound each selected from the group consisting of Compound 2, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 3, or Compound 4, or Compound 5 or Compound 6. The second compound may be Compound 2 and the third compound may be Compound 4. The second compound may be Compound 3 and the third compound may be Compound 4. The second compound may be Compound 2 and the third compound may be Compound 6. The second compound may be Compound 3 and the third compound may be Compound 6. The second compound may be Compound 4 and the third compound may be Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 2 and further comprising administering a second compound and a third compound each selected from the group consisting of Compound 1, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 4. The second compound may be Compound 1 and the third compound may be Compound 4. The second compound may be Compound 1 and the third compound may be Compound 6. The second compound may be Compound 4 and the third compound may be Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 3 and further comprising administering a second compound and a third compound each selected from the group consisting of Compound 1, Compound 2, Compound 4, Compound 5, Compound 6, Compound 7, Compound 9, Compound 10, Compound 11, Compound 12, Compound 13, Compound 14, Compound 15 and Compound 16. The second compound may be Compound 1 or Compound 6. The second compound may be Compound 1 and the third compound may be Compound 4. The second compound may be Compound 1 and the third compound may be Compound 6. The second compound may be Compound 4 and the third compound may be Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 4 and further comprising administering a second compound and a third compound each selected from the group consisting of Compound 1, Compound 2, Compound 3, Compound 5, Compound 6 and Compound 7. The second compound may be Compound 1, Compound 2, Compound 3 or Compound 6. The second compound may be Compound 1 and the third compound may be Compound 2. The second compound may be Compound 1 and the third compound may be Compound 3. The second compound may be Compound 1 and the third compound may be Compound 6. The second compound may be Compound 2 and the third compound may be Compound 6. The second compound may be Compound 3 and the third compound may be Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 5 and further comprising administering a second compound and a third compound each selected from the group consisting of Compound 1, Compound 2, Compound 3, Compound 4, Compound 6, Compound 7, Compound 9, Compound 10, Compound 11, Compound 12, Compound 13, Compound 14, Compound 15 and Compound 16. The second compound may be Compound 1.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 6 and further comprising administering a second compound and a third compound each selected from the group consisting of Compound 1, Compound 2, Compound 3, Compound 4, Compound 5, Compound 7, Compound 9, Compound 10, Compound 11, Compound 12, Compound 13, Compound 14, Compound 15 and Compound 16. The second compound may be Compound 1, Compound 2, Compound 3 or Compound 4. The second compound may be Compound 1 and the third compound may be Compound 2. The second compound may be Compound 1 and the third compound may be Compound 3. The second compound may be Compound 4 and the third compound may be Compound 6. The second compound may be Compound 2 and the third compound may be Compound 4. The second compound may be Compound 3 and the third compound may be Compound 4.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 7 and further comprising administering a second compound and a third compound each selected from the group consisting of Compound 1, Compound 2, Compound 3, Compound 4, Compound 5, Compound 6, Compound 9, Compound 10, Compound 11, Compound 12, Compound 13, Compound 14, Compound 15 and Compound 16.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 9 and further comprising administering a second compound and a third compound each selected from the group consisting of Compound 1, Compound 2, Compound 3, Compound 5, Compound 6 and Compound 7.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 10 and further comprising administering a second compound and a third compound each selected from the group consisting of Compound 1, Compound 2, Compound 3, Compound 5, Compound 6 and Compound 7.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 11 and further comprising administering a second compound and a third compound each selected from the group consisting of Compound 1, Compound 2, Compound 3, Compound 5, Compound 6 and Compound 7.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 1 and further comprising administering a second compound, a third compound and a fourth compound each selected from the group consisting of Compound 2, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 3, Compound 4, Compound 5, or Compound 6. The second compound may be Compound 2 and the third compound may be Compound 4. The second compound may be Compound 3 and the third compound may be Compound 4. The second compound may be Compound 2 and the third compound may be Compound 6. The second compound may be Compound 3 and the third compound may be Compound 6. The second compound may be Compound 4 and the third compound may be Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 2 and further comprising administering a second compound, a third compound and a fourth compound each selected from the group consisting of Compound 1, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 4. The second compound may be Compound 1 and the third compound may be Compound 4. The second compound may be Compound 1 and the third compound may be Compound 6. The second compound may be Compound 4 and the third compound may be Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 3 and further comprising administering a second compound, a third compound and a fourth compound each selected from the group consisting of Compound 1, Compound 2, Compound 4, Compound 5, Compound 6, Compound 7, Compound 9, Compound 10, Compound 11, Compound 12, Compound 13, Compound 14, Compound 15 and Compound 16. The second compound may be Compound 1 or Compound 6. The second compound may be Compound 1 and the third compound may be Compound 4. The second compound may be Compound 1 and the third compound may be Compound 6. The second compound may be Compound 4 and the third compound may be Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 4 and further comprising administering a second compound, a third compound and a fourth compound each selected from the group consisting of Compound 1, Compound 2, Compound 3, Compound 5, Compound 6 and Compound 7. The second compound may be Compound 1, Compound 2, Compound 3, or Compound 6. The second compound may be Compound 1 and the third compound may be Compound 2. The second compound may be Compound 1 and the third compound may be Compound 3. The second compound may be Compound 1 and the third compound may be Compound 6. The second compound may be Compound 2 and the third compound may be Compound 6. The second compound may be Compound 3 and the third compound may be Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 5 and further comprising administering a second compound, a third compound and a fourth compound each selected from the group consisting of Compound 1, Compound 2, Compound 3, Compound 4, Compound 6, Compound 7, Compound 9, Compound 10, Compound 11, Compound 12, Compound 13, Compound 14, Compound 15 and Compound 16. The second compound may be Compound 1.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 6 and further comprising administering a second compound, a third compound and a fourth compound each selected from the group consisting of Compound 1, Compound 2, Compound 3, Compound 4, Compound 5, Compound 7, Compound 9, Compound 10, Compound 11, Compound 12, Compound 13, Compound 14, Compound 15 and Compound 16. The second compound may be Compound 1, Compound 2, Compound 3, or Compound 4. The second compound may be Compound 1 and the third compound may be Compound 2. The second compound may be Compound 1 and the third compound may be Compound 3. The second compound may be Compound 4 and the third compound may be Compound 6. The second compound may be Compound 2 and the third compound may be Compound 4. The second compound may be Compound 3 and the third compound may be Compound 4.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 7 and further comprising administering a second compound, a third compound and a fourth compound each selected from the group consisting of Compound 1, Compound 2, Compound 3, Compound 4, Compound 5, Compound 6, Compound 9, Compound 10, Compound 11, Compound 12, Compound 13, Compound 14, Compound 15 and Compound 16.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 9 and further comprising administering a second compound, a third compound and a fourth compound each selected from the group consisting of Compound 1, Compound 2, Compound 3, Compound 5, Compound 6 and Compound 7.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 10 and further comprising administering a second compound, a third compound and a fourth compound each selected from the group consisting of Compound 1, Compound 2, Compound 3, Compound 5, Compound 6 and Compound 7.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 11 and further comprising administering a second compound, a third compound and a fourth compound each selected from the group consisting of Compound 1, Compound 2, Compound 3, Compound 5, Compound 6 and Compound 7.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 1 and further comprising administering a second compound, a third compound, a fourth compound and a fifth compound each selected from the group consisting of Compound 2, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 3, Compound 4, Compound 5 or Compound 6. The second compound may be Compound 2 and the third compound may be Compound 4. The second compound may be Compound 3 and the third compound may be Compound 4. The second compound may be Compound 2 and the third compound may be Compound 6. The second compound may be Compound 3 and the third compound may be Compound 6. The second compound may be Compound 4 and the third compound may be Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 2 and further comprising administering a second compound, a third compound, a fourth compound and a fifth compound each selected from the group consisting of Compound 1, Compound 3, Compound 4, Compound 5, Compound 6, Compound 7, Compound 9, Compound 10, Compound 11, Compound 12, Compound 13, Compound 14, Compound 15 and Compound 16. The second compound may be Compound 4. The second compound may be Compound 1 and the third compound may be Compound 4. The second compound may be Compound 1 and the third compound may be Compound 6. The second compound may be Compound 4 and the third compound may be Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 3 and further comprising administering a second compound, a third compound, a fourth compound and a fifth compound each selected from the group consisting of Compound 1, Compound 2, Compound 4, Compound 5, Compound 6, Compound 7, Compound 9, Compound 10, Compound 11, Compound 12, Compound 13, Compound 14, Compound 15 and Compound 16. The second compound may be Compound 1 or Compound 6. The second compound may be Compound 1 and the third compound may be Compound 4. The second compound may be Compound 1 and the third compound may be Compound 6. The second compound may be Compound 4 and the third compound may be Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 4 and further comprising administering a second compound, a third compound, a fourth compound and a fifth compound each selected from the group consisting of Compound 1, Compound 2, Compound 3, Compound 5, Compound 6 and Compound 7. The second compound may be Compound 1, Compound 2, Compound 3 or Compound 6. The second compound may be Compound 1 and the third compound may be Compound 2. The second compound may be Compound 1 and the third compound may be Compound 3. The second compound may be Compound 1 and the third compound may be Compound 6. The second compound may be Compound 2 and the third compound may be Compound 6. The second compound may be Compound 3 and the third compound may be Compound 6.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 5 and further comprising administering a second compound, a third compound, a fourth compound and a fifth compound each selected from the group consisting of Compound 1, Compound 2, Compound 3, Compound 4, Compound 6, Compound 7, Compound 9, Compound 10, Compound 11, Compound 12, Compound 13, Compound 14, Compound 15 and Compound 16. The second compound may be Compound 1.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 6 and further comprising administering a second compound, a third compound, a fourth compound and a fifth compound each selected from the group consisting of Compound 1, Compound 2, Compound 3, Compound 4, Compound 5, Compound 7, Compound 9, Compound 10, Compound 11, Compound 12, Compound 13, Compound 14, Compound 15 and Compound 16. The second compound may be Compound 1, Compound 2, Compound 3, and Compound 4. The second compound may be Compound 1 and the third compound may be Compound 2. The second compound may be Compound 1 and the third compound may be Compound 3. The second compound may be Compound 4 and the third compound may be Compound 6. The second compound may be Compound 2 and the third compound may be Compound 4. The second compound may be Compound 3 and the third compound may be Compound 4.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 7 and further comprising administering a second compound, a third compound, a fourth compound and a fifth compound each selected from the group consisting of Compound 1, Compound 2, Compound 3, Compound 4, Compound 5, Compound 6, Compound 9, Compound 10, Compound 11, Compound 12, Compound 13, Compound 14, Compound 15 and Compound 16.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 9 and further comprising administering a second compound, a third compound, a fourth compound and a fifth compound each selected from the group consisting of Compound 1, Compound 2, Compound 3, Compound 5, Compound 6 and Compound 7.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 10 and further comprising administering a second compound, a third compound, a fourth compound and a fifth compound each selected from the group consisting of Compound 1, Compound 2, Compound 3, Compound 5, Compound 6 and Compound 7.

Another aspect of the present invention includes a method for ameliorating one or more symptom of HCV infection in a human, a method for reducing viral load in a human diagnosed with HCV, a method of treating HCV in a human subject, and a method for reducing emergence of HCV quasispecies with resistance to coadministered oral antiviral agents, each method comprising administering Compound 11 and further comprising administering a second compound, a third compound, a fourth compound and a fifth compound each selected from the group consisting of Compound 1, Compound 2, Compound 3, Compound 5, Compound 6 and Compound 7.

Routes and Modes of Administration

Two or more of Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16 and any other components of a combination therapy can be adapted to be administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural) and the like. It will be appreciated that the preferred route may vary with, for example, the condition of the recipient.

A synergistic effect may be attained when the active ingredients are: (1) co-formulated (e.g. in a unitary dosage form) and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Co-administration of a Combination Compound with one or more Combination Compounds generally refers to simultaneous or sequential administration of one or more Combination Compounds, such that therapeutically effective amounts of two or more Combination Compounds are present in the body of the patient. In some cases, Combination Compounds (e.g. two, three or four Combinations Compounds) will be co-formulated to allow administration at the same time. In some cases, co-formulated Combination Compounds may be co-administered with one or more additional Combination Compounds.

Co-administration also includes administration of unit dosages of the Combination Compounds before or after administration of unit dosages of one or more other active ingredients, for example, administration of two or more Combination Compounds within seconds, minutes, or hours of the administration of one or more other active ingredients. For example, a unit dose of a Combination Compound can be administered first, followed within seconds or minutes by administration of a unit dose of a second Combination Compound, followed within seconds or minutes by administration of a unit dose of one or more other active ingredients. Alternatively, a unit dose of one or more other active ingredients can be administered first, followed within seconds or minutes by administration of a unit dose of a Combination Compound, followed within seconds or minutes by administration of a unit dose of a second Combination Compound. In some cases, it may be desirable to administer a unit dose of a Combination Compound first, followed, after a period of hours (e.g., 1-12 hours), by administration of a unit dose of a second Combination Compound, followed, after a period of hours (e.g., 1-12 hours), by administration of a unit dose of one or more other active ingredients. In other cases, it may be desirable to administer a unit dose of one or more other active ingredients first, followed, after a period of hours (e.g., 1-12 hours), by administration of a unit dose of a Combination Compound, followed, after a period of hours (e.g., 1-12 hours), by administration of a unit dose of a second Combination Compound. Where three or more Combinations Compounds are administered with one or more additional active ingredients, the Combination Compounds may be administered one after another within seconds, minutes, or hours (e.g. 1-12 hours) of each other and the one or more additional active ingredients may be administered before, during or after the administration of the Combination Compounds. Where Combination Compounds are co-formulated, they can be administered simultaneously, or before or after the administration of one or more additional active ingredients.

Unless otherwise specified, the combination therapy may be administered as separate dosage forms with each active ingredient, administered together or separately, sequentially or concurrently, and close in time or remote in time to each other.

The course of treatment can extend, for example, from about 12 weeks to about 48 weeks, or longer, for example, from about 12 weeks to about 24 weeks.

The present invention includes a combination of therapeutically effective components to ameliorate at least one symptom of HCV infection in a human being including, but not limited to, nausea, vomiting, loss of appetite, fatigue, jaundice, vomiting, diarrhea, dehydration, abdominal pain, cirrhosis of the liver. In addition, in some HCV infected individuals the use of combination therapy is effective to reduce the viral load of HCV viral particles present in the body of the infected person by a statistically significant amount. Viral load can be measured, for example, by measuring plasma HCV RNA levels using, for example, the COBAS TaqMan HCV assay (Roche Molecular Systems). Typically, an HCV infected person who is treated with the Combination Compounds in accordance with the present invention experiences an improvement in one or all of the symptoms associated with the HCV infection.

Combinations of Two or More of the Combination Compounds with Ribavirin but not Interferon As discussed above, some current HCV treatments include the administration of interferon, but this treatment typically produces unwanted side effects. Therefore it would be desirable to find effective HCV treatments that do not require the administration interferon.

One aspect of the present invention provides for compositions, methods, uses and the like for the treatment of HCV comprising administering two or more of the Combination Compounds or pharmaceutically acceptable salts thereof and ribavirin, without administering one or more interferons. This aspect of the invention may be particularly useful because it allows for the effective treatment of HCV without the side effects associated with the administration of one or more interferon.

In one embodiment of the present invention, the combined amount of ribavirin and Combination Compounds or pharmaceutically acceptable salts thereof, optionally with one or more additional agents, is effective to treat HCV infection.

Another aspect of the present invention includes a method for ameliorating one or more symptoms of HCV infection in a human comprising: administering two or more of the Combination Compounds or pharmaceutically acceptable salts thereof and ribavirin, without concurrent administration of one or more interferon. In this regard, the present invention does not foreclose the potential for dosing one or more interferon. Rather, the present invention may be used in conjunction with another therapy that, in fact, includes one or more interferon. An aspect of the present invention includes efficacious treatment of HCV with ribavirin without the need for one or more interferon.

Another aspect of the present invention includes a method for reducing viral load in a human diagnosed with HCV comprising: administering two or more of the Combination Compounds or pharmaceutically acceptable salts thereof and ribavirin, but not one or more interferon.

Another aspect of the present invention includes a method for treating HCV in a human subject consisting essentially of administration of ribavirin in conjunction with two or more of the Combination Compounds or pharmaceutically acceptable salts thereof.

Another aspect of the present invention includes a method for reducing emergence of HCV quasispecies with resistance to coadministered oral antiviral agents comprising: administering two or more of the Combination Compounds or pharmaceutically acceptable salts thereof and ribavirin, without concurrent administration of one or more interferon.

Similarly, another aspect of the present invention includes a composition, e.g. a pharmaceutical composition for ameliorating one or more symptom of HCV infection in a human comprising two or more of the Combination Compounds or pharmaceutically acceptable salts thereof and ribavirin, without one or more interferon. Another aspect of the present invention includes a composition for reducing viral load in a human diagnosed with HCV comprising two or more of the Combination Compounds or pharmaceutically acceptable salts thereof and ribavirin, but not one or more interferon. Another aspect of the present invention includes a composition for treating HCV in a human subject consisting essentially of ribavirin in conjunction with two or more of the Combination Compounds or pharmaceutically acceptable salts thereof. Another aspect of the present invention includes a composition for ribavirin-based HCV therapy comprising two or more of the Combination Compounds or pharmaceutically acceptable salts thereof, with the proviso that said composition does not include one or more interferon. Another aspect of the present invention includes a composition for reducing emergence of HCV quasispecies with resistance to coadministered oral antiviral agents comprising two or more of the Combination Compounds or pharmaceutically acceptable salts thereof and ribavirin, without one or more interferon.

Similarly, another aspect of the present invention includes use of: two or more of the Combination Compounds or pharmaceutically acceptable salts thereof and ribavirin, without one or more interferon, in the manufacture of a medicament for ameliorating one or more symptoms of HCV infection in a human; as well as use of: two or more of the Combination Compounds or pharmaceutically acceptable salts thereof and ribavirin, but not one or more interferon, in the manufacture of medicament for reducing viral load in a human diagnosed with HCV; as well as use of ribavirin in conjunction with two or more of the Combination Compounds or pharmaceutically acceptable salts thereof in the manufacture of a medicament for treating HCV in a human subject, wherein said use does not include use of one or more interferon; as well as use of two or more of the Combination Compounds or pharmaceutically acceptable salts thereof, in the manufacture of a medicament for ribavirin-based HCV therapy, wherein said use avoids administration of one or more interferon; as well as use of two or more of the Combination Compounds or pharmaceutically acceptable salts thereof and ribavirin, without one or more interferon in the manufacture of a medicament for reducing emergence of HCV quasispecies with resistance to coadministered oral antiviral agents.

Another aspect of the present invention includes a combination comprising ribavirin and two or more of the Combination Compounds or pharmaceutically acceptable salts thereof, which combination is substantially free of one or more interferon. In one embodiment, the combination may occur as separate dosage forms with each active ingredient, administered together or separate, sequentially or concurrently, and close in time or remote in time to each other.

Another aspect of the present invention includes a kit comprising: ribavirin, two or more of the Combination Compounds and instruction regarding a treatment regimen to treat, reduce viral load, or delay onset or progression of HCV wherein the treatment regimen includes administration of the two or more of the Combination Compounds and ribavirin without administration of one or more interferon. In one embodiment, such a kit may also include packaging, such as a blister pack. Alternatively, such a kit may provide for individual prescription and dosing of each component as separately packaged pharmaceutics, but when combined with the instruction regarding a treatment regimen to treat, reduce viral load, or delay onset or progression of HCV, such is intended to be within the scope of the present invention.

Another aspect of the present invention includes a pharmaceutical composition comprising: ribavirin; two or more of the Combination Compounds or pharmaceutically acceptable salts thereof and one or more pharmaceutically acceptable carriers. In one embodiment, the pharmaceutical composition may be a unitary dosage form.

Unless otherwise specified, the combination therapy with Ribavirin may be administered as separate dosage forms with each active ingredient administered (including the Combination Compounds), may be administered together (e.g., in the form of a unit dosage, such as a tablet) or separately, sequentially or concurrently, and close in time or remote in time to each other. If administered separately, each compound may be administered with the other(s) at the same time, or either before or after such administration of the other(s). The active ingredients can be administered daily. In one embodiment, a daily dosage of the active ingredients is administered in separate sub-doses, such as one, two, three or four times per day. Advantageously, the daily dosage of Combination Compounds or pharmaceutically acceptable salts thereof and ribavirin may be administered once per day.

Although the present invention includes compositions, methods, uses and the like for the treatment of HCV comprising administering two or more Combination Compounds or a pharmaceutically acceptable salt thereof; and ribavirin, but not one or more interferon, the present invention does not foreclose the potential for dosing one or more interferon to the human. Rather, the present invention may be used in conjunction with another therapy for another indication that, in fact, includes one or more interferon.

Combinations of Two or More of the Combination Compounds with Ribavirin and Interferon Another aspect of the present invention provides for compositions, methods, uses and the like comprising administering two or more of the Combination Compounds or pharmaceutically acceptable salts thereof and ribavirin, and one or more interferon for treatment of HCV. The administration of more interferon may be in temporal relation to the administration of the Combination Compounds and ribavirin.

Another aspect of the present invention includes a method for ameliorating one or more symptoms of HCV infection in a human comprising administering two or more of the Combination Compounds or pharmaceutically acceptable salts thereof, ribavirin, and one or more interferons. Another aspect of the present invention includes a method for reducing viral load in a human diagnosed with HCV comprising: administering two or more of the Combination Compounds or pharmaceutically acceptable salts thereof along with ribavirin and one or more interferons.

Another aspect of the present invention includes a method of ribavirin-based HCV therapy comprising administering two or more of the Combination Compounds or pharmaceutically acceptable salts thereof along with ribavirin, and one or more interferons.

Another aspect of the present invention includes a method for reducing emergence of HCV quasispecies with resistance to coadministered oral antiviral agents comprising: administering two or more of the Combination Compounds or pharmaceutically acceptable salts thereof along with ribavirin and one or more interferons.

Another aspect of the present invention includes use of two or more of the Combination Compounds or pharmaceutically acceptable salts thereof ribavirin, and one or more interferons, in the manufacture of a medicament for ameliorating one or more symptoms of HCV infection in a human. Another aspect of the present invention includes use of two or more of the Combination Compounds or pharmaceutically acceptable salts thereof along with ribavirin and one or more interferons, in the manufacture of medicament for reducing viral load in a human diagnosed with HCV. Another aspect of the present invention includes use of ribavirin in conjunction with two or more of the Combination Compounds or pharmaceutically acceptable salts thereof in the manufacture of a medicament for treating HCV in a human subject, wherein said use includes use of one or more interferons. Another aspect of the present invention includes use of two or more of the Combination Compounds or pharmaceutically acceptable salts thereof, in the manufacture of a medicament for ribavirin-based HCV therapy, wherein said use includes administration of one or more interferon. Another aspect of the present invention includes use of two or more of the Combination Compounds or pharmaceutically acceptable salts thereof, ribavirin, and one or more interferons in the manufacture of a medicament for reducing emergence of HCV quasispecies with resistance to coadministered oral antiviral agents.

Another aspect of the present invention includes a combination comprising ribavirin and two or more of the Combination Compounds or pharmaceutically acceptable salts thereof, which combination includes one or more interferons.

Another aspect of the present invention includes a kit comprising: ribavirin, two or more of the Combination Compounds and one or more interferon; and instructions regarding a treatment regimen to treat, reduce viral load, or delay onset or progression of HCV wherein the treatment regimen includes administration of the two or more of the Combination Compounds and ribavirin and administration of one or more interferon. In one embodiment, such a kit may also include packaging, such as a blister pack. Alternatively, such a kit may provide for individual prescription and dosing of each component as separately packaged pharmaceutics, but when combined with the instruction regarding a treatment regimen to treat, reduce viral load, or delay onset or progression of HCV, such is intended to be within the scope of the present invention.

Another aspect of the present invention includes a pharmaceutical composition comprising: two or more of the Combination Compounds or pharmaceutically acceptable salts thereof, ribavirin, and one or more interferon; and one or more pharmaceutically acceptable carriers. In one embodiment, the pharmaceutical composition may be a unitary dosage form.

Unless otherwise specified, the combination therapy with Ribavirin and one or more interferons may be administered as separate dosage forms with the one or more interferons administered to the patient and each of the remaining active ingredients to be employed in the combination therapy (including the Combination Compounds) are administered together (e.g., in the form of a unit dosage, such as a tablet) or separately, sequentially or concurrently, and close in time or remote in time to each other. If administered separately, each active ingredient may be administered with the other(s) at the same time, or either before or after such administration of the other(s). The active ingredients can be administered daily. In one embodiment, a daily dosage is administered in separate sub-doses, such as one, two, three or four times per day.

Combination Therapy, Including Additional Therapeutics

In another embodiment, non-limiting examples of suitable combinations include the combinations of two or more of Compound 1, Compound 2, Compound 3, Compound 4, Compound 5, Compound 6, Compound 7, Compound 9, Compound 10, Compound 11, Compound 12, Compound 13, Compound 14, Compound 15 and Compound 16 with one or more additional active ingredients including HCV NS3 protease inhibitors, alpha-glucosidase 1 inhibitors, hepatopro tectants, nucleoside or nucleotide inhibitors of HCV NS5B polymerase, non-nucleoside inhibitors of HCV NS5B polymerase, HCV NS5A inhibitors, TLR-7 agonists, cyclophilin inhibitors, HCV IRES inhibitors, HCV entry inhibitors, HCV maturation inhibitors, HCV assembly inhibitors, HCV infectivity inhibitors and pharmacokinetic enhancers, as well as other drugs for treating HCV. More specifically, one or more compounds of the present invention may be combined with one or more compounds selected from the group consisting of:

(i) HCV NS3 protease inhibitors, e.g., boceprevir (SCH-503034, SCH-7), telaprevir (VX-950), TMC-435 (IUPAC N-[(2R,3aR,10Z,11aS,12aR,14aR)-2-[2-(4-Isopropylthiazol-2-yl)-7-methoxy-8-methylquinolin-4-yloxy]-5-methyl-4,14-dioxo-1,2,3,3a,4,5,6,7,8,9,11a,12,12a,13,14,14a-hexadecahydrocyclopenta[c]cyclopropa[g][1,6]diazacyclotetradecin-12a-ylcarbonyl]cyclopropanesulfonamide], ABT-450, ACH-1625, ACH-2684, BI-201335, BI-1230, MK-5172, MK-7009, SCH-900518, VBY-376, VX-500, GS-9256, GS-9451, BMS-605339, PHX-1766, AS-101, YH-5258, YH-5530, YH-5531, and ITMN-191 (R-7227);

(ii) alpha-glucosidase 1 inhibitors, e.g., celgosivir (MX-3253), UT-231B, Miglitol;

(iii) hepatoprotectants, e.g., emericasan (IDN-6556), ME-3738, silibilin, and MitoQ;

(iv) nucleoside or nucleotide inhibitors of HCV NS5B polymerase, e.g., R1626, R7128 (R4048), IDX184, IDX-102, PSI-661, PSI-938, PSI-7851, PSI-7977, BCX-4678, valopicitabine (NM-283), MK-0608 and TMC649128;

(v) non-nucleoside inhibitors of HCV NS5B polymerase, e.g., filibuvir (PF-868554), ABT-333, ABT-072, BI-207127, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, and XTL-2125;

(vi) HCV NS5A inhibitors, e.g., ACH-2928, AZD-2836 (A-831), AZD-7295 (A-689), BMS-766, BMS-790052, BMS-824393, and PPI-461;

(vii) TLR-7 agonists, e.g., imiquimod, 852A, ANA-773, ANA-975, AZD-8848 (DSP-3025), PF-04878691, and SM-360320 and Compound 8;

(viii) cyclophilin inhibitors, e.g., DEBIO-025, SCY-635, and NIM811;

(ix) HCV IRES inhibitors, e.g., MCI-067;

(x) pharmacokinetic enhancers, e.g. roxythromycin, BAS-100, SPI-452, PF-4194477, TMC-41629;

(xi) HCV entry inhibitors (xii) HCV assembly inhibitors;

(xiii) HCV maturation inhibitors;

(xiv) HCV infectivity inhibitors; and (xv) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib).

SYNTHETIC EXAMPLES

Synthetic protocols for the preparation of Compounds 1, 2, 3, 6, 7, and 8 are known in the literature. Additionally, a synthetic protocol for preparing each of the Combination Compounds is provided in the Examples below.

Compound 1 can be prepared using synthetic methods and intermediates like those described in U.S. Pat. No. 7,754,720. Compound 1 can also be prepared as described in the following Example.

Example 1

5-({6-[2,4-bis(trifluoromethyl)phenyl]pyridazin-3-yl}methyl)-2-(2-fluorophenyl)-5H-imidazo[4,5-c]pyridine 1

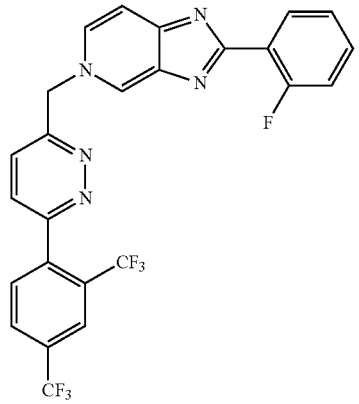 [SMILES: Fc1ccccc1-c1nc2ccn(Cc3ccc(-c4ccc(C(F)(F)F)cc4C(F)(F)F)nn3)cc-2n1]

| Compound | MW | Amount | Moles | Equivalents |
|---|---|---|---|---|
| 104 | 453.79 | 95 mg | 0.209 | 1 |
| DME | | 500 µL | | |
| 2N aq. Na$_2$CO$_3$ | | 313 µL | 0.626 | 3 |
| 105 | 257.93 | 80.9 mg | 0.313 | 1.5 |
| Pd(PPh$_3$)$_4$ | 1155 | 12 mg | 0.0104 | 0.05 |

Compound 103 was dissolved in dimethoxyethane (DME). To this solution was added 2,4-bis(trifluromethyl)phenylboronic acid 105 and a 2N aq. Na$_2$CO$_3$ solution. To the resulting biphasic mixture was added Pd(PPh$_3$)$_4$ and the reaction was then heated at 80° C. for 72 hrs. The reaction was cooled to room temperature and filtered through Celite and the Celite washed with EtOAc. The filtrate was concentrated in vacuo. The residue was purified on 6 g SiO$_2$ using MeOH/CH$_2$Cl$_2$ to elute compound. The compound thus obtained was contaminated with PPh$_3$(O). The product was repurified on a 1 mm Chromatotron plate with 0 to 5% MeOH/CH$_2$Cl$_2$ in 1% steps. The pure fractions were combined and concentrated in vacuo, then dried on high vacuum for 12 hrs. 11.8 mg of the free base of compound 1 was obtained with no PPh$_3$ contamination. $^1$H NMR (300 MHz, CD$_3$OD) δ 6.20 (s, 2), 7.32 (m, 3), 7.52 (m, 1), 7.78 (d, 1), 7.89 (d, 1), 7.95 (s, 2), 8.15 (m, 3), 8.35 (d, 1), 9.12 (s, 1); LC/MS M+H=518.

The intermediate compound 104 was prepared as follows.

a. Preparation of Compound 102

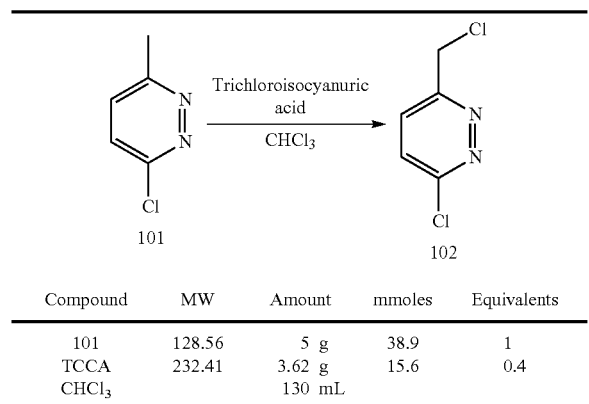

| Compound | MW | Amount | mmoles | Equivalents |
|---|---|---|---|---|
| 101 | 128.56 | 5 g | 38.9 | 1 |
| TCCA | 232.41 | 3.62 g | 15.6 | 0.4 |
| CHCl₃ | | 130 mL | | |

To a solution of the commercially available starting material 101 in CHCl₃, trichloroisocyanuric acid (TCCA) was added at 60° C. Then the solution was stirred for 1.5 hrs, cooled, and filtered with HiFlo-Celite. The filtrate was concentrated and dried with vacuum. The yield was 5.037 g of compound 102.

b. Preparation of Compound 104

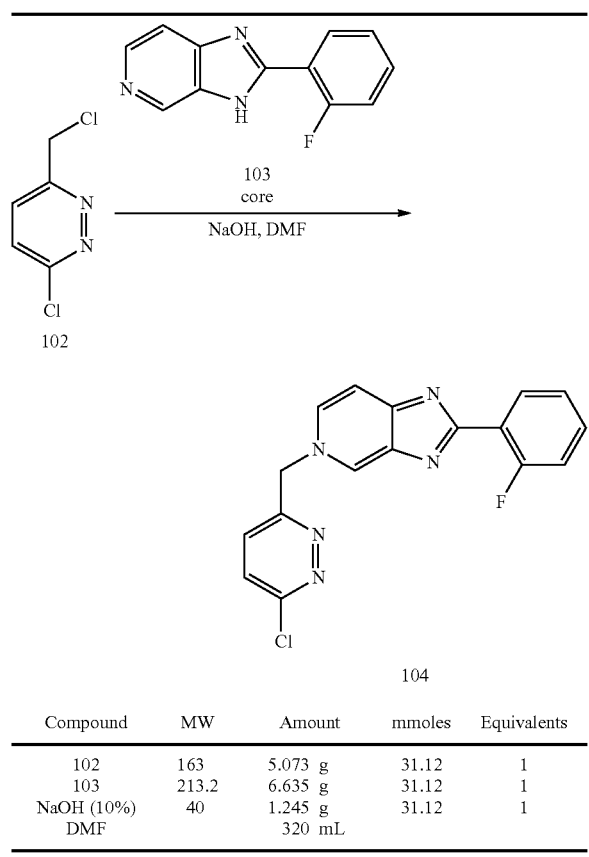

| Compound | MW | Amount | mmoles | Equivalents |
|---|---|---|---|---|
| 102 | 163 | 5.073 g | 31.12 | 1 |
| 103 | 213.2 | 6.635 g | 31.12 | 1 |
| NaOH (10%) | 40 | 1.245 g | 31.12 | 1 |
| DMF | | 320 mL | | |

To a solution of compound 103 in DMF (dimethylformamide), NaOH was added. Compound 102 was dissolved in DMF (20 mL) and added to the solution slowly. The reaction was stirred for 3 hrs, was diluted with water and extracted with EtOAc. The organic layer was dried with Na₂SO₄. The solvent was removed and the product recrystallized with dichloromethane. The yield was 5.7 g of compound 103.

Compound 2 can be prepared using synthetic methods and intermediates like those described in U.S. Ser. No. 12/202, 319 (US 20100051763 A1). Compound 2 can also be prepared as described in the following Example.

Example 2

Preparation of Compound 2

206 ⟶

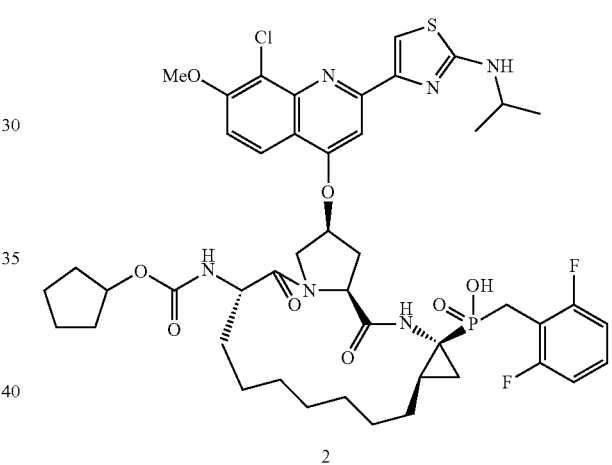

Phosphinate ester 206 (23.7 g, 24.05 mmol) was dissolved in CH₃CN (240 mL) and cooled to 0° C. Iodotrimethylsilane (17.4 mL, 122.3 mmol) was added at a fast drop-wise pace followed by, after 10 min, 2,6-lutidine (17.0 mL, 146.4 mmol). The reaction mixture was slowly warmed to room temperature and stirred for 1 h then cooled back down to 0° C. and 2,6-lutidine (11.1 mL, 95.6 mmol) followed by MeOH (24 mL) were added. The solution was concentrated in vacuo and the crude residue was purified by HPLC to afford 12.68 g of Compound 2 in 55% yield. $^1$H NMR (300 MHz, CDCl₃) δ 8.35 (d, J=9.3 Hz, 1H), 8.28 (s, 1H), 7.85 (s, 1H), 7.64 (d, J=9.6 Hz, 1H), 7.35-7.22 (m, 1H), 7.02-6.89 (m, 2H), 5.85 (bs, 1H), 4.82-4.71 (m, 2H), 4.33 (bs, 1H), 4.28-3.99 (m, 3H), 4.16 (s, 3H), 3.57-3.28 (m, 2H), 2.90-2.78 m, 1H), 2.63-2.50 (m, 1H), 2.08-1.91 (m, 1H), 1.91-170 (m, 2H), 1.70-1.13 (m, 22H), 1.37 (d, J=6.9 Hz, 6H); 31P NMR (121.4 MHz, CD₃OD) δ 42.4; LCMS (M+1): 957.35. g.

Intermediate compound 206 was prepared as follows.

a. Preparation of Compound 203

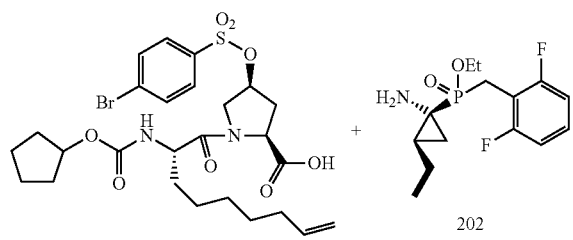

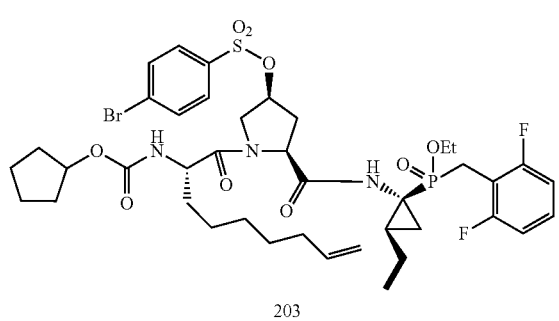

Compound 201 (17.42 g, 28.30 mmol) was dissolved in THF (136 mL) and cooled to 0° C. To the solution was added N-methylmorpholine (4.7 mL, 42.7 mmol). After 10 min at 0° C., i-butylchloroformate (4.05 mL, 30.96 mmol) was added dropwise. After an additional 1 h, (1-amino-2-vinyl-cyclopropyl)-(2,6-difluoro-benzyl)-phosphinic acid ethyl ester 202 (8.94 g, 29.70 mmol) was slowly added as a solution in THF (20 mL). The suspension was warmed to room temperature and after 2 h it was partitioned between $H_2O$ (400 mL) and ethylacetate (200 mL). The aqueous layer was extracted with ethylacetate (200 mL×2) and the combined organic layers were washed with HCl (1N, 225 mL) and $H_2O$ (200 mL). The acid wash and aqueous wash were combined and back-extracted with ethylacetate (175 mL×2, 100 mL×2). The combined organic layers were washed with brine (400 mL), dried over Na2SO4, and concentrated in vacuo providing 25.06 g of diene 203 in 98.5% crude yield. LCMS (M+1): 898.06.

b. Preparation of Compound 204

203 ⟶

-continued

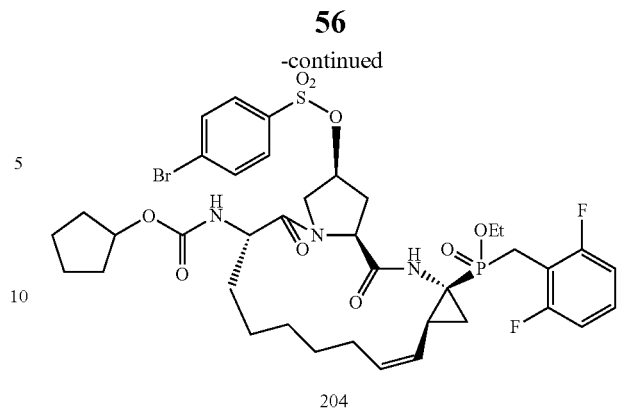

Compound 203 (12.91 g, 14.36 mmol) was dissolved in $CH_2Cl_2$ (1440 mL) and the solution was degassed for 30 minutes. The solution was heated to 40° C. and Grubb's G1 catalyst (2.95 g, 3.59 mmol) was added. The reaction was refluxed for 17 h whereupon tris-hydroxymethylphosphine (22.3 g, 18.0 mmol), TEA (50 mL, 35.9 mmol), and $H_2O$ (400 mL) were added and the reaction mixture was heated to reflux for an additional 16 hours. The reaction mixture was cooled to room temperature and the two layers were separated. The organic layer was washed with $H_2O$ (400 mL) and brine (300 mL), dried over MgSO4, and concentrated. The crude residue was purified by silica-gel chromatography to afford 8.30 g of macrocyclic olefin 204 in 66% yield. LCMS (M+1): 870.09.

c. Preparation of Compound 205

204 ⟶

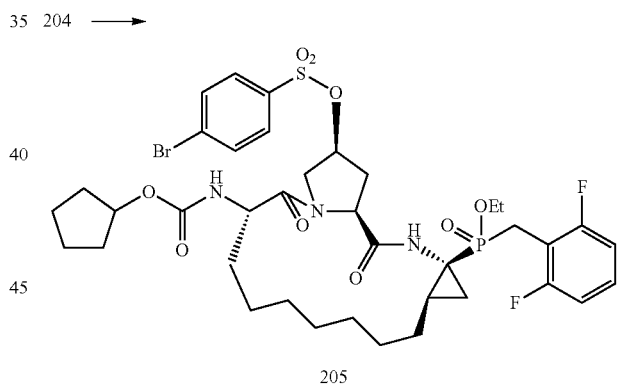

The macrocyclic olefin 204 (7.34 g, 8.42 mmol) was dissolved in ethylacetate (105 mL) and rhodium on alumina (5% wt, 2.945 g, 0.40 wt %) was added. The system was evacuated and flushed with $H_2$ (1 atm, 3×). To the system, after 3 h, was added more rhodium on alumina (5% wt, 842 mg, 0.10 wt %) and evacuated and flushed with $H_2$ (1 atm, 3×). After an additional 1 h the suspension was filtered and concentrated in vacuo providing 6.49 g of reduced macrocycle 205 in 88% crude yield. LCMS (M+1): 872.04.

d. Preparation of Compound 206

205 ⟶

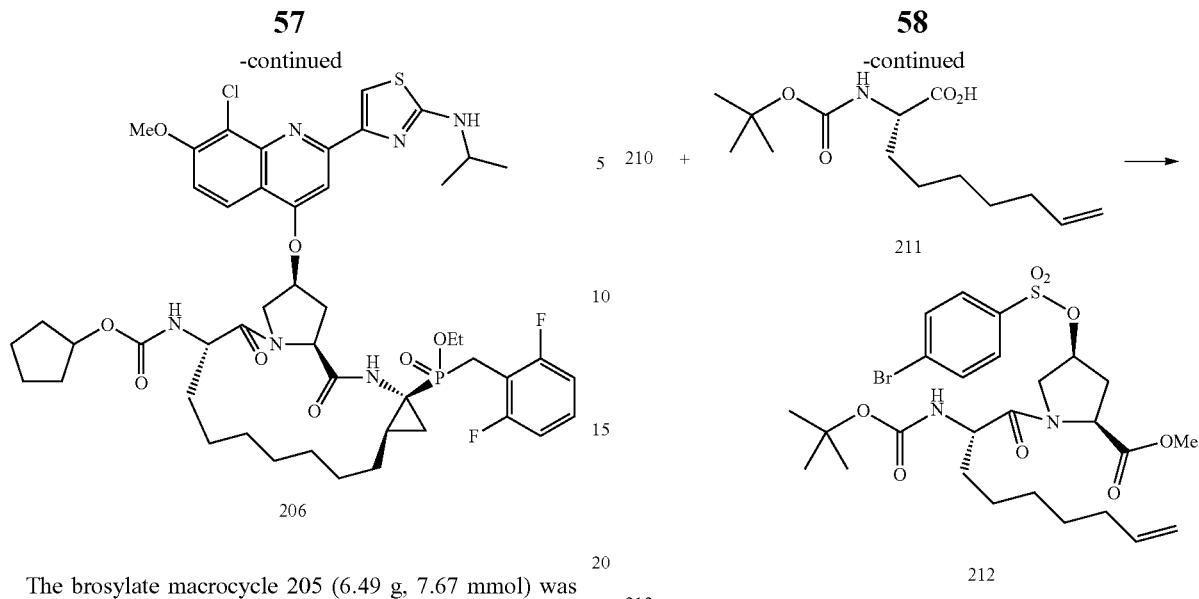

The brosylate macrocycle 205 (6.49 g, 7.67 mmol) was dissolved in N-methylpyrrolidinone (25.0 mL) and 8-chloro-2-(2-isopropylamino-thiazol-4-yl)-7-methoxy-quinolin-4-ol 207 (2.564 g, 7.33 mmol) followed by $Cs_2CO_3$ (4.40 g, 13.50 mmol) were added. The mixture was heated to 65° C. for 6 h then diluted with ethylacetate (200 mL) and washed with LiCl (5%, 250 mL). The aqueous layer was extracted with ethylacetate (100 mL×2) and the combined organic layers were washed with brine (150 mL), dried over $Na_2SO_4/MgSO_4$, and concentrated in vacuo. The crude residue was purified via silica-gel chromatography (ethylacetate-methanol) affording 4.39 g of aminothiazole 206 in 58% yield. LCMS (M+1): 985.28.

Intermediate Compound 201 can be prepared as follows.

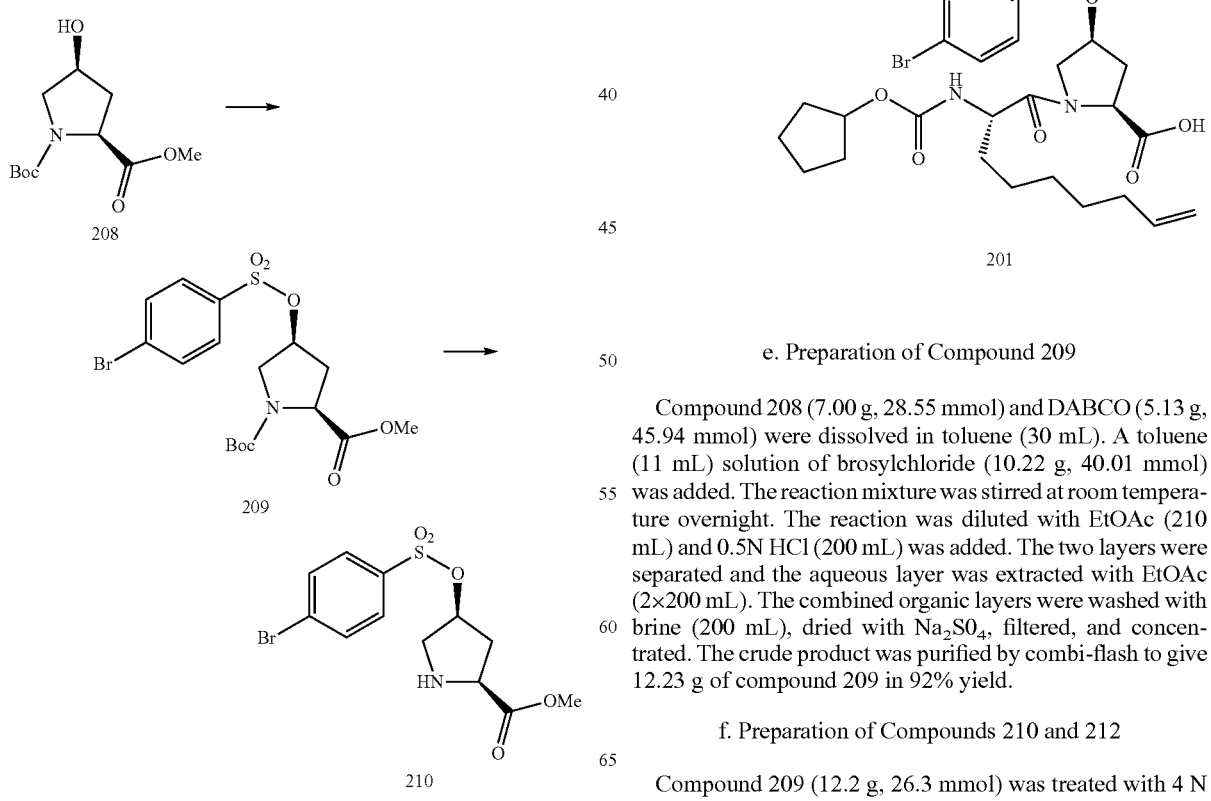

e. Preparation of Compound 209

Compound 208 (7.00 g, 28.55 mmol) and DABCO (5.13 g, 45.94 mmol) were dissolved in toluene (30 mL). A toluene (11 mL) solution of brosylchloride (10.22 g, 40.01 mmol) was added. The reaction mixture was stirred at room temperature overnight. The reaction was diluted with EtOAc (210 mL) and 0.5N HCl (200 mL) was added. The two layers were separated and the aqueous layer was extracted with EtOAc (2×200 mL). The combined organic layers were washed with brine (200 mL), dried with $Na_2SO_4$, filtered, and concentrated. The crude product was purified by combi-flash to give 12.23 g of compound 209 in 92% yield.

f. Preparation of Compounds 210 and 212

Compound 209 (12.2 g, 26.3 mmol) was treated with 4 N HCl/1,4-dioxane (60 mL) and stirred for 1 hour. The reaction mixture was concentrated and dried under vacuum for 20 minutes. The crude amine HCl salt of compound 210 was dissolved in DMF (150 mL) and acid 211 (14.2 g, 52.6 mmol) was added. HATU (20.0 g, 52.6 mmol) and NMM (13.5 g, 131.5 mmol) were added. The reaction mixture was stirred at room temperature overnight. The reaction was diluted with EtOAc (300 mL), washed with 1 N HCl (200 mL), saturated NaHCO₃, brine, dried with Na₂SO₄, and concentrated. The crude product was purified by combi-flash to give 15.1 g of compound 212 in 93% yield.

g. Preparation of Compound 213

To a solution of 212 (12.8 g, 20.7 mmol) in CH₂Cl₂ (50 mL) was added 4 N HCl in 1,4-dioxane (50 mL, 200 mmol). The reaction mixture was stirred at room temperature for 2 hours, concentrated, dried under vacuum for 20 minutes, and then dissolved in CH₃CN (50 mL). Saturated NaHCO₃ in H₂0 (50 mL) was added and stirred for 5 minutes. Freshly prepared cyclopentyichloroformate in THF (50 mL) was added. The reaction was complete within 1 h. The solvent was removed under reduced pressure and the residue was diluted with EtOAc. The mixture was brought to pH=2 with 1 N HCl and the two layers were separated. The organic layers were washed with brine, dried with Na₂SO₄, filtered, and concentrated to give crude compound 213 (3.18 g).

h. Preparation of Compound 201

The crude ester 213 (3.18 g, 5.07 mmol) was dissolved in THF (25 mL), H₂O (25 mL), and then MeOH (6 mL) and LiOH (660 mg, 25.4 mmol) was added. The reaction mixture was stirred at room temperature for 1 h and diluted with EtOAc. The reaction mixture was acidified to pH 2 with 1 N HCl and the two layers were separated. The aqueous layer was extracted with EtOAc (2×). The combined organic layers were washed with brine, dried with Na₂SO₄ concentrated and dried under vacuum to give 3.09 g of acid 201.

Intermediate 8-chloro-2-(2-isopropylamino-thiazol-4-yl)-7-methoxy-quinolin-4-ol 207 can be prepared as follows.

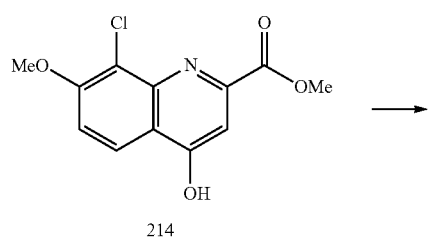

214

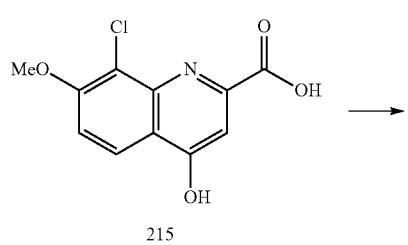

215

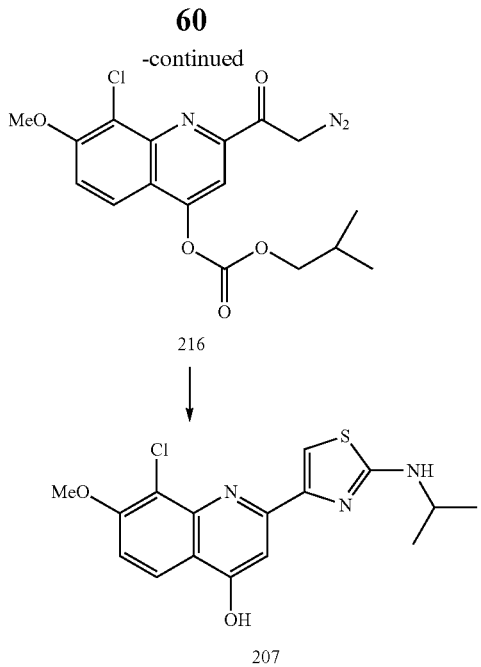

216

↓

207 i. Preparation of 8-chloro-4-hydroxy-7-methoxyquinoline-2-carboxylic acid 215

To a solution of methyl 8-chloro-4-hydroxy-7-methoxyquinoline-2-carboxylate 214 (36.5 g, 0.145 mol) in a mixture of 1:1 of MeOH:THF (160 mL total) was added a solution of LiOH (30.5 g, 0.725 mol) in H₂0 (80 mL). The mixture was stirred at room temperature for an hour when LCMS analysis showed complete conversion to the carboxylic acid. The reaction was worked up by removal of the volatiles and adjusting the pH of the solution to 6 using aqueous 6N HCl. The resulted gummy residue was filtered and dried on the lyophilizer for 2 days to provide 34.4 g (99.6%) of compound 215 as a white solid. EI MS (m/z) 253.9 [M+H].

j. Preparation of 2-(2-diazo-1-oxo)-8-chloro-7-methoxyquinolin-4-yl isobutyl carbonate 216

To a solution of 8-chloro-4-hydroxy-7-methoxyquinoline-2-carboxylic acid 215 (10.2 g, 0.04 mol) in THF (400 mL) was added triethyl amine (12.3 mL, 0.088 mol) and i-Butylchloroformate (11.6 mL, 0.088 mol) at 0° C. under an argon atmosphere. The mixture was stirred at 0° C. for 1 hour when LCMS analysis demonstrated completion of the reaction to provide the desired mixed anhydride. EI MS (m/z) 454.0 [M+H]. To the reaction mixture of the anhydride was added a 1M solution of diazomethane (121 mL, 0.121 mol) in diethyl ether via a plastic funnel at 0° C. This mixture was allowed to stir while warming up to room temperature for additional 2 hours. Analysis of the mixture by LCMS demonstrated completion of the reaction. The septum was removed and the reaction was stirred for additional 20 minutes before removal of the solvent. The residue was dried further under high vacuum to provide compound 216, which was carried on to the next step. EI MS (m/z) 377.9 [M+H].

k. Preparation of 8-chloro-2-(2-(isopropylamino) thiazol-4-yl)-7-methoxyquinoiin-4-ol 207

To a cooled solution of 2-(2-diazo-1-oxo)-8-chloro-7-methoxyquinolin-4-yl isobutyl carbonate 216 (15.2 g, 0.040 mol) at 0° C. in THF (268 mL) was added 48% HBr (23 mL, 0.201 mol) slowly over 15 minutes. The solution was stirred at 0° C. for an additional 40 minutes when LCMS analysis demonstrated complete reaction. The reaction was worked up by addition of aqueous 1N NaOH (180 mL) at 0° C. to adjust the pH of the aqueous layer to 9. The layers were separated and the aqueous layer was washed with EtOAc (2×200 mL). Combined organic extracts were washed with brine and dried over MgSO4. The solvent was removed in vacuo to provide 17.7 g of a yellow solid. EI MS (m/z) $4^{31}$.9 [M+H].

The solution of the bromoketone obtained from the previous reaction was suspended in i-propanol (270 mL) and isopropylisourea (9.4 g, 0.080 mol). The reaction mixture was heated at 72° C. for 32 hours. LCMS analysis of the reaction demonstrated complete conversion to the desired product. The reaction was allowed to cool to room temperature to allow for the product to precipitate out of the solution. The reaction was further cooled to 0° C. for 12 hours before filtration. The filtrate was washed with ether and dried on lyopholizer to provide 8.03 g of compound 207 as an orange solid. $^1$H NMR (500 MHz, CDCl$_3$): δ 8.21 (d, J=9 Hz, 1H), 7.74 (s, 1H), 7.44 (d, J=10 Hz), 1H), 7.07 (s, 1H), 4.05 (s, 3H), 3.92 (pentet, J=6 Hz, 1H), 1.25 (d, J=7 Hz, 6H): EI MS (m/z) 350.0 [M+H].

Compound 3 can be prepared using synthetic methods and intermediates like those described in U.S. Ser. No. 12/215,605 (US 20090257978 A1). Compound 3 can also be prepared as described in the following Example.

Example 3

Preparation of compound 3

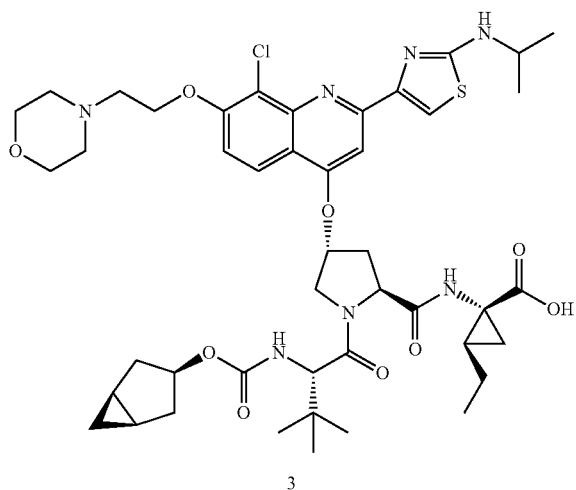

3

Compound 315 (12 g, 13 mmol) was dissolved in THF (200 ml), LiOH (11 g, 260 mmol) in H$_2$O (200 ml) was added, followed by MeOH (200 ml). The mixture was kept stirring at room temperature for 20 hours. Upon completion of the reaction, 4 N HCl in H$_2$O was added to adjust pH to 7 at 0° C. The mixture was extracted with EtOAc (2×400 ml). The combined organic layer was washed with brine, dried (Na$_2$SO$_4$) and concentrated in vacuo to give compound 3 as a yellow solid (11 g, 93%). LC/MS=911.52 (M$^+$+1). $^1$H NMR (300 MHz, CD$_3$OD) δ 7.95 (d, 1H), 7.90 (s, 1H), 7.48 (s, 1H), 7.31 (d, 1H), 5.42 (s, 1H), 4.37 (dd, 1H), 4.20 (m, 2H), 3.83-3.56 (m, 7H), 3.50 (m, 2H), 3.39 (m, 2H), 2.45 (m, 1H), 2.27 (m, 1H), 1.62 (m, 2H), 1.50 (m, 1H), 1.33 (m, 2H), 1.18 (m, 1H), 1.05 (m, 8H), 0.90 (m, 3H), 0.76 (m, 11H), 0.14-0.04 (m, 2H)

The intermediate compound 315 was prepared as follows.

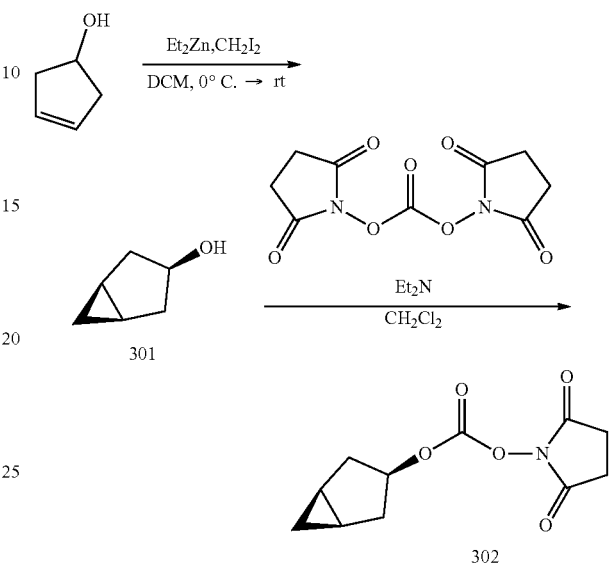

a. Preparation of Compound 301

To a dry, argon purged three-neck round bottom flask (1000 mL) were added anhydrous dichloromethane (100 mL) and Et$_2$Zn (28 mL, 273 mmol) at 0° C. (CAUTION: Source of argon can not be from needle. Use appropriate glass adapter only. A second bubbler can also be attached to the flask to prevent excessive pressure build up.) Cyclopenten-3-ol (10.0 mL, 119 mmol) was then added dropwise (large quantity of ethane gas was produced) to the flask and the reaction mixture was allowed to stir until the evolution of gas had ceased. Diiodomethane (22 mL, 242 mmol) was then added dropwise over a period of 30 minutes. The reaction was allowed to warm to room temperature and continued to stir overnight under a positive flow of argon, at which point TLC analysis had indicated complete disappearance of the starting alcohol. The reaction was then diluted with CH$_2$Cl$_2$ and quenched with 2M HCl (white precipitate should be completely dissolved). The biphasic mixture was poured into a separatory funnel and the organic layer was collected. The solvent was removed under reduced pressure until 100 mL of material containing compound 301 remained.

b. Preparation of Compound 302

Anhydrous dichloromethane (525 mL) was added to the flask followed by the dropwise addition of triethylamine (34 mL, 245 mmol). The reaction continued to stir at room temperature under a positive flow of nitrogen at which point, disuccinimidylcarbonate (40.7 g, 159 mmol) was added to the flask portion wise. The reaction was allowed to stir until TLC analysis indicated complete disappearance of the starting material (2-3 days). Upon completion, the reaction mixture was quenched with 1M HCl (200 mL×2) and washed with H$_2$0 (200 mL×2). The desired material was extracted using CH$_2$Cl$_2$ and the combined organic layers were dried using anhydrous MgSO₄ and passed through a silica plug. The solvent was removed under reduced pressure and the crude material was purified using flash chromatography (R_f=0.33, 1:1 Hex/EtOAc) to provide compound 302 (22 g, 75%): ¹H NMR (300 MHz, CDCl₃): δ 5.24 (t, 1H), 3.82 (s, 4H), 2.24 (m, 2H), 2.03 (d, 2H), 1.38 (m, 2H), 0.48 (m, 1H), 0.40 (m, 1H).

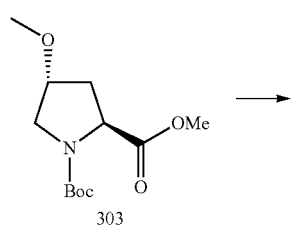

303

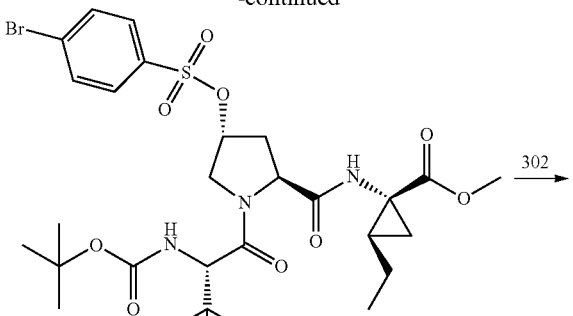

307

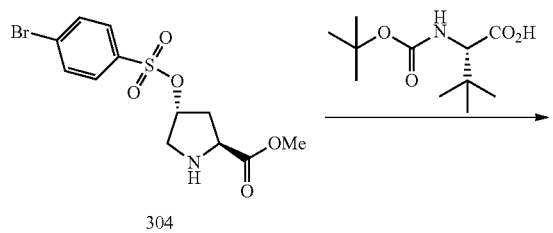

304

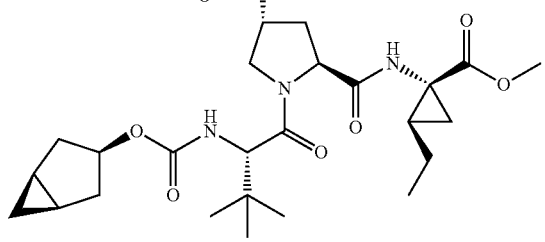

308

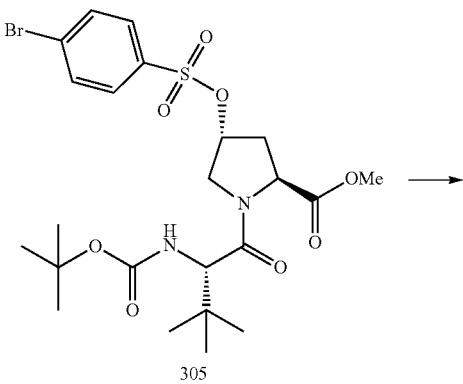

305 c. Preparation of Compound 304

N-t-Boc-cis-4-Hydroxy-L-Proline methyl ester 303 (100.0 g, 407.7 mmol) and DABCO (1.5 eq, 68.6 g, 611.6 mmol) were dissolved in anhydrous toluene (200 mL) in a 2 L three necked round bottom flask with a mechanical stirrer and an addition funnel. After cooling the solution to 0° C. under N₂, A solution of 4-Bromo-benzenesulfonyl chloride (1.3 eq, 135.6 g, 530.0 mmol) in 300 mL of toluene was added through addition funnel over 60 minutes. The reaction mixture was stirred and warmed to room temperature overnight (16 hours). The mixture was slowly poured into 2 L 1M Na₂CO₃ (aq.), and the product was extracted with EtOAc (2 L). After the organic phase was washed by 0.5 N HCl (2 L), H₂O (1 L), and brine (1 L), it was dried (MgSO₄), concentrated to give 195.45 g of a yellow oily brosylate product.

To a solution of the above brosylate (407.7 mmol) in dichloromethane (300 mL) was slowly added 4.0 M HCl in dioxane (500 mL, 5 eq) and the resulting solution was allowed to stir at room temperature for 2 hours. After ether (500 mL) was added to the reaction mixture, the mixture was stirred for 15 minutes and the white precipitate was collected by filtration. The solid was washed with ether and hexane and then dried under vacuum overnight to obtain 153.0 g of the HCl amine salt of compound 304, 381.8 mmol, in 94% yield for two steps.

d. Preparation of Compound 305

To a solution of Boc-tert-butyl-glycine (97.0 g, 420.0 mmol) in DMF (200 mL) and methylene chloride (200 mL) were added HATU (217.76 g, 572.7 mmol) and Hunig's base (126 mL, 1145.4 mmol) at room temperature. After the mixture was stirred for 20 minutes at room temperature, a solu-

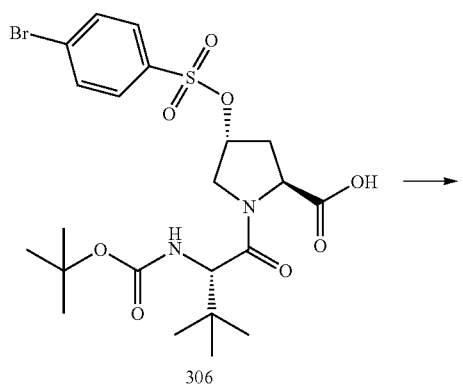

306 tion of the previous HCl salt (153.0 g, 381.8 mmol) and Hunig's base (126 mL, 1145.4 mmol) in DMF (200 mL) and dichloromethane (200 mL) was added to the above acid mixture in one portion. The reaction mixture was stirred at room temperature for 3 h, with monitoring by LCMS. The reaction mixture was concentrated to remove dichloromethane under reduced pressure and the white solid that formed was filtered off. The remaining DMF solution was diluted with ethyl acetate (1 L), washed successively with 3% LiCl (aq) (3×650 mL), sat'd NH₄Cl (2×500 mL), 0.5N HCl (aq) (2×600 mL), brine (500 mL), sat'd NaHCO₃ (3×500 mL), and brine (500 mL). The resulting organic fraction was dried (MgSO₄) and concentrated to afford compound 305 (111 g).

e. Preparation of Compound 306

To a solution of the methyl ester 305 (120 g, 207.8 mmol) in THF (300 mL), MeOH (75 mL) was added a solution of LiOH (26.18 g, 623.4 mmol) in H₂O (150 mL). The solution was allowed to stir at room temperature for 4 hours. The mixture was cooled in an ice-bath while acidifying with 3N HCl to pH about 5.5, stirred for 10 minutes, and the resulting white solids were collected by filtration. The solids were washed with more water, ether and hexane. The solids were dried under vacuum at 40° C. overnight to give 95.78 g (82%) of the acid 306.

f. Preparation of Compound 307

To a solution of the carboxylic acid 306 (81.4 g, 144.27 mmol) in DMF (200 mL) and dichloromethane (200 mL) was added HATU (82.3 g, 216.4 mmol) and Hunig's base (47.5 mL, 432.8 mmol) at room temperature. After the mixture was stirred for 20 minutes at room temperature, a solution of amine (158.7 mmol) and Hunig's base (47.5 mL, 1145.4 mmol) in DMF (200 mL) and dichloromethane (200 mL) was added to the above acid mixture in one portion. The reaction mixture was stirred at room temperature for 3 hours and monitored by LCMS. After the mixture was concentrated under reduced pressure to remove dichloromethane, the white solids that formed were filtered off. The remaining DMF solution was diluted with ethyl acetate (600 mL) and successively washed with 3% LiCl (aq) (2×550 mL), sat'd NH₄Cl (500 mL), 1N HCl (aq) (500 mL), sat'd NaHCO₃ (500 mL), and brine (300 mL). The resulting organic fraction was dried (Na₂SO₄) and concentrated to afford compound 307 (111 g).

g. Preparation of Compound 308

Compound 307 was dissolved in 4N HCl in dioxane (300 mL) at room temperature and stirred for 2 hours. It was then concentrated under vacuum, and co-evaporated with dichloromethane (2×200 mL) to dryness. The residue was dissolved in EtOAc (600 mL) and sat'd aq. NaHCO₃ (1 L). It was stirred vigorously. After 10 minutes, carbonic acid bicyclo[3.1.0] hex-3-yl ester 2,5-dioxo-pyrrolidin-1-yl ester 302 (41.4 g, 173.1 mmol) was added in one portion. After the resulting mixture was stirred for another 30 minutes, the organic layer was collected and washed with brine (500 mL), dried (Na₂SO₄), and concentrated. The crude product was purified by flash chromatography on silica gel with ethyl acetate/hexane to afford 94.44 g (92%) of compound 308.

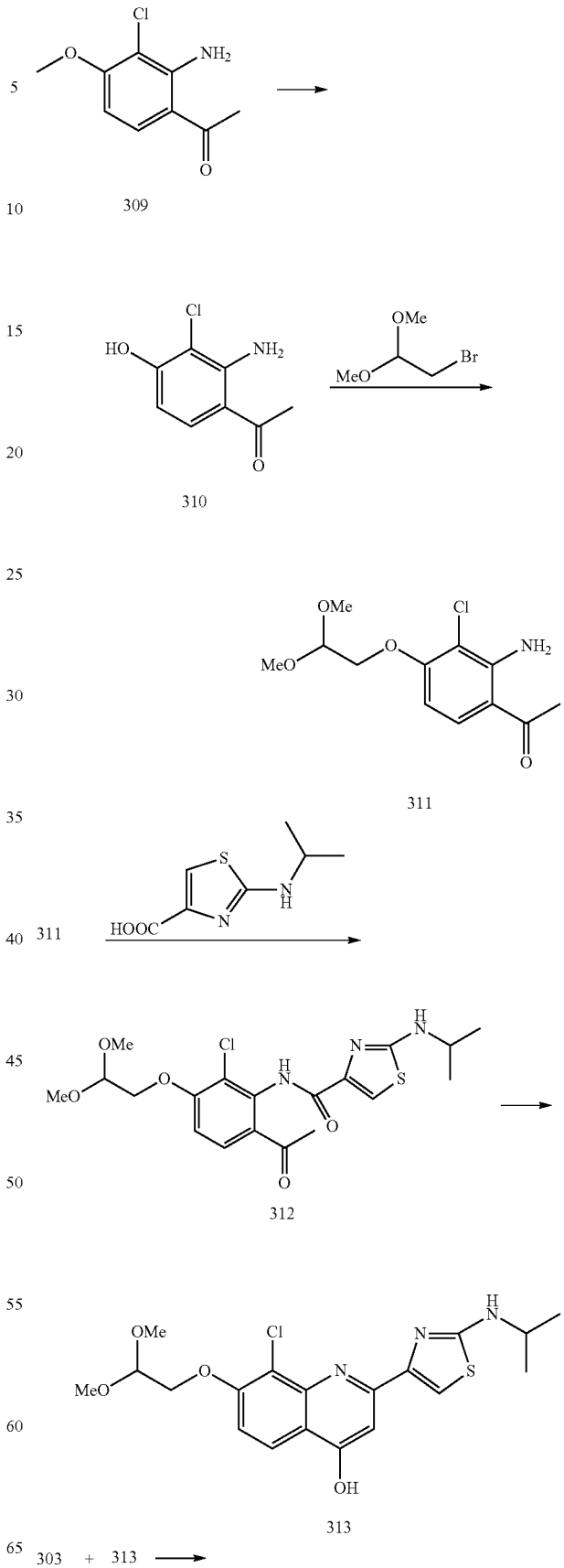

-continued

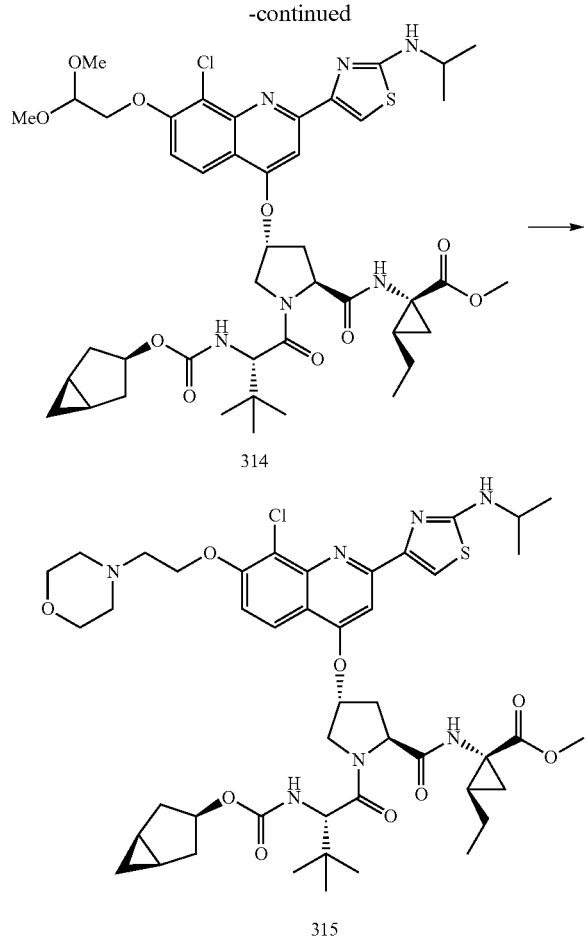

314

315 h. Preparation of Compound 310

1-(2-Amino-3-chloro-4-hydroxy-phenyl)-ethanone 309 (70.7 g, 354 mmol) was stirred in 48% aq. HBr (500 mL) at 110° C. for 72 hours. After the mixture was cooled to 0° C. with stirring, the solids were filtered and washed with water. The resulting solids were triturated with a saturated NaHCO$_3$ solution (~350 mL), filtered, washed with water, and dried under vacuum to give ~40 g (61%) of crude 310 as a dark brown solid. LC/MS=186 (M$^+$+1).

i. Preparation of Compound 311

1-(2-Amino-3-chloro-4-hydroxy-phenyl)-ethanone 310 (40 g, 215 mmol) was dissolved in DMF (360 ml). Cesium carbonate (140 g, 430 mmol) was added, followed by bromoacetaldehyde dimethyl acetal (54.5 g, 323 mmol). The mixture was then vigorously stirred at 65° C. for 24 hours. Upon cooling to room temperature, EtOAc (1 L) and H$_2$O (1 L) were added to the mixture. The organic layer was extracted with EtOAc (1×400 ml). The combined organic layer was washed with aqueous 3% LiCl solution (2×1 L), brine, dried (Na$_2$SO$_4$) and concentrated in vacuo. The residue was purified by silica gel chromatography to give compound 311 as a white solid (39 g, 67%).

j. Preparation of Compound 312

To a mixture of 1-[2-Amino-3-chloro-4-(2,2-dimethoxy-ethoxy)-phenyl]-ethanone 311 (13 g, 47.5 mmol) and isopropylaminothiazole-4-carboxylic acid hydrobromide (12.64 g, 47.5 mmol) in pyridine (150 ml) was slowly added phosphorus oxychloride (9.47 g, 61.8 mmol) at −40° C. The mixture was then stirred at 0° C. for 4 hours. Upon completion of the reaction, H$_2$O (30 ml) was added dropwise to the mixture. The mixture was then stirred at 0° C. for another 15 minutes. The mixture was concentrated in vacuo. The residue was diluted with EtOAc, washed with a sat. NaHCO$_3$ aqueous solution. The organic layer was dried (Na$_2$SO$_4$) and concentrated in vacuo. The residue was dissolved in CH$_2$Cl$_2$, hexanes were added slowly to the solution, and a yellow solid started to crash out. More hexanes were added until not much product was left in the mother liquid to provide compound 312 (18 g, 85%).

k. Preparation of Compound 313

2-Isopropylamino-thiazole-4-carboxylic acid [6-acetyl-2-chloro-3-(2,2-dimethoxy-ethoxy)-phenyl]-amide 312 (18 g, 40.7 mmol) was suspended in toluene (400 ml). NaH (2.4 g, 61 mmol) was added to the vigorously stirred mixture while monitoring H$_2$ evolution. The mixture became a clear solution during heating to reflux. The reaction was complete after refluxing for 3 hours. The mixture was cooled to room temperature. A solution of AcOH (69.2 mmol) in H$_2$O (3 vol) was added to the mixture. After vigorous agitation for 1 hour at 0° C., the solids were collected by filtration, rinsed forward with H$_2$O. The wet cake was dried under high vacuum to a constant weight to provide compound 313 (15 g, 86%).

l. Preparation of Compound 314

To a mixture of brosylate intermediate 303 (15 g, 35 mmol) and compound 313 (27.5 g, 38.5 mmol) in NMP (200 ml) was added cesium carbonate (25.1 g, 77 mmol). The mixture was stirred at 65° C. for 5 hours. The reaction was cooled to room temperature and EtOAc (600 ml) and an aqueous solution of 3% LiCl (600 ml) were added to the mixture. The organic layer was washed with aqueous 3% LiCl (1×600 ml), brine, dried (Na$_2$SO$_4$) and concentrated in vacuo. The residue was purified by silica gel chromatography to give the desired methyl ester as a yellow solid (23.6 g, 75%). LC/MS=900.13 (M$^+$+1).

m. Preparation of Compound 315

Methyl ester 314 (23.6 g, 26 mmol) was dissolved in glacial acetic acid (200 ml), 1.4 N HCl in H$_2$O (75 ml) was added to the solution. The mixture was stirred at 60° C. for 1 hour. Upon completion of the reaction, the mixture was concentrated to remove the solvents, coevaporated with toluene (×2) to remove residual acetic acid. The residue was then dissolved in EtOAc (500 ml) and sat. NaHCO$_3$ aqueous solution (enough to neutralize the mixture) while monitoring CO$_2$ evolution. The organic layer was washed with brine, dried (Na$_2$SO$_4$) and concentrated in vacuo. The residue was further dried under high vacuum for 1 h and used as is for the next step. The crude was dissolved in CH$_2$Cl$_2$ (360 ml), morpholine (3.4 g, 39 mmol) and sodium triacetoxyborohydride (7.2 g, 34 mmol) were added to the mixture at 0° C. Then glacial acetic acid (0.47 g, 7.8 mmol) was added dropwise to the mixture. The reaction was complete in 10 minutes at 0° C. Sat. NaHCO$_3$ aqueous solution was added to quench the reaction. After stirring for another 20 minutes, the organic layer was washed with brine, dried (Na$_2$SO$_4$) and concentrated in vacuo. The residue was purified by silica gel chromatography to give the desired amine product 315 as a yellow solid (12 g, 50%). LC/MS=924.63 (M$^+$+1).

Compound 4 can be prepared as described in the following Example.

Example 4

Preparation of Compound 4

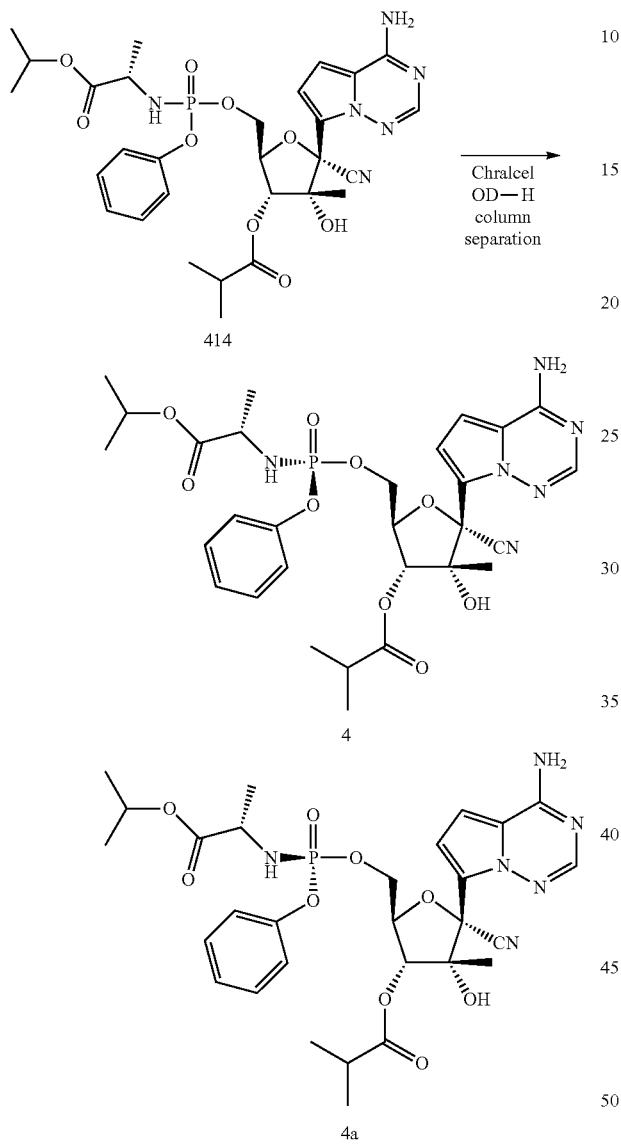

Diastereomeric mixture 414 was dissolved in heptane and isopropanol (70%:30%, 230 mg in 4.5 mL of the mixed solvents) and subjected to chiral column separation under the following conditions:

Column: Chiralcel OD-H, 2×25 cm
Solvent system: 70% heptane and 30% isopropanol
Flow rate: 6 mL/min.
Loading volume per run: 2.5 mL Compound 4 had a retention time of 20 minutes. $^1$H NMR (300 MHz, CDCl$_3$): δ 8.00 (s, 1H), 7.1-7.3 (m, 5H), 6.83 (d, 1H), 6.71 (d, 1H), 6.09 (brs, 2H), 5.95 (s, 1H), 5.04 (m, 2H), 4.67 (q, 1H), 4.35-4.52 (m, 2H), 4.00 (m, 2H), 2.74 (m, 1H), 1.40 (d, 3H), 1.2-1.3 (12H), 0.98 (s, 3H). $^{31}$P NMR (121.4 MHz, CDCl$_3$): δ 2.72 (s). Compound 4 was subsequently recrystallized from MTBE for x-ray quality crystals.

Compound 4a had a retention time 50 min. $^1$H NMR (300 MHz, CDCl$_3$): δ 7.98 (s, 1H), 7.1-7.3 (m, 5H), 6.83 (d, 1H), 6.73 (d, 1H), 6.02 (brs, 2H), 5.95 (s, 1H), 5.08 (d, 1H), 5.00 (m, 1H), 4.68 (q, 1H), 4.38-4.56 (m, 2H), 3.98 (m, 2H), 2.74 (m, 1H), 1.40 (d, 3H), 1.2-1.3 (12H), 0.99 (s, 3H). $^{31}$P NMR (121.4 MHz, CDCl$_3$): δ 2.61 (s).

The intermediate diastereomeric mixture 414 was prepared as follows.

a. Preparation of Compound 402

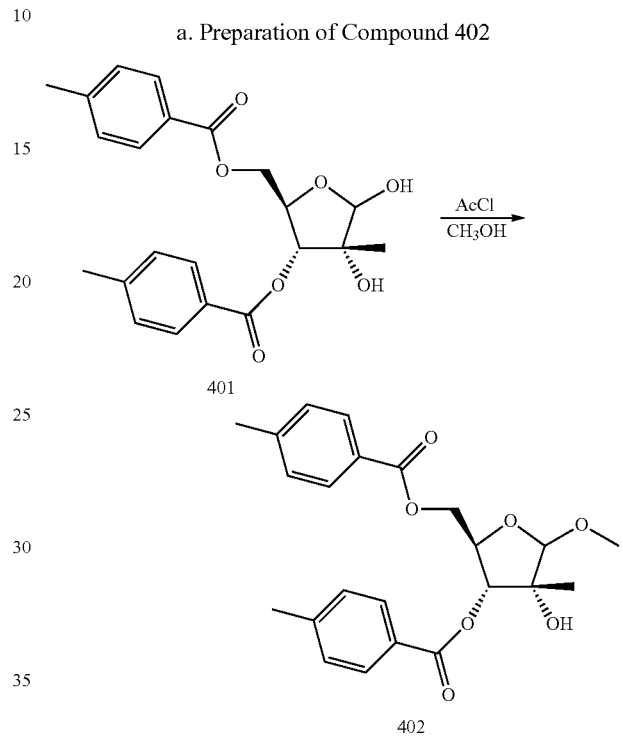

To a solution of compound 401 (22.0 g, 54.9 mmol, prepared according to the procedures described in J.O.C., 2004, 6257) in methanol (300 mL) was dropwise added acetyl chloride (22 mL) at 0° C. using a dropping funnel over a period of 30 minutes and then stirred at room temperature for 16 hours. The mixture was concentrated, re-dissolved in ethyl acetate (400 mL), washed with ice-cold 2 N NaOH, and concentrated to dryness, affording the crude methyl ether 402 as an oil. MS=437.2 (M+Na$^+$).

b. Preparation of Compound 403

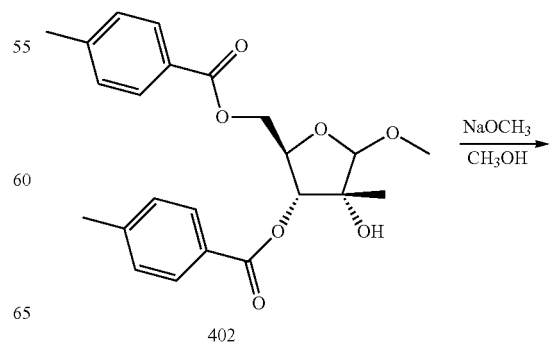

-continued

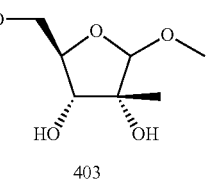

403

To a solution of compound 402 in methanol (300 mL) was added 0.5 M sodium methoxide solution in methanol (20 mL, 10 mmol), and stirred for 16 hours at room temperature. The reaction was quenched with 4.0 N HCl solution in dioxane (2.5 mL, 10 mmol). The mixture was then concentrated, affording the crude compound 403. MS=201.0 (M+Na$^+$).

c. Preparation of Compound 404

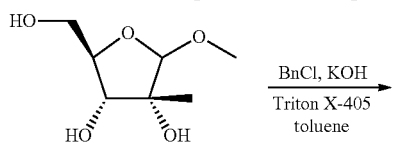

403

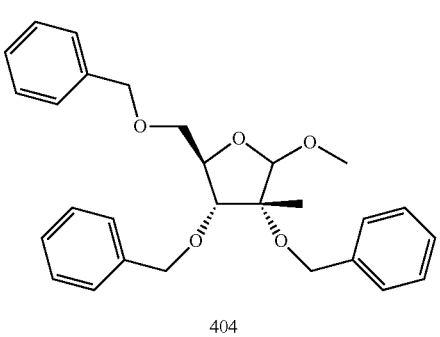

404

A mixture of compound 403, Tritron X-405 (70% in water, 6.0 g), 50% KOH (in water, 85 g) in toluene (500 mL) was heated to reflux with a Dean-Stark trap attached. After 1 hour collecting 25 mL of water, benzyl chloride (33 g, 260 mmol) was added and continued to reflux with stirring for 16 hours. The mixture was then cooled and partitioned between ethyl acetate (400 mL) and water (300 mL). The organic layer was washed with water (300 mL), and concentrated. The residue was purified by silica gel column chromatography (20% EtOAc/hexanes), affording the methyl ether 404 as an oil (22.0 g, 89% in three steps). $^1$H NMR (300 MHz, CDCl$_3$): δ, 7.3 (m, 15H), 4.5-4.9 (m, 7H), 4.37 (m, 1H), 3.87 (d, 1H), 3.56 (m, 2H), 3.52 (s, 3H), 1.40 (s, 3H).

d. Preparation of Compound 405

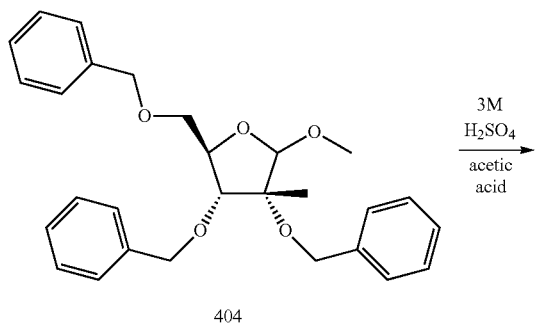

404

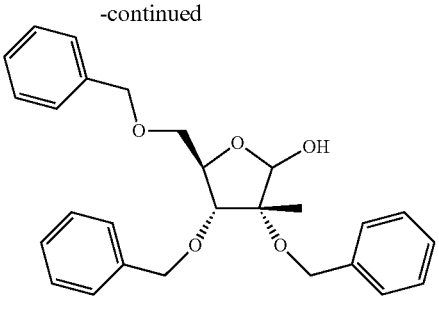

405

To a solution of 404 (22.0 g, 49.0 mmol) in acetic acid (110 mL) was added 3 M sulfuric acid (prepared by mixing 4.8 g of concentrated sulfuric acid with 24 mL of water) and stirred at 70° C. for 8 hours. The mixture was concentrated to a volume of 20 mL, and partitioned between ethyl acetate and ice-cold 2N NaOH. The ethyl acetate layer was concentrated, and purified by silica gel column chromatography (~35% EtOAc/hexanes), affording compound 405 as an oil (17.0 g, 80%). MS=457.2 (M+Na$^+$).

e. Preparation of Compound 406

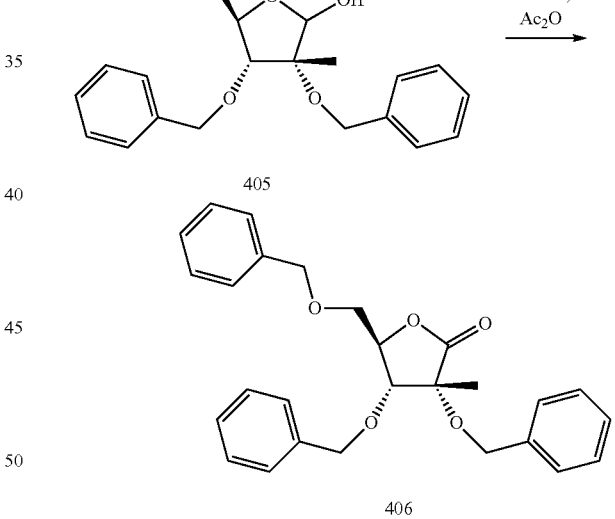

406

To a solution of compound 405 (45 g, 104 mmol) in DMSO (135 mL) was dropwise added acetic anhydride (90 mL, 815 mmol) at room temperature under argon. The mixture was stirred for 16 hours at room temperature, and then poured into ice-water (1 L) while stirring. After ice was completely melted (30 minutes), ethyl acetate (500 mL) was added. The organic layer was separated. This extraction process was repeated three times (3×500 mL). The organic extracts were combined and concentrated. The residue was purified by silica gel column chromatography (20% EtOAc/hexanes), affording compound 406 as an oil (39 g, 88%). $^1$H NMR (300 MHz, DMSO-d$_6$): δ 7.3 (m, 15H), 4.4-4.8 (m, 7H), 4.08 (d, J=7.5 Hz, 1H), 3.75 (dd, J=2, 4, 11.4 Hz, 1H), 3.64 (dd, J=5.4, 11.4 Hz, 1H), 1.51 (s, 3H).

f. Preparation of Compound 407

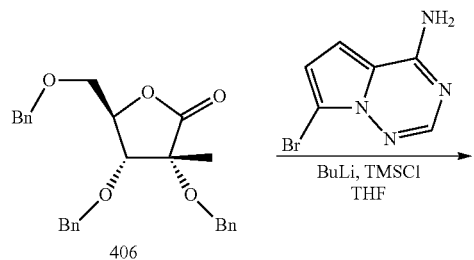

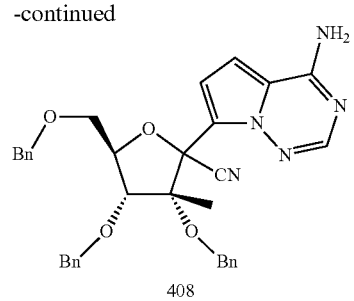

To a dry, argon purged round bottom flask (100 mL) were added 7-bromo-pyrrolo[2,1-f][1,2,4]triazin-4-ylamine (234 mg, 1.10 mmol) (prepared according to WO2007056170) and anhydrous THF (1.5 mL). TMSCl (276 µL, 2.2 mmol) was then added and the reaction mixture stirred for 2 hours. The flask was placed into a dry ice/acetone bath (−78° C.) and BuLi (2.5 mL, 4.0 mmol, 1.6M in hexanes) was added dropwise. After 1 hour, a solution of compound 406 (432.5 mg, 1.0 mmol) in THF was cooled to 0° C. and then added to the reaction flask dropwise. After 1 hour of stirring at −78° C., the flask was warmed to 0° C. and sat. NH$_4$Cl (5 mL) was added to quench the reaction. The organics were extracted using EtOAc (3×10 mL) and the combined organic layers were dried using MgSO$_4$. The solvent was removed under reduced pressure and the crude material was purified using flash chromatography (hexanes/EtOAc). 560 mg (90%) of compound 407 was isolated as a mixture of two anomers. LC/MS=567.2 (M+H$^+$). $^1$H NMR (300 MHz, CDCl$_3$): δ 7.85 (m, 1H), 7.27 (m, 15H), 7.01 (m, 1H), 6.51 (m, 1H), 4.66 (m, 8H), 4.40 (m, 2H), 3.79 (m, 3H), 1.62 (s, 2'-O—CH$_3$ from the one anomer), 1.18 (s, 2'-O—CH$_3$ from the other anomer).

g. Preparation of Compound 408

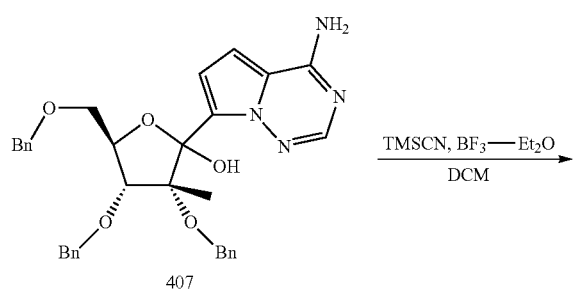

To a solution of Compound 407 (1 g, 1.77 mmol) in CH$_2$Cl$_2$ (20 mL) at 0° C. was added TMSCN (1.4 mL, 10.5 mmol) and BF$_3$-Et$_2$O (1 mL, 8.1 mmol). The reaction mixture was stirred at 0° C. for 0.5 hours, then at room temperature for additional 0.5 hour. The reaction was quenched with NaHCO$_3$ at 0° C., and diluted with CH$_3$CO$_2$Et. The organic phase was separated, washed with brine, dried over Na$_2$SO$_4$, filtered and concentrated. The residue was purified by chromatography on silica gel, eluted with CH$_3$CO$_2$Et-hexanes (1:1 to 2:1), to give compound 408 (620 mg, 61%) as an isomeric mixture. MS=576.1 (M+H$^+$).

h. Preparation of Compound 409

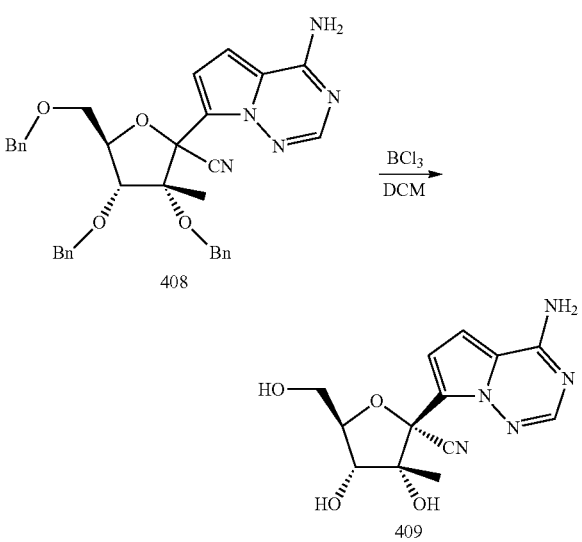

To a solution of compound 408 (150 mg, 0.26 mmol) in CH$_2$Cl$_2$ (4 mL) at −78° C. was added BCl$_3$ (2 mL, 1M in CH$_2$Cl$_2$). The reaction mixture was stirred at −78° C. for 1 hour. The reaction was quenched at −78° C. by dropwise addition of TEA (2 mL) and MeOH (5 mL). The mixture was allowed to warm up to room temperature, evaporated, and co-evaporated with MeOH several times. The residue was treated with NaHCO$_3$ (1 g in 10 mL H$_2$O), concentrated and purified by HPLC to give the desired product compound 409 (48 mg, 60%). $^1$H NMR (300 MHz, D$_2$O): δ 7.74 (s 1H), 6.76 (d, J=5 Hz, 1H), 6.73 (d, J=5 Hz, 1H), 4.1 (m, 1H), 3.9 (m, 1H), 3.8 (m, 2H), 0.84 (s, 3H). MS=305.9 (M+H$^+$). The other alpha-anomer was also obtained (9 mg, 11%): $^1$H NMR (300 MHz, D$_2$O): δ 7.70 (s 1H), 6.8 (d, J=5 Hz, 1H), 6.7 (d, J=5 Hz, 1H), 4.25 (d, J=9 Hz, 1H), 4.07 (m, 1H), 3.85 (m, 1H), 3.7 (m, 1H), 1.6 (s, 3H). MS=306.1 (M+H⁺).

i. Preparation of Compound 412

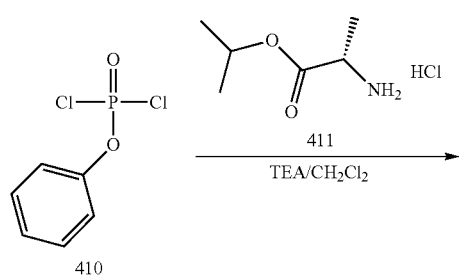

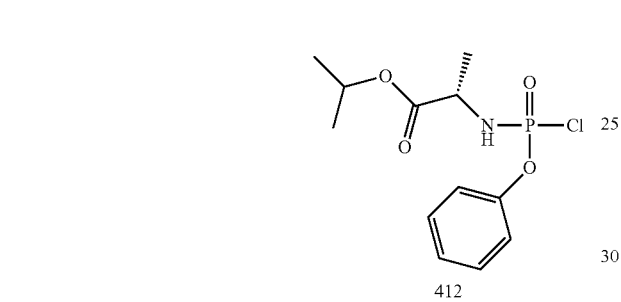

Compound 410 (commercially available, 4.99 g, 23.8 mmol) was dissolved in dichloromethane (100 mL) and alanine isopropyl ester hydrochloride 411 (3.98 g, 23.8 mmol) was added. The resulting clear solution was cooled −78° C. for 30 min. Triethylamine (6.63 mL, 47.5 mmol) was added dropwise over 15 minutes. The mixture was then allowed to warm to room temperature. After 16 hours, the solvent was removed by argon stream. The residue was re-dissolved in MTBE (25 mL) and the insoluble was removed by filtration under argon. The filtrate was condensed by argon stream and the crude product 412 was used for the next reaction without further purification. ¹H NMR (300 MHz, CDCl₃): 7.1-7.4 (m, 5H), 5.1 (m, 1H), 4.35 (m, 1H), 4.15 (m, 1H), 1.5 (d, 3H), 1.2 (m, 6H). ³¹P NMR (121.4 MHz, CDCl₃): δ 7.8 and 8.4 (2s).

j. Preparation of Compound 413

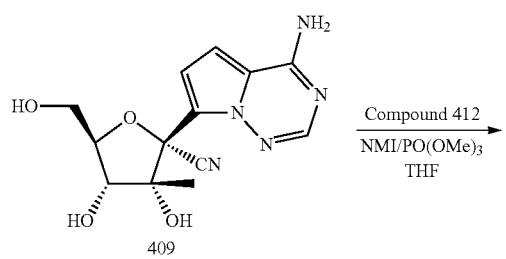

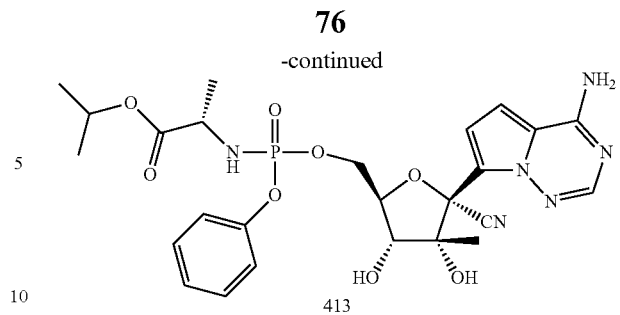

To a solution of compound 409 (1.03 g, 3.37 mmol) in trimethyl phosphate (2.0 mL) and THF (20 mL) was added N-methyl imidazole (1.5 g, 18.3 mmol) at 0° C. A solution of compound 412 (2.5 g, 8.18 mmol) in THF (3 mL) was dropwise added. The resulting mixture was allowed to warm to room temperature over 1.5 hours. The mixture was partitioned between ethyl acetate and water. The ethyl acetate layer was concentrated and the residue was purified by silica gel chromatography (ethyl acetate to 10% ethanol/ethyl acetate), affording 1.15 g (59%) of compound 413 as 1:1 diastereomeric mixture at phosphorous. ¹H NMR (300 MHz, CDCl₃): δ 8.02 (s, 1H), 7.1-7.4 (m, 5H), 6.8 (2d, 1H), 6.7 (2d, 1H), 6.08 (brs, 2H), 5.03 (m, 1H), 4.6 (m, 1H), 4.4 (m, 2H), 3.9-4.1 (m, 3H), 1.31 (d, 3H), 1.2 (m, 6H), 0.83 (s, 3H). ³¹P NMR (121.4 MHz, CDCl₃): δ 2.78 (s). MS=575.1 (M+H⁺).

k. Preparation of Compound 414

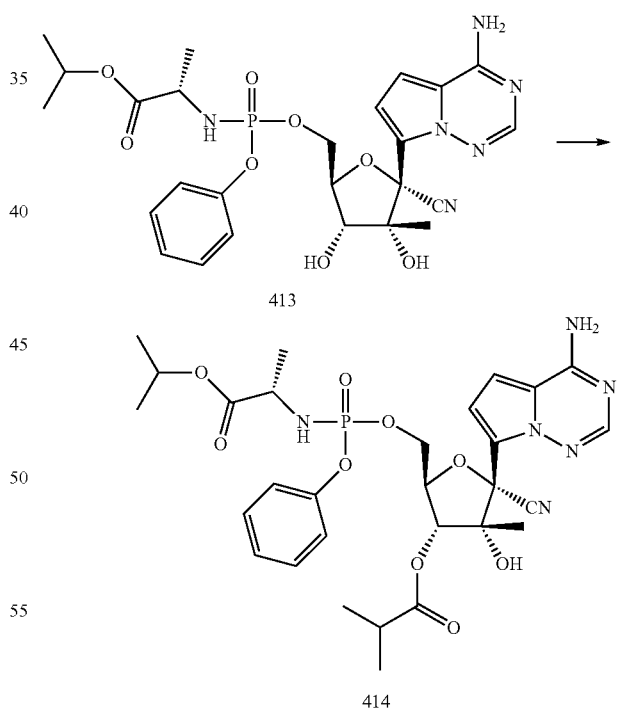

To a solution of compound 413 (175 mg, 0.305 mmol) in acetonitrile (2 mL) was added N,N-dimethylformamide dimethyl acetal (41 μL, 0.34 mmol, 1.1 eq.) and stirred at room temperature for 1 hour. The reaction was complete (by LCMS). The mixture was then concentrated to dryness. To the residue were added DCC (250 mg, 1.21 mmol, 4 eq.), acetonitrile (5 mL) and isobutyric acid (55 mg, 58 μL, 2 eq.). The mixture was stirred at room temperature for 48 hours. Water (0.2 mL) and trifluoroacetic acid (0.1 mL) were added at 0° C. and stirred at room temperature for 64 hours. Sodium bicarbonate (500 mg) was added at 0° C. The mixture was stirred at room temperature for 0.5 hour and filtered. The filtrate was concentrated and the residue was purified by silica gel column chromatography (5% methanol/dichloromethane), affording 144 mg (73%) of compound 414 as 1:1 diastereomeric mixture at phosphorus. $^1$H NMR (300 MHz, CDCl$_3$): δ 8.00 (s, 1H), 7.1-7.4 (m, 5H), 6.83 (d, 1H), 6.71 (2d, 1H), 5.97 (brs, 2H), 5.94 (d, 1H), 5.07 (2d, 1H), 5.01 (m, 1H), 4.68 (m, 1H), 4.4 (m, 2H), 4.0 (m, 2H), 2.74 (m, 1H), 1.4 (2d, 3H), 1.2-1.3 (12H), 0.98 and 0.99 (2s, 3H). $^{31}$P NMR (121.4 MHz, CDCl$_3$): δ 2.56 and 2.65 (2s). MS=645.1 (M+H$^+$).

Compound 5 can be prepared as described in the following Example.

Example 5

Preparation of 5: 5-(3,3-dimethylbut-1-yn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid 5

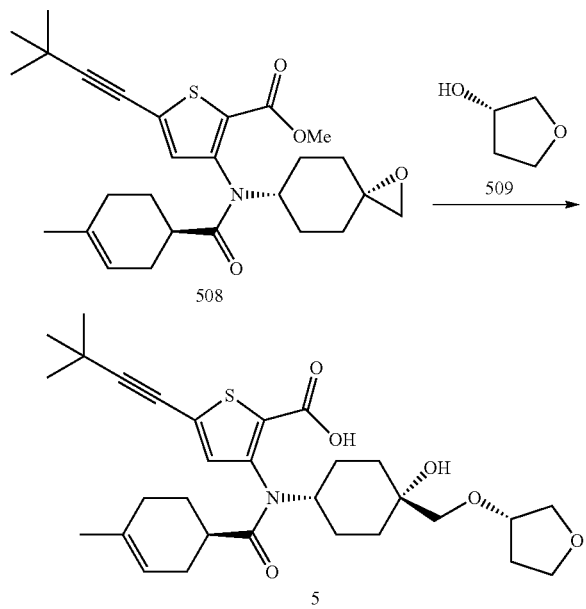

5-(3,3-dimethyl-but-1-ynyl)-3-[((1R)-4-methyl-cyclohex-3-enecarbonyl)-(1-oxa-spiro[2.5]oct-6-yl)-amino]-thiophene-2-carboxylic acid methyl ester 508 (132 mg, 0.28 mmol) and (S)-tetrahydro-furan-3-ol 509 (247 mg, 2.8 mmol) in 1-methyl-pyrrolidin-2-one (3 mL) were treated with potassium tert-butoxide (251 mg, 2.24 mmol), sealed at heated to 40° C. for 16 hours. After cooling the mixture was treated with 2 M HCl until pH 3, partitioned between ethyl acetate and water and separated. The organic layer was washed with 5% lithium chloride solution, water, brine, and dried over sodium sulfate. After filtration and concentration the residue was purified by HPLC with CH$_3$CN (0.1% TFA)/H$_2$O (0.1% TFA) to afford 107 mg (70% yield) of compound 5 as a white powder: MS (m/z): 544.0 [M+H]+; HPLC retention time 4.22 min (2-98% acetonitrile:water with 0.05% trifluoroacetic acid).

The intermediate compound 508 was prepared as follows.

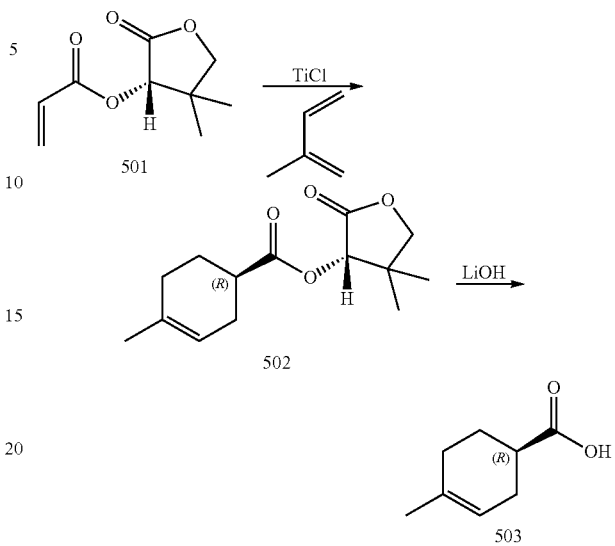

a. Preparation of Compound 502

(S)-3-hydroxy-4,4-dimethyldihydrofuran-2(3H)-one (2.60 g, 20 mmol) and diisopropylethylamine (5.2 mL, 30 mmol) in dichloromethane (25 mL) was cooled to −10° C. and treated dropwise with acryloyl chloride (2.03 mL, 25 mmol) and stirred for 2 h. 1M HCl (20 mL) was added and the organic layer was washed with sodium bicarbonate and water. The organic layer was dried over sodium sulfate, filtered and concentrated. Flash chromatography (10-40% EtOAc, hexanes) afforded 2.09 g (57% yield) of the desired (S)-4,4-dimethyl-2-oxotetrahydrofuran-3-ylacrylate 501 as a clear oil.

(S)-4,4-dimethyl-2-oxotetrahydrofuran-3-ylacrylate 501 (2.05 g, 11.1 mmol) in dichloromethane (17.5 mL) and hexanes (2.5 mL) was cooled to −10° C. and treated with titanium tetrachloride (2.2 mL, 1 M in dichloromethane, 2.2 mmol). The yellow solution was stirred for 15 minutes and treated with isoprene (1.67 mL, 16.7 mmol) dropwise over 5 minutes. After stirring for 2 hours, an additional portion of isoprene (1.67 mL, 16.7 mmol) was added and the reaction mixture was stirred at −10 to 0° C. for 3.5 hours. The reaction mixture was quenched with ammonium chloride (sat. aq.). Water and ethyl acetate:hexanes (1:1) were added. The organic layer was separated and the aqueous layer was extracted again with ethyl acetate:hexanes (1:1). The combined organic layers were dried over sodium sulfate, filtered and concentrated. The residue was purified by flash chromatography (10-50% EtOAc:Hex, 80 g column) to afford 1.30 g (46% yield) of (R)—((S)-4,4-dimethyl-2-oxotetrahydrofuran-3-yl) 4-methylcyclohex-3-enecarboxylate 502 as a clear oil.

b. Preparation of Compound 503

(R)—((S)-4,4-dimethyl-2-oxotetrahydrofuran-3-yl) 4-methylcyclohex-3-enecarboxylate 502 (1.30 g, 5.15 mmol) in THF (10 mL), water (1 mL) and methanol (1 mL) was treated with lithium hydroxide monohydrate (2.16 g, 51.5 mmol) and warmed to 50° C. with stirring. After 1 hour, the reaction mixture treated with 1M HCl. The mixture was extracted with hexanes:THF (10:1), dried over sodium sulfate, filtered and concentrated to 0.738 g (quantitative yield) of (R)-4-methylcyclohex-3-enecarboxylic acid 503 as a white powder.

c. Preparation of Compound 504

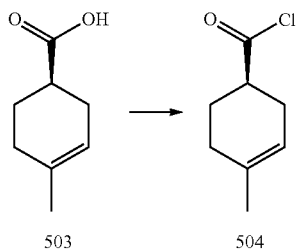

(R)-4-methylcyclohex-3-enecarboxylic acid 503 (371 mg, 2.65 mmol), azeotropically dried by evaporation from toluene, was treated with potassium phosphate tribasic (1.13 g, 7.94 mmol), suspended in dichloromethane (7.6 mL) and treated with dimethylformamide (4 drops). The reaction mixture was cooled to 0° C. and treated dropwise with oxalyl chloride (0.75 mL, 7.9 mmol). The reaction mixture was allowed to warm to ambient temperature while stirring for 2 hours. After filtering the solids, the solution was concentrated, treated with hexanes and concentrated again to afford (R)-4-methylcyclohex-3-enecarbonyl chloride 504 as a light yellow oil which was used immediately in the next step.

d. Preparation of Compound 506

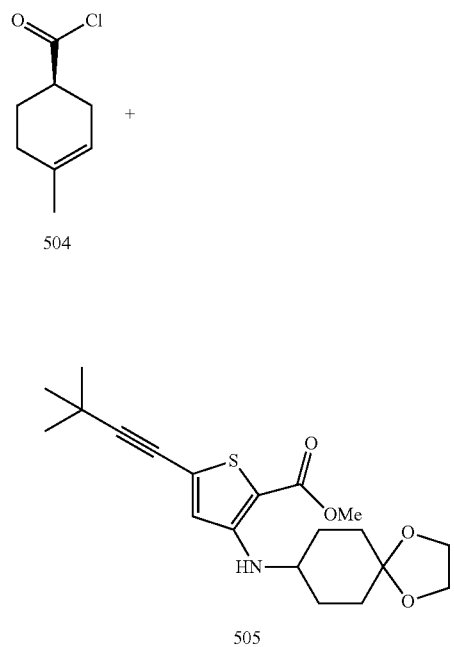

(R)-4-methylcyclohex-3-enecarbonyl chloride 504 (2.65 mmol), 5-(3,3-dimethyl-but-1-ynyl)-3-(1,4-dioxa-spiro[4.5]dec-8-ylamino)-thiophene-2-carboxylic acid methyl ester 505 (250 mg, 0.66 mmol) and potassium phosphate tribasic (562 mg, 2.65 mmol) were suspended in dichloroethane (1.7 mL), sealed with a cap and heated to 90° C. After 16 hours, the reaction mixture was cooled and partitioned between ethyl acetate and water. The organic layer was separated and the aqueous extracted again with ethyl acetate. The combined organic layers were dried over sodium sulfate, filtered and concentrated. Flash chromatography (10-40% EtOAc:Hexanes) afforded 220 mg (67% yield) of the desired 5-(3,3-dimethyl-but-1-ynyl)-3-[(1,4-dioxa-spiro[4.5]dec-8-yl)-((1R)-4-methyl-cyclohex-3-enecarbonyl)-amino]-thiophene-2-carboxylic acid methyl ester 506 as a beige foam.

e. Preparation of Compound 507

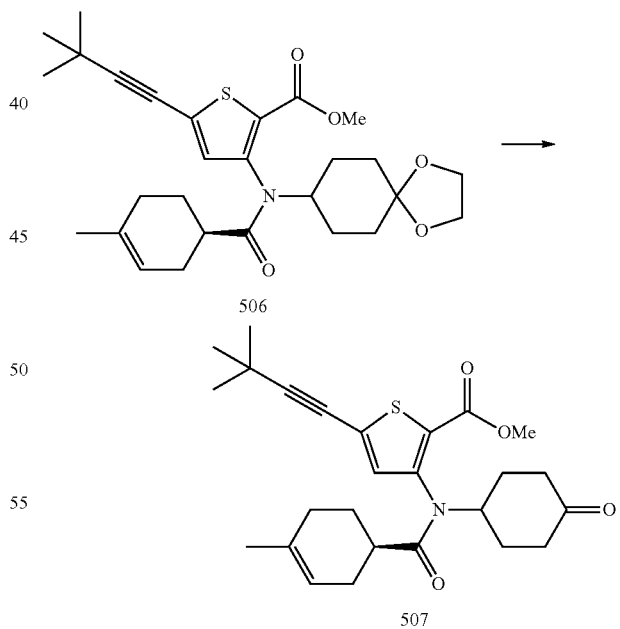

5-(3,3-Dimethyl-but-1-ynyl)-3-[(1,4-dioxa-spiro[4.5]dec-8-yl)-((1R)-4-methyl-cyclohex-3-enecarbonyl)-amino]-thiophene-2-carboxylic acid methyl ester 506 (219 mg, 0.438 mmol) was dissolved in THF (3.5 mL) and treated with 4M HCl (1.75 mL, 7.01 mmol). The reaction mixture was heated to 45° C. and stirred 2 h. Ethyl acetate was added and the organic layer was separated then washed with water, sodium bicarbonate (sat aq), water, and brine. The organic layer was dried over sodium sulfate, filtered and concentrated to 0.190 g (95% yield) of the desired 5-(3,3-dimethyl-but-1-ynyl)-3-[((1R)-4-methyl-cyclohex-3-enecarbonyl)-(4-oxo-cyclohexyl)-amino]-thiophene-2-carboxylic acid methyl ester 507 as a white foam.

f. Preparation of Compound 508

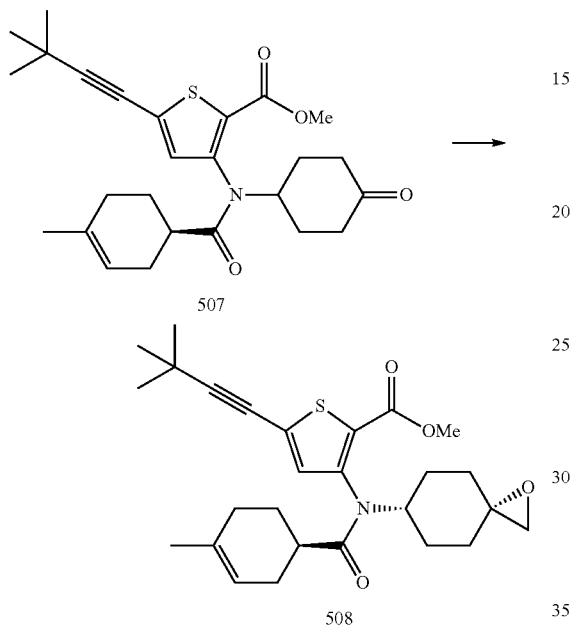

Trimethylsulfoxonium chloride (79 mg, 0.62 mmol) in DMSO (1.5 mL) was treated with sodium hydride (21 mg, 60% oil dispersion, 0.53 mmol) and stirred at ambient temperature for 10 min. 5-(3,3-Dimethyl-but-1-ynyl)-3-[((1R)-4-methyl-cyclohex-3-enecarbonyl)-(4-oxo-cyclohexyl)-amino]-thiophene-2-carboxylic acid methyl ester 507 in THF (1 mL+0.5 mL) was added dropwise and the reaction mixture was stirred for 45 min. The orange solution was treated with 5% citric acid until pH 3 and partitioned between water and ethyl acetate. The organic layer was separated and the aqueous was extracted again with ethyl acetate. The combined organics were washed with 5% LiCl, water and brine, and dried over sodium sulfate. After filtration and concentration, the residue was purified by flash chromatography (20-75% EtOAc:hexanes) to afford 0.134 g (70% yield) of 5-(3,3-dimethyl-but-1-ynyl)-3-[((1R)-4-methyl-cyclohex-3-enecarbonyl)-(1-oxa-spiro[2.5]oct-6-yl)-amino]-thiophene-2-carboxylic acid methyl ester 508 as a white powder.

Compound 6, Can be prepared using synthetic methods and intermediates like those described in U.S. Ser. No. 12/779,023 (US 20100310512 A1). Compound 6, Can also be prepared as described in the following Example.

Example 6

Preparation of (1-{3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester 6

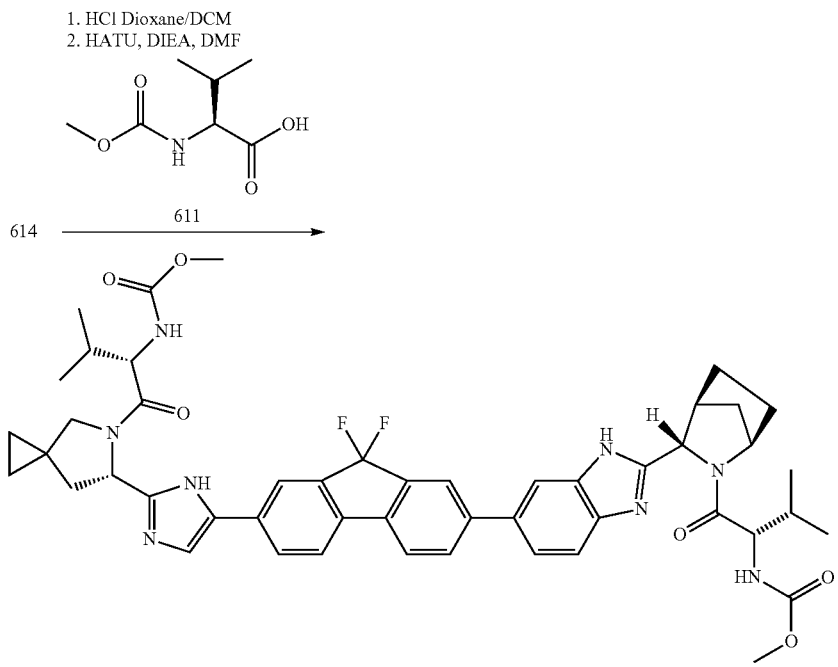

3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carboxylic acid tert-butyl ester 614 (115 mg, 0.138 mmol) was dissolved in methylene chloride (2 mL) and HCl in dioxane (4M, 2 mL) was added and stirring at room temperature was continued. After 20 minutes, all volatiles were removed in vacuo. The crude material was used in the next step without further purification. The crude material was dissolved in DMF (1.5 mL) and DIEA (53.4 mg, 0.414 mmol) was added. A solution of 2-(L) Methoxycarbonylamino-3-methyl-butyric acid 611 (24.2 mg, 0.138 mmol), HATU (52.4 mg, 0.138 mmol) and DIEA (17.8 mg, 0.138 mmol) in DMF (1 mL) was added. The reaction was stirred at room temperature. After 20 minutes, the reaction was diluted with EtOAc and was washed with aqueous bicarbonate solution, aqueous LiCl solution (5%), brine, and was dried over sodium sulfate. Filtration and removal of solvents in vacuo gave the crude material, which was purified by RP-HPLC (eluent: water/MeCN w/ 0.1% TFA) to yield compound 6 (76 mg). LCMS-ESI$^+$: calc'd for $C_{49}H_{64}F_2N_8O_6$: 888.9 (M$^+$). Found: 890.0 (M+H$^+$). $^1$H-NMR: 300 MHz, (dmso-d$_6$) δ: 8.20-7.99 (m, 8H), 7.73 (s, 2H), 7.37-7.27 (m, 2H), 5.25 (dd, J=7.2 Hz, 1H), 4.78 (s, 1H) 4.54 (s, 1H), 4.16 (m, 1H), 4.02 (m, 1H), 3.87 (m, 1H), 3.74 (m, 1H), 3.55 (s, 3H), 3.53 (s, 3H), 2.75 (m, 1H), 2.25 (m, 2H), 2.09-2.04 (m, 2H), 1.88-1.79 (m, 2H), 1.54 (m, 1H), 0.94-0.77 (m, 15H) 0.63 (m, 4H) ppm. $^{19}$F-NMR: 282 MHz, (dmso-d$_6$) δ: −109.1 ppm [−74.8 ppm TFA].

The intermediate compound 614 was prepared as follows.

temperature and the solution was washed with water and aqueous HCl (1 M). The solution was dried over sodium sulfate. Filtration and evaporation of solvents gave crude product, which was purified by silica gel chromatography (eluent:EtOAc/hexanes) to yield compound 602 (10.2 g). LCMS-ESI$^+$: calc'd for $C_{15}H_{17}NO_4$: 275.3 (M$^+$). Found: 276.4 (M+H$^+$).

b. Preparation of a Mixture of Compounds 603 and 604

An oven-dried 3-neck round bottom flask was equipped with a nitrogen inlet adaptor and a 250 mL addition funnel. The third neck was sealed with a septum. The flask was charged with a stir bar, dichlorormethane (120 mL) and diethyl zinc (1.0 M in hexane, 118 mL, 118 mmol) then cooled to 0° C. in an ice bath. The addition funned was charged with dichloromethane (40 mL) and trifluoroacetic acid (9.1 mL, 118 mmol). After the diethyl zinc solution had cooled to 0° C. (about 25 minutes), the trifluoroacetic acid solution was added dropwise over 20 min to the stirred reaction mixture. After stirring for another 20 min at 0° C., diiodomethane (9.5 mL, 118 mmol) was added slowly over 4 minutes. After another 20 min, 4-methylene-pyrrolidine-1,2-dicarboxylic acid 1-benzyl ester 2-methyl ester 602 (8.10 g, 29.4 mmol) was added in 30 mL dichloromethane by cannula. The flask containing 4-methylene-pyrrolidine-1,2-dicarboxylic acid 1-benzyl ester 2-methyl ester was then rinsed with another 10 mL dichloromethane and this solution was also transferred to the reaction mixture by cannula. The reac-

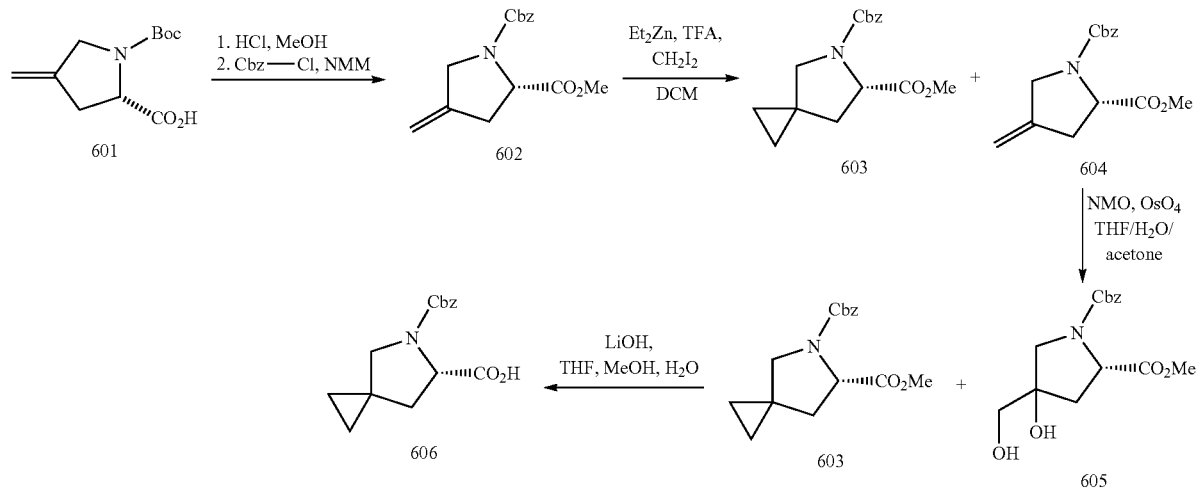

a. Preparation of compound 4-Methylene-pyrrolidine-1,2-dicarboxylic acid 1-benzyl ester 2-methyl ester 602

4-Methylene-pyrrolidine-1,2-dicarboxylic acid 1-tert-butyl ester 601 (10.0 g, 44 mmol) was dissolved in MeOH (75 mL) at room temperature and HCl (4M in dioxane, 75 mL) was added. Stirring at room temperature was continued for 4 hours. All volatiles were removed in vacuo and a beige solid was obtained. The crude material was suspended in methylene chloride (100 mL) and N-Methyl morpholine (13.3 g, 132 mmol) was added. The mixture was cooled to 0° C. and benzyl chloroformate (8.26 g, 48.4 mmol) was added while stirring. After 30 minutes, the reaction was warmed to room tion mixture was allowed to warm to RT and stirred for 110 h (about 5 days) after which the reagents were quenched with saturated aqueous ammonium chloride (~150 mL). The contents of the flask were slowly poured into a 2 L sep funnel containing saturated aqueous sodium bicarbonate (800 mL). The aqueous phase was extracted three times with 300 mL ethyl acetate. The combined organics were dried over magnesium sulfate and concentrated to provide a mixture of Compounds 603 and 604.

c. Preparation of a Compound 603

The crude material from sub-part b was dissolved in 3:1:1 THF/water/acetone (165 mL) then treated with N-methylmorpholine-N-oxide (3.45 g, 29.4 mmol) and osmium tetroxide (4 wt % in water, 5 mL, 0.818 mmol). After stirring at RT for 7 h, the reagents were quenched with 1 M aqueous sodium thiosulfate (~100 mL). The contents of the flask were then poured into a 1 L sep funnel containing water (~300 mL). The aqueous phase was extracted three times with 300 mL dichloromethane. The combined organics were dried over magnesium sulfate and concentrated. The crude residue was purified by silica column chromatography (5% to 45% EtOAc/hexane) to provide 5-aza-spiro[2.4]heptane-5,6-dicarboxylic acid 5-benzyl ester 6-methyl ester 603 as a clear oil (5.54 g, 19.15 mmol, 65%) as a clear oil. $^1$H NMR (CDCl$_3$) δ 7.36-7.29 (m, 5H), 5.21-5.04 (m, 2H), 4.56-4.47 (m, 1H), 3.75 (s, 1.5H), 3.60 (m, 1.5H), 03.51-3.37 (m, 2H), 2.32-2.25 (m, 1H), 1.87-1.80 (m, 1H), 0.64-0.51 (m, 4H).

d. Preparation of 5-Aza-spiro[2.4]heptane-5,6-dicarboxylic acid 5-benzyl ester 606

5-Aza-spiro[2.4]heptane-5,6-dicarboxylic acid 5-benzyl ester 6-methyl ester 603 (244 mg, 0.840 mmol) was dissolved in THF (2.0 mL)/MeOH (1.5 mL). An aqueous solution of LiOH (35.5 mg, 0.84 mmol) was added and stirring at room temperature was continued. After 3 hours, the reaction was neutralized with aqueous HCl (1 M) and the organic solvents were removed in vacuo. The crude mixture was diluted with water and EtOAc and the organic layer was collected. All volatiles were removed in vacuo and the crude acid 606 was used without further purification. LCMS-ESI$^+$: calc'd for C$_{15}$H$_{17}$NO$_4$: 275.3 (M$^+$). Found: 276.3 (M+H$^+$).

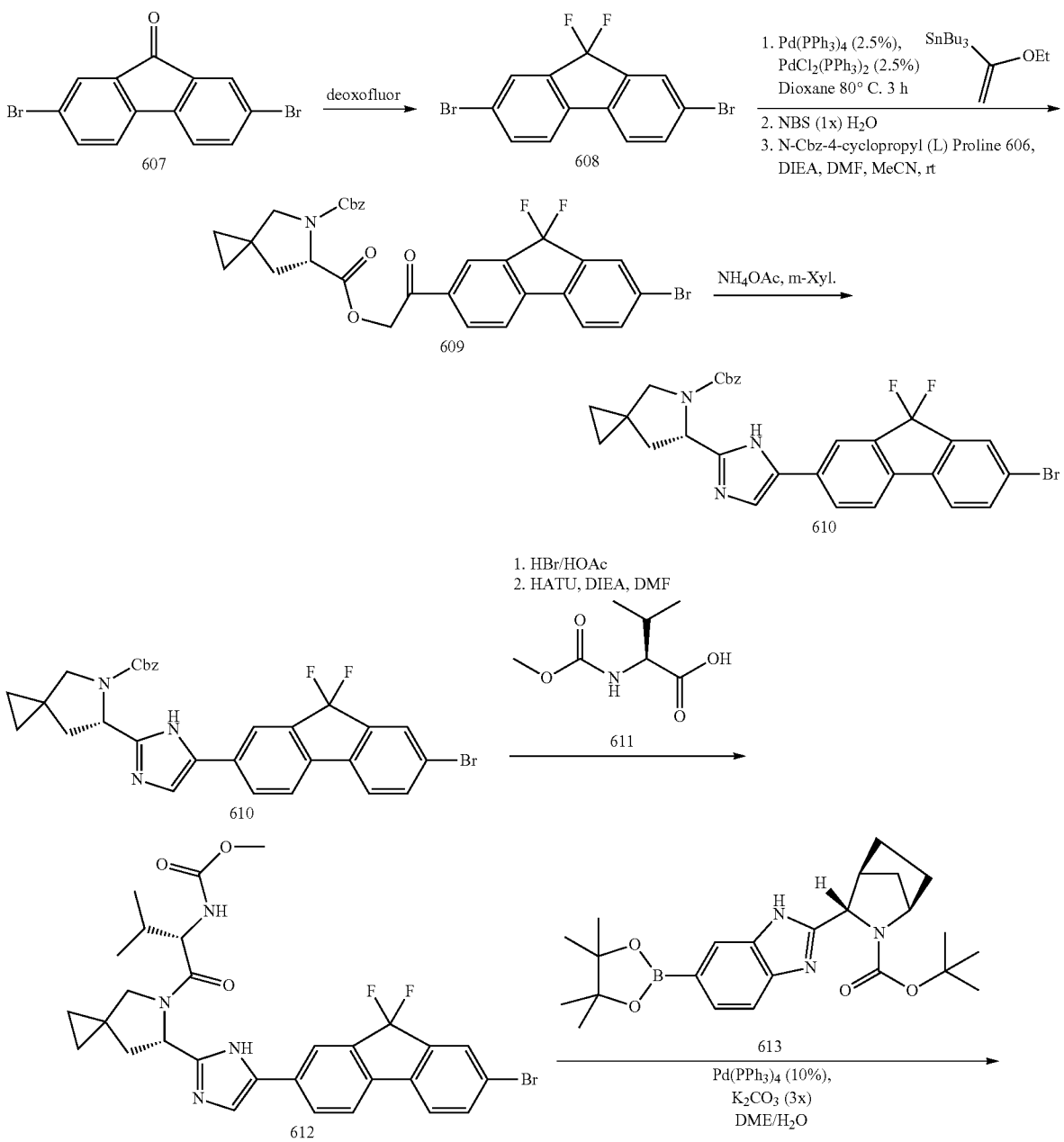

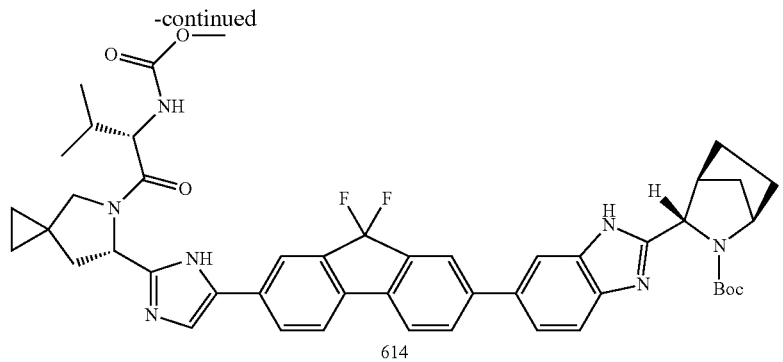

614 e. Preparation of a 2,7-Dibromo-9,9-difluoro-9H-fluorene 608

2,7-Dibromo-fluoren-9-one 607 (4.0 g, 11.8 mmol) was suspended in deoxofluor (12 mL) at room temperature and EtOH (4 drops) was added. The stirred suspension was heated at T=90° C. for 24 hours (CAUTION: Use of deoxofluor at elevated temperatures, as described above, is cautioned as rapid and violent exotherms may occur). The reaction was cooled to room temperature and poured onto ice containing sodium bicarbonate. A solid formed and was collected via filtration. The crude material was taken into EtOAc and was washed with aqueous HCl (1 M) and brine. The solution was dried over sodium sulfate. Filtration and evaporation of solvents gave crude product, which was purified by silica gel chromatography (eluent:EtOAc/hexanes) to yield 608 (3.2 g). $^{19}$F-NMR: 282 MHz, (dmso-$d_6$) δ: −111.6 ppm. Before using the material in the next step, it was exposed as a solution in EtOAc to charcoal.

f. Preparation of 5-Aza-spiro[2.4]heptane-5,6-dicarboxylic acid 5-benzyl ester 6-[2-(7-bromo-9,9-difluoro-9H-fluoren-2-yl)-2-oxo-ethyl] ester 609

2,7-Dibromo-9,9-difluoro-9H-fluorene 608 (372 mg, 1.04 mmol), Pd(PPh$_3$)$_4$ (30.0 mg, 0.026 mmol), PdCl$_2$(PPh$_3$)$_2$ (18.2 mg, 0.026 mmol), As(PPh$_3$)$_3$ (5.0 mg) were dissolved in dioxane (10 mL) under an argon atmosphere. Ethoxyvinyl-tributyl tin (376.4 mg, 1.04 mmol) was added. The mixture was heated for 140 minutes at 85° C. (oil bath). The reaction was cooled to room temperature. N-bromo succinimide (177 mg, 1.0 mmol) was added followed by water (2 mL). The reaction was stirred at room temperature for 3 hours, after which the majority of the dioxane was removed in vacuo. The crude reaction mixture was diluted with EtOAc and was washed with water. All volatiles were removed in vacuo. Toluene was added and all volatiles were removed in vacuo for a second time. The crude material was dissolved in DMF/MeCN (2 mL, 1:1) at room temperature. A solution of N-Cbz-4-cyclopropyl (L) proline 606 (0.84 mmol) and DIEA (268 mg, 2.08 mmol) in MeCN (2 mL) was added and stirring at room temperature was continued. After 14 hours, most of the MeCN was removed in vacuo and the crude reaction mixture was diluted with EtOAc. The mixture was washed with aqueous HCl (1M), aqueous LiCl solution (5%), brine, and was dried over sodium sulfate. Filtration and evaporation of solvents gave the crude reaction product, which was purified via silica gel chromatography (eluent:EtOAc/hexanes) to yield compound 609 (176 mg). LCMS-ESI$^+$: calc'd for $C_{30}H_{24}BrF_2NO_5$: 596.4 (M$^+$). Found: 595.2/597.2 (M+H$^+$).

g. Preparation of 6-[5-(7-Bromo-9,9-difluoro-9H-fluoren-2-yl)-1H-imidazol-2-yl]-5-aza-spiro[2.4]heptane-5-carboxylic acid benzyl ester 610

5-Aza-spiro[2.4]heptane-5,6-dicarboxylic acid 5-benzyl ester 6-[2-(7-bromo-9,9-difluoro-9H-fluoren-2-yl)-2-oxo-ethyl] ester 609 (172 mg, 0.293 mmol) was dissolved in m-xylenes (6.0 mL). Ammonium acetate (226 mg, 2.93 mmol) was added and the reaction was stirred at 140° C. for 60 minutes under microwave conditions. The reaction was cooled to room temperature and all volatiles were removed in vacuo. The crude material was purified via silica gel chromatography (eluent:EtOAc/hexanes) to yield compound 610 (80.3 mg). LCMS-ESI$^+$: calc'd for $C_{30}H_{24}BrF_2N_3O_2$: 576.4 (M$^+$). Found: 575.2/577.2 (M+H$^+$).

h. Preparation of (1-{6-[5-(7-Bromo-9,9-difluoro-9H-fluoren-2-yl)-1H-imidazol-2-yl]-5-aza-spiro[2.4]heptane-5-carbonyl}-2-methyl-propyl)-carbamic acid methyl ester 612

6-[5-(7-Bromo-9,9-difluoro-9H-fluoren-2-yl)-1H-imidazol-2-yl]-5-aza-spiro[2.4]heptane-5-carboxylic acid benzyl ester 610 (800 mg, 1.38 mmol) was dissolved in methylene chloride (15 mL) and HBr in AcOH (37%, 2 mL) was added and stirring at room temperature was continued. After 180 minutes, the suspension was diluted with hexanes and the solid was collected via filtration and was washed with hexanes and subjected to vacuum. The crude material was used in the next step without further purification. The crude material was dissolved in DMF (4.0 mL) and DIEA (356 mg, 2.76 mmol) was added. A solution of 2-(L)-Methoxycarbonylamino-3-methyl-butyric acid 611 (242 mg, 1.38 mmol), HATU (524 mg, 1.38 mmol) and DIEA (178 mg, 1.38 mmol) in DMF (1 mL) was added. The reaction was stirred at room temperature. After 50 minutes, the reaction was diluted with EtOAc and was washed with aqueous bicarbonate solution, aqueous LiCl solution (5%), brine, and was dried over sodium sulfate. Filtration and removal of solvents in vacuo gave the crude material, which was purified by silica gel chromatography (eluent:EtOAc/hexanes) to yield the slightly impure compound 612 (878 mg). LCMS-ESI$^+$: calc'd for $C_{29}H_{29}BrF_2N_4O_3$: 599.5 (M$^+$). Found: 598.5/600.5 (M+H$^+$).

i. Preparation of 3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carboxylic acid tert-butyl ester 614

(1-{6-[5-(7-Bromo-9,9-difluoro-9H-fluoren-2-yl)-1H-imidazol-2-yl]-5-aza-spiro[2.4]heptane-5-carbonyl}-2-methyl-propyl)-carbamic acid methyl ester 612 (840 mg, 1.4 mmol), 3-[6-(4,4,5,5-Tetramethyl-[1,3,2]dioxaborolan-2-yl)-1H-benzoimidazol-2-yl]-2-aza-bicyclo[2.2.1]heptane-2-carboxylic acid tert-butyl ester 613 (615 mg, 1.4 mmol), Pd(PPh$_3$)$_4$ (161 mg, 0.14 mmol), K$_2$CO$_3$ (579 mg, 4.2 mmol), were dissolved in DME (15 mL)/water (3 mL) under an argon atmosphere. The mixture was heated for 120 minutes at 85-90° C. (oil bath). After 120 minutes additional boronate ester (61 mg, 0.14 mmol) was added and heating was continued. After 3 hours, the reaction was cooled to room temperature. Most of the DME was removed in vacuo and the crude reaction mixture was diluted with EtOAc. The mixture was washed with brine and was dried over sodium sulfate. Filtration and evaporation of solvents gave the crude reaction product, which was purified via silica gel chromatography (eluent: EtOAc/hexanes) to yield compound 614 (878 mg). LCMS-ESI$^+$: calc'd for C$_{47}$H$_{51}$F$_2$N$_7$O$_5$: 831.9 (M$^+$). Found: 832.7 (M+H$^+$).

The intermediate compound 613 can be prepared as follows

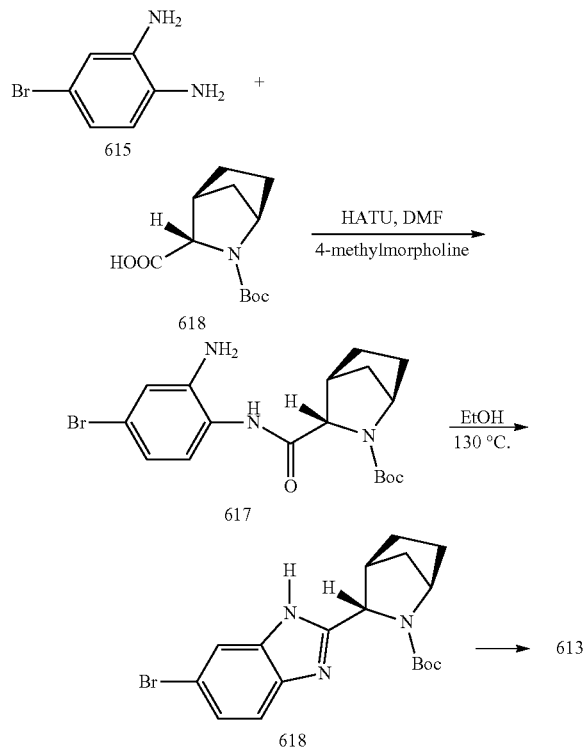

j. Preparation of 3-(2-Amino-4-bromo-phenylcarbamoyl)-2-aza-bicyclo[2.2.1]heptane-2-carboxylic acid tert-butyl ester 617

To a solution of 2-Aza-bicyclo[2.2.1]heptane-2,3-dicarboxylic acid 2-tert-butyl ester 616 (0.327 g, 1.36 mmol, 1 eq.), 4-Bromo-benzene-1,2-diamine 615 (0.507 g, 2.71 mmol, 2 eq.) and 4-methylmorpholine (0.299 mL, 2 eq.) in 10 mL DMF was added HATU (0.543 g, 1.05 eq.). The reaction mixture was stirred at room temperature for 1 hour then concentrated. The reaction mixture was diluted with ethyl acetate and washed with diluted NaHCO$_3$ aqueous solution and brine. The organic layer was concentrated down and purified by flash column chromatography (silica gel, 20 to 80% ethyl acetate/hexane) to give a mixture of regioisomer 3-(2-Amino-4-bromo-phenylcarbamoyl)-2-aza-bicyclo[2.2.1]heptane-2-carboxylic acid tert-butyl ester 617.

k. Preparation of 3-(6-Bromo-1H-benzoimidazol-2-yl)-2-aza-bicyclo[2.2.1]heptane-2-carboxylic acid tert-butyl ester 618

The above mixture of regioisomer 3-(2-Amino-4-bromo-phenylcarbamoyl)-2-aza-bicyclo[2.2.1]heptane-2-carboxylic acid tert-butyl ester 617 was dissolved in ethanol and heated to 130° C. in sealed tube overnight and continue heating at 170° C. for 3 days. LC-MS showed desired product and Boc cleaved product (about 1:1 ratio). The mixture was concentrated down and dissolved HCL. Di-tert-butyl dicarbonate (0.6 eq.) was added and reaction was stirred overnight at room temperature. The reaction mixture was concentrated down and purified by flash column chromatography (silica gel, 20 to 80% ethyl acetate/hexane) to give 3-(6-Bromo-1H-benzoimidazol-2-yl)-2-aza-bicyclo[2.2.1]heptane-2-carboxylic acid tert-butyl ester 618 (0.383 g, 72%) as an orange foam.

l. Preparation of Compound 613

A mixture of 3-(6-Bromo-1H-benzoimidazol-2-yl)-2-aza-bicyclo[2.2.1]heptane-2-carboxylic acid tert-butyl ester 618 (264 mg, 0.673 mmol), benzene-1,4-diboronic acid dipinocal ester (5 eq., 3.36 g, 6.95 mmol), tetrakis(triphenylphosphine) palladium (5%, 39 mg) and 2M potassium carbonate aqueous solution (3 eq., 1.01 mL) in 5 mL DME was heated to 90° C. under Ar for 4 hours. The reaction mixture was cooled and diluted in ethyl acetate and washed with saturated sodium bicarbonate solution. The organic layer dried (MgSO4), concentrated and purified by flash column chromatography (silica gel, 20 to 60% ethyl acetate/hexane) to give 3-{6-[4-(4,4,5,5-Tetramethyl-[1,3,2]dioxaborolan-2-yl)-phenyl]-1H-benzoimidazol-2-yl}-2-aza-bicyclo[2.2.1]heptane-2-carboxylic acid tert-butyl ester 613 (295 mg, yield 85%). LCMS-ESI$^-$: calc'd for C$_{30}$H$_{38}$BN$_3$O$_4$: 515.45. Found: 516.1 (M+H$^+$).

Compound 7 can be prepared using synthetic methods and intermediates like those described in U.S. Pat. No. 7,429,572. Compound 7 can also be prepared as described in the following Example.

Example 7

Preparation of Compound 7

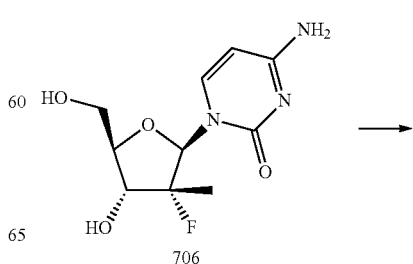

-continued

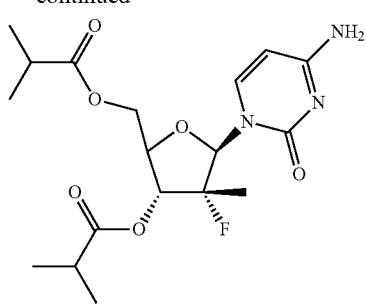

7

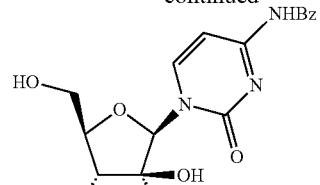

703

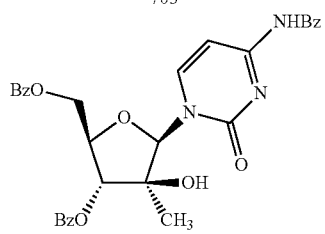

704

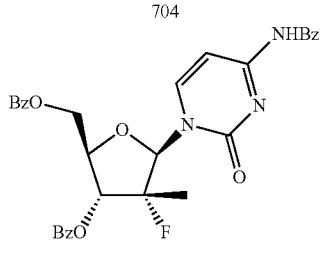

705

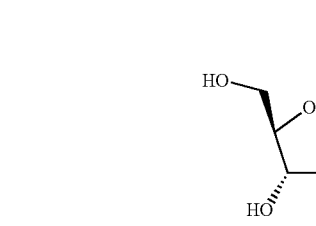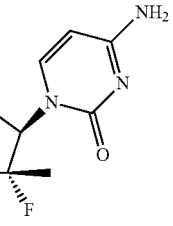

706

To an ice-cold suspension of compound 701 (970 g, 3.74 mol) and DMAP (50 g, 0.412 mol) in THF (10 L) is added TEA (2.3 kg, 16.5 mol) and water (7 L) which produces a clear solution. Isobutyryl chloride (3 equivalents) is added slowly to the stirred mixture while maintaining the temperature at about 0° C. An additional 1.2 then 0.7 equivalents of isobutyl chloride is added until the HPLC indicates the reaction had proceeded essentially to completion (a total of about 1.95 kg). The reaction mixture is acidified with concentrated HCl to a pH of about 6.4 and the organic phase is washed with EtOAc (2×10 L). The combined extracts are washed with water (1×15 L). The organic phase is filtered and concentrated in vacuo. The residue is dissolved in IPA (ca. 20 kg) and heptane (14.2 kg) is added. The solution is heated to about 74-75° C. to produce a clear solution, then about 5 L is removed by distillation. The resulting solution is cooled slowly to RT. A precipitate is formed at about 42-43° C. Cooling is continued slowly to 5° C. then stirred overnight. The resulting solid is filtered and the filtrate is washed with IPA/heptane (1:8) mixture (13.4 kg), and dried under vacuum at about 60-70° C. to afford 1.295 kg (86.65%) of compound 7 which is 99.45% pure by HPLC.

The intermediate compound 706 can be prepared as follows.

Cytidine ⟶

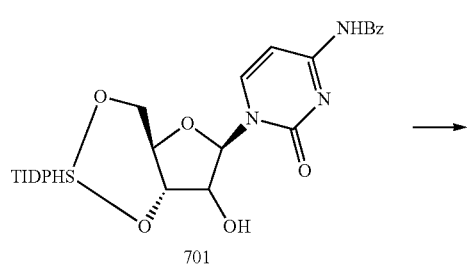

701

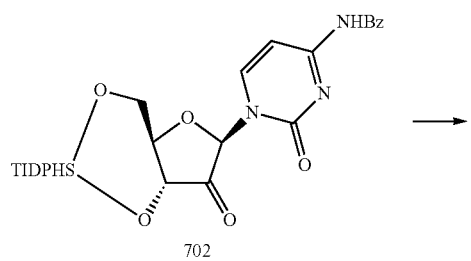

702 a. Preparation of Compound 701

To a suspension of cytidine (100 g, 0.411 mol) in DMF (2.06 L) is added benzoic anhydride (102.4 g, 0.452 mol). The mixture was stirred at room temperature for 20 hours. The DMF was removed in vacuo and the residue was triturated with diethyl ether. The resulting solid was collected by suction filtration and washed with diethyl ether (2×200 mL). Further drying in vacuo at room temperature gave the $N^4$ benzamide (140.6 g, 98.3%). A portion of this material (139.3 g, 0.401 mol) was dissolved in anhydrous pyridine (1.2 L) and was treated with 1,3-dichloro-1,1,3,3-tetraisopropyl-disiloxane (141.4 mL, 0.441 mol) at room temperature. The solution was stirred at room temperature overnight. The mixture was concentrated to near dryness in vacuo and coevaporated with toluene (3×200 mL). The residue was treated with EtOAc (1.8 L) and washed with HCl (2×200 mL, 0.05 N), NaHCO$_3$ (5%, 2×400 mL). The organic layer was washed dried (Na$_2$SO$_4$), filtered, and evaporated to dryness. Compound 701 (256.5 g, >100%) was isolated as a white foam and used without further purification.

b. Preparation of Compound 702

Compound 701 (236.5 g, 0.40 mol) was dissolved in dry THF (1.22 L). Anhydrous DMSO (180.8 mL, 2.1 mol) was added and the resulting solution was cooled to between −20° C. and −15° C. Trifluoroacetic anhydride (90.6 mL, 0.64 mol) was added dropwise over 45 minutes and the solution was stirred between −20° C. and −15° C. for 2 hrs after which anhydrous triethylamine (223.5 mL, 1.6 mol) was added over 20 minutes. The crude reaction containing ketone 702 was dissolved in EtOAc (500 mL), and the resulting solution was washed with $H_2O$ (3×400 mL), dried ($Na_2SO_4$) and the solvents were removed in vacuo to give a yellow solid that was purified on a silica gel column eluting with a stepwise gradient of $Et_2O$ (0-60%) in hexanes followed by a stepwise gradient of EtOAc (50-100%) in hexanes. The crude ketone so-obtained (~192 g) was crystallized from petroleum ether to give ketone 702 (138.91 g, 57.5% from cytidine) as a white solid and 22 g of unreacted starting material, 701, as a yellow solid.

c. Preparation of Compound 703

Compound 702 (48.57 g, 8.26 mmol) was dissolved in anhydrous toluene (~400 mL) and the solvent was removed in vacuo with exclusion of moisture. The residue was then further dried in vacuo (oil pump) for another 2 hours. With strict exclusion of moisture, the residual foam was dissolved in anhydrous diethyl ether (1.03 L) under argon. The resulting solution was cooled to −78° C. under argon and MeLi (1.6 M, 258.0 mL, 0.413 mol) was added dropwise via additional funnel. After the addition was complete, the mixture was stirred for 2 hours at −78° C. Aqueous 1M $NH_4Cl$ (500 mL) was added slowly. After warming to room temperature, the mixture was washed with $H_2O$ (2×500 mL), dried ($Na_2SO_4$), and then concentrated to dryness to give a brown foam (~60 g, >100%).

The reaction was performed two more times using 37.62 g and 56.4 g of compound 702. The combined crude products (128.0 g, 0.212 mol) were dissolved in THF (1.28 L) and treated with concd HOAc (23 mL, 0.402 mol). To the solution was added TBAF (384.0 mL, 1 M in THF). The solution was stirred at room temperature for 0.75 hours and the mixture was treated with silica gel (750 g) and concentrated to dryness. The powder was placed on a silica gel column packed in $CH_2Cl_2$. Elution with 1:7 EtOH—$CH_2Cl_2$ afforded a dark waxy solid that was pre-adsorbed on silica gel (300 g) and chromatographed as before. Compound 703 (46.4 g, 53.0% from 702) was isolated as an off-white solid. $^1H$ NMR (DMSO-$d_6$): δ 1.20 (s, 3H, $CH_3$), 3.62-3.69 (m, 2H,), 3.73-3.78 (m, 2H,), 5.19 (t, 1H, J=5.4 Hz, OH-5'), 5.25 (s, 1H, OH-2'), 5.52 (d, 1H, J=5.0 Hz, OH-3'), 5.99 (s, 1H, H-1'), 7.32 (d, 1H, J=5.8 Hz), 7.50 (ψt, 2H, J=7.7 Hz), 7.62 (ψ, 1H, J=7.3 Hz), 8.00 (d, 2H, J=7.3 Hz), 8.14 (d, 1H, J=6.9 Hz), 11.22 (s, 1H, NH). Anal. Calcd for $C_{17}H_{19}N_3O_6$.0.5 H2O: C, 55.13; H, 5.44; N, 11.35. Found: C, 55.21; H, 5.47; N, 11.33.

d. Preparation of Compound 704

Compound 703 (46.0 g, 0.13 mol) was dissolved in anhydrous pyridine and concentrated to dryness in vacuo. The resulting syrup was dissolved in anhydrous pyridine under argon and cooled to 0° C. with stirring. The brown solution was treated with benzoyl chloride (30 mL, 0.250 mol) dropwise over 10 minutes. The ice bath was removed and stirring continued for 1.5 hours whereby TLC showed no remaining starting material. The mixture was quenched by the addition of water (5 mL) and concentrated to dryness. The residue was dissolved in a minimal amount of $CH_2Cl_2$ and washed with satd $NaHCO_3$ (1×500 mL) and $H_2O$ (1×500 mL). The organic phase was dried ($Na_2SO_4$) and filtered, concentrated to dryness and chromatographed on silica gel eluting with a stepwise gradient of EtOAc-hexanes (25-60%) to provide compound 704 as yellow foam (48.5 g, 67%). $^1H$ NMR (CDCl$_3$): δ 1.64 (s, 3H, $CH_3$), 4.50 (m, 1H, H-4), 4.78-4.85 (m, 2H, H-5',5a'), 5.50 (d, 1H, J=3.4 Hz, H-3'), 6.42 (s, 1H, H-1'), 7.44-7.54 (m, 7H, Ar), 7.57-7.66 (m, 3H, Ar), 7.94 (d, 2H, J=7.8 Hz), 8.05-8.09 (m, 4H, Ar), 8.21 (d, 1H, J=7.3 Hz). Anal. Calcd for $C_{31}H_{27}NO_8$: C, 65.37; H, 4.78; N, 7.38. Found: C, 65.59; H, 4.79; N, 7.16.

e. Preparation of Compound 705

Compound 704 (7.50 g, 0.013 mol) was dissolved in anhydrous toluene (150 mL) under argon and cooled to −20° C. DAST (2.5 mL, 18.9 mmol) was added slowly and the cooling bath was removed after the addition was complete. Stirring was continued for 1 hours and the mixture was poured into satd $NaHCO_3$ (100 mL) and washed until gas evolution ceased. The organic phase was dried (Na2SO4), concentrated, and purified by silica gel chromatography eluting with 1:1 EtOAc-hexanes. Yield was 1.22 g (16.3%) of pure 705 as a white solid. mp 241° C. ($CH_2Cl_2$-hexanes); $^1H$ NMR (CDCl$_3$)): δ 1.49 (d, 3H, J=22.4 Hz, $CH_3$), 4.64 (dd, 1H, J=3.44, 12.9 Hz, H-5'), 4.73 (d, 1H, J=9.5 Hz, H-4'), 4.90 (dd, 1H, J=2.4, 12.7 Hz, H-5a'), 5.56 (dd, 1H, J=8.6, 20.7 Hz, H-3'), 6.52 (d, 1H, J=18.0 Hz, H-1'), 7.47-7.57 (m, 7H, Ar), 7.62-7.71 (m, 3H, Ar), 7.89 (d, 2H, J=6.9 Hz), 8.07-8.11 (m, 5H, Ar), 8.67 (bs, 1H, NH). $^{19}F$ NMR (CDCl$_3$)): δ 3.3 (m). Anal. Calcd for $C_{31}H_{26}FN_3O_7$.0.7 $H_2O$: C, 63.74; H, 4.72; N, 7.20. Found: C, 63.71; H, 4.54; N, 7.20.

f. Preparation of Compound 706

Compound 705 (6.30 g, 0.011 mol) was suspended in methanolic ammonia (ca 7 N, 150 mL) and stirred at room temperature overnight. The solvent was removed in vacuo, co-evaporated with methanol (1×20 mL), and pre-adsorbed onto silica gel. The white powder was placed onto a silica gel column (packed in CHCl$_3$) and the column was eluted with 9% EtOH in CHCl$_3$), then 17% EtOH and finally 25% EtOH in CH Cl$_3$). Concentration of the fractions containing the product, filtration through a 0.4 μm disk, and lyophilization from water afforded compound 706, 2.18 g (76%). $^1H$ NMR (DMSO-$d_6$): δ 1.17 (d, 3H, J=22.3 Hz, $CH_3$), 3.63 (dd, 1H, J=2.7, 13.7 Hz, H-5'), 3.70-3.84 (m, 3H, H-3', H-4', H-5a'), 5.24 (app s, 1H, OH-3'), 5.60 (d, 1H, J=5.4 Hz, H-5'), 5.74 (d, 1H, J=7.71 Hz, H-5), 6.07 (d, 1H, J=18.9 Hz, H-1'), 7.31 (s, 1H, NH2), 7.42 (s, 1H, NH2), 7.90 (d, 1H, J=7.3 Hz, H-6). $^{19}F$ NMR (DMSO-$d_6$): δ 2.60 (m). Anal. Calcd for $C_{10}H_{14}FN_3O_4$.1.4 $H_2O$: C, 44.22; H, 5.95; N, 14.77. Found: C, 42.24; H, 5.63; N, 14.54. Compound 706 (0.10 g, 0.386 mmol) was converted to the hydrochloride salt by dissolving in water (2 mL) and adjusting the pH to approximately 3.0 with 1 M HCl. The water was removed in vacuo and the residue was crystallized from aqueous EtOH to give Compound 706 as the hydrochloride salt (71.0 mg). mp 243° C. (dec); $^1H$ NMR (DMSO-$d_6$): δ 1.29 (d, 3H, J=22.6 Hz, $CH_3$), 3.65 (dd, 1H, J=2.3, 12.7 Hz, H-5'), 3.76-3.90 (m, 3H, H-3', H-4', H-5a'), 5.96 (d, 1H, J=17.3 Hz, H-1'), 6.15 (d, 1H, J=7.9 Hz, H-5), 8.33 (d, 1H, J=7.9 Hz, H-6), 8.69 (s, 1.5H, NH), 9.78 (s, 1.5H, NH). $^{19}F$ NMR (DMSO-$d_6$): δ 1.69 (m). Anal. Calcd for $C_{10}H_{14}FN_3O_4$.HCl: C, 40.62; H, 5.11; N, 14.21. Found: C, 40.80; H, 5.09; N, 14.23.

Compound 8 can be prepared using synthetic methods and intermediates like those described in U.S. Ser. No. 12/632,194. Compound 8 can also be prepared as described in the following Example.

Example 8

Preparation of 4-amino-2-n-butoxy-8-[3'-(pyrrolidin-1''-ylmethyl)-benzyl]-5,6,7,8-tetrahydropteridin-6-one 8. (R=n-butyl)

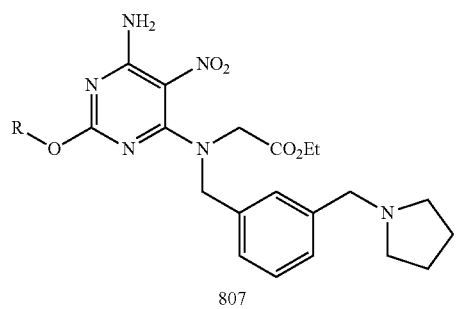

To a solution of nitro compound 807 (730 mg, 1.5 mmol) in MeOH (10 mL) was added a Raney Nickel (—200 μL, slurry in H₂O). The reaction vessel was flushed with H₂ and then stirred under an H₂ atmosphere for 1.5 hours. The mixture was filtered through celite with CH₂Cl₂ and MeOH (1:1). The filtrate was concentrated under vacuum and left on lyophilizer overnight. The free base of compound 8 was obtained as a white solid. To obtain the HCl salt of 8, a sample of the filtrate above was spiked with 1.0 M HCl to pH=1-2 and lyophilized. $^1$H NMR (CD₃OD, 300 MHz): δ 7.65 (s, 1H), 7.50 (m, 3H), 4.96 (s, 2H), 4.44 (t, J=7 Hz, 2H), 4.40 (s, 2H), 4.16 (s, 2H), 3.48 (m, 2H), 3.19 (m, 2H), 2.02-2.17 (m, 4H), 1.74 (m, 2H), 1.45 (m, 2H), 0.94 (t, J=7 Hz, 3H)—[HCl salt]. LCMS-ESI⁺: calc'd for $C_{22}H_{31}N_6O_2$: 411.5 (M+H⁺). Found: 411.3 (M+H⁺).

The intermediate compound 807 was prepared as follows.

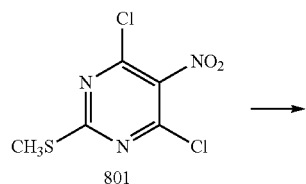

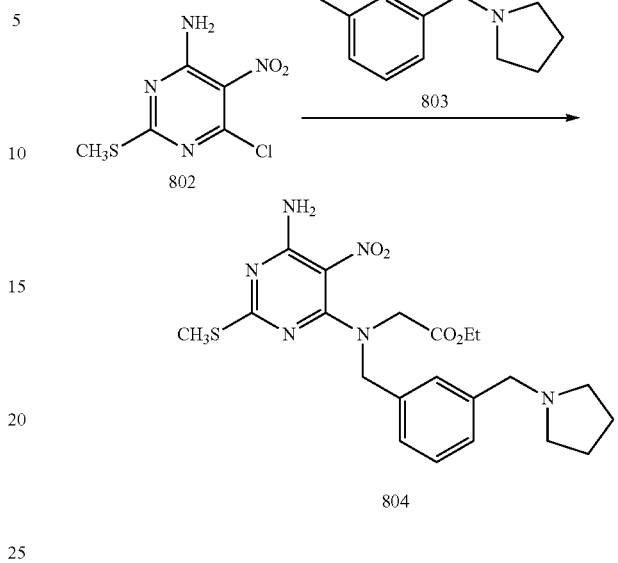

a. Preparation of Compound 802

To a solution of compound 801 (2.46 g, 10.2 mmol) in THF (34 mL) at −20° C. was added Et₃N (3.14 mL, 22.5 mmol) followed by a solution of NH₃ (2.0 M in MeOH, 5.4 mL, 11 mmol). The mixture was stirred while warming to 0° C. for 1.5 h (LC/MS indicated consumption of starting materials). The reaction mixture containing compound 802 was taken forward without work-up.

b. Preparation of Compound 803

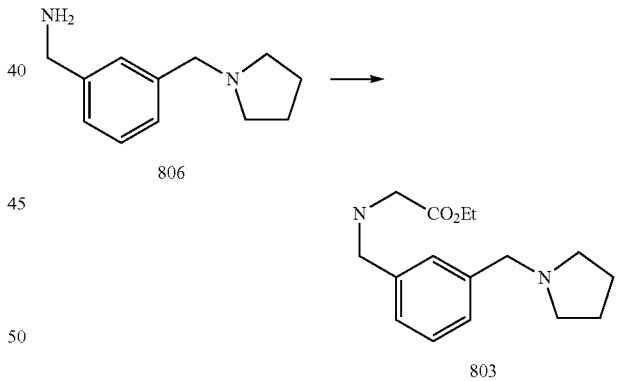

To a solution of 3-((1-pyrrolidinylmethyl)phenyl)methanamine 806 (1.95 g, 10.2 mmol) in THF (34 mL) at 0° C. was added Et₃N (3.14 mmol, 22.5 mmol) followed by methyl bromoacetate (1.04 mL, 22.3 mmol) dropwise. The reaction mixture was stirred until LC/MS indicated consumption of starting materials, approximately 2 hours. The mixture containing compound 803 was taken forward without work up.

c. Preparation of Compound 804

The reaction mixture containing compound 803 was added to the reaction mixture containing compound 802 at 0° C. The reaction mixture was stirred until LC/MS indicated the consumption of compound 802, approximately 45 minutes. A saturated solution of NH₄Cl (50 mL) was added. The layers were separated, and the aqueous layer was extracted with EtOAc (2×30 mL). The combined organic layers were dried over MgSO$_4$, filtered, and concentrated under vacuum. Purification by silica gel chromatography provided 2.11 g of compound 804. $^1$H NMR (CD$_3$OD, 300 MHz): δ (ppm) 7.32-7.16 (m, 4H), 4.69 (s, 2H), 4.19 (q, J=7 Hz, 2H), 4.07 (s, 2H), 3.60 (s, 2H), 2.49 (m, 4H), 2.40 (s, 3H), 1.78 (m, 4H), 1.23 (t, 3H, J=7 Hz). LCMS-ESI$^+$: calc'd for C$_{21}$H$_{29}$N$_6$O$_4$S: 461.2 (M+H$^+$). Found: 461.0 (M+H$^+$).

d. Preparation of Ethyl-N$_\alpha$-[4-amino-2-methanesulfonyl-5-nitropyrimidin-6-yl],N$_\alpha$-[3'-(pyrrolidin-1"-ylmethyl)-benzyl]-glycinate 805

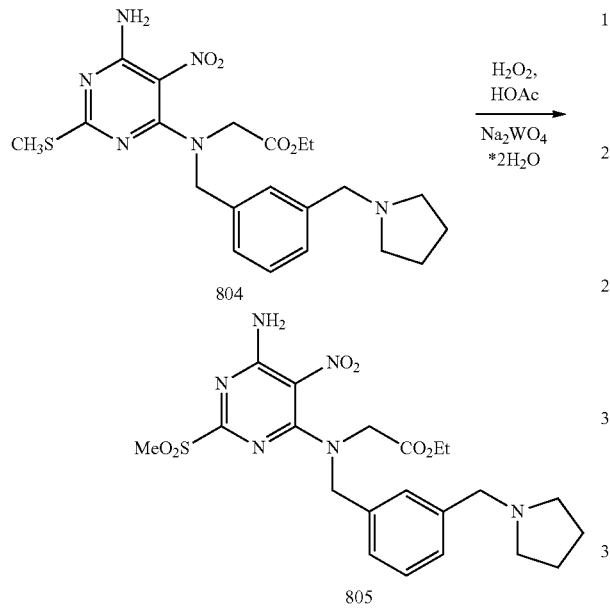

To a solution a suspension of the sulfide 804 (3.68 g, 8.00 mmol) in EtOH (40 mL) at 0° C. was added sodium tungstate dihydrate (792 mg, 2.40 mmol), acetic acid (4.6 mL, 80 mmol), and hydrogen peroxide (3.4 mL, ~40 mmol, 35% w/w in H$_2$O) sequentially. After 3 hours, additional acetic acid (4.6 mL) and hydrogen peroxide (3.4 mL) were added. The reaction was maintained at 0° C. for 16 hours. A saturated solution of Na$_2$SO$_3$ (50 mL) was added carefully while at 0° C. followed by CH$_2$Cl$_2$ (75 mL). The layers were separated, and the aqueous layer was extracted with CH$_2$Cl$_2$ (4×50 mL). The combined organic layers were dried over MgSO$_4$, filtered, and concentrated under vacuum to provide a material containing compound 805 that was used without further purification.

e. Preparation of Compound 807. (R=n-butyl)

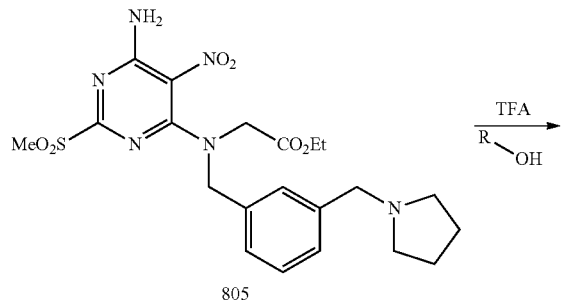

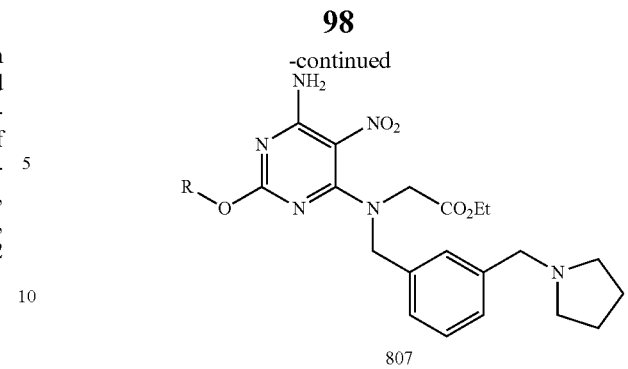

To a solution of sulfone 805 (1.0 g, 2.0 mmol) in n-butanol (10 mL) was added TFA (470 µL, 6.1 mmol). The reaction was stirred at 100° C. for 1 hour. The reaction mixture was poured onto a saturated solution of NaHCO$_3$ (20 mL) and CH$_2$Cl$_2$ (30 mL). The layers were separated, and the aqueous layer was extracted with CH$_2$Cl$_2$ (30 mL). The combined organic layers were dried over MgSO$_4$, filtered, and concentrated under vacuum. Purification was conducted by silica gel chromatography (1 g substrate/10 g SiO$_2$) (2-15% MeOH/CH$_2$Cl$_2$) to provide compound 807.

Example 9

Preparation of Compound 9 (from US2010/0298257)

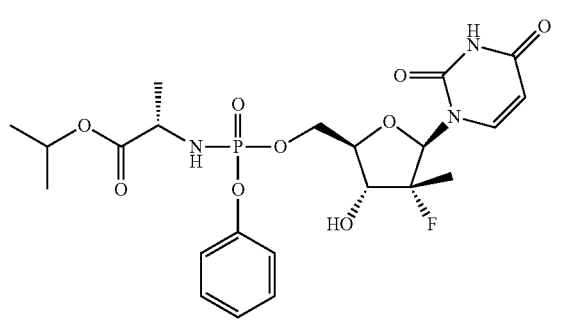

Preparation of (S)-2-{[(1R,4R,5R)-5-(2,4-Dioxo-3,4-dihydro-2H-pyrimidin-1-yl)-4-(R)-fluoro-3-hydroxy-4-methyl-tetrahydro-furan-2-yl-methoxy]-phenoxy-phosphorylamino}-propionic acid isopropyl ester (from US2010/0298257 Example 2)

Synonym: 5'-O-(Isopropyl-L-alanate, phenyl phosphoramidyl)-2'-deoxy-2'-fluoro-2'-C-methyl-uridine diastereomeric mixture.

A 5 L 3-necked flask was fitted with a mechanical stirrer, brine ice bath, internal thermometer, and a nitrogen atmosphere. The flask was charged with L-alanine isopropyl ester hydrochloride (82.0 g, 0.490 moles) and anhydrous dichloromethane (0.80 L). While this was stirring, phenyl dichlorophosphate (85.0 g, 0.40 moles) was added in one lot and stirred. While maintaining the internal temperature between −5 to 5° C., a solution of N-methylimidazole (NMI, 250 g, 3.07 moles) in dichloromethane (250 mL) was added over a period of a half hour. The solution was allowed to stir for 1 h in this temperature range. 2'-Deoxy-2'-fluoro-2'-C-methyluridine (3, 80.0 g, 0.307 moles) was added at 0° C. in one portion and then the reaction flask was allowed to warm up slowly in the brine bath. At 1 h, the internal temperature was up to −2° C. TLC (5% Methanol in HCL) at 1 h showed that more than 50% of nucleoside was consumed. The bath was removed and the reaction flask reached ambient temperature over 1 h more. TLC after 3 h and at 5 h total showed 95% of the starting nucleoside was consumed. The reaction mixture was quenched by adding methanol (100 mL) and stirring the reaction for 5 minutes. The reaction mixture was washed with 1N HCl (2×500 mL) followed by saturated sodium bicarbonate solution (2×500 mL). The separated organic layer was dried over anhydrous sodium sulfate (50 g) and filtered. The solution was evaporated under reduced pressure and then under high vacuum to dryness to give the crude product as a viscous oil (170 g). NMRs of the crude product ($^{31}$P and $^1$H) were taken. The $^{31}$P-NMR indicated about 1% of the total phosphorus integration was due to the presence of the 3' isomer 5.

To the crude product was added anhydrous pyridine (1700 mL). The solvent was evaporated under reduced pressure and then under high vacuum in order to reduce the water content of the crude mixture through co-evaporation. The resulting oil was re-dissolved in anhydrous pyridine (500 ml) and then was added excess t-butyldimethylsilyl chloride (9.0 g, 60 mM). The reaction was stirred at ambient temperature. Reaction progress was monitored by UPLC/MS.

After 3 hours, the 3' impurity 5 could no longer be detected and the reaction was quenched by the addition of methanol (50 mL).

The reaction was evaporated under reduced pressure to an oil. The residue was dissolved in ethyl acetate (1.5 L) and washed with 1N HCl (2×500 mL), followed by saturated sodium bicarbonate solution (2×500 mL). The organic layer was dried over anhydrous sodium sulfate (50 g), filtered and evaporated under reduced pressure to give the crude product as a pale yellow oil.

The crude oil was diluted with the same volume of dichloromethane and loaded onto a 2.5 Kg silica gel cartridge n a radial compression module at 100 psi of air pressure. Using a gradient pump at 60 psi and a flow rate of 400 ml/min, the cartridge was washed with methylene chloride (4 L) followed by a gradient 1-4% methanol in methylene chloride (48 L). Most of the major impurities (di-(isopropylalanyl)phenyl phosphate, 3',5'-bis phosphoramidate, 3'-phosphoramidate-5'-TBDMS adduct (7)) eluted with ~3% gradient. The desired product eluted between 3 and 4% methanol. The product containing fractions were sorted into two lots. The first contained small amounts of upper impurities and the latter was pure product. The first set of fractions contained small amounts of less polar impurities (upper impurities) such as the 3',5'-bis phosphoramidate and the di-alanylphenyl phosphate and a mostly the Rp diastereomer and required a second column purification. (The relative terminology, upper vs. lower refers to the elution on normal phase silica-gel chromatography, where the "upper isomer" means the first eluting isomer.) The second set of fractions did not have a significant amount of impurities-just the remaining Rp and mostly the Sp diasterereomers. It was later recombined with the twice-columned fractions. The solvent was evaporated under reduced pressure and the resulting white foam was further dried (0.20 mmHg) for 1 h to give 42 g of the impure lot (4:1 upper vs lower isomer based on $^{31}$P-NMR) and 38 g of the pure lot (1:3 upper vs lower isomer). The impure lot was recolumned in a similar manner to give 3.8 g of 97% pure upper isomer (fraction set aside) and 36 g of pure product in a 4:1 ratio. The two main lots were dissolved in HCL, combined, evaporated under reduced pressure and dried (50° C., 0.2 mmHg, 24 h) to get 74 g (45.7%) of pure product (Compound 9) with a diastereomeric ratio of 48:51, as a white foam, mp about 75-85° C.

In order to produce an amorphous solid of the diastereomeric mixture, 74 g of the white foam was stirred in with t-butyl methyl ether (750 mL) resulting in a partial solution and a gummy solid residue. While stirring, heptanes (750 mL) was added slowly and the suspension was mechanically stirred for 1 hour until most of the gum was converted to a white solid. The solid was scraped up with a spatula and the resulting slurry was filtered. The solid was washed with heptanes (4×50 mL) and dried under vacuum (50° C., 0.2 mmHg, 24 h) to give a white, amorphous powder (64 g) with a broad melting range of ca 70-80° C. $^1$H and $^{31}$P NMR conformed to structure and HPLC showed a purity of 99.8% with a diastereomeric ratio of 46:54 (also confirmed by $^{31}$P NMR).

Alternative method to make a solid mixture of Compound 9. After chromatography, the residue was co-evaporated with dichloromethane twice (5 mL/g) and dried for 24 h at 35-40° C. at 35-45 mTorr. The foam residue was sieved through a 250 micron screen and further dried under the same conditions until the residual dichloromethane fell below 400 ppm as measured by headspace GC. The resulting fine off-white to white amorphous powder has a glass transition temperature range of 53.7 to 63.5° C.

Characterization of Compound 9 (Mixture of Isomers):
$^1$H-NMR (CDCl$_3$) 010.05 (brs, 1H, NH, Sp), 10.00 (brs, 1H, NH, Rp), 7.49 (d, 1H, C6-H, Sp), 7.36 (m, 5H, C6-H, Rp, aromatic), 7.23-7.14 (m, 6H, Rp/Sp, aromatic), 6.18 (br d, 2H, Cl'—H, Rp/Sp), 5.63 (d, 1H, C5-H, Sp), 5.58 (d, 1H, C5-H, Rp), 5.01 (m, 2H, CH—(CH3)$_2$ Rp/Sp), 4.46-4.33 (m, 8H, C-5'-H$_2$, ala-NH, C3'-OH, Rp/Sp), 4.12 (m, 2H, ala-CHCH$_3$, Rp/Sp), 4.01-3.85 (m, 4H, C3'-H, C4'-H, Rp/Sp), 1.391.22 (m, 12H, all CH$_3$, Rp/Sp). $^{31}$P-NMR (CDCl$_3$) 03.60 (Rp), 3.20 Sp relative to triphenylphosphate at −17.80 ppm. ES-MS M+1 530.2. Elemental Analysis: Calculated % (including 0.29% water as found by Karl Fisher analysis) C, 49.75; H, 5.54; N, 7.90; F, 3.58; P, 5.84. Found %: C, 49.50; H, 5.44; N, 7.85; F, 3.62; P, 6.05.

Preparation of 2'-deoxy-2'-fluoro-2'-C-methyluridine (from US2010/0298257 Example 1) In a 10 L flask, was added 3',5'-O-dibenozyl-2'deoxy-2'-fluoro-2'-C-methyl-N4-benzoylcytidine (500 g, 0.874 mol) and 70% aqueous acetic acid (7.5 L). The solution was heated to reflux (110° C.) for 20 h. TLC indicated a complete reaction (RfO.6 in 5% methanol in dichloromethane (HCL)). The mixture was cooled to ambient temperature and diluted with water (2 L). After stirring for 2 h, the resulting precipitate was collected by filtration and the solid was rinsed with water (5 L) and dried in the atmosphere at ambient temperature for 12 h to afford 360 g (88%). This dibenzoyluridine intermediate was used directly in the next step by adding it all to freshly prepared methanolic ammonia (5.4 L, ca 25%) at 0° C. This temperature was maintained for 3 h and then allowed to warm to 15° C. for 24 h. TLC indicated a complete reaction (Rf 0.4 in 10% methanol in HCL). The reaction mixture was filtered through a Celite bed and concentrated under reduced pressure to give the crude product (216 g). The crude product was stirred with ethyl acetate (325 mL) for 3 h at ambient temperature. The resulting solid was collected by filtration and washed with ethyl acetate (216 mL). The solid was dried under vacuum at ambient temperature for 4 h to afford 160 g (78%) of the desired product in 98.7% HPLC purity. 1H-NMR (DMSO-d6) 011.44 (br s, 1H, NH), 7.95 (d, 1H, C-6H), 5.97 (d, 1H, C-1'H), 5.64 (d, 1H, C-5H), 3.84-3.77 (m, 3H, C-5'-Ha, C-3'H. C-4'H), 3.63-3.60 (m, 1H, C5'-Hb), 1.23 (d, 3H, C-2'-CH3). ES-MS M-I 259.

Example 10

Preparation of Compound 10 (from US2010/0298257)

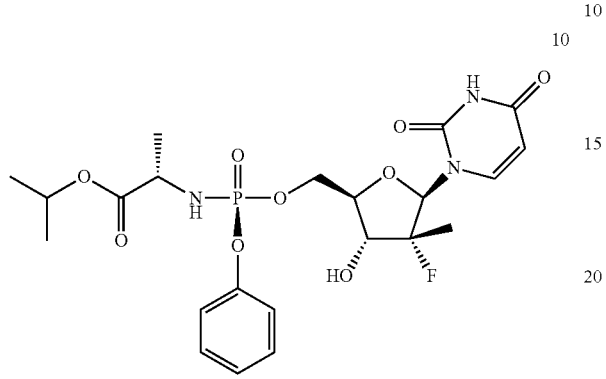

Direct precipitation of Compound 10 (from US2010/ 0298257; Example 4): To a stirred solution of L-alanine isopropyl ester hydrochloride (10.5 g, 61.5 mmol, azeotropically dried, two times, with 50 mL of toluene each time) in dichloromethane (100 mL) was added phenydichlorophosphate (7.5 mL, 50 mmol) at room temperature. The mixture was cooled to −10° C. and then was added a solution of N-Methylimidazole (30.5 mL, 384.3 mmol) in 30 mL of dichloromethane over a period of 30 min. After completion of the addition, the mixture was stirred between −10 and −15° C. for 1 h. To the above mixture was added 2'-deoxy-2'-fluoro-2'-C-methyluridine (10 g, 38.4 mmol) (see US2010/0298257 Example 1) in one lot and the mixture was stirred below −10° C. for 3 h and then slowly allowed to warm to 20° C. (6 h). The mixture was stirred at this temperature overnight (15 h) and then quenched with 10 mL of methanol. The solvent was evaporated and the residue was re-dissolved in EtOAc (200 mL). The EtOAc layer was washed with water (100 mL), 1N HCl (3×75 mL), 2% aqueous $NaHCO_3$ solution (50 mL) and brine (50 mL). The organic layer was dried over $Na_2SO_4$, filtered and concentrated. The residue was dried under high vacuum for 2 h to give white foam (22 g).

The above foam was dissolved in 33 mL of HCl and then was added 65 mL of isopropyl ether to give a saturated solution. The solution was filtered though a small pad of Celite and the filtrate was stirred with seeds of Compound 10 for 72 h at ambient temperature (about 22° C.-note that cooling the suspension to 0° C. led to oiling out the crude product). The white solid was filtered, washed with isopropyl ether (20 mL) and dried to give 4.58 g (85:15 mixture of Compound 10: R isomer at P respectively as determined by $^{31}P$ NMR) of a white powder. The above solid was suspended in 23 mL of HCL and then refluxed for 3 h. The mixture was cooled to room temperature and stirred for 15 h. The white solid was filtered, washed with 4.5 mL of cold HCl and dried under high vacuum at 45° C. to give pure Compound 10, mp 93.9-104.7° C. HPLC purity 99.74% (3.11 g, 15.2% from the uridine nucleoside).

Compound 10:

$^1$H-NMR (CDCl$_3$) δ 8.63 (br s, $^1$H, NH), 7.47 (d, 1H, C6-H), 7.30 (m, 2H, o-aromatic), 7.26-7.18 (m, 3H, m, p-aromatic), 6.18 (br d, IH, Cl'—H), 5.70 (d, IH, C5-H), 5.02 (sept, CH—(CH$_3$)$_2$), 4.53 (m, 2H, C-5-H$_2$), 4.11 (d, IH, C3'-H), 3.97 (m, 3H, C3'-OH, C4'-H, ala-CH—CH$_3$), 3.77 (br s, IH, ala-NH), 1.39 (d, 3H, C2'-CH$_3$), 1.37 (d, 3H, ala-CH$_3$) 1.24 (d, 6H, CH—(CH$_3$)$_2$).

Example 11

Preparation of Compound 11 (from US 2010/0081628)

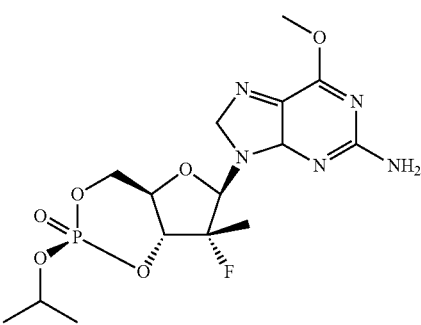

Synthesis of 6-Ethoxy-9-((4aR,6R,7R,7aR)-7-fluoro-2-isopropoxy-7-methyl-2-oxo-tetrahydro-2,5-furo[3,2-d][1,3,2]dioxaphosphinin-6-yl)-9H-purin-2-yl-amine (Compound 11) (Compound 19, US 2010/0081628)

(2R,3R,4R,5R)-5-(2-Amino-6-ethoxy-purin-9-yl)-4-fluoro-2-hydroxymethyl-4-methyl-tetrahydro-furan-3-ol (150 mg, 0.46 mmol) was dissolved in anhydrous pyridine (2 ml) at 0° C. A solution of 0.45 M IH-tetrazole in acetonitrile (2.55 mL) was added followed by bis(N,N-diisopropylamino) ispropylphosphoramidite (0.16 mL, 0.55 mmol, 1.2 eq). The mixture was allowed to slowly warm to ambient temperature over 3 h. TLC indicated a complete reaction. The reaction was quenched upon the addition of water (0.1 mL). The reaction solution was concentrated under reduced pressure and then the residue was triturated with ethyl acetate (5 mL). The resulting white precipitate was removed by filtration and the filtrate was concentrated under reduced pressure.

The resulting intermediate cyclic phosphite residue was dissolved in acetonitrile (2 mL) and then treated with t-butyl hydroperoxide (70% in water, 0.19 mL) for 5 h at ambient temperature. TLC indicated a complete reaction. The reaction solution was concentrated under reduced pressure and the residue was purified by column chromatography (Analogix using a gradient of 0 to 5% IPA in HCL). The two diastereomers (Compound 11 and R-isomer at P) were separable. Fractions containing each diastereomer were separately combined and concentrated under reduced pressure to white solids to give 20 mg of each diastereomer (combined yield 20%).

Compound 11

$^{31}P$_NMR (162 MHz, DMSO): δ-6.49;

$^1$H-NMR (400 MHz, DMSO): δ=8.17 (s, 1H), 6.47 (bs, 2H), 6.27 (d, J=21.2 Hz, 1H), 4.73-4.62 (m, 4H), 4.45 (q, J=7.0 Hz, 2H), 4.27-4.21 (m, 1H), 1.39-1.34 (m, 9H), 1.20 (d, J=22.8 Hz, 3H). MS (ESI): m/z 432.4 [M+H]$^+$

R-Isomer at P $^{31}P$_NMR (162 MHz, DMSO): δ=−4.68;

$^1$H-NMR (400 MHz, DMSO): δ=8.15 (s, 1H), 6.63 (s, 2H), 6.27 (d, J=21.2 Hz, 1H), 4.74-4.58 (m, 4H), 4.45 (q, J=6.4 Hz, 2H), 4.42-4.37 (m, 1H), 1.36 (t, J=7.2 Hz, 3H), 1.32 (d, J=3.6 Hz, 3H), 1.30 (d, J=3.6 Hz, 3H), 1.22 (d, J=22.8 Hz, 3H).

MS (ESI): m/z 432.4 [M+H]$^+$

The structures for Compound 11 and the R-Isomer at P are represented below.

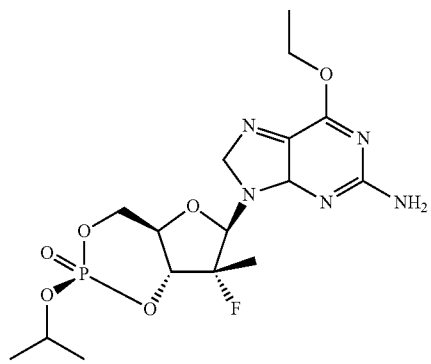

11

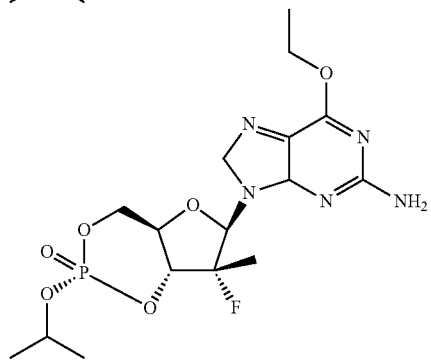

R-isomer at P

Synthesis of (2R,3R,4R,5R)-5-(2-amino-6-ethoxy-9H-purin-9-yl)-4-fluoro-2-(hydroxymethyl)-4-methyltetrahydro-furan-3-ol (Compound 16, US 2010/0081628)

To a 500 mL of dry round-bottomed flask was loaded (2R,3R,4R,5R)-5-(2-amino-6-chloro-9H-purin-9-yl)-2-(benzoyloxymethyl)-4-fluoro-4-methyltetrahydrofuran-3-yl benzoate (11 g, 20.92 mmol). Anhydrous absolute ethanol (210 mL) was added and followed by anhydrous K$_2$CO$_3$ (28.91 g, 209.2 mmol). The suspension was stirred and heated at 75° C. under nitrogen for 5.5 h. All the starting material was consumed at that time by TLC test. The mixture was cooled to room temperature and solid was filtered out. The filtrate was neutralized by addition of glacial acetic acid (2.52 g) to pH-7 and concentrated under reduced pressure. The residue was dissolved in methanol and mixed with silica gel (15 g). The dried mixture of crude product and silica gel was transferred to an empty cartridge and separated through column chromatography (Analogix 220 g, gradient of 0 to 15% MeOH in DCM) to afford product (5% MeOH in DCM) as a white foam solid (3.73 g, 54.5%). A second white solid was isolated from column (10% MeOH in DCM, 1.44 g) and it is a mixture of two dimers of nucleoside. A more polar, third white solid was collected from column (15% MeOH in DCM, 0.47 g) and it is a mixture of trimers of nucleoside. HPLC purity of product 99.94%.

$^1$H-NMR (DMSO-d6): δ 8.16 (s, IH, 8-H), 6.55 (s, 2H, NH$_2$), 6.04 (d, IH, C1'-H), 5.66 (d, IH, 3'-OH), 5.24 (m, IH, 5'-OH), 4.44 (q, 2H, 6-OCH$_2$), 4.23-4.08 (m, IH, C3'-H), 3.91-3.82 (m, 2H, C4'-H and C5'-H$_a$,), 3.71-3.66 (m, IH, C5'-Hb), 1.36 (t, 3H, CH$_3$ of ethyl), 1.06 (d, 3H, C2'-CH$_3$).

Synthesis of (2R,3R,4R,5R)-5-(2-amino-6-chloro-9H-purin-9-yl)-2-(benzoyloxymethyl)-4-fluoro-4-methyltetrahydrofuran-3-yl benzoate (Compound 12, US 2010/0081628)

To a 12 L of three-neck round-bottomed flask was charged 6-chloro-2-aminopurine (225.4 g, 1.329 mol). Anhydrous tert-BuOH (4.5 L) was added and the solution was stirred with a mechanical stirrer at ambient temperature. Potassium tert-butoxide (solid, 151.6 g, 1.35 mol) was added portion-wise under a flow of nitrogen gas while stirring. The mixture was stirred at RT for an additional 30 min. To a 5 L round-bottomed flask was loaded the α-bromide (10, 197 g, 0.451 mol) and 3 L of anhydrous acetonitrile at ambient temperature. The bromide solution was added to the purine base suspension over 1 min at ambient temperature. The 5 L flask was rinsed with acetonitrile (2×1 L) to transfer bromide completely to the reaction mixture. The mixture was heated gradually to 50° C. over 2 h with a heating mantle and controller, and stirred for 20 h. The reaction was almost complete as shown by TLC beta (R, 0.28, 30% EtOAc in hexanes). The reaction was quenched by the addition of sat. NH4Cl (200 mL) to form a suspension. The suspended solid was removed by filtration through a 3 cm pad of Celite in a 2.5 L porcelain Buchner funnel. The solid was washed with toluene (3×100 mL). The combined filtrate was neutralized by adding 6 N HCl solution until pH 7 (approx 220 mL). The mixture was concentrated under reduced pressure. When the volume of mixture was reduced to about one-third volume, additional precipitated solid was removed by filtration in a similar manner. The filtrate was further concentrated to a volume of about 800 mL. The residue was loaded onto a plug column (1.6 kg flash grade silica gel in a 6 L sintered glass Buchner funnel) and eluted (via suction) with a gradient of 10% ethyl acetate in hexanes (6 L) to remove non-polar impurities, 30% ethyl acetate in hexanes to afford a small amount of lactol (6 L), and then 40%-45% ethyl acetate in hexanes (4 L) to elute the main amount of product. The product containing fractions were combined, concentrated under reduced pressure and dried under vacuum (0.2 mmHg, 24 h, ambient temp.) to a white foam solid (150.7 g, β/α=14:1 by NMR. $^1$H-NMR. (CDCl$_3$) beta: δ=1.33 (d, 22.4 Hz, 2'-C—CH$_3$), alpha: 1.55 (d, 22 Hz, 2'-C—CH$_3$).

The product mixture foam was dissolved in methanol (700 mL) at ambient temperature. Upon standing, a solid slowly formed over 2 h. The suspension was cooled in a freezer to −5° C. for 17 h. The resulting white solid was collected by filtration and washed with cold MeOH (−5° C. 3×60 mL) and ethyl ether (3×100 mL). The solid was dried under vacuum (0.2 mmHg, 24 h, ambient temp.) to afford 110.5 g of β-product with excellent de (β/α 99.8:1 by HPLC). The filtrate was partially concentrated (ca. 400 mL) and then diluted with more MeOH (400 mL) while heating to 60° C. The solution was cooled down to ambient temperature, seeded and the cooled to −5° C. The second crop was collected, washed and dried in a similar manner to give more product as a white solid (12.26 g) with similar diastereomeric purity. The mother liquor was concentrated to dryness under reduced pressure (ca. 25 g). The residue was a mixture of β and α-isomers. It was subjected to automated silica gel column chromatography (Analogix, 240 g cartridge, 40% to 50% ethyl acetate in hexanes) to afford 14.52 g of product foam which was recrystallized from MeOH, washed and dried in a similar manner to afford an additional 8.46 g of product in high purity.

The three solids were judged to be of similar purity and they were combined to give 131.2 g of white crystalline product, (55% from bromosugar, 49% from lactol). Mp 160.5-162.0° C. HPLC purity 99.5% including 0.20% alpha.

$^1$H-NMR (pure β-anomer, CDCl$_3$): δ=8.03 (m, 2H, arom.), 7.93 (m, 2H, arom.), 7.88 (s, 1H, C8-H), 7.60 (m, 1H, arom.), 7.50 (m, 1H, arom.), 7.44 (m, 2H, arom.), 7.33 (m, 2H, arom.), 6.44 (dd, 1H, Cl'—H), 6.12 (d, 1H, C3'-H), 5.35 (s, 2H, NH2), 5.00 (dd, 1H, C5'-Ha), 4.76 (m, 1H, C4'-H), 4.59 (dd, 1H, C5'-Hb), 1.33 (d, 3H, CH$_3$).

Example 12

Preparation of Compound 12 (from US20110015146)

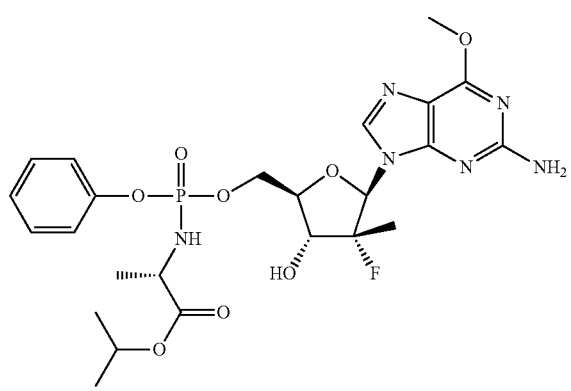

12

Synthesis of (2S)-isopropyl 2-(((((2R,3R,4R,5R)-5(2-amino-6-methoxy-9H-purin-9-yl)-4-fluoro-3hydroxy-4-methyltetrahydrofuran-2-yl)methoxy)(phenoxy)phosphorylamino)propanoate To a 250 mL dry round-bottomed flask were loaded phenyl dichlorophosphate (2.66 g, 12.61 mmol) and anhydrous dichloromethane (40 mL). The amino ester salt (2.60 g, 15.53 mmol) was added to the solution and the mixture was cooled to −5° C. N-Methyl imidazole (7.7 mL, 97 mmol) was then added quickly via a dry syringe at −5° C. and the solution was stirred at −5° C. for 1 h. The nucleoside ((2R,3R,4R,5R)-5-(2-amino-6-methoxy-9H-purin-9-yl)-4-fluoro-2-(hydroxymethyl)-4-methyltetrahydrofuran-3-ol), 3.04 g, 9.7 mmol) was added from a vial in one portion at −5° C. and the solid was slowly dissolved in 20 minutes. The reaction temperature was allowed to rise to ambient temperature over 2 h. After 17 h, the reaction was not complete. More reagents were made (from phosphate (2.66 g), aminoester (2.60 g), and N-Methyl imidazole (3.8 mL, 48 mmol)) and added to the reaction mixture at −5° C. The reaction was stirred at room temperature for 2 more hours. The reaction was almost complete as shown by TLC result and diluted with 70 mL of dichloromethane. HCl solution (1 N, 70 mL) was added. The aqueous layer was separated and extracted with dichloromethane. The organic layer was washed with saturated NaHCO$_3$, water, brine and dried over MgSO$_4$. After removal of the solvent under reduced pressure, the sticky residue was purified through automated column chromatography using a 240 g cartridge and a gradient of 0-8% 2-PrOH in dichloromethane to afford product as a foam solid (4.16 g, 7.14 mmol, 73% yield). HPLC purity 97.4%. NMR spectra of product showed it is a mixture of two diastereoisomers with a ratio of 1.2:1.

$^1$H-NMR (DMSO-d$_6$): δ=7.98 (1H, s, 8-H of one isomer), 7.95 (1H, s, 8-H of another isomer), 7.37-7.32 (2H, m, arom-H), 7.22-7.15 (3H, m, arom-H), 6.6 (2H, s, NH$_2$), 6.11 (1H, d, Cl'—H of one isomer), 6.09 (1H, d, Cl'—H of another isomer), 6.09-5.98 (1H, m, amide NH), 5.88 (1H, d, 3'-OH of one isomer), 5.81 (1H, d, 3'-H of another isomer), 4.85-4.75 (1H, hepta, methine H of iso-propyl), 4.46-4.27 (2H, m, C4'-H, α-H of amino ester), 4.15-4.07 (1H, m, C3'-H), 3.96 (3H, s, OCH$_3$), 3.82-3.72 (2H, m, C5'-H, and C5'H$_b$), 1.23-1.06 (9H, m, CH$_3$'s of amino ester), 1.03 (3H, d, C2'-O—CH$_3$).

$^{31}$P-NMR (DMSO-d6): 0=4.91 (one isomer), 4.72 (another isomer).

An alternate purification method is to chemically alter the minor 3' phosphoramidate by-product in order to simplify the chromatographic separation. The crude phosphoramidate product is dissolved in anhydrous pyridine (5 mL/g), and is treated with 0.5 molar equivalents of t-butyldimethylsilyl chloride at ambient temperature to react selectively with the free 5' primary hydroxyl of the 3' isomer impurity. Reaction progress can be monitored by LC/MS. Once the 3' isomer is converted to a 5'-tBDMS-3'-phosphoramidate derivative, the reaction is quenched with methanol (3 eq), concentrated under reduced pressure, partitioned between ethyl acetate and 5% citric acid and then the organic layer is concentrated. The residue is then subjected to chromatography which can now be done with a higher loading and a faster gradient and achieve a higher purity.

Example 13

Preparation of Compound 13 (from US20110015146)

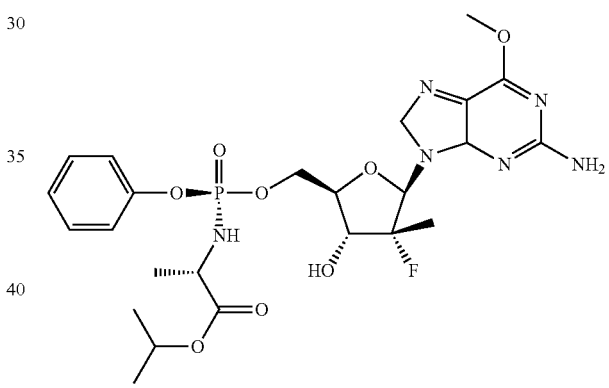

13

Example 14

Preparation of Compound 14 (From U.S. Pat. No. 7,964,580, Example 5)

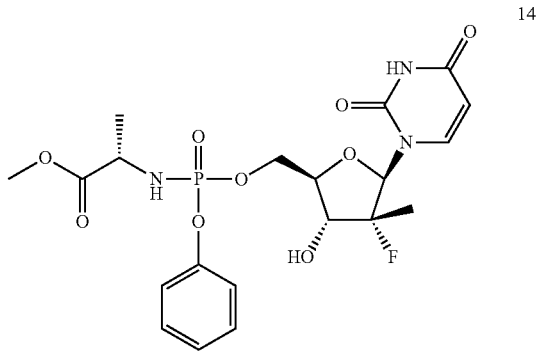 [SMILES: COC(=O)[C@H](C)NP(=O)(OC[C@H]1O[C@@H](n2ccc(=O)[nH]c2=O)[C@](C)(F)[C@@H]1O)Oc1ccccc1]

14

Preparation of 2'-Deoxy-2'-fluoro-2'-C-methyluridine-5'-phenyl methoxy-alanyl phosphate Phenyl methoxyalaninyl phosphorochloridate (1 g, 6.5 eq) dissolved in 3 mL of THF was added to a mixture of 2'-Deoxy-2'-fluoro-2'-C-methyluridine (0.15 g, 1 eq) and N-methylimidazole (0.3 g, 8 eq) in 3 mL THF with vigorous stirring at room temperature, then the reaction was stirred overnight. Solvent was removed by reduced pressure. The resulting crude product was dissolved in methanol purified by prep-HPLC on a YMC 25×30×2 mm column using a water/acetonitrile gradient elution mobile phase. The acetonitrile and water were removed under reduce pressure to give the desired product (50.1 mg, 15.6%). $^1$H NMR (DMSO-$d_6$) 1.20-1.27 (m, 6H), 3.58 (d, J=16.0 Hz, 3H), 3.75-3.92 (m, 2H), 4.015-4.379 (m, 2H), 5.54 (t, J=10.2 Hz, 1H), 5.83-5.91 (m, 1H), 6.00-616 (m, 1H), 7.18 (d, J=8.0 Hz, 2H), 7.22 (s, 1H), 7.35 (t, J=4.4 Hz, 2H), 7.55 (s, 1H), 11.52 (s, 1H); MS, m/e 502 (M+1)$^+$.

Example 15

Preparation of Compound 15 (Example 55, from U.S. Pat. No. 7,964,580)

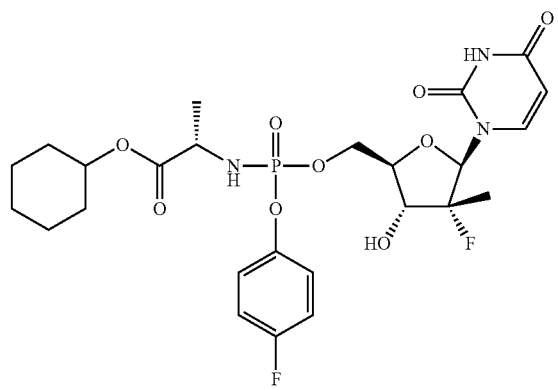

$^1$H NMR (DMSO-$d_6$) δ>1.20-1.44 (m, 12H), 1.60-1.71 (m, 4H), 3.75-4.02 (m, 2H), 3.94-4.02 (m, 1H), 4.19-4.26 (m, 2H), 4.59-4.61 (m, 1H), 5.57 (t, J=8.4 Hz, 1H), 5.85-6.06 (m, 3H), 7.17-7.23 (m, 4H), 7.54 (d, J=8.4 Hz, 1H), 11.50 (s, 1H); MS, m/e 587.92 (M+1)$^+$

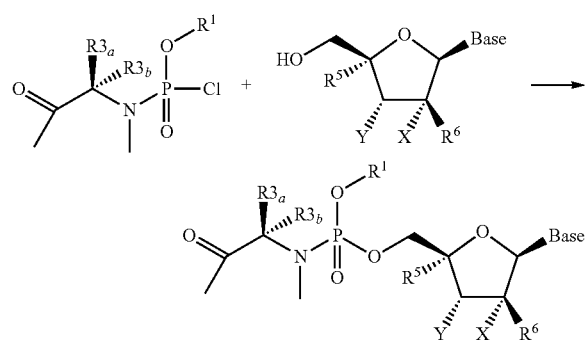

A general procedure for nucleoside phosphoramidate derivatives is reported at column 461 of U.S. Pat. No. 7,964,580. A solution of the appropriate phosphorochloridate (6.5 equivalents) in anhydrous tetrahydrofuran (THF) may be added to a mixture of nucleoside (1 equivalent) and N-methylimidazole (8 equivalents) in anhydrous THF with vigorous stirring at room temperature with the reaction mixture stirred overnight. Solvent may be removed in vacuo and the crude purified by column chromatography and/or preparative thin layer chromatography to give the desired compound.

Example 16

Preparation of Compound 16 (From U.S. Pat. No. 7,429,572)

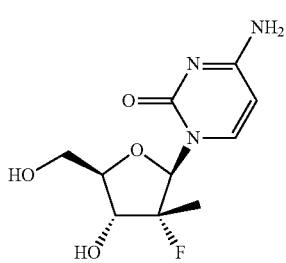

Synthesis of (2'R)-2'-Deoxy-2'-Fluoro-2'-C-Methylcytidine Starting from Cytidine Step 1: To a suspension of cytidine (100 g, 0.411 mol) in DMF (2.06 L) is added benzoic anhydride (102.4 g, 0.452 mol). The mixture was stirred at room temperature for 20 h. The DMF was removed in vacuo and the residue was triturated with diethyl ether. The resulting solid was collected by suction filtration and washed with diethyl ether (2×200 mL). Further drying in vacuo at room temperature gave the N$^4$ benzamide (140.6 g, 98.3%). A portion of this material (139.3 g, 0.401 mol) was dissolved in anhydrous pyridine (1.2 L) and was treated with 1,3-dichloro-1,1,3,3-tetraisopropyl-disiloxane (141.4 mL, 0.441 mol) at room temp. The solution was stirred at room temperature overnight. The mixture was concentrated to near dryness in vacuo and coevaporated with toluene (3×200 mL). The residue was treated with EtOAc (1.8 L) and washed with HCl (2×200 mL, 0.05 N), NaHCO$_3$ (5%, 2×400 mL). The organic layer was washed, dried (Na$_2$SO$_4$), filtered, and evaporated to dryness. Compound 16-1 (Compound 4-1 from U.S. Pat. No. 7,429,572) (256.5 g, >100%) was isolated as a white foam and used without further purification.

Step 2: Compound 16-1 (236.5 g, 0.40 mol) was dissolved in dry THF (1.22 L). Anhydrous DMSO (180.8 mL, 2.1 mol) was added and the resulting solution was cooled to between −20° C. and −15° C. Trifluoroacetic anhydride (90.6 mL, 0.64 mol) was added dropwise over 45 minutes and the solution was stirred between −20° C. and −15° C. for 2 hrs after which anhydrous triethylamine (223.5 mL, 1.6 mol) was added over 20 min. The crude reaction containing ketone 16-2 was dissolved in EtOAc (500 mL), and the resulting solution was washed with H$_2$O (3×400 mL), dried (Na$_2$SO$_4$) and the solvents were removed in vacuo to give a yellow solid that was purified on a silica gel column eluting with a stepwise gradient of Et$_2$O (0-60%) in hexanes followed by a stepwise gradient of EtOAc (50-100%) in hexanes. The crude ketone so-obtained (~192 g) was crystallized from petroleum ether to give ketone 16-2 (Compound 4-2 from U.S. Pat. No. 7,429, 572) (138.91 g, 57.5% from cytidine) as a white solid and 22 g of unreacted starting material, 16-1, as a yellow solid.

Step 3: Compound 16-2 (48.57 g, 8.26 mmol) was dissolved in anhydrous toluene (~400 mL) and the solvent was removed in vacuo with exclusion of moisture. The residue was then further dried in vacuo (oil pump) for another 2 h. With strict exclusion of moisture, the residual foam was dissolved in anhydrous diethyl ether (1.03 L) under argon. The resulting solution was cooled to −78° C. under argon and MeLi (1.6 M, 258.0 mL, 0.413 mol) was added dropwise via additional funnel. After the addition was complete, the mixture was stirred for 2 h at −78° C. Aqueous 1M $NH_4Cl$ (500 mL) was added slowly. After warming to room temperature, the mixture was washed with $H_2O$ (2×500 mL), dried ($Na_2SO_4$), and then concentrated to dryness to give a brown foam (~60 g, >100%).

The reaction was performed two more times using 37.62 g and 56.4 g of compound 16-2. The combined crude products (128.0 g, 0.212 mol) were dissolved in THF (1.28 L) and treated with concd HOAc (23 mL, 0.402 mol). To the solution was added TBAF (384.0 mL, 1 M in THF). The solution was stirred at room temp for 0.75 h and the mixture was treated with silica gel (750 g) and concentrated to dryness. The powder was placed on a silica gel column packed in $CH_2Cl_2$. Elution with 1:7 EtOH—$CH_2Cl_2$ afforded a dark waxy solid that was pre-adsorbed on silica gel (300 g) and chromatographed as before. Compound 16-3 (Compound 4-3 from U.S. Pat. No. 7,429,572) (46.4 g, 53.0% from 16-2) was isolated as an off-white solid. $^1$H NMR (DMSO-$d_6$): δ 1.20 (s, 3H, $CH_3$), 3.62-3.69 (m, 2H,), 3.73-3.78 (m, 2H,), 5.19 (t, 1H, J=5.4 Hz, OH-5'), 5.25 (s, 1H, OH-2'), 5.52 (d, 1H, J=5.0 Hz, OH-3'), 5.99 (s, 1H, H-1'), 7.32 (d, 1H, J=5.8 Hz), 7.05 (ψt, 2H, J=7.7 Hz), 7.62 (ψt, 1H, J=7.3 Hz), 8.00 (d, 2H, J=7.3 Hz), 8.14 (d, 1H, J=6.9 Hz), 11.22 (s, 1H, NH). Anal. Calcd for $C_{17}H_{16}N_3O_6.0.5\ H_2O$: C, 55.13; H, 5.44; N, 11.35. Found: C, 55.21; H, 5.47; N, 11.33.

Step 4: Compound 16-3 (46.0 g, 0.13 mol) was dissolved in anhydrous pyridine and concentrated to dryness in vacuo. The resulting syrup was dissolved in anhydrous pyridine under argon and cooled to 0° C. with stirring. The brown solution was treated with benzoyl chloride (30 mL, 0.250 mol) dropwise over 10 min. The ice bath was removed and stirring continued for 1.5 h whereby TLC showed no remaining starting material. The mixture was quenched by the addition of water (5 mL) and concentrated to dryness. The residue was dissolved in a minimal amount of $CH_2Cl_2$ and washed with satd $NaHCO_3$ (1×500 mL) and $H_2O$ (1×500 mL). The organic phase was dried ($Na_2SO_4$) and filtered, concentrated to dryness and chromatographed on silica gel eluting with a stepwise gradient of EtOAc-hexanes (25-60%) to provide compound 16-4 as yellow foam (Compound 4-4 from U.S. Pat. No. 7,429,572) (48.5 g, 67%). $^1$H NMR (CDCl$_3$): δ 1.64 (s, 3H, $CH_3$), 4.50 (m, 1H, H-4), 4.78-4.85 (m, 2H, H-5',5a'), 5.50 (d, IH, J=3.4 Hz, H-3'), 6.42 (s, IH, H-1'), 7.44-7.54 (m, 7H, Ar), 7.57-7.66 (m, 3H, Ar), 7.94 (d, 2H, J=7.8 Hz), 8.05-8.09 (m, 4H, Ar), 8.21 (d, 1H, J=7.3 Hz). Anal. Calcd for $C_{31}H_{27}N_3O_8$. C, 65.37; H, 4.78; N, 7.38.

Found: C, 65.59; H, 4.79; N, 7.16.

Step 5: Compound 16-4 (7.50 g, 0.013 mol) was dissolved in anhydrous toluene (150 mL) under argon and cooled to −20° C. DAST (2.5 mL, 18.9 mmol) was added slowly and the cooling bath was removed after the addition was complete.

Stirring was continued for 1 h and the mixture was poured into satd $NaHCO_3$ (100 mL) and washed until gas evolution ceased. The organic phase was dried ($Na_2SO_4$), concentrated, and purified by silica gel chromatography eluting with 1:1 EtOAc-hexanes. Yield was 1.22 g (16.3%) of pure 16-5 (Compound 4-5 from U.S. Pat. No. 7,429,572 as a white solid. mp 241° C. ($CH_2Cl_2$-hexanes); $^1$H NMR (CDCl$_3$): δ 1.49 (d, 3H, J=22.4 Hz, $CH_3$), 4.64 (dd, 1H, J=3.44, 12.9 Hz, H-5'), 4.73 (d, 1H, J=9.5 Hz, H-4'), 4.90 (dd, 1H, J=2.4, 12.7 Hz, H-5a'), 5.56 (dd, 1H, J=8.6, 20.7 Hz, H-3'), 6.52 (d, 1H, J=18.0 Hz, H-1'), 7.47-7.57 (m, 7H, Ar), 7.62-7.71 (m, 3H, Ar), 7.89 (d, 2H, J=6.9 Hz), 8.07-8.11 (m, 5H, Ar), 8.67 (bs, 1H, NH). $^{19}$F NMR (CDCl$_3$): δ 3.3 (m). Anal. Calcd for $C_{31}H_{26}FN_3O_7.0.7\ H_2O$: C, 63.74; H, 4.72; N, 7.20. Found: C, 63.71; H, 4.54; N, 7.20.

Step 6: Compound 16-5 (6.30 g, 0.011 mol) was suspended in methanolic ammonia (ca 7 N, 150 mnL) and stirred at room temperature overnight. The solvent was removed in vacuo, co-evaporated with methanol (1×20 mL), and pre-adsorbed onto silica gel. The white powder was placed onto a silica gel column (packed in CHCl$_3$) and the column was eluted with 9% EtOH in CHCl$_3$, then 17% EtOH and finally 25% EtOH in CHCl$_3$. Concentration of the fractions containing the product, filtration through a 0.4 1 am disk, and lyophilization from water afforded compound 16-6 (Compound 4-6 from U.S. Pat. No. 7,429,572), 2.18 g (76%). $^1$H NMR (DMSO-$d_6$): δ 1.17 (d, 3H, J=22.3 Hz, $CH_3$), 3.63 (dd, 1H, J=2.7, 13.7 Hz, H-5'), 3.70-3.84 (m, 3H, H-3', H-4', H-5a'), 5.24 (app s, 1H, OH-3'), 5.60 (d, 1H, J=5.4 Hz, H-5'), 5.74 (d, 1H, J=7.71 Hz, H-5), 6.07 (d, 1H, J=18.9 Hz, H-1'), 7.31 (s, 1H, NH$_2$), 7.42 (s, 1H, NH$_2$), 7.90 (d, 1H, J=7.3 Hz, H-6). $^{19}$F NMR (DMSO-$d_6$): δ 2.60 (m). Anal. Calcd for $C_{10}H_{14}FN_3O_4.4.1.4\ H_2O$: C, 44.22; H, 5.95; N, 14.77. Found: C, 42.24; H, 5.63; N, 14.54. Compound 16-6 (0.10 g, 0.386 mmol) was converted to the hydrochloride salt by dissolving in water (2 mL) and adjusting the pH to approximately 3.0 with 1 M HCl. The water was removed in vacuo and the residue was crystallized from aqueous EtOH to give 16-6 as the hydrochloride salt (71.0 mg). mp 243° C. (dec); $^1$H NMR (DMSO-$d_6$): δ 1.29 (d, 3H, J=22.6 Hz, $CH_3$), 3.65 (dd, 1H, J=2.3, 12.7 Hz, H-5'), 3.76-3.90 (m, 3H, H-3', H-4', H-5a'), 5.96 (d, 1H, J=17.3 Hz, H-1'), 6.15 (d, 1H, J=7.9 Hz, H-5), 8.33 (d, 1H, J=7.9 Hz, H-6), 8.69 (s, 1.5H, NH), 9.78 (s, 1.5H, NH). $^{19}$F NMR (DMSO-$d_4$): δ 1.69 (m). Anal. Calcd for $C_{10}H_{14}FN_3O_4.HCl$: C, 40.62; H, 5.11; N, 14.21. Found: C, 40.80; H, 5.09; N, 14.23.

BIOLOGICAL EXAMPLES

Assay Protocol

High Throughput Replicon Assay (HTBS)

Replicon cells harboring H77 (genotype 1a) or Con1 (genotype 1b) HCV RNA and *Renilla* luciferase reporter were seeded in 384-well black plates at a density of 1.6×10³ cells per well in 90 µl of DMEM culture medium, excluding G-418. Compounds were serially diluted in 100% DMSO and added to cells at a 1:225 dilution, achieving a final concentration of 0.44% DMSO in a total volume of 90 µL with a Biotek µFlow Workstation. Cell plates were incubated at 37° C. with 5% CO2 for 3 days, after which culture media were removed and cells were assayed for luciferase activity as a marker for replication level. Luciferase expression was measured using Dual-Glo luciferase assay reagents (Promega, Madison, Wis.). Briefly, 20 µL of Dual-Glo luciferase buffer was added to lyse the cells for 10 min and subsequently 20 µL of a diluted Dual-Glo Stop & Glo substrate (1:100) was added to each well. Luminescence signal was measured on a Perkin Elmer Envision Plate Reader after incubation for 10 minute. Luciferase levels were converted into percentages relative to the untreated controls (defined as 100%) and data were fit to the logistic dose response equation $y=a/(1+(x/b)c)$ using XLFit4 software (IDBS, Emeryville, Calif.). $EC_{50}$ values were calculated from the resulting equations. Alternatively, antiviral activity may be analyzed by HCV NS3 Protease $IC_{50}$ Determination. HCV NS3 protease activity was monitored using a fluorescence resonance energy transfer (FRET) depsipeptide substrate (RET S1, Anaspec, San Jose, Calif.) based on the method of Taliani, Taliani M, Bianchi E, Narjes F, Fossatelli M, Urbani A, Steinkuhler C, et al. A continuous assay of hepatitis C virus protease based on resonance energy transfer depsipeptide substrates. Anal. Biochem. 1996; 240 (1):60-7, herein incorporated by reference with regard to performing such assay.

Briefly, 2-10 nM of purified NS3 protease domains were pre-incubated at 37° C. for 10 minutes with 20 μM isogenic NS4A peptide cofactors (Sigma, St. Louis, Mo.), in 40% glycerol buffer with 50 mM HEPES pH 7.5 and 10 mM DTT. Compounds were diluted serially 1:3 in DMSO, incubated with the enzyme/cofactor mixture for 10 minutes and reactions were started by the addition of 2 μM RET S1 substrate (final concentration). Fluorescence increase was measured continuously over one hour using a Victor3 V fluorescence plate reader (Perkin Elmer, Waltham, Mass.). Initial velocities were calculated for each inhibitor concentration using Workout 1.5 software (DAZDAQ, East Sussex, UK) with the maximal slope algorithm. Velocity data were converted into percentages relative to the untreated control (defined as 100%) and non-linear regression was performed to calculate 50% inhibitory concentrations ($IC_{50}$ values).

NS3 Enzymatic Potency:

Purified NS3 protease is complexed with NS4A peptide and then incubated with serial dilutions of the compounds (DMSO used as solvent). Reactions are started by addition of dual-labeled peptide substrate and the resulting kinetic increase in fluorescence is measured. Non-linear regression of velocity data is performed to calculate $IC_{50}$s. Activity is initially tested against genotype 1b protease. Depending on the potency obtained against genotype 1b, additional genotypes (1a, 2a, 3) and or protease inhibitor resistant enzymes (D168Y, D168V, or A156T mutants) may be tested. BILN-2061 is used as a control during all assays. Compounds of the Examples were evaluated in this assay and were found to have $IC_{50}$ values of less than about 1 μM.

Replicon Potency and Cytotoxicity:

Huh-luc cells (stably replicating Bartenschlager's I389luc-ubi-neo/NS3-3'/ET genotype 1b replicon) are treated with serial dilutions of compound (DMSO is used as solvent) for 72 hours. Replicon copy number is measured by bioluminescence and non-linear regression is performed to calculate $EC_{50}$s. Parallel plates treated with the same drug dilutions are assayed for cytotoxicity using the Promega CellTiter-Glo cell viability assay. Depending on the potency achieved against the 1b replicon, compounds may be tested against a genotype 1a replicon and/or inhibitor resistant replicons encoding D168Y or A156T mutations. BILN-2061 is used as a control during all assays. Compounds of the Examples were evaluated in this assay and were found to have $EC_{50}$ values of less than about 5 μM.

Effect of Serum Proteins on Replicon Potency

Replicon assays are conducted in normal cell culture medium (DMEM+10% FBS) supplemented with physiologic concentrations of human serum albumin (40 mg/mL) or α-acid glycoprotein (1 mg/mL). $EC_{50}$s in the presence of human serum proteins are compared to the $EC_{50}$ in normal medium to determine the fold shift in potency.

Enzymatic Selectivity:

The inhibition of mammalian proteases including Porcine Pancreatic Elastase, Human Leukocyte Elastase, Protease 3, and Cathepsin D are measured at $K_m$ for the respective substrates for each enzyme. $IC_{50}$ for each enzyme is compared to the $IC_{50}$ obtained with NS3 1b protease to calculate selectivity.

MT-4 Cell Cytotoxicity:

MT4 cells are treated with serial dilutions of compounds for a five day period. Cell viability is measured at the end of the treatment period using the Promega CellTiter-Glo assay and non-linear regression is performed to calculate $CC_{50}$.

Compound Concentration Associated with Cells at $EC_{50}$:

Huh-luc cultures are incubated with compound at concentrations equal to $EC_{50}$. At multiple time points (0-72 hours), cells are washed 2× with cold medium and extracted with 85% acetonitrile; a sample of the media at each time-point is also extracted. Cell and media extracts are analyzed by LC/MS/MS to determine the molar concentration of compounds in each fraction Solubility and Stability:

Solubility is determined by taking an aliquot of 10 mM DMSO stock solution and preparing the compound at a final concentration of 100 μM in the test media solutions (PBS, pH 7.4 and 0.1 N HCl, pH 1.5) with a total DMSO concentration of 1%. The test media solutions are incubated at room temperature with shaking for 1 hr. The solutions are then centrifuged and the recovered supernatants are assayed on the HPLC/UV. Solubility can be calculated by comparing the amount of compound detected in the defined test solution compared to the amount detected in DMSO at the same concentration. The stability of compounds after 1 hour incubation in the test media at 37° C. is also determined.

Stability in Cryo-preserved Human, Dog, and Rat Hepatocytes:

Each compound is incubated for up to 1 hour in hepatocyte suspensions (100 μl, 80,000 cells per well) at 37° C. Cryo-preserved hepatocytes are reconstituted in the serum-free incubation medium. The suspension is transferred into 96-well plates (50 μL/well). The compounds are diluted to 2 μM in incubation medium and then are added to hepatocyte suspensions to start the incubation. Samples are taken at 0, 10, 30 and 60 minutes after the start of incubation and reaction can be quenched with a mixture consisting of 0.3% formic acid in 90% acetonitrile/10% water. The concentration of the compound in each sample is analyzed using LC/MS/MS. The disappearance half-life of the compound in hepatocyte suspension is determined by fitting the concentration-time data with a monophasic exponential equation. The data is also scaled up to represent intrinsic hepatic clearance and/or total hepatic clearance.

Stability in Hepatic S9 Fraction from Human, Doc, and Rat:

Each compound is incubated for up to 1 hour in S9 suspension (500 μl, 3 mg protein/mL) at 37° C. (n=3). The compounds are added to the S9 suspension to start the incubation. Samples are taken at 0, 10, 30, and 60 minutes after the start of incubation. The concentration of the compound in each sample is analyzed using LC/MS/MS. The disappearance half-life of the compound in S9 suspension is determined by fitting the concentration-time data with a monophasic exponential equation.

Caco-2 Permeability:

Both forward (A-to-B) and reverse (B-to-A) permeability is measured. Caco-2 monolayers are grown to confluence on collagen-coated, microporous, polycarbonate membranes in 12-well Costar Transwell® plates. The compounds are dosed on the apical side for forward permeability (A-to-B), and are dosed on the basolateral side for reverse permeability (B-to-A). The cells are incubated at 37° C. with 5% $CO_2$ in a humidified incubator. At the beginning of incubation, at 1 hr and 2 hr after incubation, a 200-μL aliquot is taken from the receiver chamber and replaced with fresh assay buffer. The concentration of the compound in each sample is determined with LC/MS/MS. The apparent permeability, Papp, is calculated.

Plasma Protein Binding:

Plasma protein binding is measured by equilibrium dialysis. Each compound is spiked into blank plasma at a final concentration of 2 μM. The spiked plasma and phosphate buffer is placed into opposite sides of the assembled dialysis cells, which is then rotated slowly in a 37° C. water bath. At the end of the incubation, the concentration of the compound in plasma and phosphate buffer is determined. The percent unbound is calculated using the following equation:

$$\% \text{ Unbound} = 100 \cdot \left(\frac{C_f}{C_b + C_f}\right)$$

Where $C_f$ and $C_b$ are free and bound concentrations determined as the post-dialysis buffer and plasma concentrations, respectively.

CYP450 Profiling:

Each compound is incubated with each of 5 recombinant human CYP450 enzymes, including CYP1A2, CYP2C9, CYP3A4, CYP2D6 and CYP2C19 in the presence and absence of NADPH. Serial samples can be taken from the incubation mixture at the beginning of the incubation and at 5, 15, 30, 45 and 60 min after the start of the incubation. The concentration of the compound in the incubation mixture is determined by LC/MS/MS. The percentage of the compound remaining after incubation at each time point is calculated by comparing with the sampling at the start of incubation.

Stability in Rat, Dog, Monkey and Human Plasma:

Compounds are incubated for up to 2 hour in plasma (rat, dog, monkey, or human) at 37° C. Compounds are added to the plasma at final concentrations of 1 and 10 μg/mL. Aliquots are taken at 0, 5, 15, 30, 60, and 120 min after adding the compound. Concentration of compounds and major metabolites at each timepoint are measured by LC/MS/MS. Biological data (antiviral potency [$EC_{50}$] is determined using a *Renilla* luciferase (RLuc)-based HCV replicon reporter assay—HCV 1b RLuc).

Biological Example 1

Anti-HCV Activity of the Combination of Compound 1 and Compound 2

Materials and Methods

Compound 1 and Compound 2 were synthesized by Gilead Sciences (Foster City, Calif.).

Cell Lines

HCV genotype 1b replicon cells (Huh-luc) were obtained from Reblikon (Mainz, Germany). The replicon in these cells is designated l389luc-ubi-neo/NS3-3'/ET and encodes a selectable resistance marker (neomycin phosphotransferase) as well as the firefly luciferase reporter gene. Huh-luc cells were maintained in Dulbecco's Modified Eagle's Medium (DMEM; GIBCO, Carlsbad, Calif.) supplemented with 10% fetal bovine serum (FBS; Hyclone, Logan, Utah) and 0.5 mg/mL of G-418 (GIBCO). Cells were passaged twice a week and maintained at subconfluent levels.

$EC_{50}$ Determinations

Replicon cells were seeded in 96-well plates at a density of $5\times10^3$ cellsper well in 100 μL of DMEM culture medium, excluding G-418. Compounds 1 and 2 were serially diluted 1:3 in 100% DMSO (Sigma). These serial dilutions were added to the cells at a 1:200 dilution to achieve a final concentration of 0.5% DMSO in a total volume of 200 μL. Plates were incubated at 37° C. for 3 days, after which culture media were removed and cells were lysed and assayed for luciferase activity using a commercial luciferase assay (Promega, Madison, Wis.).

HCV replication levels in drug-treated samples were expressed as a percentage of those in untreated controls (defined as 100%), and data were fit to the logistic dose response equation y=a/(1+(x/b)c) using XLFit4 software (IDBS, Emeryville, Calif.). $EC_{50}$ values were calculated from the resulting equations as described previously (Delaney, W. E., et al., Antimicrobial Agents Chemotherapy, 45(6):1705-1713 (2001)).

Antiviral Combination Studies

Replicon cells were seeded in 96-well plates at a density of $5\times10^3$ cells per well in 100 μL of culture medium. Compounds 1 and 2 were serially diluted in 100% DMSO as described above and added in a matrix format to 96-well plates, achieving a defined set of different drug concentrations and ratios in a final volume of 200 μL and a final DMSO concentration of 0.5%. For each individual drug, the $EC_{50}$ value was selected as the midpoint for the concentration range tested. Cells were incubated for three days and analyzed for luciferase expression as indicated above. For the combination study, two independent experiments were performed in triplicate.

Combination Data Analysis

Data were analyzed using the MacSynergy II program developed by Prichard and Shipman (Prichard M N, Aseltine K R, Shipman C, Jr., MacSynergy™ II, Version 1.0. University of Michigan, Ann Arbor, Mich., 1993; Prichard M. N., Shipman C., Jr., Antiviral Res 14 (4-5):181-205 (1990); Prichard M. N., Shipman C, Jr., Antivir Ther 1 (1):9-20 (1996); Prichard M. N., et al., Antimicrob Agents Chemother 37 (3):540-5 (1993). The software calculates theoretical inhibition assuming an additive interaction between drugs (based on the Bliss Independence model) and quantifies statistically significant differences between the theoretical and observed inhibition values. Plotting these differences in three dimensions results in a surface where elevations in the Z-plane represent antiviral synergy and depressions represent antiviral antagonism between compounds. The calculated volumes of surface deviations are expressed in $nM^2\%$. Per Prichard and Shipman, combination effects are defined as:

Highly synergistic if volumes >100 $nM^2$.

Slightly synergistic if volumes are >50 and ≤100 $nM^2$.

Additive if volumes are >−50 $nM^2$ and ≤50 $nM^2$.

Slightly antagonistic if volumes are >−100 $nM^2$ and ≤−50 $nM^2$.

Antagonistic if volumes are ≤−100 $nM^2$.

Results

Prior to initiating combination experiments, $EC_{50}$ values in Huh-luc replicon cells were determined for Compound 1 and Compound 2 and results are shown in Table II. Both compounds had an antiviral effect.

TABLE II

Individual EC$_{50}$s for Anti-HCV Compounds 1 and 2 in Huh-luc Replicon Cells

| Compound | EC$_{50}$ (nM)[a] |
|---|---|
| Compound 1 | 3 ± 2 |
| Compound 2 | 11 ± 3 |

[a]EC$_{50}$ indicates average ± standard deviation for two or more independent experiments. The antiviral effect of the combination of Compound 1 and Compound 2 was measured the resulting data were analyzed using MacSynergy II, which provides surface plots displaying significant deviations from additivity. Quantification of statistically significant deviations from additivity indicated that the combination of Compounds 1 and 2 had synergy/antagonism volumes between −50 nM$^2$ and 50 nM$^2$ indicating additive antiviral effects as shown in Table III.

TABLE III

Quantification of Antiviral Synergy and Antagonism and Drug Interactions for Combination Compound 1 and Compound 2

| Drug(s) Used in Combination with Compound 2 | Synergy Volume (nM$^2$)[a] | Antagonism Volume (nM$^2$)[a] | Interaction |
|---|---|---|---|
| Compound 1 | 13.5 ± 10.5 | 0.07 ± 0.07 | Additive |

[a]Values represent the mean ± standard deviation of two independent experiments performed in triplicate
The results of the in vitro experiments set forth in Table III indicate that Compound 2 has additive antiviral activity when combined with Compound 1.

Biological Example 2

Combinations with Compound 3

Materials and Methods

Antiviral Compounds

Compound 1 and Compound 3 were synthesized by Gilead Sciences (Foster City, Calif.). Ribavirin and IFN-α were purchased from Sigma (St. Louis, Mo.).

Cell Lines

HCV genotype 1b replicon cells (Huh-luc) were obtained from Reblikon (Mainz, Germany). The replicon in these cells is designated 1389luc-ubi-neo/NS3-3'/ET and encodes a selectable resistance marker (neomycin phosphotransferase) as well as the firefly luciferase reporter gene. Huh-luc cells were maintained in Dulbecco's Modified Eagle Medium (D-MEM) with GlutaMAX™ (Invitrogen, Carlsbad, Calif.) supplemented with 10% fetal bovine serum (FBS, Hyclone, Logan, Utah) and 0.5 mg/mL of G-418 (Invitrogen). Cells were passaged twice a week and maintained at subconfluent levels.

EC$_{50}$ Determinations

Replicon cells were seeded in 96-well plates at a density of 5×10$^3$ cells per well in 100 μL of DMEM plus 10% FBS culture medium, excluding G-418. Compounds were serially diluted 1:3 in 100% DMSO (Sigma). These serial dilutions were added to the cells at a 1:200 dilution to achieve a final concentration of 0.5% DMSO in a total volume of 200 μL. Plates were incubated at 37° C. for 3 days, after which culture media were removed and cells were lysed and assayed for luciferase activity using a commercial luciferase assay (Promega, Madison, Wis.). HCV replication levels in drug-treated samples were expressed as a percentage of those in untreated controls (defined as 100%), and data were fit to the logistic dose response equation $y=a/(1+(x/b)c)$ using XLFit4 software (IDBS, Emeryville, Calif.). EC$_{50}$ values were calculated from the resulting equations as described previously.

Antiviral Combination Studies

Replicon cells were seeded in 96-well plates at a density of 5×10$^3$ cells per well in 100 4 of culture medium, excluding G-418. Compound 3 and other compounds were serially diluted in 100% DMSO as described above and added in a matrix format to 96-well plates, achieving a defined set of different drug concentrations and ratios in a final volume of 200 4 and a final DMSO concentration of 0.5%. For each individual drug (with the exception of Ribavirin), the EC$_{50}$ value was selected as the midpoint for the concentration range tested. For Ribavirin, which did not have a selective antiviral effect, a top dose of 6.2 μM was selected since this was approximately 3-fold below the concentration at which cytotoxicity started to be observed. Cells were incubated with drugs for three days and analyzed for luciferase expression as indicated above. For each combination study, two independent experiments were performed in triplicate.

Combination Data Analysis

Data were analyzed using the MacSynergy II program developed by Prichard and Shipman. The software calculates theoretical inhibition assuming an additive interaction between drugs (based on the Bliss Independence model) and quantifies statistically significant differences between the theoretical and observed inhibition values. Plotting these differences in three dimensions results in a surface where elevations in the Z-plane represent antiviral synergy and depressions represent antiviral antagonism between compounds. The calculated volumes of surface deviations are expressed in nM$^2$%. Per Prichard and Shipman, combination effects are defined as follows:

Strong synergy if volumes >100 nM$^2$; this amount of synergy is probably important in vivo
Moderate synergy if volumes are >50 and 100 nM$^2$; this amount of synergy may be important in vivo
Minor synergy if volumes are >25 and <50 nM$^2$
Additivity if volumes are >−25 nM$^2$ and ≤25 nM$^2$
Minor antagonism if volumes are <−25 and >−50 nM$^2$
Moderate antagonism if volumes are >−100 nM$^2$ and ≤−50 nM$^2$; this amount of antagonism may be important in vivo
Strong antagonism if volumes are ≤−100 nM$^2$; this amount of antagonism is probably important in vivo Results EC$_{50}$ Values for Individual Compounds in Huh-luc Replicon Cells.

Prior to initiating combination experiments, EC$_{50}$ values in Huh-luc replicon cells were determined for each compound as shown in Table IV. All compounds had an antiviral effect with the exception of Ribavirin, which had no antiviral activity up to concentrations which were beginning to show cytotoxicity.

TABLE IV

Individual EC$_{50}$s for Anti-HCV Compounds in Huh-luc Replicon Cells

| Compound | EC$_{50}$ (nM)[a] |
|---|---|
| Compound 3 | 2.3 ± 2.6 |
| IFN-α | 0.105 ± .003 (U/mL)[b] |
| Ribavirin | >12,500 |
| Compound 1 | 0.4 ± 0.14 |

[a]EC$_{50}$ indicates average ± standard deviation for two or more independent experiments.
[b]INF-α EC$_{50}$ is expressed in Units (U) per milliliter (mL) instead of a nanomolar concentration.

Combination Antiviral Effects and Drug Interactions

The antiviral effects of Compound 3 when combined with IFN-α, Ribavirin, and Compound 1 were assayed. The resulting data were analyzed using MacSynergy II, which provides surface plots displaying significant deviations from additivity. Quantification of statistically significant deviations from additivity indicated that combinations of Compound 3 with IFN-α resulted in minor synergy (synergy volumes of 32 and 36.5 nM$^2$, respectively; Table V). The combination of Compound 3 with the non-nucleoside NS5B inhibitor Compound 1 yielded an synergy volume of 14.5 nM$^2$ which indicates an additive antiviral interaction. None of the compounds yielded antiviral antagonism volumes outside of the additive range (>−25 nM$^2$) when combined with Compound 3 as shown in Table V.

TABLE V

Quantification of Antiviral Synergy and Antagonism and Drug Interactions for Drug Combinations with Compound 3

| Drug(s) Used in Combination with Compound 3 | Synergy Volume (nM$^2$)$^a$ | Antagonism Volume (nM$^2$)$^a$ | Interaction |
|---|---|---|---|
| IFN-α | 32 ± 4.2 | 0.15 ± 0.2 | Minor synergy |
| Ribavirin | 54 ± 14.1 | 1.6 ± 2.3 | Moderate synergy |
| Compound 1 | 14.5 ± 0.7 | 4.22 ± 5.0 | Additive |

$^a$Values represent the mean ± standard deviation of two independent experiments performed in triplicate These in vitro antiviral combination experiments indicate that the novel HCV NS3 protease inhibitor Compound 3 has minor synergy when combined with IFN-α and moderate synergy when combined with Ribavirin. These results suggest that Compound 3 could potentially be used in combination with the current standard of care (PEG-IFN-α plus ribavirin) in HCV patients to achieve enhanced viral load suppression without reducing the efficacy of any of the individual drugs. Combinations of Compound 3 with non-nucleoside (Compound 1) NS5B polymerase inhibitors resulted in additivity. These results indicate that Compound 3 may also be suitable for exploring drug combinations comprised of multiple classes of specific HCV inhibitors in patients.

Biological Example 3

Compound 4 Combinations

Materials and Methods
Anti-HCV Agents

Compound 1, Compound 2, Compound 3, Compound 4, Compound 5, and Compound 6 were synthesized by Gilead Sciences (Foster City, Calif.). Puromycin, IFN-α and Ribavirin were purchased from Sigma (St. Louis, Mo.). Calcein AM was purchased from Anaspec (Fremont, Calif.).

Cell Line and Cell Culture

The HCV genotype 1a replicon cell line used in this study was described previously. The cells were grown in cell culture medium containing Dulbecco's Modified Eagle Medium (DMEM) with GlutaMAX (Gibco, Carlsbad, Calif., Cat#10569-044), supplemented with 10% FBS (HyClone, Logan, Utah, Cat#SH30071.03), 100 Units/mL Penicillin, 100 μg/mL Streptomycin (Gibco, Carlsbad, Calif., Cat#15140-122), and 0.1 mM non-essential amino acids (Gibco, Carlsbad, Calif., Cat#11140-050). Replicon cells were maintained in 0.5 mg/mL Geneticin (Invitrogen, Carlsbad, Calif., Cat#10131-035) to prevent the loss of HCV replicon. The cells were passaged every 3-4 days before reaching confluency.

HCV Replicon Assay for $EC_{50}$, $CC_{50}$ Determinations and Combination Studies All compounds were supplied in 100% DMSO except for IFN-α, which was supplied in buffer specified by the manufacture (Sigma, St. Louis, Mo., Cat#I4276). Compound serial dilutions were performed in 100% DMSO except for IFN-α, which was serially diluted in cell culture medium described in section 3.2. All serial dilutions were performed in 384-well polypropylene plates (Thermo Scientific, Hudson, N.H., Cat#4341) using a Biomek FX Workstation. For $EC_{50}$ and $CC_{50}$ determinations, test compounds were serially diluted in ten steps of 1:3 dilutions in columns 3-20 of the 384-well plates. For combinational studies, one compound was serially diluted in nine steps of 1:2 dilutions toward the horizontal direction with the other compound serially diluted in seven steps of 1:2 dilutions toward the vertical direction. This achieved a defined set of different drug concentrations and ratios. For each individual drug, the $EC_{50}$ value was selected as the midpoint for the concentration range tested. All serial dilutions were performed in four replicates per compound within the same 384-well plate. 100% DMSO was added into column 1-2 of each serial dilution 384-well plate. A HCV protease inhibitor ITMN-191 at 100 μM was added into column 23 as a control of 100% inhibition of HCV replication while puromycin at 10 mM was added into column 24 as a control of 100% cytotoxicity.

To each well of a black polystyrene 384-well plate (Greiner Bio-one, Monroe, N.C., Cat#781086, cell culture treated), 90 μL of cell culture medium (without geneticin) containing 2000 suspended HCV replicon cells was added with a Biotek μFlow Workstation. For compound transfer into cell culture plates, 0.4 μL of compound solution from the compound serial dilution plate was transferred to the cell culture plate on a Biomek FX Workstation. The DMSO concentration in the final assay wells was 0.44%. The plates were incubated for 3 days at 37° C. with 5% $CO_2$ and 85% humidity.

The HCV replicon assay was a multiplex assay which can assess both cytotoxicity and anti-replicon activity from the same well. The $CC_{50}$ assay was performed first. The media in the 384-well cell culture plate was aspirated and the wells were washed four times with 100 μL 1×PBS each, using a Biotek ELX405 plate washer. A volume of 50 μL of a solution containing 400 nM calcein AM (Anaspec, Fremont, Calif., Cat#25200-056) in 1×PBS was added to each well of the plate with a Biotek μFlow Workstation. The plate was incubated for 30 minutes at room temperature before the fluorescence signal (excitation 490 nm, emission 520 nm) was measured with a Perkin Elmer Envision Plate Reader.

$EC_{50}$ assay was performed in the same wells as $CC_{50}$ assay. The calcein-PBS solution in the 384-well cell culture plate was aspirated with a Biotek ELX405 plate washer. A volume of 20 μL of Dual-Glo luciferase buffer (Promega, Madison, Wis., Cat#E298B) was added to each well of the plate with a Biotek μFlow Workstation. The plate was incubated for 10 minutes at room temperature. A volume of 20 μL of a solution containing 1:100 mixture of Dual-Glo Stop & Glo substrate (Promega, Madison, Wis., Cat#E313B) and Dual-Glo Stop & Glo buffer (Promega, Madison, Wis., Cat#E314B) was then added to each well of the plate with a Biotek μFlow Workstation. The plate was then incubated at room temperature for 10 minutes before the luminescence signal was measured with a Perkin Elmer Envision Plate Reader.

Data Analysis

The cytotoxicity effect was determined by calcein AM conversion to fluorescent product. The percent cytotoxicity was calculated by equation 1:

$$\% \text{ cytotoxicity or } \% \text{ inhibition} = 100 \times \left(1 - \frac{X_C - M_B}{M_D - M_B}\right) \quad (1)$$

where $X_C$ is the fluorescence signal from the compound-treated well; $M_B$ is the average fluorescence signal from puromycin-treated wells; $M_D$ is the average fluorescence signal from DMSO-treated wells. The anti-HCV replication activity was determined by the luminescence signal generated from the reporter *renilla* luciferase of the HCV replicon. The percent inhibition on HCV replicon was calculated using equation 1, where $X_C$ is the luminescence signal from compound-treated well; $M_B$ is average luminescence signal from the ITMN-191-treated wells; $M_D$ is the average luminescence signal from DMSO-treated wells.

The $CC_{50}$ values were determined as the testing compound concentration that caused a 50% decrease of cell viability. The $EC_{50}$ values were determined as the testing compound concentration that caused a 50% decrease in HCV replication. Both $CC_{50}$ and $EC_{50}$ values were obtained using Pipeline Pilot 5.0 software package (Accelrys, San Diego, Calif.) by nonlinear regression fitting of experimental data to equation 2:

$$y = d + \frac{a-d}{\left[1 + \left(\frac{x}{c}\right)^b\right]} \quad (2)$$

where y is the observed % inhibition of HCV replicon at x concentration of compound; d is estimated response at zero compound concentration; a is estimated response at infinite compound concentration; c is the mid-range concentration ($CC_{50}$ or $EC_{50}$); b is the Hill slope factor.

The combination study experimental data were analyzed using the MacSynergy II program developed by Prichard and Shipman. The software (MacSynergy™ II, University of Michigan, Mich.) calculates theoretical inhibition assuming an additive interaction between drugs (based on the Bliss Independence model) and quantifies statistically significant differences between the theoretical and observed inhibition values. Plotting these differences in three dimensions results in a surface where elevations in the Z-plane represent antiviral synergy and depressions represent antiviral antagonism between compounds. The calculated volumes of surface deviations are expressed in nM²%. Per Prichard and Shipman, combination effects are defined as:

Strong synergy: >100 nM²%
Moderate synergy: >50 and ≤100 nM²%
Minor synergy: >25 and ≤50 nM²%
Additivity: ≤25 and >−25 nM²%
Minor antagonism: ≤−25 and >−50 nM²%
Moderate antagonism: ≤−50 and >−100 nM²%
Strong antagonism: ≤−100 nM²%

For each combination study, three independent experiments were performed with four replicates in each experiment.

Results

Antiviral Activity and Cytotoxicity of Individual Compounds in HCV Genotype 1a Replicon Assay.

The anti-HCV activity and cytotoxicity of Compound 4 and other compounds were tested in Huh-7 cells carrying a HCV genotype 1a replicon. The $EC_{50}$ and $CC_{50}$ values are listed in Table VI. There is no significant cytotoxicity observed for all compounds up to the highest concentrations tested.

TABLE VI $EC_{50}$ and $CC_{50}$ of Compounds used in this Study against HCV Genotype 1a Replicon

| Compounds | $EC_{50}$[a] (nM) | $CC_{50}$[a] (nM) |
|---|---|---|
| Compound 1 | 19 ± 8 | >44400 |
| Compound 2 | 496 ± 135 | >22200 |
| Compound 3 | 49 ± 18 | >22200 |
| Compound 4 | 201 ± 74 | >44400 |
| Compound 5 | 15 ± 2.4 | >44400 |
| Compound 6 | 0.033 ± 0.011 | >44400 |
| IFN-α | 1.4 ± 0.3[b] | >50[b] |
| Ribavirin | 36482 ± 17507 | >88800 |

[a]Values are average ± standard deviation for three or more independent experiments
[b]IFN-α values are expressed in Units (U) per milliliter (mL) instead of a nanomolar concentration Antiviral Activity and Cytotoxicity of Compound 4 in Combination with Other Classes of Anti-HCV Agents.

The antiviral effects of Compound 4 in combination with other anti-HCV compounds were evaluated using the HCV genotype 1a replicon. The results were analyzed using MacSynergy II, which provides surface plots displaying significant deviations from additivity. Synergy and antagonism volumes (nM²%) calculated from deviations from additive surface are summarized in Table VII. At 95% confidence interval, the mean synergy and antagonism volumes are between 25 and −25 nM²% when Compound 4 was combined with IFN-α, Compound 2 and Compound 6, indicative of additive interaction with those compounds. Furthermore, Compound 4 shows synergy volumes in the range of 25 to 50 nM²% when combined with Compound 1, Compound 5 or Compound 3, suggesting minor synergistic interaction.

TABLE VII

Quantification of Antiviral Synergy and Antagonism and Drug Interactions for Drug Combinations with Compound 4

| Drug(s) Used in Combination with Compound 4 | Synergy Volume (nM²%)[a] | Antagonism Volume (nM²%)[a] | Interaction |
|---|---|---|---|
| Compound 1 | 34 ± 26 | −1 ± 2 | Minor synergy |
| Compound 2 | 22 ± 14 | −2 ± 3 | Additivity |
| Compound 3 | 26 ± 6 | −3 ± 2 | Minor synergy |
| Compound 5 | 26 ± 28 | −1 ± 3 | Minor synergy |
| Compound 6 | 19 ± 17 | −7 ± 7 | Additivity |
| IFN-α | 12 ± 6 | 0 ± 0 | Additivity |
| Ribavirin | 1 ± 1 | −43 ± 20 | Minor antagonism |

Values represent the mean ± standard deviation of three independent experiments performed in four replicates In all combination studies, the cell viability is higher than 85% at all concentration ratios and all drug combinations show additive effects on the cytotoxicity as shown in Table VIII.

TABLE VIII

Quantification of Cytotoxicity Synergy and Antagonism and Drug Interactions for Drug Combinations with Compound 4

| Drug(s) Used in Combination with Compound 4 | Synergy Volume (nM²%)[a] | Antagonism Volume (nM²%)[a] | Interaction |
|---|---|---|---|
| Compound 1 | 13 ± 11 | 0 ± 1 | Additivity |
| Compound 2 | 17 ± 14 | 0 ± 0 | Additivity |
| Compound 3 | 3 ± 5 | 0 ± 0 | Additivity |
| Compound 5 | 15 ± 8 | −10 ± 7 | Additivity |

TABLE VIII-continued

Quantification of Cytotoxicity Synergy and Antagonism and
Drug Interactions for Drug Combinations with Compound 4

| Drug(s) Used in Combination with Compound 4 | Synergy Volume (nM² %)[a] | Antagonism Volume (nM² %)[a] | Interaction |
|---|---|---|---|
| Compound 6 | 8 ± 4 | 0 ± 0 | Additivity |
| IFN-α | 8 ± 12 | −7 ± 13 | Additivity |
| Ribavirin | 4 ± 3 | −1 ± 2 | Additivity |

[a]Values represent the mean ± standard deviation of three independent experiments performed in four replicates However, Compound 4 shows an antagonism volume of −43 nM²% when combined with Ribavirin, suggesting a minor antagonistic interaction.

TABLE IX

Quantification of Cytotoxicity Synergy and Antagonism and
Drug Interactions for Drug Combinations with Ribavirin

| Drug Used in Combination with Ribavirin | Synergy Volume (μM² %)[a] | Antagonism Volume (μM² %)[a] | Interaction |
|---|---|---|---|
| Compound 4 | 4 ± 3 | −1 ± 2 | Additivity |

[a]Values represent the mean ± standard deviation of three independent experiments performed in four replicates The Ribavirin concentration that shows the highest antagonism with Compound 4 is around 0.5 to 1 µM, which is about 10-fold lower than the steady-state plasma concentration of Ribavirin (6-11 µM) observed in human at a dose of 800 mg/day. At this physiological concentration of Ribavirin (6-11 µM), the antagonistic interaction between Ribavirin and Compound 4 is minimal across a wide range of Compound 4 concentrations (0-0.44 µM). Therefore, the observed minor antagonism between Ribavirin and Compound 4 in the in vitro replicon system is unlikely to have clinical significance.

Conclusions

The antiviral activity of Compound 4 (in a diastereomeric mixture) was tested in combination with the current standard of care (IFN-α/Ribavirin), as well as Gilead Sciences' internal developmental candidates Compound 1 and Compound 5 (non-nucleoside NS5B inhibitors), Compound 2 and Compound 3 (NS3 protease inhibitors), and Compound 6 (NS5A inhibitor). As summarized in Table VIII, Compound 4 showed additive antiviral activity in combination with IFN-α, Compound 2 and Compound 6 and minor synergy with Compound 1, Compound 5 and Compound 3.

The combination of Compound 4 with Ribavirin resulted in a minor antagonism at Ribavirin concentrations between 0.5 to 1 µM, which is approximately 10-fold lower than its steady-state physiological concentration (6-11 µM) in human plasma. At the clinically relevant Ribavirin concentration, the antagonistic interaction between the two compounds became negligible.

Biological Example 4

Compound 5 Combinations

The antiviral activity of Compound 5 was tested in GT-1b Huh-lunet cells (using substantially the same methods as in the assays for Compound 4) in combination with the internal developmental compounds Compound 1, Compound 2 and Compound 3 (NS3 protease inhibitors), Compound 6 (NS5A inhibitor), Compound 4 (C-nuc NS5B inhibitor) and also the approved HCV therapeutics PEG-IFN-α and Ribavirin. Combination data were analyzed based on the Bliss Independence model using MacSynergy II software. Results of the combination assays were expressed as mean synergy and antagonism volumes (nM²) calculated at 95% confidence from two independent experiments performed in triplicate. Combination effects are defined as:

Strong synergy if volumes >100 nM²; this amount of synergy is probably important in vivo Moderate synergy if volumes are >50 and ≤100 nM²; this amount of synergy may be important in vivo Minor synergy if volumes are >25 and <50 nM²

Additivity if volumes are >−25 and ≤25 nM²

Minor antagonism if volumes are <−25 and >−50 nM²

Moderate antagonism if volumes are >−100 nM² and ≤−50 nM²; this amount of antagonism may be important in vivo Strong antagonism if volumes are ≤−100 nM²; this amount of antagonism is probably important in vivo.

The combination of the allosteric NS5B inhibitors Compound 1 and Compound 5 resulted in moderate synergy in the replicon assay. Studies with other HCV inhibitors, including PEG-IFN-α and Ribavirin, revealed additive to minor synergistic interactions.

TABLE X

Antiviral effects of Compound 5 in combination with other
anti-HCV drugs in 1b Huh-luc replicon cells

| Drug used in combination with Compound 5 | Synergy Volume (nM²)[a] | Antagonism Volume (nM²)[a] | Interaction |
|---|---|---|---|
| Compound 1 | 70 ± 26 | 0 ± 0 | Moderate synergy |
| Compound 2 | 22 ± 12 | −7 ± 7 | Additive |
| Compound 3 | 19 ± 13 | −2 ± 2 | Additive |
| Compound 4 | 26 ± 28 | −1 ± 3 | Minor synergy |
| Compound 6 | 34 ± 19 | 0 ± 0 | Minor synergy |
| PEG-IFN-α | 31 ± 23 | −2 ± 4 | Minor synergy |
| Ribavirin | 12 ± 8 | −12 ± 9 | Additive |

[a]Values represent the mean ± standard deviation of two independent experiments performed in triplicate Biological Example 5

Compound 6, Combinations

Materials and Methods

Compounds

Compound 1, Compound 2, Compound 3, Compound 6 and Compound 7 were synthesized by Gilead Sciences (Foster City, Calif.). IFN-α and Ribavirin were purchased from Sigma (St. Louis, Mo.).

Cell Lines

HCV genotype 1b replicon cells (Huh-luc) were obtained from Reblikon (Mainz, Germany). The replicon in these cells is designated I389luc-ubi-neo/NS3-3'/ET and encodes a selectable resistance marker (neomycin phosphotransferase) as well as the firefly luciferase reporter gene. Huh-luc cells were maintained in Dulbecco's Modified Eagle's Medium GlutaMax (DMEM; Invitrogen, Carlsbad, Calif.) supplemented with 10% fetal bovine serum (FBS; Hyclone, Logan, Utah), 1× penicillin/streptomycin, 1× nonessential amino acids and 0.5 mg/mL of G-418 (all from Invitrogen, Carlsbad, Calif.). Cells were passaged twice a week and maintained at subconfluent levels.

Assays
Antiviral Activity Assay in HCV Huh-luc Replicon Cells

Replicon cells were seeded in 96-well plates at a density of $7\times10^3$ cells per well in 1004 of DMEM culture medium, excluding G-418. Compounds were serially diluted 1:2 in 100% DMSO. Serial dilutions were added to the cells at a 1:200 dilution to achieve a final concentration of 0.5% DMSO in a total volume of 200 µL. Plates were incubated at 37° C. for 3 days, after which culture media were removed and cells were lysed and assayed for luciferase activity using a commercial luciferase assay (Promega, Madison, Wis.).

Antiviral Combination Studies

Replicon cells were seeded in 96-well plates at a density of $7\times10^3$ cells per well in 100 µL culture medium, excluding G-418. Compound 6 and other compounds were serially diluted 1:2 in 100% DMSO and added in a matrix format to 96-well plates, achieving a defined set of different drug concentrations and ratios in a final volume of 200 µL and a final DMSO concentration of 0.5%. For each individual drug, the $EC_{50}$ value was selected as the midpoint for the concentration range tested. Cells were incubated for 3 days and analyzed for luciferase expression using a commercial luciferase assay (Promega). For each combination study, two independent experiments were performed in triplicate.

Cellular Cytotoxicity Determination

Replicon cells were seeded and treated with drugs as described for the antiviral combination studies above. After three day incubation at 37° C., the culture media was removed and cells were lysed and assayed for cytotoxicity using a CellTiter-Glo Luminescent Cell Viability Assay (Promega) according to the manufacturer's instructions. Relative Light Units were converted into percentages relative to the untreated controls (defined as 100%).

Data Analysis $EC_{50}$ Calculations

Following $EC_{50}$ assays, luciferase levels in drug-treated samples were expressed as a percentage of those in untreated controls (defined as 100%). $EC_{50}$ values were calculated by nonlinear regression analysis of replicate data sets using XLfit 4 software (IDBS, Emeryville, Calif.).

Calculation of Antiviral Synergy and Antagonism

Following combination assays, luciferase levels in drug-treated samples were expressed as a percentage of those in untreated controls (defined as 100%). Replicate data sets were then analyzed using the MacSynergy II program developed by Prichard and Shipman. The software (MacSynergy™ II, University of Michigan, Mich.) calculates theoretical inhibition assuming an additive interaction between drugs (based on the Bliss Independence model) and quantifies statistically significant differences between the theoretical and observed inhibition values. Plotting these differences in three dimensions results in a surface where elevations in the Z-plane represent antiviral synergy and depressions represent antiviral antagonism between compounds. The calculated volumes of surface deviations are expressed in $nM^2\%$. Per Prichard and Shipman, combination effects are defined as:

Strong synergy if volumes >100 $nM^2$; this amount of synergy is probably important in vivo
Moderate synergy if volumes are >50 and ≤100 $nM^2$; this amount of synergy may be important in vivo
Minor synergy if volumes are >25 and <50 $nM^2$
Additivity if volumes are >−25 and ≤25 $nM^2$
Minor antagonism if volumes are <−25 and >−50 $nM^2$
Moderate antagonism if volumes are >−100 $nM^2$ and ≤−50 $nM^2$; this amount of antagonism may be important in vivo
Strong antagonism if volumes are ≤−100 $nM^2$; this amount of antagonism is probably important in vivo.

Results

Antiviral Activity of Individual Compounds in Huh-luc Replicon Cells.

Prior to initiating combination experiments, the antiviral activity of individual compounds was determined in Huh-luc replicon cells. $EC_{50}$ values consistent with historical results were observed with all seven compounds.

TABLE XI

Individual $EC_{50}$ Values for Anti-HCV Compounds in Huh-luc Replicon Cells

| Compound | $EC_{50}$ (nM)[a] |
|---|---|
| IFN-α[b] | 0.05 U/ml ± 0.04 |
| Ribavirin | >12 ± 2.4 |
| Compound 1 | 0.96 ± 0.39 |
| Compound 2 | 5.0 ± 0.0 |
| Compound 3 | 3.0 ± 1.2 |
| Compound 6 | 0.0018 ± 0.0007 |
| Compound 7 | 1245 ± 341 |

[a]$EC_{50}$ indicates arithmetic mean ± standard deviation for three or more independent experiments.
[b]IFN-α $EC_{50}$ is expressed in Units (U) per milliliter (mL) instead of a nanomolar concentration.

Combination Antiviral Effects and Drug Interactions

The antiviral effects of Compound 6 in combination with other HCV inhibitors were evaluated using the HCV 1b replicon system. The resulting data were analyzed using MacSynergy II, which provides surface plots displaying significant deviations from additivity. Quantification of statistically significant deviations from additivity from two independent experiments is summarized in Table XII. Combinations of Compound 6 with IFN-α or Compound 1 resulted in synergy volumes of 32 and 34 $nM^2$, respectively, indicating minor synergy. Ribavirin, Compound 2 and Compound 7 yielded synergy volumes of 61, 52 and 51 when combined with Compound 6, respectively, indicating a moderate synergistic interaction between Compound 6 and these three HCV inhibitors. The combination of Compound 6 with Compound 3 resulted in a synergy volume of 132 $nM^2\%$ signifying a strongly synergistic antiviral interaction. None of the compounds yielded antiviral antagonism volumes outside of the additive range (>−25 nM) when combined with Compound 6.

TABLE XII

Quantification of Antiviral Synergy and Antagonism and Drug Interactions for Drug Combinations with Compound 6

| Drug(s) Used in Combination with Compound 6 | Synergy Volume $(nM^2)$[a] | Antagonism Volume $(nM^2)$[a] | Interaction |
|---|---|---|---|
| IFN-α | 32 ± 1.4 | 0.0 ± 0.0 | Minor Synergy |
| Ribavirin | 61 ± 0.5 | −0.5 ± 0.1 | Moderate Synergy |
| Compound 1 | 34 ± 9.9 | −17 ± 0.7 | Minor Synergy |
| Compound 2 | 52 ± 5.1 | −0.7 ± 0.7 | Moderate Synergy |
| Compound 3 | 132 ± 44 | −0.1 ± 0.2 | Strong Synergy |
| Compound 7 | 51 ± 7.8 | −0.2 ± 0.1 | Moderate Synergy |

[a]Values represent the arithmetic mean ± standard deviation of two independent experiments performed in triplicate.

Cell Viability Percentages for Compound 6 in Combination with Other HCV Inhibitors To ensure that antiviral combination results were not confounded by combination cytotoxicity, the cytotoxicity was investigated in parallel using the same compound concentrations tested in the antiviral assays (Table XIII). For all compounds, cell viability was at least 98% of untreated controls for combinations at the highest concentrations tested. Therefore, no significant in vitro cytotoxicity was observed while testing Compound 6 alone, or in combination with these agents.

TABLE XIII

Cell Viability Percentages for Compound 6, Combinations in Huh-luc Replicon Cells

| Compounds | Concentration(s) (nM) | Cell Viability %[a] |
|---|---|---|
| Compound 6 | 0.014 | 99 ± 1 |
| Compound 6 + IFN-α[b] | 0.014 + 0.8 | 102 ± 3 |
| Compound 6 + Ribavirin | 0.014 + 8000 | 105 ± 4 |
| Compound 6 + Compound 1 | 0.014 + 4.0 | 99 ± 3 |
| Compound 6 + Compound 2 | 0.014 + 24.0 | 103 ± 3 |
| Compound 6 + Compound 3 | 0.014 + 12.8 | 104 ± 4 |
| Compound 6 + Compound 7 | 0.014 + 8800 | 103 ± 3 |

[a]Cell viability % indicates arithmetic mean ± standard deviation for at least two independent experiments performed in triplicate.
[b]IFN-α is expressed in Units (U) per milliliter (mL) instead of a nanomolar concentration.

Conclusions

Results of these in vitro experiments indicate that Compound 6 has minor antiviral synergy when combined with IFN-α or the non-nucleoside NS5B polymerase inhibitor Compound 1. Combinations of Compound 6 with Ribavirin, the NS3 protease inhibitor Compound 2 or the nucleoside NS5B polymerase inhibitor Compound 7 resulted in moderate antiviral synergy. Strong antiviral synergy was observed between Compound 6 and the NS3 protease inhibitor Compound 3. No significant in vitro cytotoxicity was identified while testing these drug combinations. These results suggest that Compound 6, Could rationally be combined with the current standard of care.

Biological Example 6

Compounds

Compound 1, Compound 3, Compound 4, and Compound 6 were synthesized by Gilead Sciences (Foster City, Calif.)

Cell Lines

HCV genotype 1b replicon cells (Huh-luc) were obtained from Reblikon (Mainz, Germany). The replicon in these cells is designated 1389luc-ubi-neo/NS3-3'/ET and encodes a selectable resistance marker (neomycin phosphotransferase) as well as the firefly luciferase reporter gene. Huh-luc cells were maintained in Dulbecco's Modified Eagle's Medium GlutaMax (DMEM; Invitrogen, Carlsbad, Calif.) supplemented with 10% fetal bovine serum (FBS; Hyclone, Logan, Utah), 1× penicillin/streptomycin, 1× nonessential amino acids and 0.5 mg/mL of G-418 (all from Invitrogen, Carlsbad, Calif.). Cells were passaged twice a week and maintained at subconfluent levels.

Assays

Determination of Compound Concentration Required to Suppress Replicon RNA by 1-1.5 Log Over 6 Days of Treatment Genotype 1b replicon cells were seeded in T-75 flasks at a cell density of $2.5 \times 10^5$ cells/flask, excluding G418. Compounds were individually added to the cells at variable concentrations: Compound 6 was added at concentrations of either 1 pM, 2 pM, 4 pM, 6 pM, 8 pM, or 12 pM, Compound 4 was added at 125 nM, 250 nM, 375 nM, 500 nM or 1000 nM, Compound 1 was added at 1.25 nM, 2.5 nM, 5 nM, 2.75 nM or 10 nM, and Compound 3 was added at concentrations of 3.75 nM, 7.5 nM, 11.25 nM, 15 nM, 30 nM or 60 nM. Flasks were incubated at 37° C., media and compounds were refreshed every two days. After 6 days of incubation the replicon cells were collected for RNA extraction and replicon RNA QRT-PCR analysis.

Compound Combination Replicon Cure Assay

Genotype 1b replicon cells were seeded in T-75 flasks at a density of $2.5 \times 10^5$ cells/flask Compounds were added to the T-75 flasks at the following concentrations: Compound 6 at 4 pM, Compound 4 at 1000 nM, Compound 1 at 10 nM, and Compound 3 at 26.25 nM. Flasks were incubated at 37° C. and compounds and media were refreshed every two days. All experiments were performed in duplicate and will be noted in as flask 1 and flask 2. On day 6 all cells were collected form flask 1 for RNA extraction followed by HCV replicon specific QRT-PCR analysis and the cells form flask 2 were replated on a 10 cm tissue culture dishes in the presence of G418 for 14 days to record colony formation of uncured replicon cells.

QRT-PCR Assay

Total RNA was extracted with the RiboPure kit (AM1924 Life Technologies Corporation Carlsbad, Calif.) following the manufacturer's protocol. Extracted RNA samples were stored at −80° C. until use. For the Quantitative RT-PCR assay the Qiagen One-step QRT-PCR kit was used according to manufacturer's protocol (Qiagen, Valencia Calif.). The genotype 1b HCV NS3 gene specific primers, forward primer NS3_180FL 5'-CGGCGGACTGTCTATCATGGTGC [FAM]G-'3 (SEQ ID NO:1) and reverse NS3_180 5'-GGTC-CTGGTCCACATTGGTGT-'3 (SEQ ID NO:2) and 18S rRNA LUX™ [FAM] endogenous control primer set (115HM-01) were produced by Invitrogen corporation (Carlsbad, Calif.). For the reverse transcriptase step, the reactions were incubated at 44° C. for 30 min, the reverse transcriptase enzyme was then degraded by heating the sample to 94° C. for 10 min. The Q-PCR step included 38 cycles at 94° C. for 15 s and 58° C. for 30 s.

Results

Prior to initiating combination replicon cure experiments the compound concentration required to suppress genotype 1b replicon RNA by 1-1.5 log was determined for Compound 6, Compound 4, Compound 1, and Compound 3. The replicon RNA log drop is relative to the RNA levels in DMSO control treated replicon cells maintained for 6 days.

TABLE XIV

Individual compound dose able to induce replicon RNA 1-1.5 log drop in a 6 day assay

| Compound | Replicon RNA log drop | Compound concentration (nM) |
|---|---|---|
| Compound 1 | −1.0 | 10 |
| Compound 3 | −0.9 | 26.25 |
| Compound 4 | −1.2 | 1000 |
| Compound 6 | −1.4 | 0.004 |

Combination Genotype 1b Replicon Cure Assay

The replicon RNA suppression by compounds Compound 6, Compound 4, Compound 1 and Compound 3 was determined in a 6 day assay as individual compounds and in various double, triple, and quadruple combinations. The replicon RNA log drop is relative to the RNA levels in DMSO control treated replicon cells maintained for 6 days alongside the treatment flasks. The ability of the various compound combinations to cure the cells from the HCV replicon was determined by colony formation. Colony formation occurred after compound treatment was removed and G418 pressure was returned for 14 days. If a compound combination completely cures the cell population from the HCV replicon no colonies will develop since the cells lack resistance to G418.

TABLE XV

Quantification of compound combination in the replicon cure assay

| Compounds | Replicon RNA log drop | Uncured colony number |
| --- | --- | --- |
| Compound 6 | −1.4 | 634 |
| Compound 4 | −1.2 | 1054 |
| Compound 1 | −1.0 | 657 |
| Compound 3 | −0.9 | 989 |
| Compound 4 + Compound 6 | −2.67 | 15 |
| Compound 1 + Compound 4 | −2.022 | 14 |
| Compound 3 + Compound 4 | −2.26 | 23 |
| Compound 1 + Compound 6 | −2.3 | 148 |
| Compound 3 + Compound 6 | −2.62 | 13 |
| Compound 1 + Compound 3 | −1.8 | 113 |
| Compound 1 + Compound 4 + Compound 6 | −2.66 | 0 |
| Compound 3 + Compound 4 + Compound 6 | −2.71 | 0 |
| Compound 1 + Compound 3 + Compound 4 | −2.69 | 0 |
| Compound 1 + Compound 3 + Compound 6 | −2.69 | 0 |
| Compound 1 + Compound 3 + Compound 4 + Compound 6 | −2.71 | 0 |
| DMSO (0.2% to match Quadruple combination) | 0 | 6330 |

Conclusions

Results of these in vitro experiments indicate that combination of two compounds increases the viral RNA log drop over 6 day treatment and increases the rate of cured replicon cells. The dual combinations of Compound 6 with Compound 4 or Compound 3 results in larger replicon RNA log suppression and lowest number of uncured colonies compared to all other dual compound combinations. The combination of three or four compounds cures all replicon cells and the combination treatments suppress the replicon RNA levels to the assay limit of detection.

Biological Example 7

Compound 10 and Compound 6 Cross-Resistance

This study was conducted to determine the in vitro cross-resistance profiles of Compound 10 and Compound 6. A panel of HCV mutant replicons bearing the signature NS5B nucleoside HCV drug resistance mutation S282T or the most common in vitro and in vivo NS5A HCV drug resistance mutations was investigated via transient replicon assay to determine whether cross-resistance exists between mutations conferring reduced susceptibility to Compound 10 or Compound 6. No cross-resistance was observed between these compound with S282T mutant replicons remaining fully susceptible to Compound 6 and NS5A mutants showing no reduced susceptibility to Compound 10.

Materials and Methods
Reagents
Compounds

Compound 6 and Compound 10 were synthesized at Gilead Sciences, Inc. in Foster City, Calif.

Cell Lines

Huh-lunet, a Huh-7 clone that is highly permissive for HCV replication, was obtained from ReBLikon GmbH (Mainz, Germany). Huh-lunet cells were maintained in Dulbecco's Modified Eagle's Medium (DMEM; GIBCO, Carlsbad, Calif.) supplemented with 10% fetal bovine serum (FBS; Hyclone, Logan, Utah). Cells were maintained at 37° C. in humidified incubators (85% humidity) and under a 5% $CO_2$ atmosphere.

PI-hRluc, a bicistronic replicon encoding the Renilla luciferase gene downstream of the polio IRES and the genotype 1b (Con-1 strain) HCV nonstructural genes (NS3-NS5B) downstream of the EMCV IRES, was used for transient transfection studies. The plasmid pPI-hRluc was generated from the plasmid pFKI341 PI-Luc/NS3-3'/ET, which encodes a genotype 1b (Con-1 strain) subgenomic replicon and was obtained from ReBLikon (Friebe et al., J Virol 2001; 75 (24):12047-57). The hRluc gene was PCR amplified from pF9 CMV hRluc-neo Flexi® (Promega, Madison, Wis.) by PCR using Accuprime Super Mix I (Invitrogen, Carlsbad, Calif.) and the primers PV_Rluc_Top and 3'-Rluc(NotI). These two primers have the following sequences and carry restriction sites for subsequent cloning: PV_Rluc_Top: 5' ATC AGA CAA TTG TAT CAT MT GGC TTC CM GGT GTA CG 3' (SEQ ID NO:3); 3'-Rluc(NotI): 5' ACG TCA CTA TCT ACGCGGCCGCTT ACT GCT CGT TCT TC3' (NotI site underlined) (SEQ ID NO:4). The T7 Promoter, 5'UTR and Polio Virus IRES were PCR amplified from the plasmid pFKI341 PI-Luc/NS3-3'/ET using the primers 5'-P7(SbfI) and PV_Rluc_Bottom. These two primers have the following sequences and carry restriction sites for subsequent cloning: 5'-P7(SbfI): 5' CAA GCT AAG CTG CCTGCAGG T 3' (SbfI site underlined) (SEQ ID NO:5); PV_Rluc_Bottom: 5' CGT ACA CCT TGG MG CCA TTA TGA TAC MT TGT CTG AT (SEQ ID NO:6). The subsequent PCR fragments from the two above reactions were then joined together using overlapping PCR and the primers 5'-P7 (SbfI) and 3'-Rluc(NotI). The completed P7-5'UTR-Polio Virus IRES-hRluc amplification product was subcloned into pCR2.1-TOPO. The resulting plasmid was digested with SbfI and NotI, and the excised fragment (P7-5'UTR-Polio Virus IRES-hRluc) were ligated using T4 DNA ligase into pFKI341 PI-Luc/NS3-3'/ET digested with the same enzymes. The resulting vector, pPI-hRluc, was sequenced to confirm the correct orientation and sequence of the P75'UTR-Polio Virus IRES-hRluc region of the plasmid.

GT 1a and 2a replicons containing hRluc have been described previously (Robinson M, Yang H, Sun S C, Peng B, Tian Y, Pagratis N, et al. Novel HCV Reporter Replicon Cell Lines Enable Efficient Antiviral Screening against Genotype 1a. Antimicrob Agents Chemother 2010.)

The PI-hRluc replicon was used as a backbone for chimera construction. An internal deletion was made in NS5B rendering it replication deficient. The last 413 base pairs (encoding last 137 NS5A amino acids) of 1b-con-1 NS5A were synthesized in frame with NS5B sequences from genotypes 2b, 3a, 4a, 5a, and 6a (Genscript Inc. Piscataway N.J.). Consensus NS5B sequences for each of these genotypes were derived by aligning sequences deposited in the European HCV database and extracting a consensus. These novel consensus sequences for NS5B, as well as sequences derived from individual clinical isolates (Herlihy et al., Antimicrob Agents Chemother 2008; 52 (10):3523-31) were used to construct the NS5B chimeric replicons. A unique XhoI site was used at the 5' end and a unique AseI site at the 3' end to directionally clone into the 1b-hRLuc/NeoR NS5B vector via standard molecular biology techniques.

NS5B S282T mutations were introduced replicon plasmids using the QuikChange II XL mutagenesis kit according to the manufacturer's instructions (Stratagene, La Jolla, Calif.). The entire mutated replicon was sequenced to confirm the presence of the S282T mutation and absence of any secondary site mutations.

NS5A mutant replicons were created by synthesizing a sequence encoding the first 149 amino acids of NS5A containing the desired mutation flanked by a 5' and 3' BsrGI and EcoRI site, respectively (Genscript, Piscataway, N.J.). Synthesized fragments were then cloned by standard molecular biology techniques into a 1a Rluc replicon plasmid modified to enable cloning into unique BsrGI and EcoRI restriction sites. Mutations were confirmed by DNA sequencing.

Replicons were linearized using the following enzymes: Spe I (1b PI-Rluc-based replicons), Hpa I (1a-Rluc-based replicons), and XbaI/HpaI (2a Rluc replicon). Replicon RNAs were transcribed in vitro from replicon-encoding plasmids using a T7 Ribomax in vitro transcription kit (Promega; Madison, Wis.) followed by purification using an RNAeasy column (Qiagen; Valencia, Calif.).

Assays

Drug Susceptibility Determination Using Transient Transfection Replicon Assay

RNA was transfected into Huh-lunet cells using the method of Lohmann et al. (Lohmann et al., Science 1999; 285 (5424):110-3) Briefly, cells were trypsinized and washed twice with PBS. A suspension of $4\times10^6$ cells in 400 μL of PBS were mixed with 5 μg of RNA and subjected to electroporation using settings of 960 μF and 270 V. Cells were transferred into 40 mL of pre-warmed culture medium and then seeded into 96-well or 384-well plates. Compounds were 3-fold serially diluted in 100% DMSO and added to cells to achieve a final DMSO concentration of 0.5%. Cells were treated for three days after which culture media were removed, cells were lysed, and *Renilla* luciferase activity was quantified using commercially available reagents (Promega) and a Victor or Envision instrument (Perkin Elmer, Waltham, Mass.).

Data Analysis

Data were converted into percentages relative to untreated controls (defined as 100%), and $EC_{50}$ values were calculated by non-linear regression of two replicate data sets using GraphPad Prism software or Pipeline Pilot. Resistance fold changes were calculated as the ratio of mutant to wild-type replicon $EC_{50}$.

Results

Activity of Compound 10 and Compound 6 Against S282T

Previous in vitro resistance selection with Compound 10 has consistently identified S282T in NS5B as primary mutation in multiple genotypes (GT 1b, 1a and 2a). The NS5B S282T mutation was subsequently introduced into the full-length GT 1a, 1b, and 2a replicons and chimeric replicons containing a 2b, 3a, or 4a NS5B sequence cloned into a GT1b backbone. The susceptibility to Compound 10, Compound 6, and ribavirin (RBV) was evaluated using a transient replication assay. The S282T mutation displayed a reduced susceptibility to Compound 10 with $EC_{50}$ values across all five genotypes ranging from 117.1 nM to 346.1 nM. The fold increase in $EC_{50}$ for S282T ranged from 2.4 to 16.0 compared to the wild-type from the corresponding genotypes demonstrating decreased replicon susceptibility to Compound 10 when the NS5B S282T mutation is present.

For the wild-type replicon, the $EC_{50}$ values for RBV were also similar across the five genotypes tested with the lowest $EC_{50}$ being against GT 2b. Interestingly, the $EC_{50}$ values for S282T replicons were 5- to 10-fold more sensitive to treatment with RBV than their corresponding wild-type for all five genotypes. No significant differences were observed in Compound 6 $EC_{50}$s between the wild-type and S282T replicons indicating that this mutation does not alter susceptibility to Compound 6. In conclusion, while the S282T replicon conferred reduced susceptibility to Compound 10, the mutant replicon demonstrated wild-type sensitivity to Compound 6 and an increased susceptibility to inhibition by RBV over wild-type.

TABLE 7.1

Antiviral activity of Compound 10 and RBV against wild-type and S282T mutant of GT1b, 2a, 2b, 3a and 4a

| | Compound 10 | | | RBV | | | Compound 6 | | |
|---|---|---|---|---|---|---|---|---|---|
| | $EC_{50}$ nM[a] | | Fold | $EC_{50}$ nM[a] | | Fold | $EC_{50}$ nM[a] | | Fold |
| Replicon | WT | S282T | change[b] | WT | S282T | change[b] | WT | S282T | change[b] |
| GT1b | 21.5 | 189.2 | 8.8 | 6.6 | 1.6 | 0.2 | 0.5 | 0.4 | 0.8 |
| GT2a | 146.8 | 346.1 | 2.4 | 8.3 | 0.6 | 0.1 | 5165 | 2336 | 0.5 |
| GT2b | 13.3 | 215.6 | 16.2 | 2.6 | 0.6 | 0.2 | 0.5 | 0.5 | 0.9 |
| GT3a | 33.9 | 117.1 | 3.5 | 6.7 | 1.0 | 0.2 | 0.4 | 0.2 | 0.6 |
| GT4a | 35.8 | 217.5 | 6.1 | 6.2 | 0.6 | 0.1 | 0.5 | 0.4 | 0.6 |

[a]$EC_{50}$ indicates average for two or more independent experiments.
[b]Fold change from the corresponding wild type Activity of Compound 10 and Compound 6 Against NS5A Mutants To determine if NS5A drug resistance mutations are cross resistant to Compound 10, a panel of NS5A mutant replicons was assayed for susceptibility to both Compound 6 and Compound 10. All seven NS5A mutants displayed a reduced susceptibility to Compound 6 with an increase in $EC_{50}$ ranging from 25- to 3029-fold. In contrast, no significant shift in $EC_{50}$ was observed for the NS5A mutants to Compound 10 or to a RBV control.

TABLE 7.2

In Vitro Activity of Compound 10 or Compound 6 against NS5A Mutants in Genotype 1a

| | Fold Shift in $EC_{50}$ (DRM $EC_{50}$/1a-H77 $EC_{50}$) | | | | | | |
|---|---|---|---|---|---|---|---|
| Compound | M28T | Q30H | Q30R | Q30E | L31M | Y93C | Y93H |
| Compound 6 | 25 | 73 | 170 | 997 | 140 | 327 | 3029 |
| Compound 10 | 0.9 | 1.0 | 0.8 | 1.0 | 1.1 | ND | 0.7 |
| RBV | 0.4 | 0.7 | 0.8 | 0.8 | 0.5 | | 1.0 |

Conclusions

In this example, the cross-resistance profiles of Compound 10 and Compound 6 were evaluated using transient HCV replicons encoding known resistance mutations in NS5A and NS5B conferring reduced susceptibility to Compound 6 and Compound 10, respectively. NS5B S282T replicons conferred reduced susceptibility to Compound 10, while there were no significant differences in Compound 6 $EC_{50}$s measured from wild-type and S282T replicons. Reciprocally, mutations conferring reduced susceptibility to Compound 6 remained sensitive to treatment with Compound 10.

Overall, these results indicate that resistance mutations for Compound 10 and Compound 6 do not demonstrate cross-resistance and support the use of these compounds in future combination therapy for the treatment of HCV.

Biological Example 8

Combination Activity

Combination study data of Compound 10 with the NS5A inhibitor Compound 6, the non-nucleoside inhibitors Compound 1 or Compound 5, the protease inhibitor Compound 3, or ribavirin (RBV) is shown for an in vitro replicon assay which remains the standard for evaluating the cell-based antiviral activity of HCV inhibitors. These results indicated that Compound 10 has additive antiviral activity when combined with Compound 6, Compound 1, Compound 5, or Compound 3. In addition, Compound 10 demonstrated minor synergy in combination with RBV in vitro.

Materials and Methods
Cell Line and Cell Culture

The HCV genotype 1a replicon cell line used in this study was described previously (Robinson M, Yang H, Sun S C, Peng B, Tian Y, Pagratis N, et al. Novel HCV Reporter Replicon Cell Lines Enable Efficient Antiviral Screening against Genotype 1a. Antimicrob Agents Chemother 2010). The cells were grown in cell culture medium containing Dulbecco's Modified Eagle Medium (DMEM) with GlutaMAX (Gibco, Carlsbad, Calif., Cat#10569-044), supplemented with 10% FBS (HyClone, Logan, Utah, Cat# SH30071.03), 100 Units/mL Penicillin, 100 µg/mL Streptomycin (Gibco, Carlsbad, Calif., Cat#15140-122), and 0.1 mM non-essential amino acids (Gibco, Carlsbad, Calif., Cat#11140-050). Replicon cells were maintained in 0.5 mg/mL Geneticin (Invitrogen, Carlsbad, Calif., Cat#10131-035) to prevent the loss of HCV replicon. The cells were passaged every 3-4 days before reaching confluency.

HCV Replicon Assay for $EC_{50}$, $CC_{50}$ Determinations and Combination Studies All compounds were supplied in 100% DMSO. Compound serial dilutions were performed in 100% DMSO. All serial dilutions were performed in 384-well polypropylene plates (Thermo Scientific, Hudson, N.H., Cat#4341) using a Biomek FX Workstation. For $EC_{50}$ and $CC_{50}$ determinations, test compounds were serially diluted in ten steps of 1:3 dilutions in columns 3-20 of the 384-well plates. For combinational studies, one compound was serially diluted in nine steps of 1:2 dilutions toward the horizontal direction with the other compound serially diluted in seven steps of 1:2 dilutions toward the vertical direction. This achieved a defined set of different drug concentrations and ratios. For each individual drug, the $EC_{50}$ value was selected as the midpoint for the concentration range tested. All serial dilutions were performed in four replicates per compound within the same 384-well plate. 100% DMSO was added into column 1-2 of each serial dilution 384-well plate. A HCV protease inhibitor ITMN-191 at 100 µM was added into column 23 as a control of 100% inhibition of HCV replication while puromycin at 10 mM was added into column 24 as a control of 100% cytotoxicity.

To each well of a black polystyrene 384-well plate (Greiner Bio-one, Monroe, N.C., Cat#781086, cell culture treated), 90 µL of cell culture medium (without geneticin) containing 2000 suspended HCV replicon cells was added with a Biotek µFlow Workstation. For compound transfer into cell culture plates, 0.4 µL of compound solution from the compound serial dilution plate was transferred to the cell culture plate on a Biomek FX Workstation. The DMSO concentration in the final assay wells was 0.44%. The plates were incubated for 3 days at 37° C. with 5% $CO_2$ and 85% humidity.

The HCV replicon assay was a multiplex assay which can assess both cytotoxicity and anti-replicon activity from the same well. The $CC_{50}$ assay was performed first. The media in the 384-well cell culture plate was aspirated and the wells were washed four times with 100 µL 1×PBS each, using a Biotek ELX405 plate washer. A volume of 50 µL of a solution containing 400 nM calcein AM (Anaspec, Fremont, Calif., Cat#25200-056) in 1×PBS was added to each well of the plate with a Biotek µFlow Workstation. The plate was incubated for 30 minutes at room temperature before the fluorescence signal (excitation 490 nm, emission 520 nm) was measured with a Perkin Elmer Envision Plate Reader.

$EC_{50}$ assay was performed in the same wells as $CC_{50}$ assay. The calcein-PBS solution in the 384-well cell culture plate was aspirated with a Biotek ELX405 plate washer. A volume of 20 µL of Dual-Glo luciferase buffer (Promega, Madison, Wis., Cat#E298B) was added to each well of the plate with a Biotek µFlow Workstation. The plate was incubated for 10 minutes at room temperature. A volume of 20 µL of a solution containing 1:100 mixture of Dual-Glo Stop & Glo substrate (Promega, Madison, Wis., Cat#E313B) and Dual-Glo Stop & Glo buffer (Promega, Madison, Wis., Cat#E314B) was then added to each well of the plate with a Biotek µFlow Workstation. The plate was then incubated at room temperature for 10 minutes before the luminescence signal was measured with a Perkin Elmer Envision Plate Reader.

Data Analysis

The cytotoxicity effect was determined by calcein AM conversion to fluorescent product. The percent cytotoxicity was calculated by equation 1:

$$\% \text{ cytotoxicity or } \% \text{ inhibition} = 100 \times \left(1 - \frac{X_C - M_B}{M_D - M_B}\right) \quad (1)$$

where $X_C$ is the fluorescence signal from the compound-treated well; $M_B$ is the average fluorescence signal from puromycin-treated wells; $M_D$ is the average fluorescence signal from DMSO-treated wells. The anti-HCV replication activity was determined by the luminescence signal generated from the reporter *renilla* luciferase of the HCV replicon. The percent inhibition on HCV replicon was calculated using equation 1, where $X_C$ is the luminescence signal from compound-treated well; $M_B$ is average luminescence signal from the ITMN-191-treated wells; $M_D$ is the average luminescence signal from DMSO-treated wells.

The $CC_{50}$ values were determined as the testing compound concentration that caused a 50% decrease of cell viability. The $EC_{50}$ values were determined as the testing compound concentration that caused a 50% decrease in HCV replication. Both $CC_{50}$ and $EC_{50}$ values were obtained using Pipeline Pilot 5.0 software package (Accelrys, San Diego, Calif.) by nonlinear regression fitting of experimental data to equation 2:

$$y = d + \frac{a-d}{\left[1+\left(\frac{x}{c}\right)^b\right]} \quad (2)$$

where y is the observed % inhibition of HCV replicon at x concentration of compound; d is estimated response at zero compound concentration; a is estimated response at infinite compound concentration; c is the mid-range concentration ($CC_{50}$ or $EC_{50}$); b is the Hill slope factor.

The combination study experimental data were analyzed using the MacSynergy II program developed by Prichard and Shipman (Prichard M N, Aseltine K R, Shipman C, Jr. MacSynergy™ II, Version 1.0. University of Michigan, Ann Arbor, Mich., 1993). The software (MacSynergy™ II, University of Michigan, Mich.) calculates theoretical inhibition assuming an additive interaction between drugs (based on the Bliss Independence model) and quantifies statistically significant differences between the theoretical and observed inhibition values. Plotting these differences in three dimensions results in a surface where elevations in the Z-plane represent antiviral synergy and depressions represent antiviral antagonism between compounds. The calculated volumes of surface deviations are expressed in $\mu M^2\%$. Per Prichard and Shipman, combination effects are defined as:

Strong synergy: >100 $\mu M^2\%$

Moderate synergy: >50 and ≤100 $\mu M^2\%$

Minor synergy: >25 and ≤50 $\mu M^2\%$

Additivity: ≤25 and >−25 $\mu M^2\%$

Minor antagonism: ≤−25 and >−50 $\mu M^2\%$

Moderate antagonism: ≤−50 and >−100 $\mu M^2\%$

Strong antagonism: −100 $\mu M^2\%$

For each combination study, three independent experiments were performed with four replicates in each experiment.

Results

Antiviral Activity and Cytotoxicity of Individual Compounds in HCV Genotype 1a Replicon Assay The anti-HCV activity and cytotoxicity of Compound 10 combined with other anti-HCV compounds were tested in Huh-7 cells carrying an HCV genotype 1a replicon. The $EC_{50}$ and $CC_{50}$ values for all compounds are listed in the following Table. There is no significant cytotoxicity observed for all individual compounds up to the highest concentrations tested in the combination assay.

TABLE 8.1

$EC_{50}$ and $CC_{50}$ of Compounds used in this Study against HCV Genotype 1a Replicon

| Compounds | Class | $EC_{50}{}^a$ (nM) | $CC_{50}{}^a$ (nM) |
|---|---|---|---|
| Compound 10 | NS5B Nucleoside Prodrug | 39 | >82446 |
| Compound 6 | NS5A Inhibitor | 0.032 | >44400 |
| Compound 1 | NS5B Non-nucleoside | 18 | >44400 |
| Compound 5 | NS5B Non-nucleoside | 14 | >44400 |
| Compound 3 | NS3 Protease Inhibitor | 46 | >22200 |
| RBV | Nucleoside Analog | 33626 | >88800 |

$^a$Values are geometric means for three or more independent experiments

Antiviral Activity and Cytotoxicity of Compound 10 in Combination with Other Classes of Anti-HCV Agents.

The antiviral effects of Compound 10 in combination with other anti-HCV compounds were evaluated using the HCV genotype 1a replicon. The results were analyzed using MacSynergy II, which provides surface plots displaying significant deviations from additivity. Synergy and antagonism volumes ($\mu M^2\%$) calculated from deviations from additive surface are summarized in the following Table. At 95% confidence interval, the mean synergy and antagonism volumes were between 25 and −25 $\mu M^2\%$ when Compound 10 was combined with Compound 6, Compound 1, Compound 5, or Compound 3 indicative of additive interaction with Compound 10. Furthermore, Compound 10 shows a synergy volume in the range of 25 to 50 $\mu M^2\%$ when combined with RBV, suggesting a minor synergistic interaction. In combination studies using direct acting antivirals with Compound 10, cell viability was greater than 93% at the highest concentrations of compound combinations tested while studies analyzing the combined effects of Compound 10 and RBV showed cell viability greater than 85% at the highest combined drug concentrations.

TABLE 8.2

Quantification of Antiviral Synergy and Antagonism and Drug Interactions for Drug Combinations with Compound 10

| Compound Used in Combination with Compound 10 | Class | Synergy Volume $(nM^2)^a$ | Antagonism Volume $(nM^2)^a$ | Interaction |
|---|---|---|---|---|
| Compound 6 | NS5A Inhibitor | 3.3 ± 4.2 | −7.7 ± 13.3 | Additive |
| Compound 1 | NS5B Non-nucleoside | 4.7 ± 8.1 | −11.7 ± 10.0 | Additive |
| Compound 5 | NS5B Non-nucleoside | 1.3 ± 2.3 | −5.7 ± 9.0 | Additive |
| Compound 3 | NS3 Protease Inhibitor | 1.0 ± 1.7 | −3.0 ± 4.4 | Additive |
| RBV | Nucleoside Analog | 35.3 ± 3.2 | −2.0 ± 2.0 | Minor synergy |

$^a$Values represent the mean ± standard deviation of three independent experiments performed in four replicates

TABLE 8.3

Quantification of Cytotoxicity In Compound Combinations

| Compound Used in Combination with Compound 10 | Highest Concentration of Compound Used With Highest Concentration (320 nM) of Compound 10 | Cytotoxicity at Highest Concentration of Compound Combinations (% inhibition on cell growth) |
|---|---|---|
| Compound 6 | 0.16 nM | 5.0 ± 5.0 |
| Compound 1 | 120 nM | 7.0 ± 4.6 |
| Compound 5 | 64 nM | 4.3 ± 2.9 |
| Compound 3 | 240 nM | 2.0 ± 3.5 |
| RBV | 16000 nM | 14.0 ± 4.4 |

$^a$Values represent the mean ± standard deviation of three independent experiments performed in four replicates Conclusions The antiviral activity of Compound 10 was tested in combination with Compound 6, Compound 1, Compound 5, Compound 3, or RBV. Compound 10 showed additive antiviral activity in combination with Compound 6, Compound 1, Compound 5, or Compound 3, and minor synergy with RBV.

In summary, these findings support the potential of Compound 10 to be used in combination with Compound 6, Compound 1, Compound 5, Compound 3 or RBV to achieve enhanced viral suppression without reducing the efficacy of any of the individual drugs.

Clinical Example 1

Clinical Testing of Anti-HCV Activity of the Combination of Compound 1 and Compound 2

This Clinical Example shows that the combination of Compound 1 and Compound 2 plus ribavirin is more effective at reducing HCV viral load, and suppressing HCV viral rebound, than the combination of Compound 1 plus Compound 2 without ribavirin.

Clinical Trial Design:

A Phase 2, randomized, open-label trial of Compound 2 plus Compound 1 alone and in combination with ribavirin for 28 days in treatment-naive subjects with chronic genotype 1 HCV infection. Subjects in Arm 1 received Compound 2 at 75 mg+Compound 1 at 40 mg, both administered twice daily (BID) (double regimen) and subjects in Arm 2 received Compound 2 at 75 mg+Compound 1 at 40 mg, both administered BID, and plus ribavirin, also administered BID (triple regimen) for 28 days.

On Day 28, all subjects were to initiate PEG/Ribavirin. Additionally, the protocol called for subjects with an insufficient virologic response (<2 $\log_{10}$ IU/mL reduction from baseline HCV RNA by Day 5) or virologic rebound (HCV RNA increase of >0.5 $\log_{10}$ IU/mL from nadir confirmed over two time points occurring after Day 5 with an absolute value >1000 IU/mL) to initiate PEG/RIBA prior to Day 28.

For subjects with insufficient virologic response, the combination of pegylated interferon (PEG) and ribavirin (RIBA) was initiated prior to Day 28 with or without continuation Compound 2+Compound 1. As a result, by Day 28 of the study, subjects were receiving one of four treatments:
  (i) Compound 2+Compound 1,
  (ii) Compound 2+Compound 1+RIBA,
  (iii) Compound 2+Compound 1+PEG/RIBA, or
  (iv) PEG/RIBA.

A total of 31 subjects were enrolled and started dosing (16 subjects received the double regimen in Arm 1 and 15 subjects received the triple regimen in Arm 2). Preliminary subject demographics and baseline characteristics (Table XVI) were generally comparable between Arms 1 and 2, aside from a greater number of subjects with genotype 1b in Arm 2. Four subjects were identified as HCV genotype 1b at screening (one subject on the dual regimen and three subjects on the triple regimen), but have not been confirmed as genotype 1a or 1b upon further analysis, with further assessment ongoing.

No subjects have experienced serious adverse events. Study medications have been generally well-tolerated, with all adverse events being Grade 1-2 in severity, except for a single Grade 3 fatigue, which was the only treatment emergent adverse event leading to study drug discontinuation. Prior to the initiation of PEG/Ribavirin, the most common treatment-emergent adverse events occurring in more than one subject were headache (n=5), and diarrhea or nausea (n=3 each) in Arm 1 and headache (n=7), diarrhea or fatigue (n=3 each), nausea, asthenia, pruritis or insomnia (n=2 each) in Arm 2. When Compound 2+Compound 1 were given in combination with PEG/RIBA, the only adverse events occurring in more than one subject were influenza-like illness (n=5) and myalgia (n=3), both common adverse events with PEG/RIBA therapy. With regard to laboratory abnormalities, there were no Grade 4 events during the 28-day treatment period. Among subjects receiving the study drugs, there were two treatment-emergent Grade 3 elevations in total bilirubin in the ribavirin containing Arm 2 (occurring at Day 7, but resolving with continued dosing of study drug). There were also 2 Grade-1 elevations and a single Grade-2 elevation in total bilirubin among other subjects in this dosing Arm (with ribavirin). Among subjects in Arm-1 (no ribavirin), there were four Grade-1 total bilirubin elevations. ALT values were reduced approximately 40 U/L from baseline in both arms by Day 14. Median QTcF was not significantly changed from baseline in either study arm and no subjects discontinued study drugs due to QTc abnormalities. Preliminary safety data are summarized in Table XVIII.

Plasma HCV RNA was monitored approximately twice weekly to gauge virologic response in relation to the protocol-specified criteria for early initiation of PEG/RIBA. From preliminary analysis of the HCV RNA values, the median maximal decline in HCV RNA was 3.9 $\log_{10}$ IU/mL for the dual regimen and 5.0 $\log_{10}$ IU/mL for the triple regimen. The median time to maximal decline in HCV RNA was 7 days for the dual regimen and 14 days for the triple regimen, with the difference attributed to delayed incidence and onset of viral breakthrough in the ribavirin containing arm. Three of 15 (20%) subjects receiving the dual regimen and 10 of 13 (77%) subjects receiving the triple regimen had nadir HCV RNA values ≤30 IU/mL (excluding non-GT1 subjects). 13/16 (81%) subjects receiving Compound 2/Compound 1 and 6/15 (40%) subjects receiving Compound 2/Compound1/Ribavirin initiated PEG or PEG/Ribavirin prior to the scheduled start on Day 28 of the study. Additional details of virologic outcomes are provided in Results.

Compound 2+Compound 1 alone and in combination with RIBA were well-tolerated for up to 28 days by HCV subjects in this study, both before and following the addition of PEG or PEG/Ribavirin. Both regimens yielded potent suppression of HCV RNA, with greater and more sustained activity in the three drug regimen.

TABLE XVI

Preliminary Subject Demographics and Baseline Characteristics

| | Arm #1:<br>Compound 2 at<br>75 mg BID +<br>Compound 1 at<br>40 mg BID<br>(n = 16) | Arm #2:<br>Compound 2 at<br>75 mg BID +<br>Compound 1<br>at 40 mg<br>BID + RIBA<br>(n = 15) |
|---|---|---|
| Age in years - Median (range) | 47<br>(30, 66) | 55<br>(27, 63) |
| Sex | 14 male<br>2 female | 11 male<br>4 female |
| Ethnicity | 16 Non-Hispanic/<br>Latino | 15 Non-Hispanic/<br>Latino |
| Race | 13 White<br>2 Black<br>1 Asian | 13 White<br>2 Black<br>0 Asian |
| Baseline Weight in kg - Median (range) | 86.1<br>(57.8, 110.5) | 79.0<br>(51, 127.5) |
| Baseline BMI in kg/M² - Median (range) | 27.1<br>(21.5, 34.1) | 24.7<br>(19.9, 37.6) |
| Baseline $\log_{10}$ HCV RNA (IU/mL) from Central lab- Median (range) Central lab | 6.17<br>(5.25, 7.26) | 6.34<br>(5.41, 7.19) |
| Baseline HCV Genotype | 8 1a<br>8 1b | 3 1a<br>12 1b |

TABLE XVII

Preliminary Safety Results

|  | Arm 1:<br>Compound 2 at 75 mg<br>BID + Compound 1 at<br>40 mg BID<br>(n = 16) | Arm 2:<br>Compound 2 at 75 mg BID +<br>Compound 1 at 40 mg<br>BID + RIBA<br>(n = 15) |
|---|---|---|
| Grade 3 Adverse Events (AEs): | | |
| Fatigue | 1 | 0 |
| Grade 1/Grade 2 (AEs): | | |
| Headache | 5 (31%) | 7 (47%) |
| Diarrhea | 3 (19%) | 3 (20%) |
| Nausea | 3 (19%) | 2 (13%) |
| Fatigue | 0 | 3 (20%) |
| Asthenia | 0 | 2 (13%) |
| Pruritia | 1 (6%) | 2 (13%) |
| Insomnia | 0 | 2 (13%) |
| Grade 3 Laboratory Abnormalities: | | |
| Bilirubin | 0 | 2 |
| Grade 1/Grade 2 Laboratory Abnormalities: | | |
| Bilirubin | 4 | 3 |
| Hemoglobin | 0 | 2 |
| Glucose (nonfasting) | 8 | 5 |

TABLE XVIII

Preliminary Virologic Outcomes

|  | Arm 1:<br>Compound 2 at<br>75 mg BID +<br>Compound 1 at<br>40 mg BID<br>(n = 16) | Arm 1:<br>Compound 2 at<br>75 mg BID +<br>Compound 1 at<br>40 mg BID<br>Unconfirmed<br>GT1 Subjects<br>Excluded<br>(n = 15)* | Arm 2:<br>Compound 2 at<br>75 mg BID +<br>Compound 1 at<br>40 mg BID +<br>Ribavirin<br>(n = 15) | Arm 2:<br>Compound 2 at<br>75 mg BID +<br>Compound 1 at<br>40 mg BID +<br>Ribavirin<br>Unconfirmed<br>GT1 Subjects<br>Excluded<br>(n = 13) |
|---|---|---|---|---|
| Median maximal HCV RNA decline | −3.9 log$_{10}$ IU/mL | −4.0 log$_{10}$ IU/mL | −5.0 log$_{10}$ IU/mL | −5.0 log$_{10}$ IU/mL |
| Mean maximal HCV RNA decline | −3.4 log$_{10}$ IU/mL | −3.6 log$_{10}$ IU/mL | −4.5 log$_{10}$ IU/mL | −4.9 log$_{10}$ IU/mL |
| Mean time to Breakthrough | 16 days | 16 days | 23 days | 23 days |
| Subjects with HCV RNA nadir <50 IU/mL | 3/16 (19%) | 3/15 (20%) | 10/15 (63%) | 10/13 (77%) |
| Subjects with Breakthrough** Day 28 Response: | 12 (75%) | 12/15 (80%) | 6/15 (40%) | 6/13 (46%) |
| RVR at <25 IU/mL | 1/16 (6%) | 1/15 (7%) | 5/15 (33%) | 5/13 (38%) |
| RVR at <50 IU/mL | 1/16 (6%) | 1/15 (7%) | 6/15 (40%) | 6/13 (46%) |

*GT1 is an abbreviation for HCV Genotype 1. Subjects 1011, 1012, and 1043 at one French study center were excluded; Subject 1004 was not excluded
**Breakthrough defined as >1 log increase in HCV RNA above nadir value or HCV RNA >25 IU/mL following a nadir of <25 IU/mL The data presented in Table XVIII show that there was an approximately 10 fold greater decline in both the median maximal HCV RNA level and the mean maximal HCV RNA level in response to the combination of Compound 2+Compound 1 in the presence of ribavirin compared to the absence of ribavirin. Also, the number of study subjects having an HCV RNA nadir below 50 IU/mL is greater in the presence of ribavirin than in the absence of ribavirin. These results show that ribavirin, in the absence of interferon, significantly potentiates the antiviral activity of the combination of Compound 1 and Compound 2.

Additionally, the mean time to HCV breakthrough, which is a measure of the eventual increase in HCV viral load as the virus mutates and becomes less susceptible to the antiviral drugs, is greater in the presence of ribavirin than in the absence of ribavirin. Further, the number of subjects showing viral breakthrough is substantially less in the presence of ribavirin than in the absence of ribavirin. These results show that the HCV virus is less able to develop resistance to the combination of Compound 1 and Compound 2 in the presence of ribavirin.

Further, the data presented in Table XVIII shows that the number of patients achieving a Rapid Virologic Response (RVR) in the presence of ribavirin is significantly greater than in the absence of ribavirin. Achievement of RVR positively correlates with cure of HCV infection.

Taken together the data presented in Table XVIII show that the combination of Compound 1, Compound 2, and ribavirin causes a rapid and clinically significant reduction in HCV viral load, with a reduced viral rebound, even in the absence of administration of interferon.

Although specific embodiments of the present invention are herein illustrated and described in detail, the invention is not limited thereto. The above detailed descriptions are provided as exemplary of the present invention and should not be construed as constituting any limitation of the invention.

Modifications will be obvious to those skilled in the art, and all modifications that do not depart from the spirit of the invention are intended to be included with the scope of the appended claims.

What is claimed is:

1. A method of treating an HCV infection in a human, comprising administering to the human: 1) compound 10 having the structure:

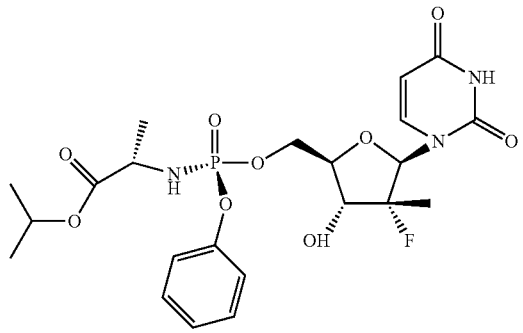 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

or a pharmaceutically acceptable salt thereof and 2) compound 6 having the structure:

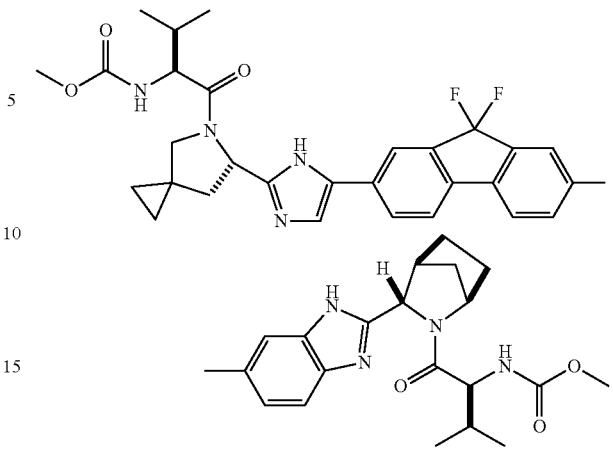

or a pharmaceutically acceptable salt thereof, wherein the method does not include administering interferon.

2. The method of claim 1 wherein compound 10 and compound 6 are administered orally.

3. The method of claim 1 wherein ribavirin an interferon is not administered to the human.

4. The method of claim 1 further comprising administering ribavirin to the human.

* * * * *